(12) United States Patent
Montalvo et al.

(10) Patent No.: US 12,339,272 B2
(45) Date of Patent: Jun. 24, 2025

(54) SENSORS INCORPORATED INTO BUILDING MATERIALS TO DETECT PHYSICAL CHARACTERISTIC CHANGES

(71) Applicant: Lyten, Inc., San Jose, CA (US)

(72) Inventors: Carlos Montalvo, Cambria, CA (US); Michael Stowell, Sunnyvale, CA (US); Bruce Lanning, Littleton, CO (US)

(73) Assignee: LYTEN, INC., San Jose, CA (US)

( * ) Notice: Subject to any disclaimer, the term of this patent is extended or adjusted under 35 U.S.C. 154(b) by 106 days.

(21) Appl. No.: 17/940,246

(22) Filed: Sep. 8, 2022

(65) Prior Publication Data

US 2023/0019088 A1    Jan. 19, 2023

Related U.S. Application Data

(63) Continuation-in-part of application No. 17/340,493, filed on Jun. 7, 2021, now Pat. No. 11,592,279, and
(Continued)

(51) Int. Cl.
*G01N 33/38* (2006.01)

(52) U.S. Cl.
CPC .................. *G01N 33/383* (2013.01)

(58) Field of Classification Search
None
See application file for complete search history.

(56) References Cited

U.S. PATENT DOCUMENTS 6,359,444 B1    3/2002   Grimes
6,525,105 B1    2/2003   Udagawa et al.
(Continued)

FOREIGN PATENT DOCUMENTS

CN    103649718 A    3/2014
CN    106129558 A    11/2016
(Continued)

OTHER PUBLICATIONS

Non-Final Office Action from U.S. Appl. No. 17/940,227, dated Nov. 14, 2022.
(Continued)

*Primary Examiner* — Eric Blount
(74) *Attorney, Agent, or Firm* — Zilka-Kotab, P.C.

(57) ABSTRACT

A disclosed construction structure unit may include at least one split-ring resonator, which may be embedded within a material. The split ring resonator may be formed from a three-dimensional (3D) monolithic carbonaceous growth and may detect an electromagnetic ping emitted from a user device. The split ring resonator may generate an electromagnetic return signal in response to the electromagnetic ping. The electromagnetic return signal may indicate a state of the material in a position proximate to a respective split ring resonator. In some aspects, the split-ring resonator may resonate at a first frequency in response to the electromagnetic ping when the material is in a first state, and may resonate at a second frequency in response to the electromagnetic ping when the material is in a second state. A resonant frequency of the 3D monolithic carbonaceous growth may be based on physical characteristics of the material.

28 Claims, 57 Drawing Sheets

Related U.S. Application Data a continuation-in-part of application No. 17/227,249, filed on Apr. 9, 2021, now Pat. No. 11,479,062, which is a continuation-in-part of application No. 16/829,355, filed on Mar. 25, 2020, now Pat. No. 11,446,966, said application No. 17/340,493 is a continuation-in-part of application No. 16/829,355, filed on Mar. 25, 2020, now Pat. No. 11,446,966.

(60) Provisional application No. 63/281,846, filed on Nov. 22, 2021, provisional application No. 63/276,274, filed on Nov. 5, 2021, provisional application No. 63/247,680, filed on Sep. 23, 2021, provisional application No. 63/242,270, filed on Sep. 9, 2021, provisional application No. 63/094,223, filed on Oct. 20, 2020, provisional application No. 63/036,796, filed on Jun. 9, 2020, provisional application No. 63/036,118, filed on Jun. 8, 2020, provisional application No. 63/008,262, filed on Apr. 10, 2020, provisional application No. 62/985,550, filed on Mar. 5, 2020, provisional application No. 62/979,215, filed on Feb. 20, 2020, provisional application No. 62/824,440, filed on Mar. 27, 2019.

(56) References Cited

U.S. PATENT DOCUMENTS

| | | | |
|---|---|---|---|
| 6,885,291 B1 | 4/2005 | Pollack et al. | |
| 6,997,039 B2 | 2/2006 | Rao et al. | |
| 7,581,439 B2 | 9/2009 | Rensel et al. | |
| 8,364,419 B2 | 1/2013 | Potyrailo et al. | |
| 8,448,496 B2 | 5/2013 | Huang et al. | |
| 8,567,232 B2 | 10/2013 | Ackley et al. | |
| 8,736,425 B2 | 5/2014 | Potyrailo | |
| 9,038,443 B1 | 5/2015 | Pace et al. | |
| 9,172,147 B1 * | 10/2015 | Manry, Jr. .............. | H01Q 1/286 |
| 9,395,343 B2 | 7/2016 | Schmid et al. | |
| 9,538,657 B2 | 1/2017 | Potyrailo et al. | |
| 9,705,469 B2 | 7/2017 | Rinaldi et al. | |
| 9,944,131 B2 | 4/2018 | Wei et al. | |
| 10,408,775 B2 | 9/2019 | Tao et al. | |
| 10,492,683 B2 | 12/2019 | Yalçinkaya et al. | |
| 10,502,705 B2 | 12/2019 | Stowell et al. | |
| 10,802,018 B2 | 10/2020 | Cubukcu et al. | |
| 11,011,282 B1 | 5/2021 | Dong et al. | |
| 11,014,413 B2 | 5/2021 | Räisänen et al. | |
| 11,137,368 B2 | 10/2021 | Stowell et al. | |
| 11,555,748 B2 | 1/2023 | Stowell et al. | |
| 11,555,761 B1 | 1/2023 | Stowell | |
| 11,585,731 B2 | 2/2023 | Stowell et al. | |
| 11,892,372 B2 | 2/2024 | Stowell et al. | |
| 11,965,803 B2 | 4/2024 | Stowell et al. | |
| 12,174,090 B2 | 12/2024 | Stowell et al. | |
| 12,196,636 B2 | 1/2025 | Stowell et al. | |
| 12,265,058 B2 | 4/2025 | Jardine et al. | |
| 12,270,785 B2 | 4/2025 | Jardine et al. | |
| 2003/0080919 A1 | 5/2003 | Forster et al. | |
| 2003/0201044 A1 | 10/2003 | Schick | |
| 2004/0113846 A1 | 6/2004 | Achim | |
| 2007/0068493 A1 | 3/2007 | Pavlovsky | |
| 2007/0090926 A1 | 4/2007 | Potyrailo et al. | |
| 2007/0175555 A1 | 8/2007 | Myatt | |
| 2007/0295069 A1 | 12/2007 | Mancosu et al. | |
| 2008/0135614 A1 | 6/2008 | Werner et al. | |
| 2009/0145233 A1 | 6/2009 | Eklund et al. | |
| 2009/0327188 A1 | 12/2009 | Ryhanen et al. | |
| 2011/0018556 A1 | 1/2011 | Le et al. | |
| 2011/0040498 A1 | 2/2011 | Huang et al. | |
| 2012/0235690 A1 | 9/2012 | Potyrailo et al. | |
| 2013/0150516 A1 | 6/2013 | Lettow | |
| 2013/0214875 A1 | 8/2013 | Duncan et al. | |
| 2014/0002111 A1 | 1/2014 | Potyrailo et al. | |
| 2014/0070935 A1 | 3/2014 | Wang et al. | |
| 2014/0134092 A1 | 5/2014 | Shankman | |
| 2014/0270937 A1 | 9/2014 | Kulkarni et al. | |
| 2014/0305191 A1 | 10/2014 | Schmid et al. | |
| 2014/0354112 A1 | 12/2014 | Rocha | |
| 2015/0118492 A1 | 4/2015 | Sitharaman et al. | |
| 2015/0123678 A1 | 5/2015 | Neikirk et al. | |
| 2015/0323482 A1 | 11/2015 | Shimoyama et al. | |
| 2016/0065169 A1 | 3/2016 | Rinaldi et al. | |
| 2016/0091544 A1 | 3/2016 | Daneshmand et al. | |
| 2016/0169824 A1 | 6/2016 | Shin et al. | |
| 2016/0282312 A1 | 9/2016 | Cable et al. | |
| 2017/0096036 A1 | 4/2017 | Guinart et al. | |
| 2017/0294698 A1 | 10/2017 | Cho et al. | |
| 2017/0294699 A1 | 10/2017 | Cho et al. | |
| 2017/0330004 A1 | 11/2017 | Gibson | |
| 2018/0042479 A1 | 2/2018 | Yalçinkaya et al. | |
| 2018/0164236 A1 | 6/2018 | Tao et al. | |
| 2018/0265666 A1 | 9/2018 | Anzelmo et al. | |
| 2018/0346684 A1 | 12/2018 | Polyzos et al. | |
| 2019/0204265 A1 | 7/2019 | Stowell et al. | |
| 2019/0242450 A1 | 8/2019 | Lin | |
| 2019/0264004 A1 | 8/2019 | Stowell et al. | |
| 2019/0277702 A1 | 9/2019 | Aleman et al. | |
| 2019/0277761 A1 | 9/2019 | Falk et al. | |
| 2020/0278304 A1 | 9/2020 | Udpa et al. | |
| 2021/0229503 A1 | 7/2021 | Stowell et al. | |
| 2021/0293521 A1 | 9/2021 | Stowell et al. | |
| 2021/0293630 A1 | 9/2021 | Stowell et al. | |
| 2021/0348909 A1 | 11/2021 | Stowell et al. | |
| 2023/0017082 A1 | 1/2023 | Stowell et al. | |
| 2023/0018475 A1 | 1/2023 | Stowell | |
| 2023/0021276 A1 | 1/2023 | Stowell et al. | |
| 2023/0107066 A1 | 4/2023 | Ram et al. | |
| 2023/0296479 A1 | 9/2023 | Stowell et al. | |
| 2023/0384264 A1 | 11/2023 | Jardine et al. | |
| 2023/0384265 A1 | 11/2023 | Jardine et al. | |
| 2023/0417685 A1 | 12/2023 | Jardine et al. | |
| 2024/0003779 A1 | 1/2024 | Stowell et al. | |
| 2024/0264043 A1 | 8/2024 | Stowell et al. | |
| 2024/0392852 A1 | 11/2024 | Biggins et al. | |
| 2025/0067720 A1 | 2/2025 | Montalvo et al. | |
| 2025/0076154 A1 | 3/2025 | Stowell et al. | |
| 2025/0093219 A1 | 3/2025 | Stowell et al. | |

FOREIGN PATENT DOCUMENTS

| | | |
|---|---|---|
| CN | 104677879 B | 6/2017 |
| CN | 108182321 A | 6/2018 |
| CN | 109840579 A | 6/2019 |
| DE | 102017208169 A1 | 11/2018 |
| EP | 1289809 B1 | 5/2007 |
| EP | 3584885 A1 | 12/2019 |
| JP | 5822282 B2 | 11/2015 |
| KR | 100721261 B1 | 5/2007 |
| TW | 201312104 A | 3/2013 |
| TW | 202223332 A | 6/2022 |
| WO | 199325400 A1 | 12/1993 |
| WO | 2009024673 A1 | 2/2009 |
| WO | 20110018556 A1 | 2/2011 |
| WO | 2013027029 A1 | 2/2013 |
| WO | 2013192335 A1 | 12/2013 |
| WO | 2014169195 A1 | 10/2014 |
| WO | 2015083073 A1 | 6/2015 |
| WO | 2016068810 A1 | 5/2016 |
| WO | 2019067488 A1 | 4/2019 |
| WO | 2019136181 A1 | 7/2019 |
| WO | 2020198451 A1 | 10/2020 |
| WO | 2021096890 A1 | 5/2021 |
| WO | 2022216403 A1 | 10/2022 |

OTHER PUBLICATIONS

Notice of Allowance from U.S. Appl. No. 17/940,240, dated Nov. 16, 2022.
Stowell et al., U.S. Appl. No. 17/340,678, filed Jun. 7, 2021.
Stowell et al., U.S. Appl. No. 17/340,514, filed Jun. 7, 2021.
Notice of Allowance from U.S. Appl. No. 17/340,514, dated Oct. 5, 2022.

(56) References Cited

OTHER PUBLICATIONS

Corrected Notice of Allowance from U.S. Appl. No. 17/340,514, dated Oct. 27, 2022.
Stowell et al., U.S. Appl. No. 17/340,493, filed Jun. 7, 2021.
Non-Final Office Action from U.S. Appl. No. 17/340,493, dated Jul. 21, 2022.
Notice of Allowance from U.S. Appl. No. 17/340,493, dated Oct. 13, 2022.
Jardine et al., U.S. Appl. No. 18/230,072, filed Aug. 3, 2023.
Jardine et al., U.S. Appl. No. 18/230,080, filed Aug. 3, 2023.
Jardine et al., U.S. Appl. No. 18/230,083, filed Aug. 3, 2023.
Corrected Notice of Allowance from U.S. Appl. No. 18/080,606, dated Dec. 6, 2023.
Notice of Allowance from U.S. Appl. No. 18/369,418, dated Dec. 5, 2023.
Corrected Notice of Allowance from U.S. Appl. No. 18/369,418, dated Jan. 17, 2024.
Stowell et al., U.S. Appl. No. 18/596,390, dated Mar. 5, 2024.
Stowell et al., U.S. Appl. No. 17/940,227, filed Sep. 8, 2022.
Stowell, M., U.S. Appl. No. 17/940,240, filed Sep. 8, 2022.
Stowell et al., U.S. Appl. No. 17/940,256, filed Sep. 8, 2022.
International Search Report and Written Opinion from PCT Application No. PCT/US2019/012224, dated Apr. 26, 2019.
International Search Report and Written Opinion from PCT Application No. PCT/US2021/042735, dated Nov. 3, 2021.
Na et al., "Graphene-Based Wireless Environmental Gas Sensor on PET Substrate," IEEE Sensor Journal, 2015, pp. 1-7.
Potyrailo et al., "A Passive Radio-Frequency Identification (RFID) Gas Sensor With Self-Correction Against Fluctuations of Ambient Temperature," Sens Actuators B Chem., vol. 185, Aug. 1, 2013, 16 pages.
Potyrailo et al., "Multivariable MHz and GHz Wireless Chem/Bio Sensors for Environmental, Industrial, and Security Applications," The 14th International Meeting on Chemical Sensors (IMCS), vol. 40, May 2012, pp. 399-402.
Potyrailo et al., "Wireless sensors and sensor networks for homeland security applications," Trends in Analytical Chemistry, vol. 40, Nov. 1, 2012, pp. 1-25.
Zhu et al., "Optoelectromechanical Multimodal Biosensor with Graphene Active Region," Nano Letters, vol. 14, 2014, pp. 5641-5649.
Corrected Notice of Allowance from U.S. Appl. No. 17/940,227, dated Jan. 5, 2022.
International Search Report and Written Opinion from PCT Application No. PCT/US 22/43125, dated Dec. 15, 2022.
Notice of Allowance from U.S. Appl. No. 17/940,227, dated Dec. 8, 2022.
Stowell et al., U.S. Appl. No. 18/080,606, filed Dec. 13, 2022.
Corrected Notice of Allowance from U.S. Appl. No. 17/940,240, dated Dec. 2, 2022.
Non-Final Office Action from U.S. Appl. No. 18/080,606, dated Jul. 20, 2023.
Reddy et al., "Split ring resonator and its evolved structures over the past decade," IEEE International Conference on Emerging Trends in Computing, Communication, and Nanotechnology (ICECCN), 2013, pp. 625-629.
Non-Final Office Action from U.S. Appl. No. 18/080,606, dated Aug. 24, 2023.
Stowell et al., U.S. Appl. No. 18/369,418, filed Sep. 18, 2023.
Notice of Allowance from U.S. Appl. No. 18/080,606, dated Sep. 29, 2023.
Non-Final Office Action from U.S. Appl. No. 18/369,418, dated Oct. 31, 2023.
Corrected Notice of Allowance from U.S. Appl. No. 18/369,418, dated Dec. 26, 2023.
International Search Report and Written Opinion from PCT Application No. PCT/US23/33178, dated Dec. 20, 2023.
Final Office Action from U.S. Appl. No. 18/596,390, dated Jun. 28, 2024.
Biggins et al., U.S. Appl. No. 18/792,423, filed Aug. 1, 2024.
Office Action from Taiwanese Application No. 112123553, dated Jul. 31, 2024, 16 pages.
Notice of Allowance from U.S. Appl. No. 18/596,390, dated Aug. 14, 2024.
Non-Final Office Action from U.S. Appl. No. 18/596,390, dated May 28, 2024.
Office Action from Taiwanese Application No. 112135663, dated May 21, 2024, 13 pages.
Corrected Notice of Allowance from U.S. Appl. No. 18/596,390, dated Oct. 31, 2024.
Notice of Preliminary Rejection from Korean Application No. 10-2024-7011607, dated Oct. 23, 2024, 4 pages.
Montalvo et al., U.S. Appl. No. 18/942,240, filed Nov. 8, 2024.
Stowell et al., U.S. Appl. No. 18/943,655, filed Nov. 11, 2024.
Corrected Notice of Allowance from U.S. Appl. No. 18/596,390, dated Nov. 20, 2024.
Notice of Allowance from U.S. Appl. No. 17/940,256, dated Nov. 27, 2024.
International Search Report and Written Opinion from PCT Application No. PCT/US2024/040628, dated Nov. 20, 2024, 24 pages.
Stowell et al., U.S. Appl. No. 18/968,785, filed Dec. 4, 2024.
Notice of Allowance from U.S. Appl. No. 18/230,072, dated Dec. 18, 2024.
Corrected Notice of Allowance from U.S. Appl. No. 18/230,072, dated Dec. 20, 2024.
Non-Final Office Action from U.S. Appl. No. 18/230,080, dated Dec. 18, 2024.
Office Action from Chinese Patent Application No. 202280067756.0, dated Aug. 23, 2024, 3 pages.
Corrected Notice of Allowance from U.S. Appl. No. 18/596,390, dated Aug. 29, 2024.
Non-Final Office Action from U.S. Appl. No. 17/940,256, dated Oct. 7, 2024.
Notice of Allowance from U.S. Appl. No. 18/230,083, dated Jan. 15, 2025.
Corrected Notice of Allowance from U.S. Appl. No. 18/230,083, dated Jan. 24, 2025.
Corrected Notice of Allowance from U.S. Appl. No. 18/230,083, dated Feb. 7, 2025.
Second Office Action from Taiwanese Application No. 112135663, dated Jan. 8, 2025, 3 pages.
Second Office Action from Chinese Patent Application No. 202280067756.0, dated Jan. 23, 2025.
International Search Report and Written Opinion from PCT Application No. PCT/US2024/036945, dated Dec. 19, 2024.
Extended European Search Report from European Application No. 22868142.5, dated Jan. 17, 2025, 9 pages.
Jardine et al., U.S. Appl. No. 19/051,045, filed Feb. 11, 2025.
Corrected Notice of Allowance from U.S. Appl. No. 18/230,083, dated Feb. 18, 2025.
Notice of Allowance from U.S. Appl. No. 18/230,072, dated Feb. 20, 2025.
Corrected Notice of Allowance from U.S. Appl. No. 18/230,072, dated Mar. 5, 2025.
Notice of Allowance from U.S. Appl. No. 18/230,080, dated Apr. 1, 2025.

\* cited by examiner

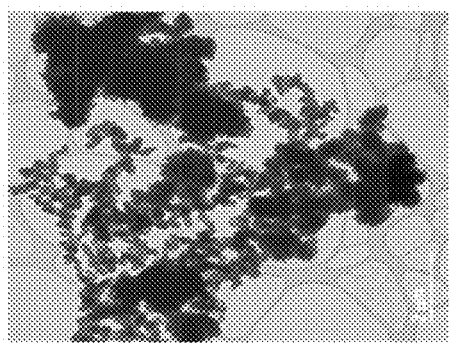
*Figure 18G*
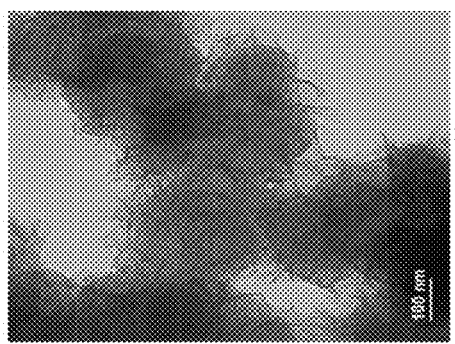
*Figure 18H*
*Figure 18I*
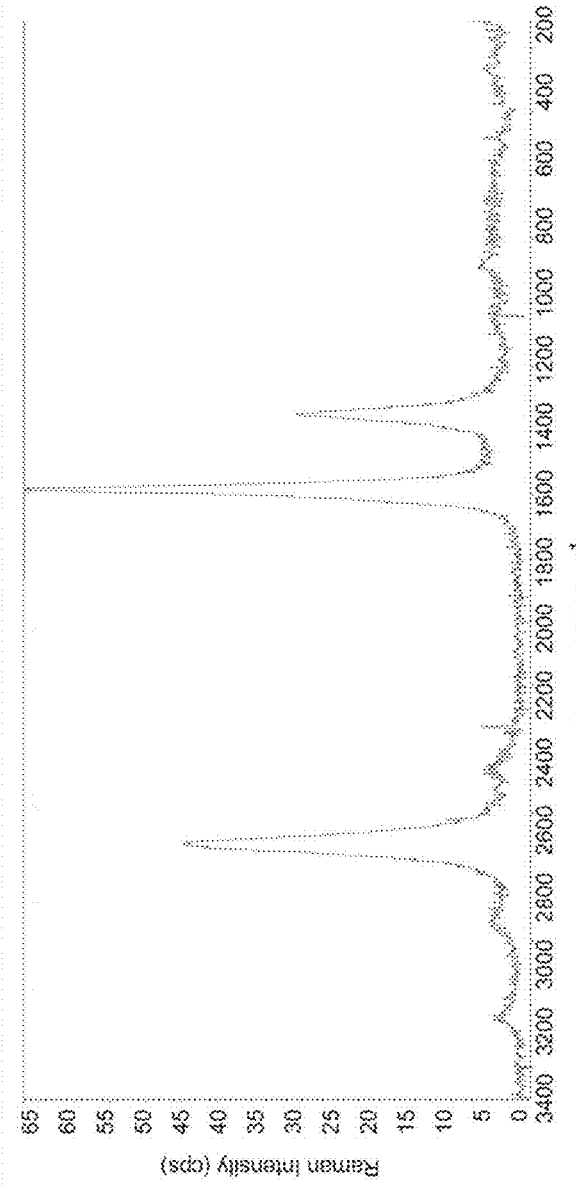
*Figure 18J*

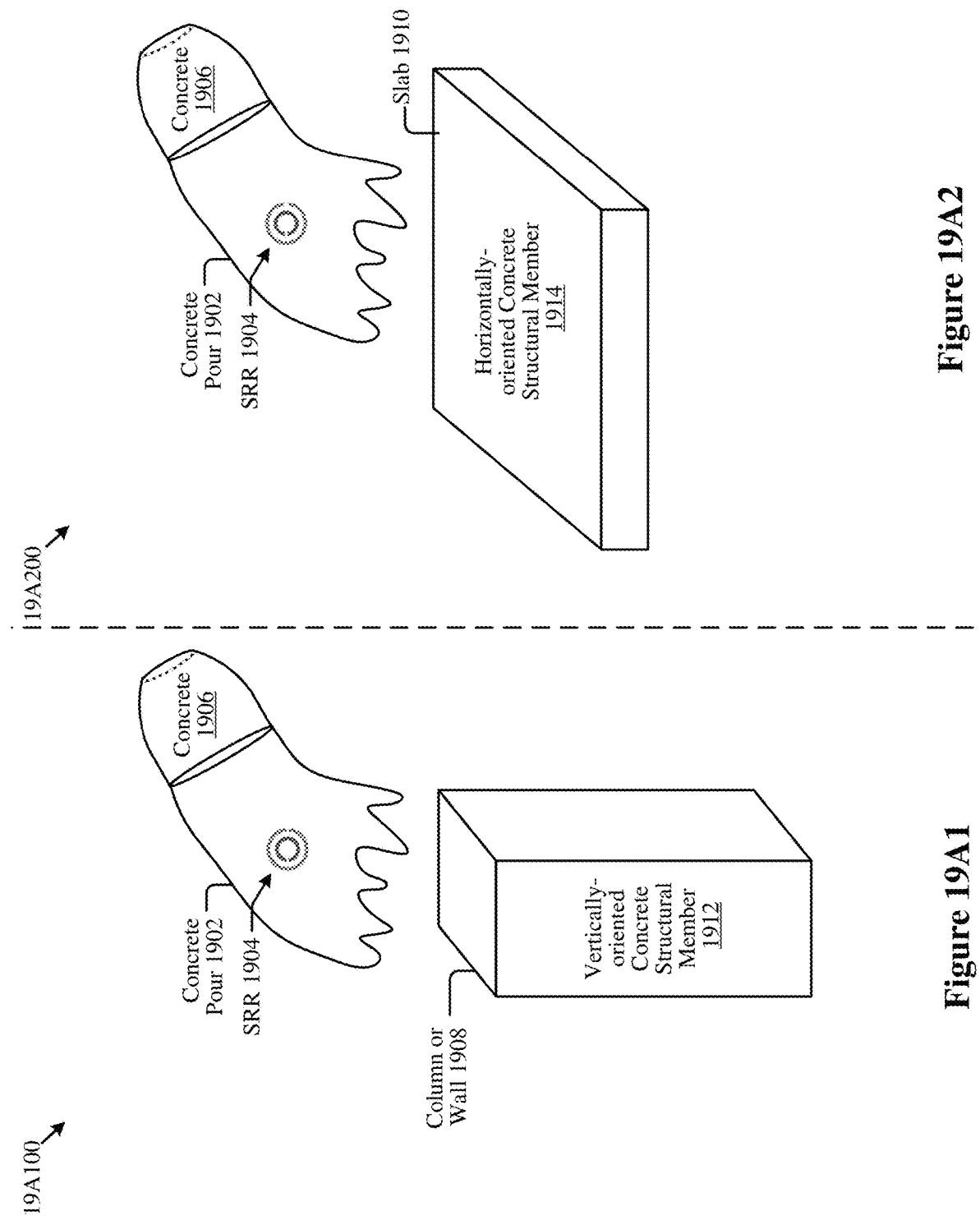
Figure 19A2
Figure 19A1

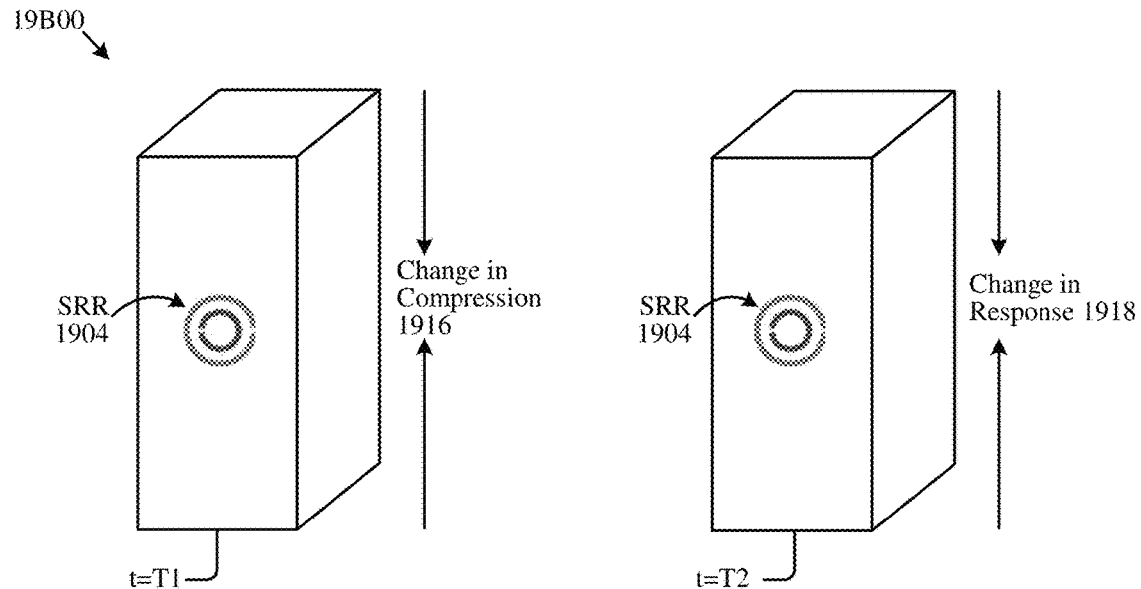
Figure 19B1
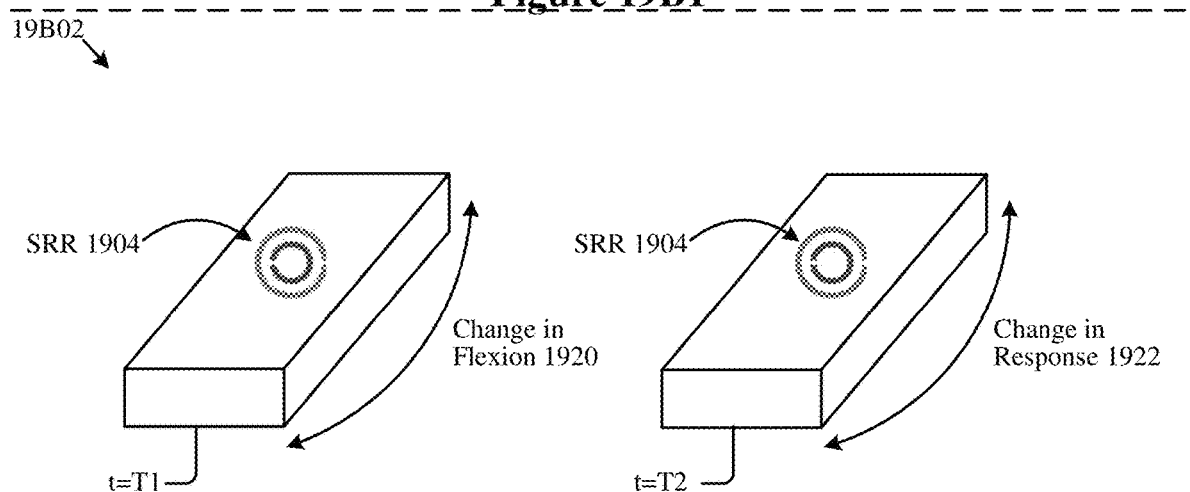
Figure 19B2

| Size = f(size of member) | Eq. 8 |

| Orientation = f(flexure vectors, compression vectors, expansion vectors) | Eq. 9 |

| Location = f(flexure points, compression maxima, expansion maxima) | Eq. 10 |

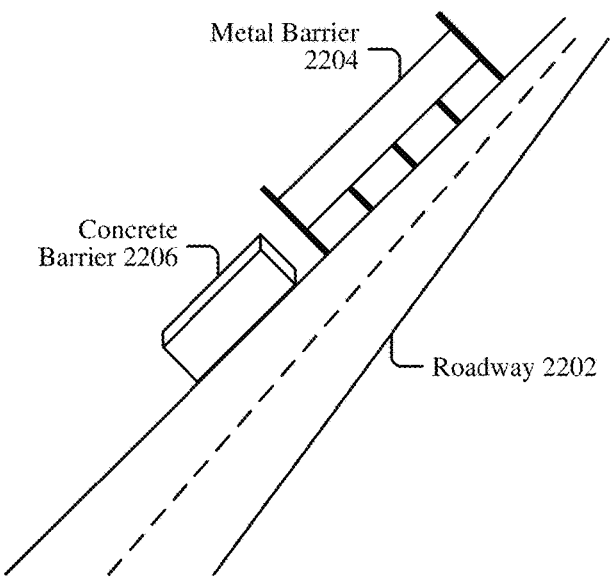
Figure 22A1
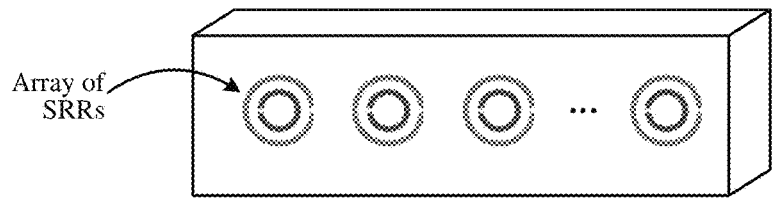
Figure 22A2
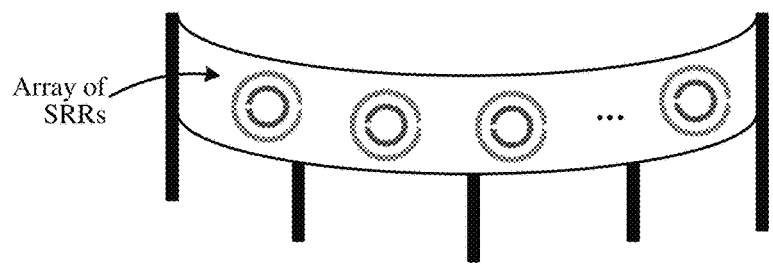
Figure 22A3

24A00
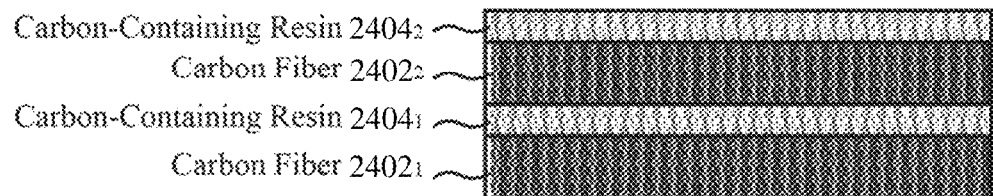
Carbon-Containing Resin 2404₂
Carbon Fiber 2402₂
Carbon-Containing Resin 2404₁
Carbon Fiber 2402₁
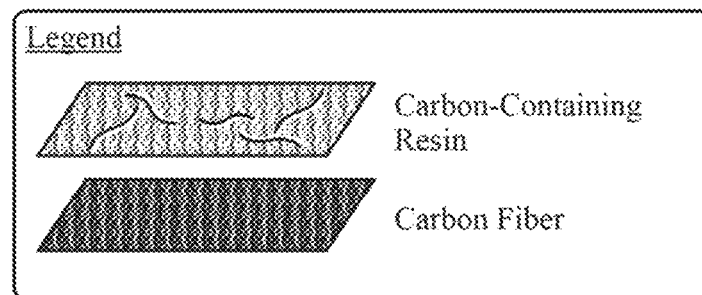
Figure 24A

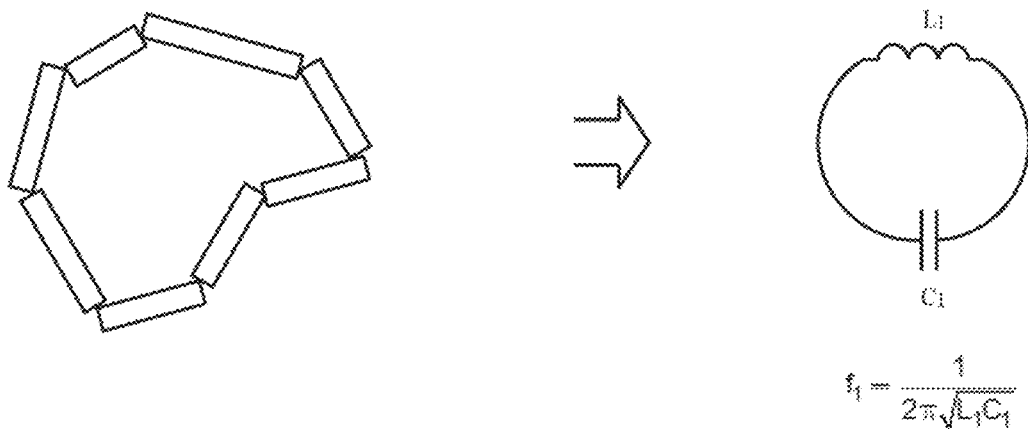
Figure 24B1
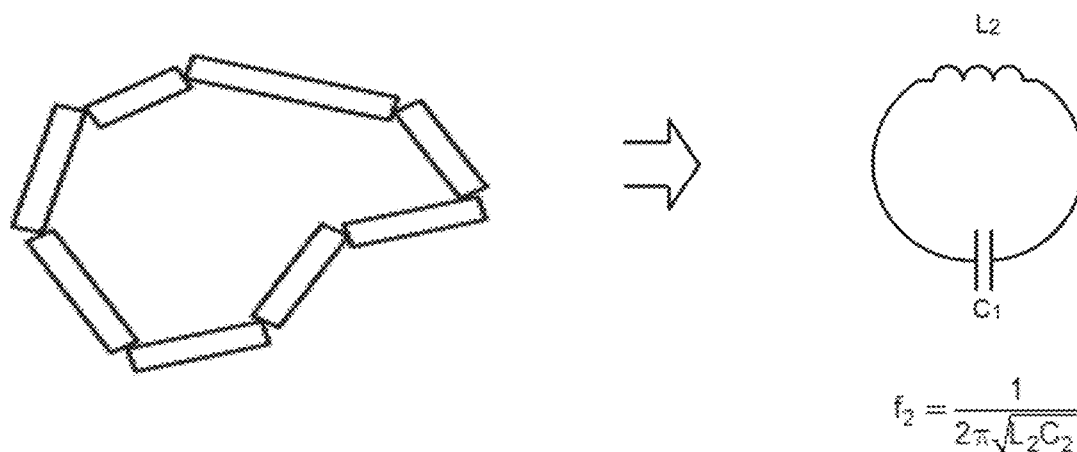
Figure 24B2

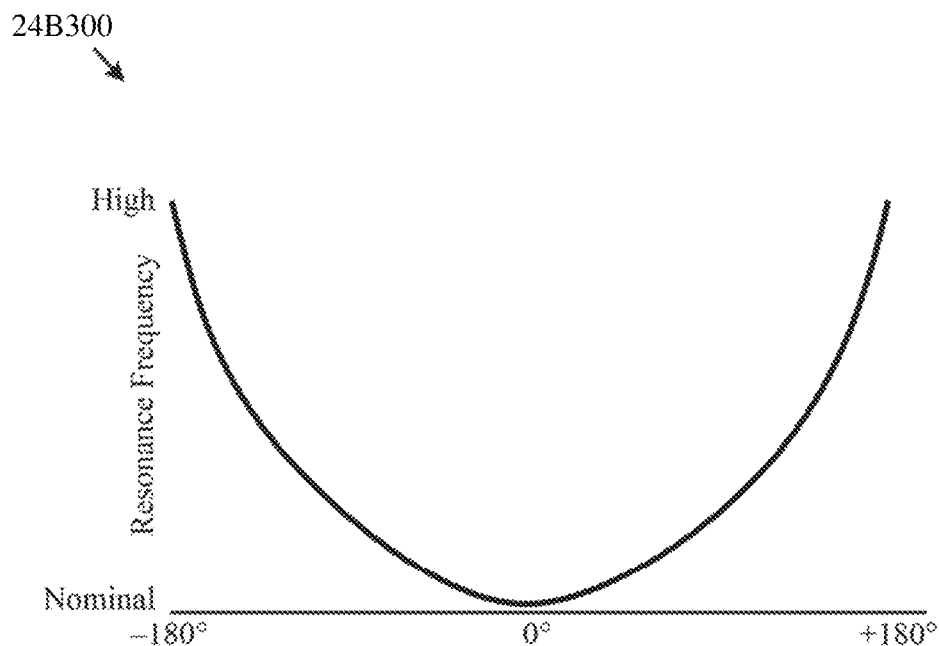
Figure 24B3
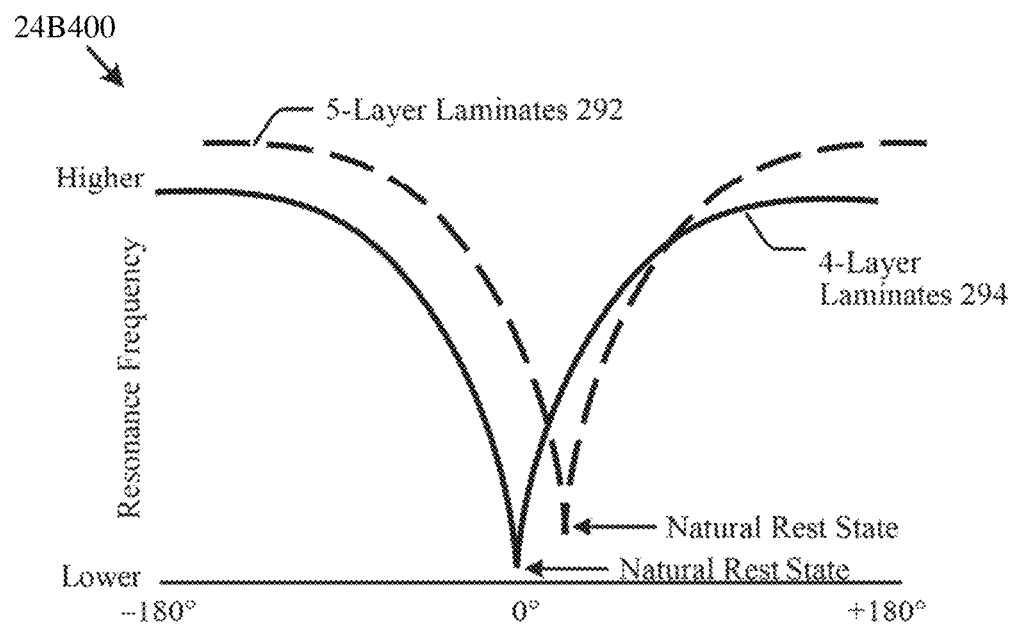
Figure 24B4

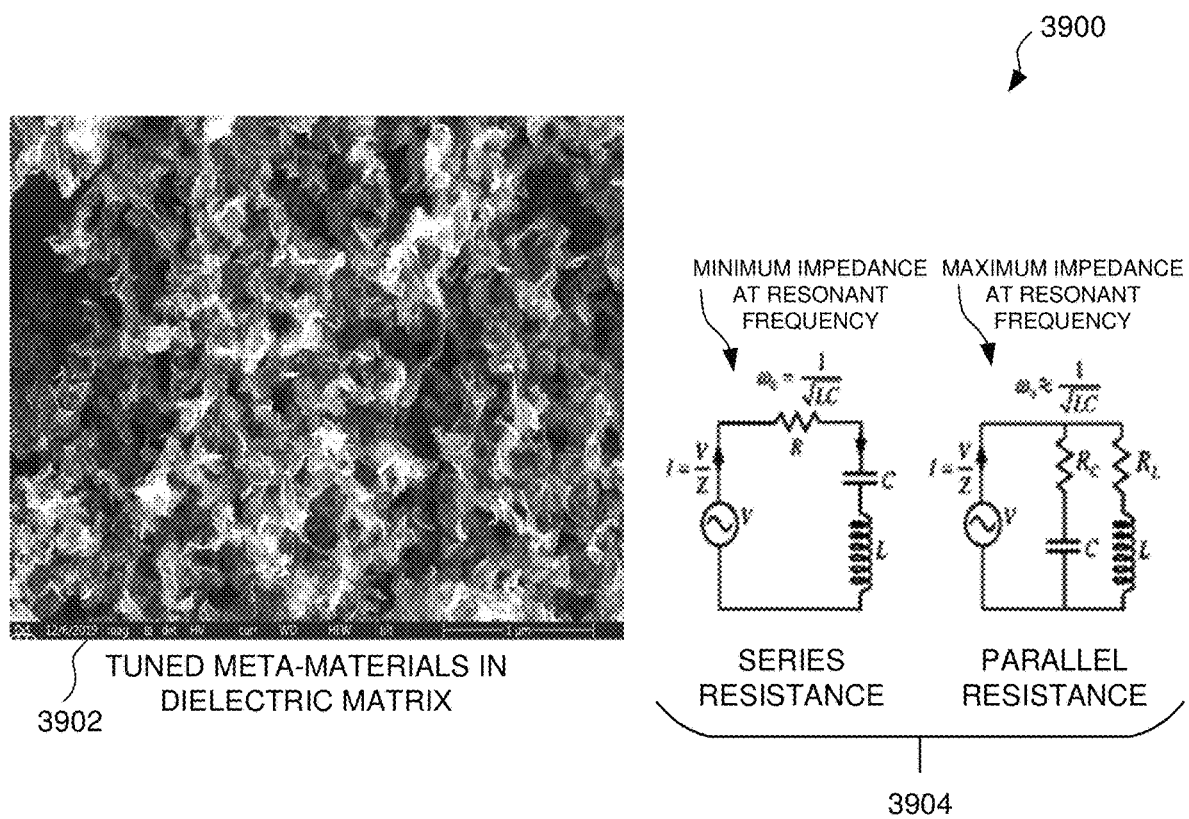
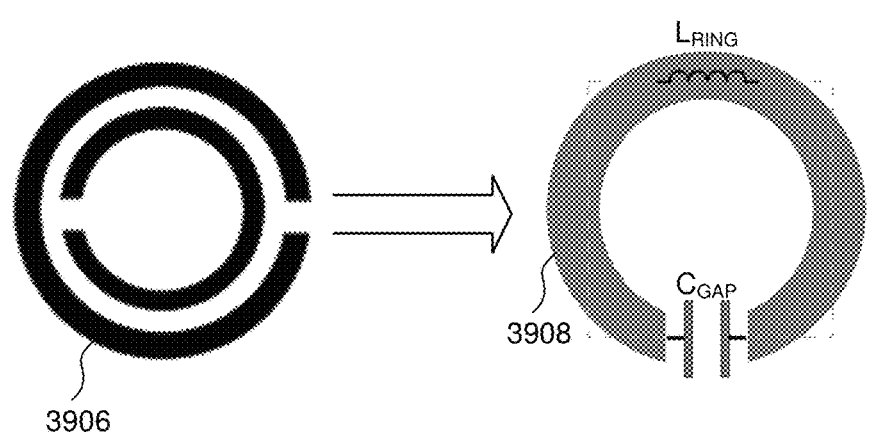
Figure 39

SENSORS INCORPORATED INTO BUILDING MATERIALS TO DETECT PHYSICAL CHARACTERISTIC CHANGES

CROSS-REFERENCE TO RELATED APPLICATIONS

This Patent Applications claims the benefit of priority to: U.S. Provisional Patent Application No. 63/242,270, entitled "SENSORS INCORPORATED INTO SEMI-RIGID STRUCTURAL MEMBERS TO DETECT PHYSICAL CHARACTERISTIC CHANGES" filed Sep. 9, 2021; U.S. Provisional Patent Application No. 63/247,680, entitled "SENSORS INCORPORATED INTO SEMI-RIGID STRUCTURAL MEMBERS TO DETECT PHYSICAL CHARACTERISTIC CHANGES" and filed Sep. 23, 2021; U.S. Provisional Patent Application No. 63/276,274, entitled "SENSORS INCORPORATED IN VEHICLE COMPONENTS TO DETECT PHYSICAL CHARACTERISTIC CHANGES, and filed Nov. 5, 2021; and U.S. Provisional Patent Application No. 63/281,846, entitled "SENSORS INCORPORATED INTO AIRBORNE VEHICLE COMPONENTS TO DETECT PHYSICAL CHARACTERISTIC CHANGES" and filed Nov. 22, 2021, all of which are assigned to the assignee hereof; the disclosures of all prior Applications are considered part of and are incorporated by reference in this Patent Application.

This Patent Application is also a continuation-in-part of and claims the benefit of priority to U.S. patent application Ser. No. 17/227,249, entitled "TUNED RADIO FREQUENCY (RF) RESONANT MATERIALS AND MATERIAL CONFIGURATIONS FOR SENSING IN A VEHICLE" and filed on Apr. 9, 2021, which in turn, claims the benefit of priority to U.S. Provisional Patent Application No. 63/008,262, entitled "RESONANCE SENSING IN TIRES" and filed on Apr. 10, 2020, and to U.S. Provisional Patent Application No. 63/036,796, entitled "RESONANCE SENSING IN ELASTOMER-CONTAINING PRODUCTS" and filed on Jun. 9, 2020, all of which are assigned to the assignee hereof; the disclosures of all prior Applications are considered part of and are incorporated by reference in this Patent Application.

U.S. patent application Ser. No. 17/227,249 is also a continuation-in-part of and claims the benefit of priority to U.S. patent application Ser. No. 16/829,355, entitled "TIRES CONTAINING RESONATING CARBON-BASED MICROSTRUCTURES" and filed on Mar. 25, 2020, which in turn, claims the benefit of priority to U.S. Provisional Patent Application No. 62/985,550, entitled "RESONANT SERIAL NUMBER IN VEHICLE TIRES" and filed on Mar. 5, 2020, to U.S. Provisional Patent Application No. 62/979,215, entitled "WASTE ENERGY HARVESTING AND POWERING IN VEHICLES" and filed on Feb. 20, 2020, and to U.S. Provisional Patent Application No. 62/824,440, entitled "TUNING RESONANT MATERIALS FOR VEHICLE SENSING" and filed on Mar. 27, 2019, all of which are assigned to the assignee hereof; the disclosures of all prior Applications are considered part of and are incorporated by reference in this Patent Application.

This Patent Application is a continuation-in-part of and claims the benefit of priority to U.S. patent application Ser. No. 17/340,493, entitled "SENSORS INCORPORATED INTO ELASTOMERIC MATERIALS TO DETECT ENVIRONMENTALLY-CAUSED PHYSICAL CHARACTERISTIC CHANGES" and filed on Jun. 7, 2021, which in turn, claims the benefit of priority to U.S. Provisional Patent Application No. 63/036,118, entitled "CARBON-CONTAINING STICTION SENSORS" and filed on Jun. 8, 2020, to U.S. Provisional Patent Application No. 63/094,223, entitled "SENSORS FOR ELASTOMER PROPERTY CHANGE DETECTION" and filed on Oct. 20, 2020, and to, U.S. Provisional Patent Application No. 63/036,796, entitled "RESONANCE SENSING IN ELASTOMER-CONTAINING PRODUCTS" and filed on Jun. 9, 2020, all of which are assigned to the assignee hereof; the disclosures of all prior Applications are considered part of and are incorporated by reference in this Patent Application.

U.S. patent application Ser. No. 17/340,493 is also a continuation-in-part of and claims the benefit of priority to U.S. patent application Ser. No. 16/829,355, entitled "TIRES CONTAINING RESONATING CARBON-BASED MICROSTRUCTURES" and filed on Mar. 25, 2020, which in turn, claims the benefit of priority to U.S. Provisional Patent Application No. 62/824,440, entitled "TUNING RESONANT MATERIALS FOR VEHICLE SENSING" and filed on Mar. 27, 2019, all of which are assigned to the assignee hereof; the disclosures of all prior Applications are considered part of and are incorporated by reference in this Patent Application.

TECHNICAL FIELD

This disclosure generally relates to sensors and, more specifically, to incorporating split ring resonators in or on structural members of building materials to detect changes properties of the structural members.

DESCRIPTION OF RELATED ART

Advances in construction materials, including self-healing concrete, use of graphene, and zero-emissions construction, at a minimum, have created an opportunity for further technological integration. This is true especially as businesses seek to create sustainable and greener construction solutions. Further, the expectation and requirements of construction material safety continue to increase. However, current systems fail to anticipate construction failures until they are often too late. For example, a microscopic crack in a foundation may not be seen for many years as the crack slowly propagates, causing the building to eventually collapse. Such applications and issues can present unique challenges, including detecting material wear and fatigue before it can be visually seen or cause a physical effect, or failing to have a human inspector always present to assess the safety of a structure or of its materials.

Recent developments in sensors allow for the detection of material property changes in many new applications. However, further improvements in sensor technology are desirable.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter.

One innovative aspect of the subject matter described in this disclosure may be implemented as an electromagnetic state sensing device (EMSSD) including split-ring resonators (split ring resonators) configured to be embedded within a material. Each split ring resonator may be formed from a three-dimensional (3D) monolithic carbonaceous growth and respond to an electromagnetic stimulus signal emitted from a user device (e.g., a smartphone, a radio frequency identification (RFID) reader, or a near-field communication (NFC) device) to generate an electromagnetic return signal in response to the electromagnetic stimulus signal. The electromagnetic return signal may indicate a state of the material in a position proximate to a respective split ring resonator. The split ring resonator may resonate at a first frequency in response to the electromagnetic stimulus signal when the material is in a first state and may resonate at a second frequency in response to the electromagnetic stimulus signal when the material is in a second state. A natural resonant frequency of the 3D monolithic carbonaceous growth may be based on physical characteristics of the material, e.g., permittivity and/or permeability. In this way, an extent of shift of a natural resonance frequency in response to the electromagnetic stimulus signal of the first split ring resonator and the second split ring resonator may be indicative of an amount of deformation of the material.

In various implementations, each split ring resonator may indicate a first condition of the material by generating a first electromagnetic return signal in response to the electromagnetic stimulus signal, and may indicate a second condition of the material by generating a second electromagnetic return signal in response to the electromagnetic ping. In addition, the first electromagnetic return signal may have a first frequency, and the second electromagnetic return signal may have a second frequency different than the first frequency.

The state of the material may include a deformation of the material. In some aspects, the split ring resonator may indicate deformation of the material by generating a first electromagnetic return signal in response to the electromagnetic stimulus signal, and may indicate a lack of deformation of the material by generating a second electromagnetic return signal in response to the electromagnetic ping.

In some implementations, at least one split ring resonator includes a resonance portion, which may resonate at a first frequency in response to the electromagnetic stimulus signal when the state of the material exceeds a threshold, and may resonate at a second frequency in response to the electromagnetic stimulus signal when the state of the material is beneath the threshold. Some of the split ring resonators may each have a first split-ring resonator (split ring resonator) with first carbon particles that may uniquely resonate in response to an electromagnetic stimulus signal based on a concentration level of the first carbon particles within the first split ring resonator. Some split ring resonators may have a second split ring resonator adjacent to the first split ring resonator with second carbon particles that may uniquely resonate in response to the electromagnetic stimulus signal based at least in part on a concentration level of the second carbon particles within the second split ring resonator.

Each of the first carbon particles and second carbon particles may be chemically bonded with the material. In some aspects, first carbon particles may include first aggregates forming a first porous structure, and the second carbon particles may include second aggregates forming a second porous structure. In this way, an amplitude of resonance of the first split ring resonator or the second split ring resonator may be indicative of an extent of wear of the material. In addition, the first split ring resonator may resonate at a first frequency in response to the electromagnetic ping, and the second split ring resonator may resonate at a second frequency in response to an electromagnetic ping, where the first frequency is different than the second frequency. Each of the first split ring resonator and the second split ring resonator may each have an attenuation point associated with a frequency response to the electromagnetic ping.

In some implementations, split ring resonators are disposed in structural members of an EVTOL. Further, techniques are disclosed to show how resonant sensors play a significant role in the safety and maneuverability of EVTOL vehicles as well as pertaining to the safety and maneuverability of other types of airborne vehicles.

In one implementation, a construction structural unit may comprise at least one split-ring resonator (SRR) embedded within a material of the construction structural unit, or placed on a surface of the material. Additionally, the at least one SRR is formed from a three-dimensional (3D) monolithic carbonaceous growth and wherein the at least one SRR is configured to respond to a wireless electromagnetic stimulus. Further, the at least one SRR is configured to resonate at one or more corresponding unique frequencies, the frequencies indicating a state of the material at a position proximate to the at least one SRR.

In various embodiments, the material may be concrete or steel. A first frequency of the one or more corresponding unique frequencies may be associated with a calibration signature of the material, and the calibration signature may be measured after the concrete has been poured, cured, and hardened, and/or a second signature may be measured at a time after the calibration signature was measured. The second signature may be associated with a second frequency, and the second signature may indicate at least one of a deformation, a change in compression, a change in flexion, a change in response, a fracture, a strain, or a stress.

The at least one SRR may be configured to resonate at a first frequency in response to the wireless electromagnetic stimulus when the material is in a first state, and may be configured to resonate at a second frequency in response to the wireless electromagnetic stimulus when the material is in a second state. Additionally, a tuned resonant frequency of the 3D monolithic carbonaceous growth may be based at least in part on one or more physical characteristics of the material. The at least one SRR may be configured to indicate a first condition of the material by generating a first wireless electromagnetic return signal in response to the wireless electromagnetic stimulus, and may be configured to indicate a second condition of the material by generating a second wireless electromagnetic return signal in response to the wireless electromagnetic stimulus. Further, the first wireless electromagnetic return signal may have a first frequency, and the second wireless electromagnetic return signal may have a second frequency different than the first frequency.

In some implementations, the state of the material may include a deformation of the material. Additionally, the at least one SRR may be configured to indicate the deformation of the material by generating a first electromagnetic return signal in response to the wireless electromagnetic stimulus, and may be configured to indicate a lack of deformation of the material by generating a second electromagnetic return signal in response to the wireless electromagnetic stimulus. At least one SRR may include a resonance portion, and/or the resonance portion may be configured to resonate at a first frequency in response to the wireless electromagnetic stimulus when the state of the material exceeds a threshold, and may be configured to resonate at a second frequency in response to the wireless electromagnetic stimulus when the state of the material is beneath the threshold.

A resonant frequency of 3D monolithic carbonaceous growth may be based at least in part on either or both of a permittivity and a permeability of the material. Additionally, the at least one SRR may further comprise a first SRR including a plurality of first carbon particles configured to uniquely resonate in response to the wireless electromagnetic stimulus based at least in part on a concentration level of the first carbon particles within the first SRR, the at least one SRR further may comprise a second SRR and includes a plurality of second carbon particles configured to uniquely resonate in response to the wireless electromagnetic stimulus based at least in part on a concentration level of the second carbon particles within the second SRR, each of the first carbon particles and second carbon particles may be chemically bonded with the material, the first carbon particles may include first aggregates forming a first porous structure, and/or the second carbon particles may include second aggregates forming a second porous structure.

Still yet, the at least one SRR may comprise a first SRR and a second SRR. Additionally, the first SRR may be configured to resonate at a first frequency in response to the wireless electromagnetic stimulus, the second SRR may be configured to resonate at a second frequency in response to the wireless electromagnetic stimulus, the first frequency may be different than the second frequency, an amplitude of resonance of the first SRR or the second SRR may be indicative of an extent of wear of the material, and/or an extent of shift of a natural resonance frequency in response to the wireless electromagnetic stimulus of the first SRR and the second SRR may be indicative of an amount of deformation of the material. Further, each of the first SRR and the second SRR may have an attenuation point, and the attenuation point of each the first SRR and the second SRR may be associated with a frequency response to the wireless electromagnetic stimulus.

Details of one or more implementations of the subject matter described in this disclosure are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

FIGS. 19A1 and 19A2 provide a depiction of a split ring resonator, or plurality of split ring resonators, being placed in concrete before the concrete is to be poured into a given structural form, in accordance with one embodiment.

FIGS. 19B1 and 19B2 show a depiction of columns containing the split ring resonator, or plurality of split ring resonators, and an equation for measuring the change within the structural members, in accordance with one embodiment.

FIG. 20 also displays examples of possible factors and equations that may be vital in determining the size, orientation, location, and application of the split ring resonator or split ring resonators on the structural member, in accordance with one embodiment.

FIG. 22A1 through 22A3 are being presented to illustrate use of split ring resonators or a plurality of split ring resonators within roadside barriers, in accordance with one embodiment.

FIG. 24A depicts a sensing laminate including alternating layers of carbon-containing resin and carbon fiber in contact with one-another, in accordance with one embodiment.

FIGS. 24B1 and 24B2 depict a frequency-shifting phenomenon as demonstrated by a sensing laminate including carbon-containing tuned RF resonance materials, in accordance with one embodiment.

FIG. 24B3 is a graph depicting idealized changes in RF resonance as a function of deflection, in accordance with one embodiment.

FIG. 24B4 is a graph depicting changes in RF resonance for 4-layer and 5-layer laminates, in accordance with one embodiment.

FIG. 39 shows a depiction of meta-materials in a dielectric matrix, and circuitry relating thereto, in accordance with one embodiment.

Like reference numbers and designations in the various drawings indicate like elements.

DETAILED DESCRIPTION

Figure 1:
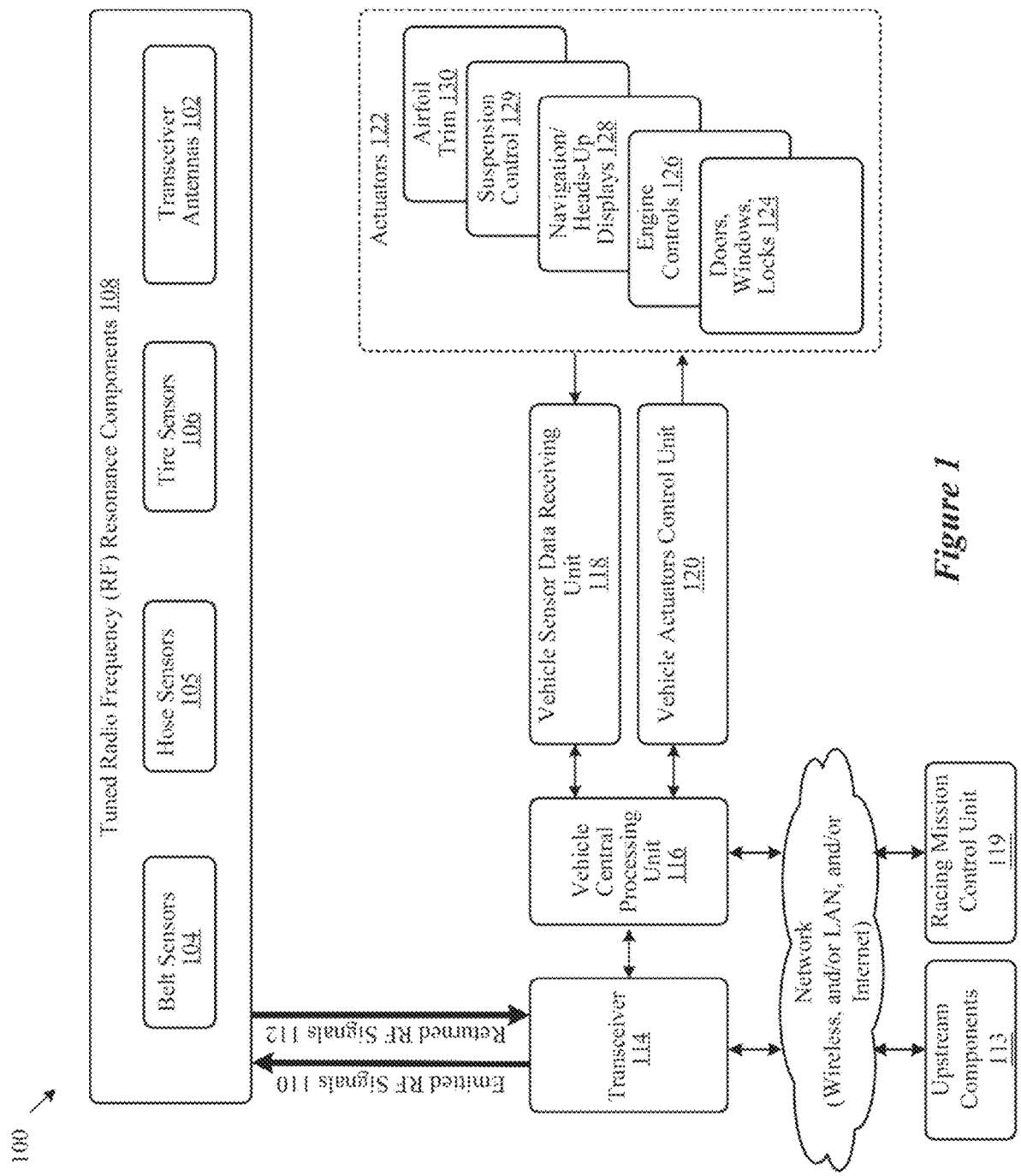
FIG. 1 presents an in-situ vehicle control system including various sensors formed of carbon-containing composites tuned to demonstrate desirable radio frequency (RF) signal resonance and response upon being pinged, in accordance with one embodiment.

Various implementations of the subject matter disclosed herein relate generally to deploying durable sensors (e.g., split-ring resonators, split ring resonators), made from carbonaceous microstructures. The sensors may be incorporated within vehicle components, e.g., within the plies of the body of a conventional, currently commercially available pneumatic (referring to air, nitrogen or other gas-filled) tire, next-generation airless solid tires, as well as in other positions, e.g., within vehicle bodywork. The sensors may be embedded within portions of tire plies and/or tire tread, e.g., rubber in contact with pavement or ground. Routine tire usage results in degradation of contact surfaces, eventually resulting in bald (treadles) tires incapable of adequately adhering to road surfaces, especially in inclement weather conditions, e.g., snow, heavy rain, etc. Deterioration of tire plies containing sensors produces corresponding detectable changes in sensor response behavior, e.g., relative to both forward rotation and tire strain encountered in lateral tire sliding, e.g., "drifting," a common maneuver in some enthusiast communities. In this way, both routine (e.g., forward-rotation) tire deterioration can be detected by changes in expected sensor resonance response behavior and loss of tire stiction (e.g., during drift maneuvers) by observing shifts in expected sensor resonance response behavior (e.g., as accomplished through frequency shift-keying, a concept explained further below). Stiction, as commonly understood, may imply the static friction that needs to be overcome to enable relative motion of stationary objects in contact, e.g., as may be encountered during performance driving maneuvers involving lateral movement, such as drifting. This is comparison to kinetic and/or dynamic friction, which may imply concurrent movement between both contacting surfaces, etc.

It is to be appreciated that, as described herein, the sensors may also be incorporated as well within building materials, construction materials, metallic materials, polymers, plastics, foams (both open and closed cell), etc. Further, application of such materials may be within industries beyond the automobile (e.g. aerospace, construction, mining, etc.).

The carbonaceous materials can be tuned during synthesis to achieve specific expected radio frequency (RF) signal shift (referring to frequency shift) and signal attenuation (referring to the diminishment of signal magnitude) behavior relative to RF signals emitted. Equipment capable of emitting the RF signals may include, for example, a transceiver mounted within one or wheel wells of a vehicle equipped with the disclosed systems and/or by an inductor-capacitor (LC) circuit, also referred to (interchangeably) as a tank circuit, LC circuit or resonator. The presently disclosed implementations do not require moving parts and are thereby less susceptible to wear and tear resultant of routine road usage. Split ring resonators function with pre-existing vehicle electronic components, aerial vehicle electronic components, construction (including concrete) components, etc., Target RF resonance frequency values of disclosed ingredient carbonaceous materials may be tuned within a reaction chamber or a reactor to demonstrate interaction to yield target performance characteristics. The characteristics may be for any number of applications, e.g., knobby, low-pressure off-road tires as well as race-track only slicks without tread. Split ring resonators formed of unique carbonaceous materials demonstrate frequency shifting and/or signal attenuation at specified radio frequencies (RF), e.g., 0.01 GHz to 100 GHz, which may be tuned pursuant to desired applications. Regarding tunability, the carbonaceous materials may be innately grown (e.g., self-nucleated) in a reactor from a carbon-containing gaseous species without requiring a seed particle to generate ornate 3D structures.

Changes in the environment (e.g., snow, rain, etc.) surrounding a vehicle equipped with the disclosed materials and systems may affect the resonance, frequency shifting, and/or signal attenuation behavior of the split ring resonators. As a result, even minute tire condition changes can be detected and communicated to the driver. For example, should a tire ply containing one or more split ring resonators contact a road surface (e.g., forward-rotation) and thereby deteriorate and/or deform over time, resonance of that split ring resonator within the deteriorating and/or deforming tire ply may change. Further, other detectable changes may occur during drifting (e.g., sideways movement) scenarios, such that signal response of the affected tire ply and/or tread layer containing the split ring resonator may indicate the presence or absence of that tread layer, as well as the degree of wear. As a result, split ring resonators may accurately and precisely detect both abrupt or gradual transitions in weather or other environmental conditions (e.g., performance driving maneuvers).

Detectable changes and/or shifts in in RF range resonant frequency response of split ring resonators may be detected by stimulating the RF resonant materials within each split ring resonator with an electromagnetic (EM) signal having a known frequency. In some configurations, EM signals may be initially output by an antennae (also mounted on the vehicle) and/or further propagated by patterned resonant circuits (referred to herein as "resonators", which can be 3D printed onto the tire body plies) mounted within one or more wheel wells. In this way, attenuation and/or frequency shifts associated with respective split ring resonators relative to the emitted signal may be electronically observed and analyzed to gauge current environmental conditions. In addition, changes in the RF resonant frequency (or frequencies) may be observed and compared to known and discrete calibration points to determine tire air pressure as measured at one or more defined detection points on the vehicle's bodywork at a given moment in time.

Conventional use of tires, such as that encountered during on-road driving for most road tires, or off- for off-road tires, can cause slight deformations of portions of the tire, which can cause a change in the natural RF resonance frequency of a respective split ring resonator (at the time y being 'pinged' by a RF signal). Such changes in the natural resonance frequencies (as associated with presently disclosed carbons forming various split ring resonators) can be detected and compared to known calibration points to determine conditions inside the tire. Systems employing antennae in combination with the presently disclosed split ring resonators incorporated within tire plies may accommodate both the sensing of tire ply property changes and reporting-out to associated telemetry equipment in the vehicle.

Of course, it is to be appreciated that although the application of split ring resonators is described in detail with respect to tires (and the automotive industry), such application may equally apply to other industries (e.g. aerospace, construction, materials, mining, oil, concrete, etc.).

Presently disclosed split ring resonators may be tuned to detect even minute changes in physical properties of respective tire plies (and/or any material or substance in which the split ring resonators are embedded in or on), including changes due to air pressure on a vehicle skin, or due to any external application of forces in/on a tire. Such changes can be detected by "pinging" (e.g., e.g., emitting, and later observation and analysis of RF signals) for then processing the unique set of detected properties (e.g., the "signature") of a given tire ply, tread layer, or other surface or region as demonstrated by, for example, frequency domain return. Various mechanisms for calibrating an observed signal signature and processing a return signature are discussed. Methods for fabrication of a tire with passive embedded sensors in the form of tuned carbon structures that interact with the elastomer are disclosed. For example, mechanisms used for making a tire from multiple plies may influence split ring resonator natural resonance frequency behavior. In addition, tires may be constructed including multiple tire plies, each tire ply incorporating a distinct tuned carbon having a unique tuned carbonaceous microstructure, which may be micron-sized, or alternatively in any one or more of the nanometer, micro, even meso-particle sizes up to the millimeter (mm) level.

Disclosed split ring resonators may permit for self-powered signatures from resonance in the GHz and MHz range as made possible by tribological power generators (e.g., generating electric current upon, for example, rotation of a vehicle tire and its repeated friction and/or contact with the pavement or ground). Such tribological components can be integrated or otherwise incorporated within multiple steel belts in between elastomer layers in one or more vehicle tire plies. In this way, the split ring resonators may be charged (and/or powered) by the triboelectric generator for the resonator to resonate (and thus emit RF signals) and discharge. The resonator can be configured to accommodate repeated charge-discharge cycles and be in any one or more of a variety of shapes and/or patterns, including ovals that have an inherent resonant value or properties (based on its formative materials and/or construction).

Changes in the shape or orientation of the resonator may result in a corresponding change of any associated resonation constants. As a result, any change in tire physical properties due to deformation (or any similar deformation of the material in which or on which the split ring resonators are found), e.g., under static conditions like internal tire pressure, or under dynamic conditions such as those encountered while running over Bots Dots, can change the shape or orientation of a respective split ring resonator. Different resonator patterns (e.g., in addition, or the alternative, to split ring resonators) can be used to respond with greater sensitivity to one type of deformation over another (such as referring to lateral deformation encountered while moving around a curve compared to vertical motion encountered while running over gravel or a rough surface). In addition to configurations where split ring resonators change in signal response behavior based on tire deformation, split ring resonators may also electronically communicate with other signal attenuation detection capabilities, e.g., as associated with a digital signal processing, DSP, computer chip and/or transducers placed within the wheel well, or even within the rim, of a wheel. DSP may function with external transceiver (a semiconductor chip) for both stimulus and response; while option. Split ring resonators may also communicate with tribological generators incorporated in individual tire plies and demonstrate resonance behavior that can detected by an external receiver.

As found through the detailed description, illustrative information presented is intended to set forth various architectures (including those optional) and uses. It should be strongly noted that the information is set forth for illustrative purposes (to provide as thorough a description as possible) and should not be construed as limiting in any manner. Any of the following features may be optionally incorporated with or without the exclusion of other features described.

FIG. 1 is a schematic diagram a vehicle condition detection system 100 e.g., intended to be equipped onto a vehicle such as an automobile and/or truck. The vehicle condition detection system 100 may include sensors, such as tuned RF resonance components 108 (e.g., split-ring resonators, such as that shown in FIG. 8). Each of the as tuned RF resonance components 108 may be formed from multiple carbon-based microstructural materials, aggregates, agglomerations, and/or the like such as those disclosed by Stowell, et al., in U.S. patent application Ser. No. 16/785,020 entitled "3D Self-Assembled Multi-Modal Carbon-Based Particle" filed on Feb. 7, 2020 (referred to collectively as "carbonaceous materials"), the disclosure of which is incorporated by reference for all purposes. The tuned RF resonance components 108 can be incorporated into any one or more of belt sensors 104, hose sensors 105, tire sensors 106, and transceiver antennas 102 on a vehicle, such as a conventional driver-driven automobile or a fully-autonomous transport pod or vehicle capable of operating to move vehicle occupants without a human driver.

The tuned RF resonance components 108 can be configured to electronically and/or wirelessly communicate, such as by measurement of signal frequency shift or attenuation, with any one or more of a transceiver 114, a vehicle central processing unit 116, a vehicle sensor data receiving unit 118, a vehicle actuators control unit 120, and actuators 122 including doors, windows, locks (collectively 124), engine controls 126, navigation/heads-up displays 128, suspension control 129, and an airfoil trim 130. The tuned RF resonance components 108 can cause a shift in observed frequencies of emitted RF signals (referred to as a "frequency-shift", implying any change in frequency) via emitted RF signals 110 and/or returned RF signals 112 with the transceiver 114. Reference to the returned RF signals 112 corresponding to emitted RF signals 110 may refer to the electronic detection of frequency shift or attenuation of the emitted RF signals 110 relative to one or more of the tuned RF resonance components 108 integrated into any one or more of the belt sensors 104, the hose sensors 105, the tire sensors 106, the transceiver antennas 102 on a vehicle, and/or the like (e.g., rather than an actual physical reflection or return of a signal from a sensor). The emitted RF signals 110 and the returned RF signals 112 can be in communication with (and therefore also assessed by) any one or more of the vehicle central processing unit 116, the vehicle sensor data receiving unit 118, the vehicle actuators control unit 120, and/or the actuators 122. The vehicle condition detection system 100 can be implemented using any suitable combination of software and hardware.

Any one or more of the depicted various sensors of the vehicle condition detection system 100 can be formed of carbon-based microstructures tuned to achieve a specific RF resonance behavior upon being "pinged" (referring to being hit or otherwise contacted by) emitted RF signals. The vehicle condition detection system 100 (or any aspect thereof) can be configured to be implemented in any conceivable vehicle use application, area, or environment, such as during inclement weather conditions including sleet, hail, snow, ice, frost, mud, sand, debris, uneven terrain, water and/or the like.

The tuned RF resonance components 108 can be disposed around and/or on the vehicle (such as within the cabin, engine compartment, or the trunk, or on the body of the vehicle). As shown in FIG. 1, the tuned RF resonance components can include belt sensors 104, hose sensors 105, tire sensors 106, and transceiver antennas 102, any one or more of which can be implemented in modern vehicles during their production, or (alternatively) retro-fitted to pre-existing vehicles, regardless of their age and/or condition. The tuned RF resonance components 108 can be formed, in part, using readily available materials such as fiberglass (such as, for airfoils) or rubber (such as, for tires) or glass (such as, for windshields). These conventional materials can be combined with carbon-based materials, growths, agglomerates, aggregates, sheets, particles and/or the like, such as those self-nucleated in-flight in a reaction chamber or reactor from a carbon-containing gaseous species and formulated to: (1) improve the mechanical (such as tensile, compressive, shear, strain, deformation and/or the like) strength of a composite material in which they are incorporated; and/or, (2) to resonate at a particular frequency or set of frequencies (within the range of 10 GHz to 100 GHz). Variables that dominate RF resonance properties and behavior of a material can be controlled independently from the variables responsible for control of material strength.

Radio Frequency (RF) based stimulation (such as that emitted by the transceiver 114 or emitted by a resonator) can be used to emit RF signals to the tuned RF resonance components 108, the actuators 122 (and/or the like, such as sensors implemented in or on the tuned RF resonance components 108) to detect their respective resonance frequency or frequencies, as well as frequency shifts and patterns observed in the attenuation of emitted signals (which may be affected by internal or external conditions). For example, if a tuned RF resonance component (such as the tire sensors 106) has been specially prepared (referred to as being "tuned") to resonate at a frequency of approximately 3 GHZ, then the tire sensors 106 can emit sympathetic resonance or sympathetic vibrations (referring to a harmonic phenomenon wherein a formerly passive string or vibratory body responds to external vibrations to which it has a harmonic likeness) when stimulated by a 3 GHz RF signal.

These sympathetic vibrations can occur at the stimulated frequency as well in overtones or sidelobes deriving from the fundamental 3 GHz tone. If a tuned resonance component (of the tuned RF resonance components 108) has been tuned to resonate at 2 GHZ, then when the tuned resonance component is stimulated by a 2 GHz RF signal, that tuned resonance component will emit sympathetic vibrations as so described. These sympathetic vibrations will occur at the stimulated frequency as well as in overtones or sidelobes (in engineering, referring to local maxima of the far field radiation pattern of an antenna or other radiation source, that are not the main lobe) deriving from the fundamental 2 GHz tone. Many additional tuned resonance components can be situated proximally to an RF emitter. An RF emitter might be controlled to first emit a 2 GHz ping, followed by a 3 GHz ping, followed by a 4 GHz ping, and so on. This succession of pings at different and increasing frequencies may be referred to as a "chirp".

Figure 5:
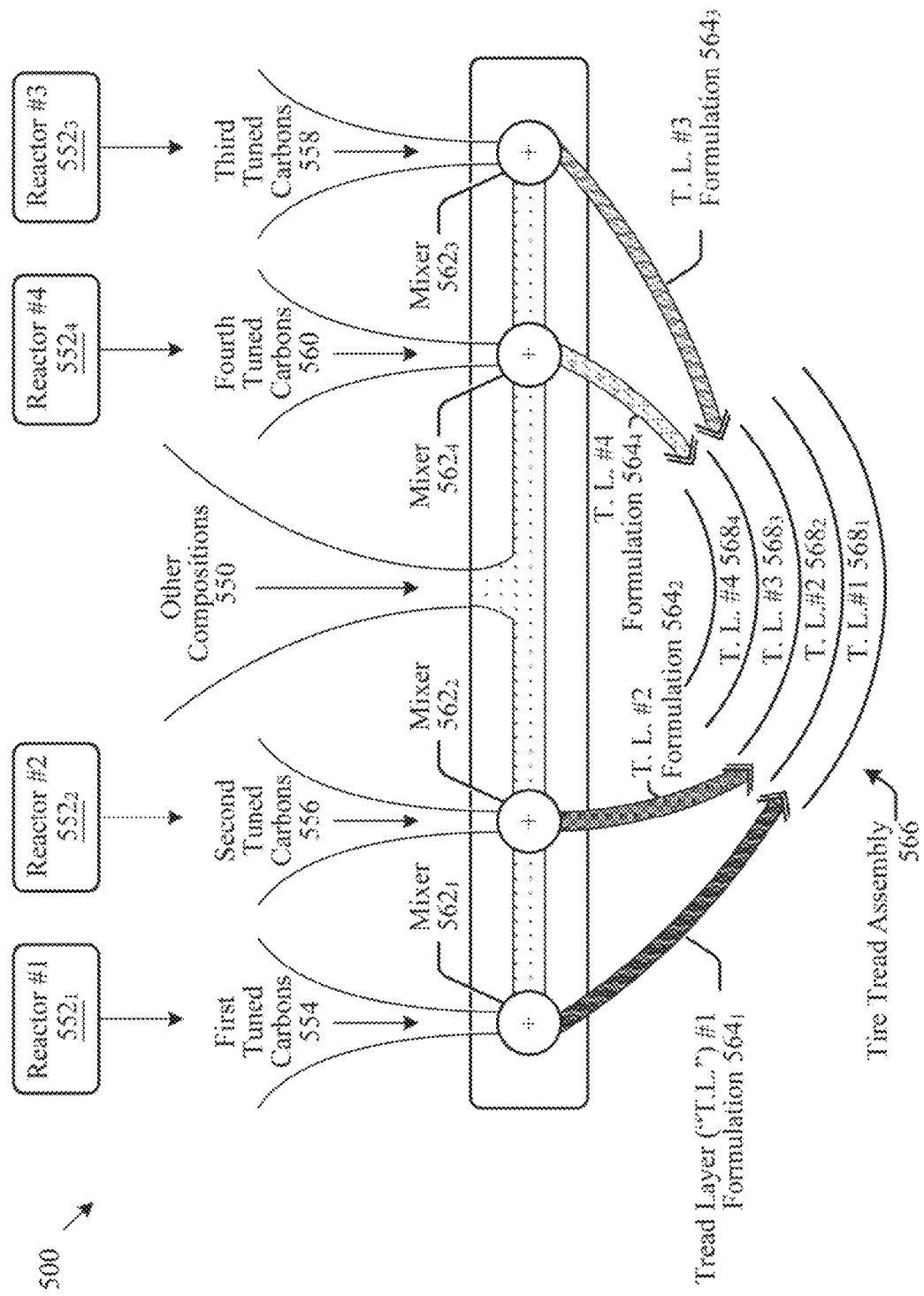
FIG. 5 depicts a schematic diagram of an apparatus used for tuning multiple plies of a tire by selecting carbon-containing tuned RF resonance materials from separate and independent reactors for incorporation into the body of a single tire assembly, in accordance with one embodiment.
Figures 6, 7:
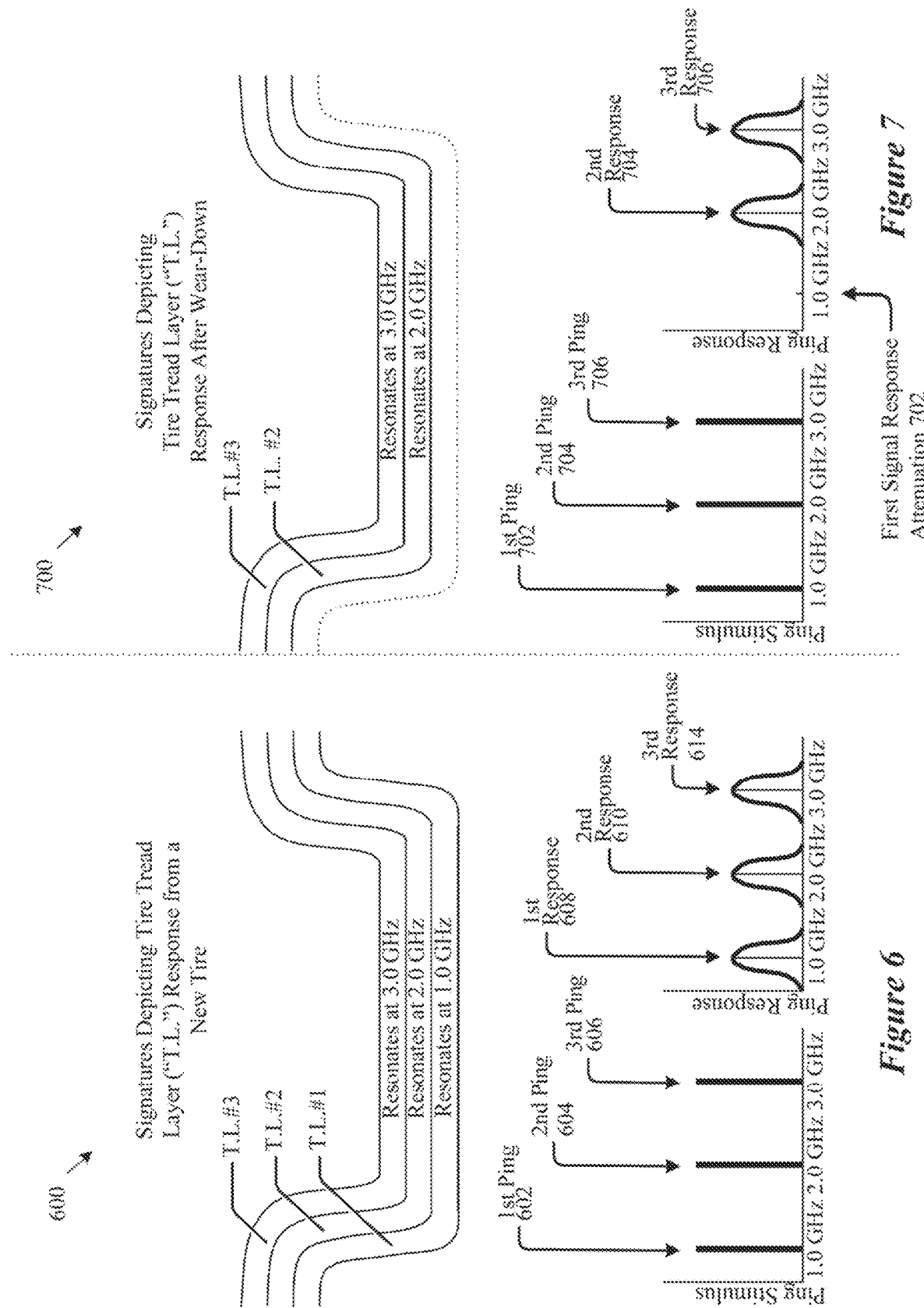
FIGS. 6 and 7 depict sets of example condition signatures that may be emitted from new tires formed of layers of carbon-containing tuned RF resonance materials, in accordance with one embodiment.

Adjacent tire plies (such as those in contact with each other) within a tire body, such as that generally shown by FIGS. 5-7, can have varying concentration levels or configurations of carbon-based microstructures to define sensors incorporated within that (referring to the respective) tire body ply and/or tread layer to resonate at varying distinct frequencies that are not harmonic with one-another. That is, non-harmonic plies can ensure a distinct and easily recognizable detection of a particular tire body ply and/or tread layer (or other surface or material) relative to others with minimal risk of confusion due to signal interference caused by (or otherwise associated with) harmonics.

The transceiver 114 (and/or a resonator, not shown in FIG. 1) can be configured to transmit the emitted RF signals 110 to any one or more of the tuned RF resonance components 108 to digitally recognize frequency shift and/or attenuation of the returned RF signals 112 from any one or more of the tuned RF resonance components 108. Such "returned" signals 112 can be processed into digital information that can be electronically communicated to a vehicle central processing unit 116, that interacts with a vehicle sensor data receiving unit 118 and/or a vehicle actuators control unit 120, which send further vehicle performance related signals based on sensor data received. The returned signals 112 can at least partially control the actuators 122. That is, the vehicle actuators control unit 120 can control the actuators 122 to operate any one or more of the doors, windows, locks 124, the engine controls 126, the navigation/heads-up displays 128, the suspension control 129, and/or the airfoil trim 130 according to feedback received from the vehicle sensor data receiving unit 118 regarding vehicle component wear or degradation as indicated by the tuned RF components in communication with the transceiver 114.

Detection of road debris and inclement weather conditions upon monitoring behavior (such as frequency shift and/or attenuation) of the returned RF signals 111 can, for example, result in the actuators 122 triggering a corresponding change in the suspension control 129. Such changes can, for example, include softening suspension settings to accommodate driving over the road debris, while later tightening suspension settings to accommodate enhanced vehicle responsiveness as may be necessary to travel during heavy rain (and thus low traction) conditions. The variations of such control by the vehicle actuators control unit 120 are many, where any conceivable condition exterior to the vehicle can be detected by the transceiver (as demonstrated by frequency shifting and/or attenuation of the emitted RF signals 110 and/or the returned RF signals 112).

Any of the tuned RF resonance components 108 forming the described sensors can be tuned to resonate when stimulated at particular frequencies, where a defined shift in frequency or frequencies (as caused by the carbon-based microstructures) can form one or more signal signatures indicative of the material, or condition of the material, into which the sensor is incorporated.

Time variance or deviation (TDEV) (referring to the time stability of phase x versus observation interval t of the measured clock source; the time deviation thus forms a standard deviation type of measurement to indicate the time instability of the signal source) of frequency shifts in the returned RF signals 112 (such as that shown in a signal signature) can correspond to time variant changes in the environment of the sensor and/or time variant changes in the sensor itself. Accordingly, signal processing systems (such as any one or more of the vehicle central processing unit 116, the vehicle sensor data receiving unit 118, and/or the vehicle actuators control unit 120, etc.) can be configured to analyze signals (such as the emitted RF signals 110 and returned RF signals 112) associated with the sensors according to TDEV principles. Results of such analysis (such as a signature analysis) can be delivered to the vehicle central processing unit 116, which (in turn) can communicate commands to the vehicle actuators control unit 120 for appropriate responsive action. In some configurations such responsive action by the actuators 122 can involve at least some human driver input, while in other configurations the vehicle condition detection system 100 can function entirely in a self-contained manner allowing for a so-equipped vehicle to address component performance issues as they arise in an entirely driverless setting. In addition, the vehicle central processing unit 116 may electronically communicate with one or more upstream components 113 (e.g., computational equipment associated with racing applications housed in stationary areas) and/or a racing mission control unit 119 responsible for intake and/or processing of all data associated with the tuned RF resonance components 108.

Figure 2:
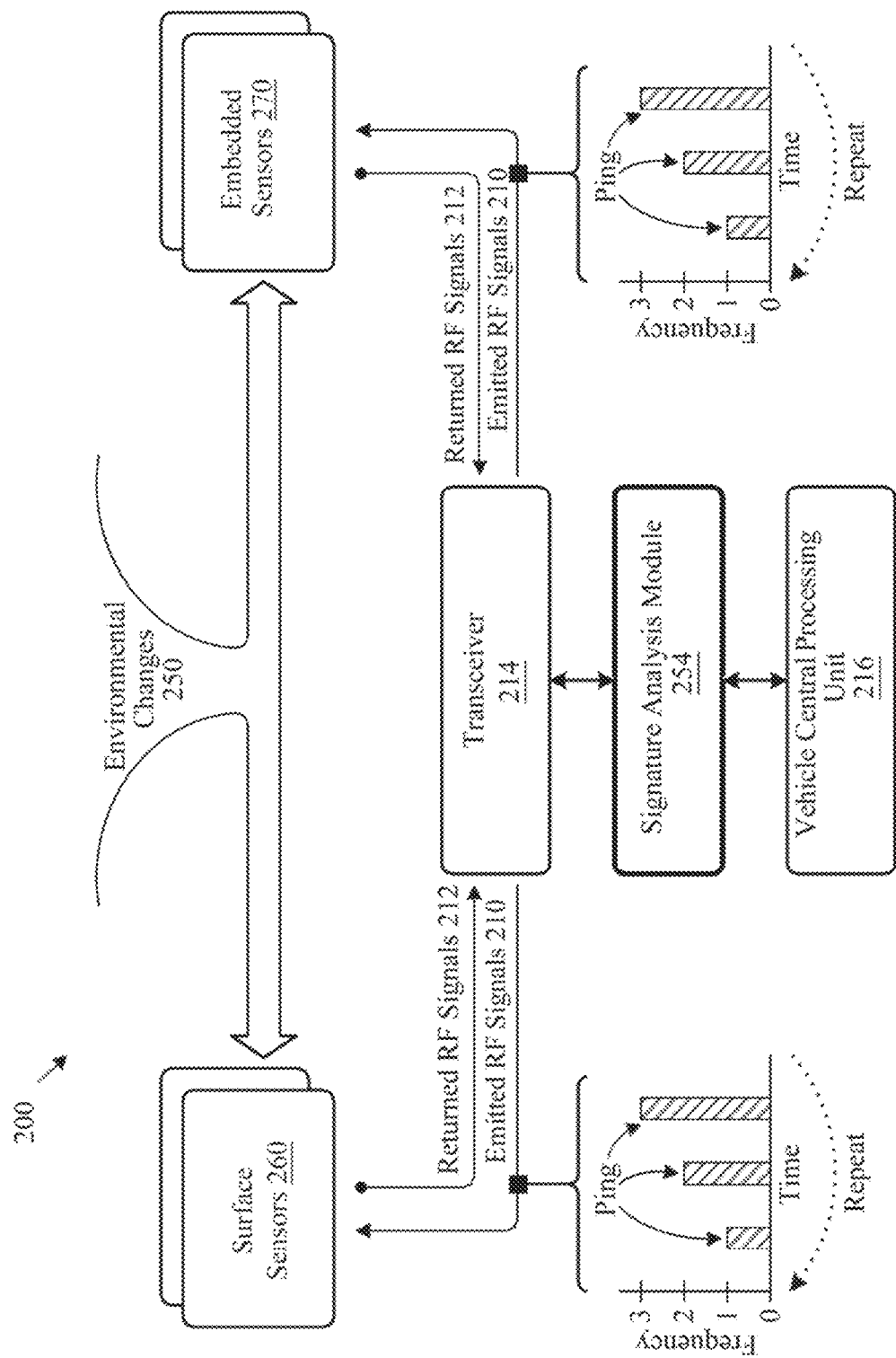
FIG. 2 depicts a signal processing system that analyzes emitted and/or returned RF signals that are frequency-shifted and/or attenuated by sensors formed of carbon-containing tuned RF resonance materials, in accordance with one embodiment.

FIG. 2 depicts a signal processing system 200 that analyzes emitted and/or returned RF signals that are frequency-shifted and/or attenuated by sensors formed of carbon-containing tuned RF resonance materials, in accordance with one embodiment. As an option, the signal processing system 200 may be implemented in the context of any one or more of the embodiments set forth in any previous and/or subsequent figure(s) and/or description thereof. Of course, however, the signal processing system 200 may be implemented in the context of any desired environment. Further, the aforementioned definitions may equally apply to the description below.

As shown, FIG. 2 shows a block diagram of a signal processing system 200, which can include surface sensors 260 and embedded sensors 270, any one or more of which may electronically communicate with the other concerning environmental changes 250 for a so-equipped vehicle (referring to a vehicle equipped with the surface sensors 260 and the embedded sensors 270). The signal processing system 200 may also include a transceiver 214, a signature analysis module 254, and a vehicle central processing unit 216, any one or more of which may be in electronic communication with the other.

In some implementations, the embedded sensors 270 (which can be embedded within materials such as tire plies) can employ and/or be powered by self-powered telemetry including tribological energy generators (not shown in FIG. 2) also incorporated within the material enclosed the respective sensor. Accordingly, the tribological energy generators can generate usable electric current and/or power by harvesting static charge buildup between, for example, a rotating tire or wheel and the pavement it contacts, to power a resonant circuit (to be described in further detail herein), which can then resonate to emit a RF signal at a known frequency. As a result, an externally-mounted transceiver unit (such as that mounted within each wheel well of a vehicle) can emit RF signals which are further propagated by the resonant circuits that are tribologically-powered and embedded in the plies of a tire body in this configuration. Frequency shifts and/or attenuation of the magnitude of the emitted signals are likewise received and analyzed, for example, by a signature analysis module 254 and/or a vehicle central processing unit 216.

Self-powered telemetry (referring to collection of measurements or other data at remote or inaccessible points and their automatic transmission to receiving equipment for monitoring) can be incorporated in vehicle tires. Self-powering telemetry, as referred to herein, includes exploiting tribological charge generation inside a tire, storage of that charge, and later discharge of the stored charge to or through a resonant circuit, to make use of the "ringing" (referring to oscillation of the resonant circuit responsible for further emission of RF signals) that occurs during discharge of the resonant circuit (referring to an electric circuit consisting of an inductor, represented by the letter L, and a capacitor, represented by the letter C, connected together, used to generate RF signals at a particular frequency or frequencies).

Ping stimulus can be provided, generally, in one of two possible configurations of the presently disclosed vehicle component wear detection systems, including reliance on signals or 'pings' generated by a stimulus source, such as a conventional transceiver, located outside the tire (or other vehicle component intended for monitoring regarding wear from ongoing use) such as being incorporated within each wheel well of a so-equipped vehicle; or usage of an intra-tire (referring to also being embedded in the tire plies, similar to the sensors having carbon-based microstructures) tribological energy generation devices that harvest energy resultant from otherwise wasted frictional energy between the rotating wheel and/or tire and the ground or pavement in contact therewith. Tribology, as commonly understood and as referred to herein, implies the study of the science and engineering of interacting surfaces in relative motion. Such tribological energy generation devices can provide electrical power to intra-tire resonance devices which in turn self-emit tire property telemetry.

Either of the above-discussed two 'ping' stimulus generators or providers can have complex resonance frequencies (CRf) components ranging from approximately 10 to 99 GHz (due, for example, resonance frequency of small dimensions of structures like graphene platelets) as well as lower frequency resonance in KHz range due to the relatively much larger dimensions of the discussed intra-tire resonance. Generally, CRf can be equated to a function of elastomer component innate resonance frequency, carbon component innate resonance frequency, ratio/ensemble of the constituent components, and the geometry of the intra-tire resonance device.

The signal processing system 200 functions to analyze a signal signature (defined by digitally observing frequency shifting and/or attenuation of any one or more of the emitted RF signals 210 and/or returned RF signals 212) once sensors formed of carbon-based microstructures have been stimulated. As a result of stimulation with a chirp signal sensor that resonate at one of the chirp/ping frequencies "respond" by resonating at or near its corresponding tuned frequency, shifting the emitted frequency, and/or attenuating the amplitude of the emitted signal. When an environmental change (such as that resulting in the wear of a tire body ply and/or tread layer) occurs while the chirp/ping is emitted, "returned" signals can monitored for variations in modulation-either higher or lower than the tuned frequency. Accordingly, the transceiver 214 can be configured to receive returned RF signals 212 that are representative of the surfaces that they are pinged on or against, etc.

Of course, it is to be again appreciated that although the context of FIGS. 1-18 relate predominately to automobile application of split ring resonators, such teachings may also apply equally to other scenarios and industries detailed herein (including concrete, materials science, aerospace, drone and aerial vehicles, mining materials, oil industry components, etc.). Thus, the teachings herein with respect to automobiles (and tires in particular) may be applied in the context of these other industries, some of which are described in detailed hereinbelow.

The foregoing chirp/ping signals can be emitted (such as by non-audible RF signal, pulse, vibration and/or the like transmission) by the transceiver 214. Also, the "return" signals can be received by the transceiver 214. As shown, chirp signals can occur in a repeating sequence of chirps (such as, the emitted RF signals 210). For example, a chirp signal sequence might be formed of a pattern comprising a 1 GHz ping, followed by a 2 GHz ping, followed by a 3 GHz ping, and so on. The entire chirp signal sequence can be repeated in its entirety continuously. There can be brief periods between each ping such that the returned signals from the resonant materials (returned RF signals 212) can be received immediately after the end of a ping. Alternatively, or in addition, signals corresponding to ping stimulus and signals of the observed "response" can occur concurrently and/or along the same general pathway or route. The signature analysis module can employ digital signal processing techniques to distinguish signals of the observed "response" from the ping signals. In situations where the returned response comprises energy across many different frequencies (such as, overtones, sidelobes, etc.), a notch filter can be used to filter the stimulus. Returned signals that are received by the transceiver can be sent to the signature analysis module 254, which in turn can send processed signals to vehicle central processing unit 216. The foregoing discussion of FIG. 2 includes discussion of sensors formed of carbon-containing tuned resonance materials and can also refer to sensing laminates as well.

Disclosed sensors may be incorporated into tire layers, e.g., including layers of resin can be layered interstitially between additional layers of carbon fiber within tire plies. Each layer of carbon-containing resin can be formulated differently to resonate at a different expected or desired tuned frequency. The physical phenomenon of material resonation can be described with respect to a corresponding molecular composition. For example, a layer having a first defined structure, such as a first molecular structure will resonate at a first frequency, whereas a layer having a second, different molecular structure can resonate at a second, different frequency Material having a particular molecular structure and contained in a layer will resonate at a first tuned frequency when that layer is in a low energy state and will resonate at a second different frequency when the material in the layer is in an induced higher-energy state. For example, material in a layer that exhibits a particular molecular structure can be tuned to resonate at a 3 GHz when the layer is in a natural, undeformed, low energy state. In contrast, that same layer can resonate at 2.95 GHz when the layer is at least partially deformed from its natural, undeformed, low energy state. As a result, this phenomenon can be adjusted to accommodate the needs for detecting, with a high degree of fidelity and accuracy, even the most minute aberration to, for example, a tire surface contacting against a road surface such as pavement and experiencing enhanced wear at a certain localized region of contact. Race cars racing on demanding race circuits (referring to highly technical, windy tracks featuring tight turns and rapid elevational changes) can benefit from such localized tire wear or degradation information to make informed tire-replacement decisions, even in time-sensitive race-day conditions.

The frequency-shifting phenomenon referred to above (such as transitioning from resonating at a frequency of 3 GHz to 2.95 GHZ) may be shown and discussed with reference to FIGS. 24B1-24B2, which will be discussed hereinbelow.

Carbon-containing materials (such as those including carbon-based microstructures) tuned to demonstrate a specific resonance frequency upon being pinged by a RF signal can be tuned to exhibit a particular resonance profile by tailoring specific compounds that make up the materials to have particular electrical impedances. Different electrical impedances in turn correspond to different frequency response profiles.

Impedance describes how difficult it is for an alternating (AC) current to flow through an element. In the frequency domain, impedance is a complex number having a real component and an imaginary component due to the structures behaving as inductors. The imaginary component is an inductive reactance (the opposition of a circuit element to the flow of current due to that element's inductance or capacitance; larger reactance leads to smaller currents for the same voltage applied) component $X_L$, which is based on the frequency f and the inductance L of a particular structure:

$$X_L = 2\pi f L \quad \text{(Eq. 1)}$$

As the received frequency increases, the reactance also increases such that at a certain frequency threshold the measured intensity (amplitude) of the emitted signal can attenuate. Inductance L is affected by the electrical impedance Z of a material, where Z is related to the material properties of permeability u and permittivity & by the relationship:

$$Z = \sqrt{\frac{\mu' + j\mu''}{\varepsilon' + j\varepsilon''}} = \sqrt{\frac{\mu_0}{\varepsilon_0}}, \quad \text{(Eq. 2)}$$

Thus, tuning of material properties changes the electrical impedance Z, which affects the inductance L and consequently affects the reactance $X_L$.

Carbon-containing structures such as those disclosed by Anzelmo, et al., in U.S. Pat. No. 10,428,197 entitled "Carbon and Elastomer Integration" issued on Oct. 1, 2019, incorporated herein by reference in its entirety with different inductances can demonstrate different frequency responses (when used to create sensors for the aforementioned systems). That is, a carbon-containing structure with a high inductance L (being based on electrical impedance Z) will reach a certain reactance at a lower frequency than another carbon-containing structure with a lower inductance.

The material properties of permeability, permittivity and conductivity can also be considered when formulating a compound to be tuned to a particular electrical impedance. Still further, it is observed that a first carbon-containing structure will resonate at a first frequency, whereas second carbon-containing structure will resonate at a second frequency when that structure is under tension-inducing conditions, such as when the structure is slightly deformed (such as, thereby slightly changing the physical characteristics of the structure).

Figure 18B:
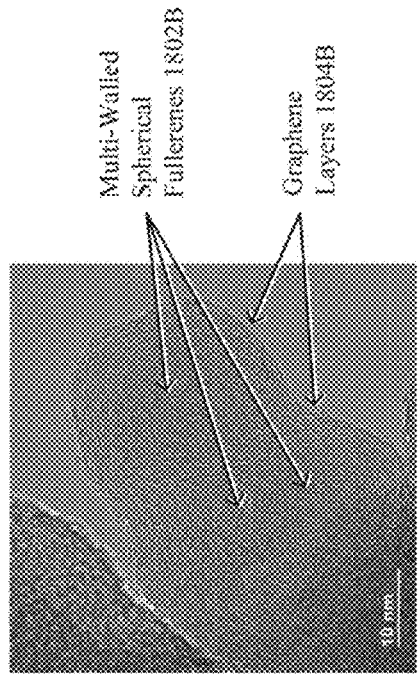
FIG. 18A through FIG. 18Y depict carbonaceous materials used as a formative material to produce any of the presently disclosed resonators (e.g., split ring resonators), in accordance with one embodiment.
Figure 18A:
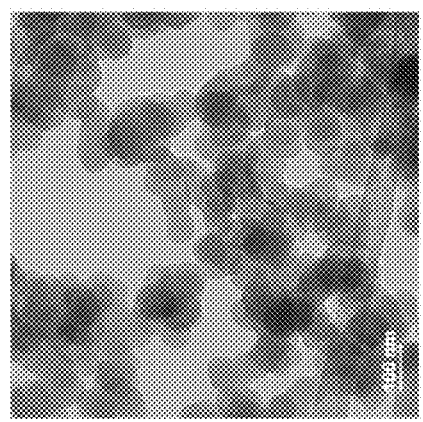
Figure 18C:
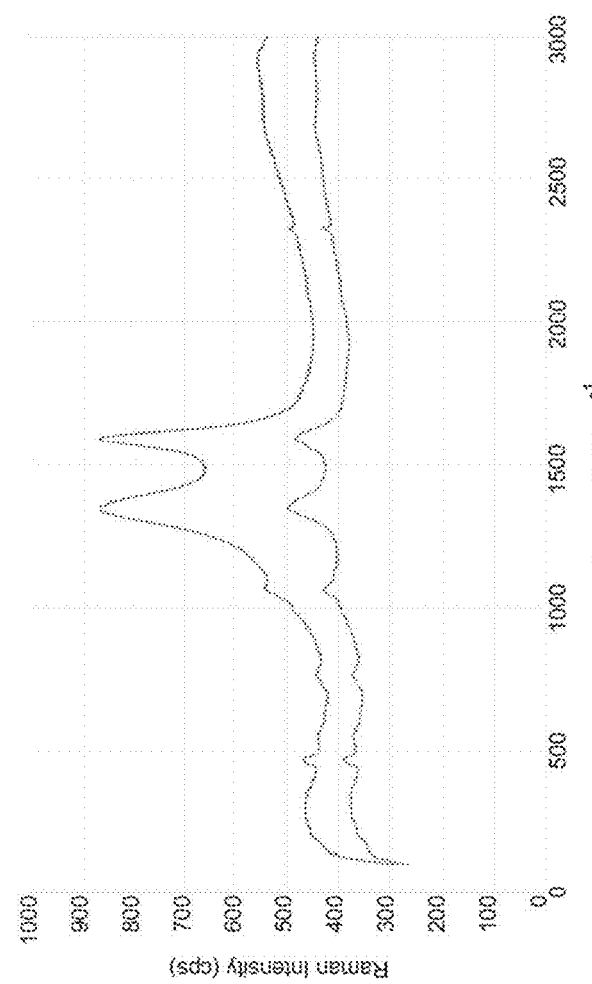
Figure 18E:
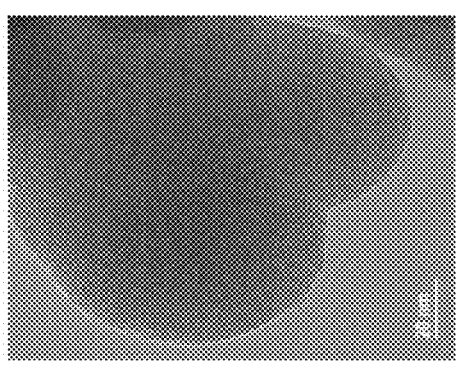
Figure 18D:
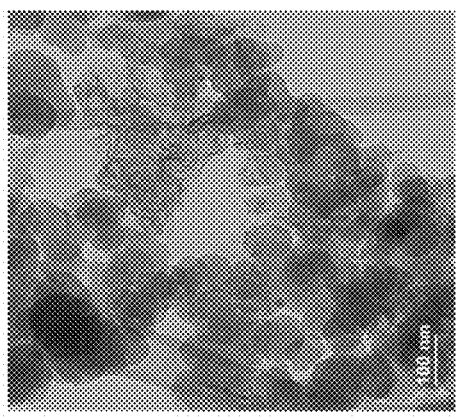
Figure 18F:
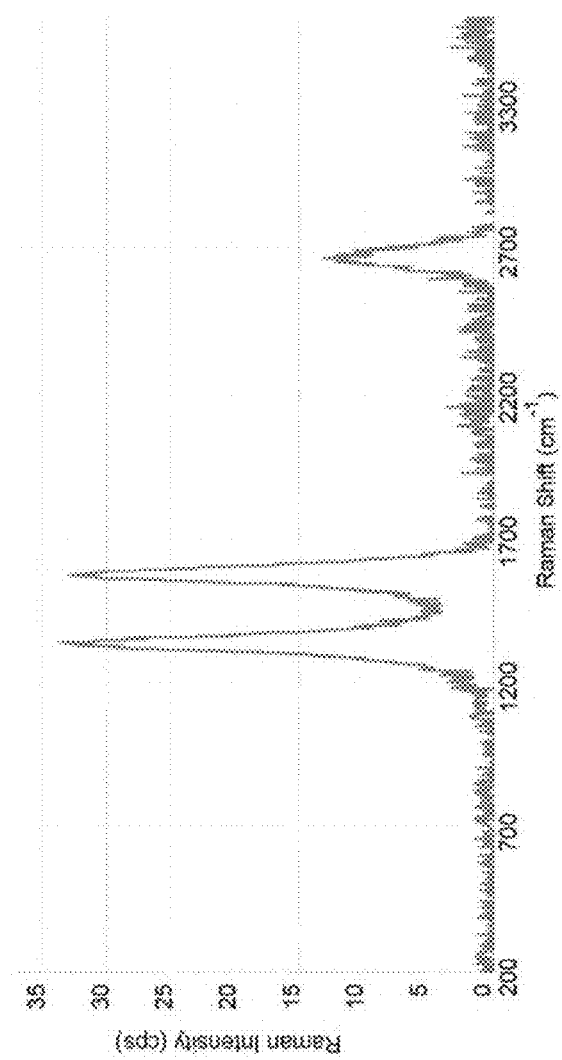
Figure 18K:
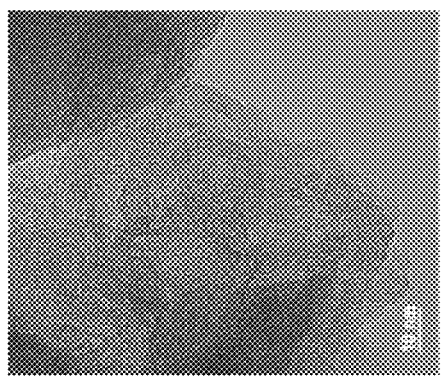
Figure 18L:
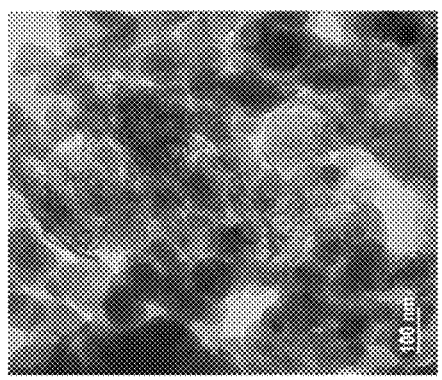
Figure 18M:
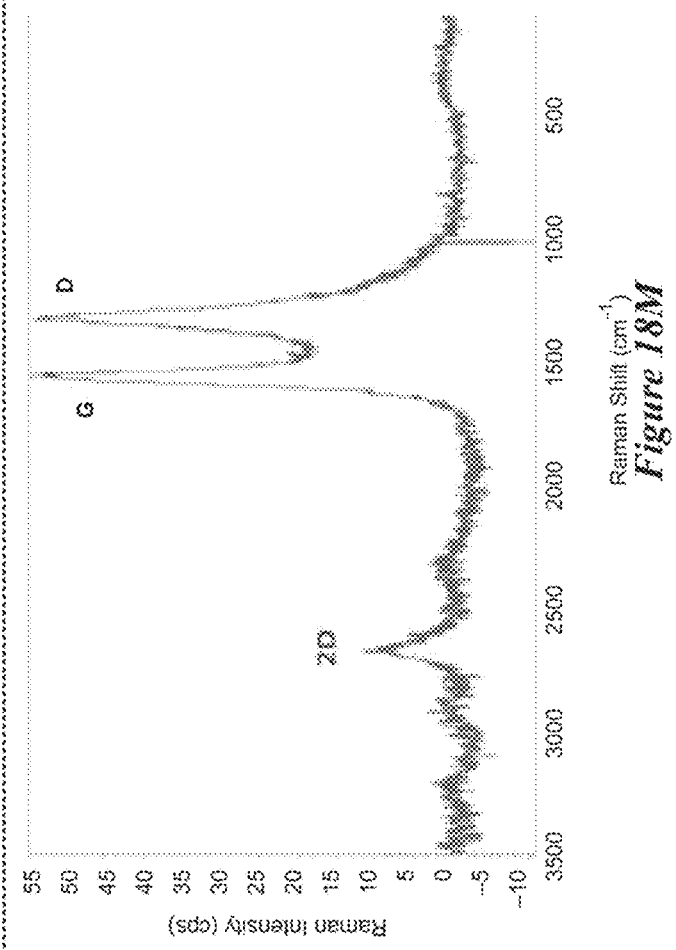
Figure 18O:
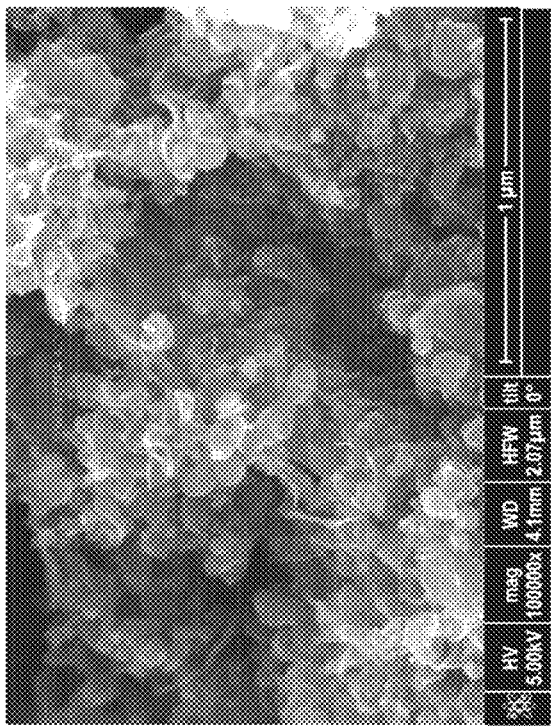
Figure 18N:
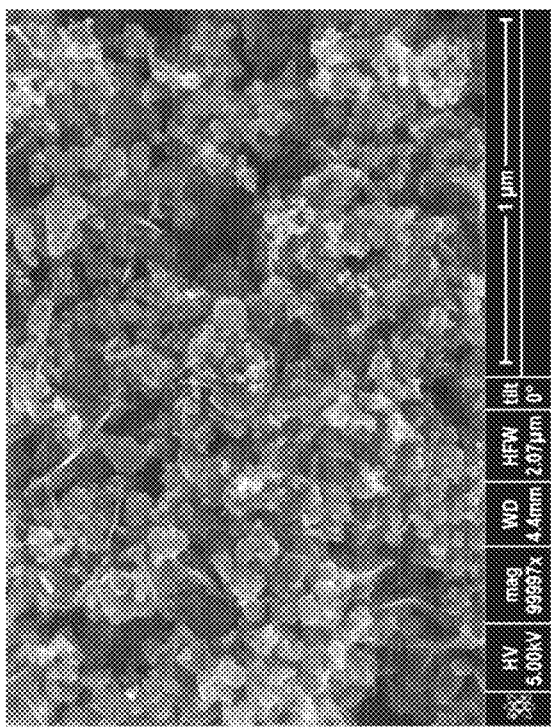
Figure 18P:
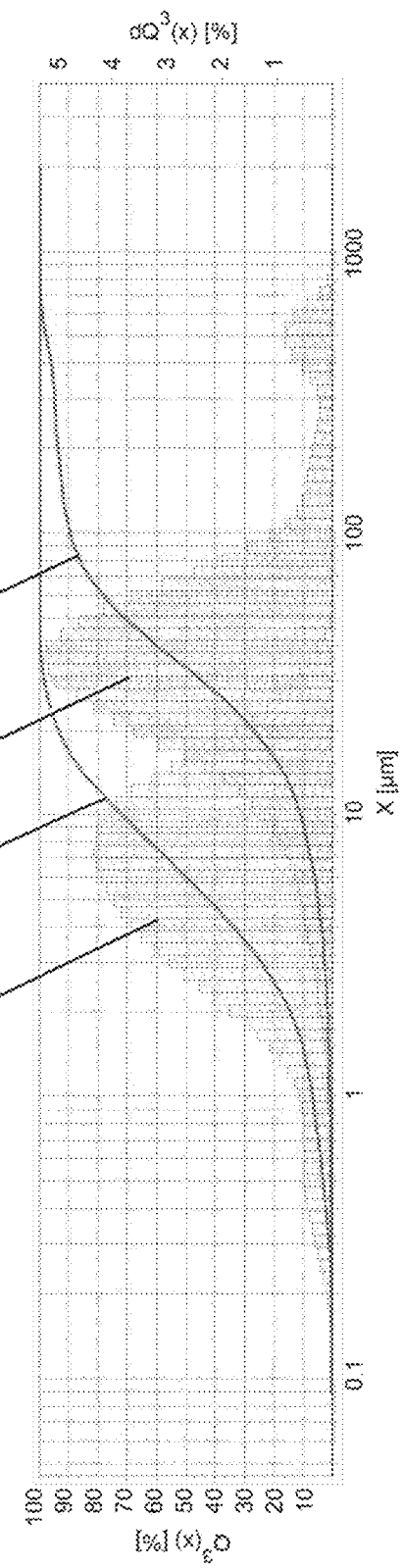
Figure 18Q:
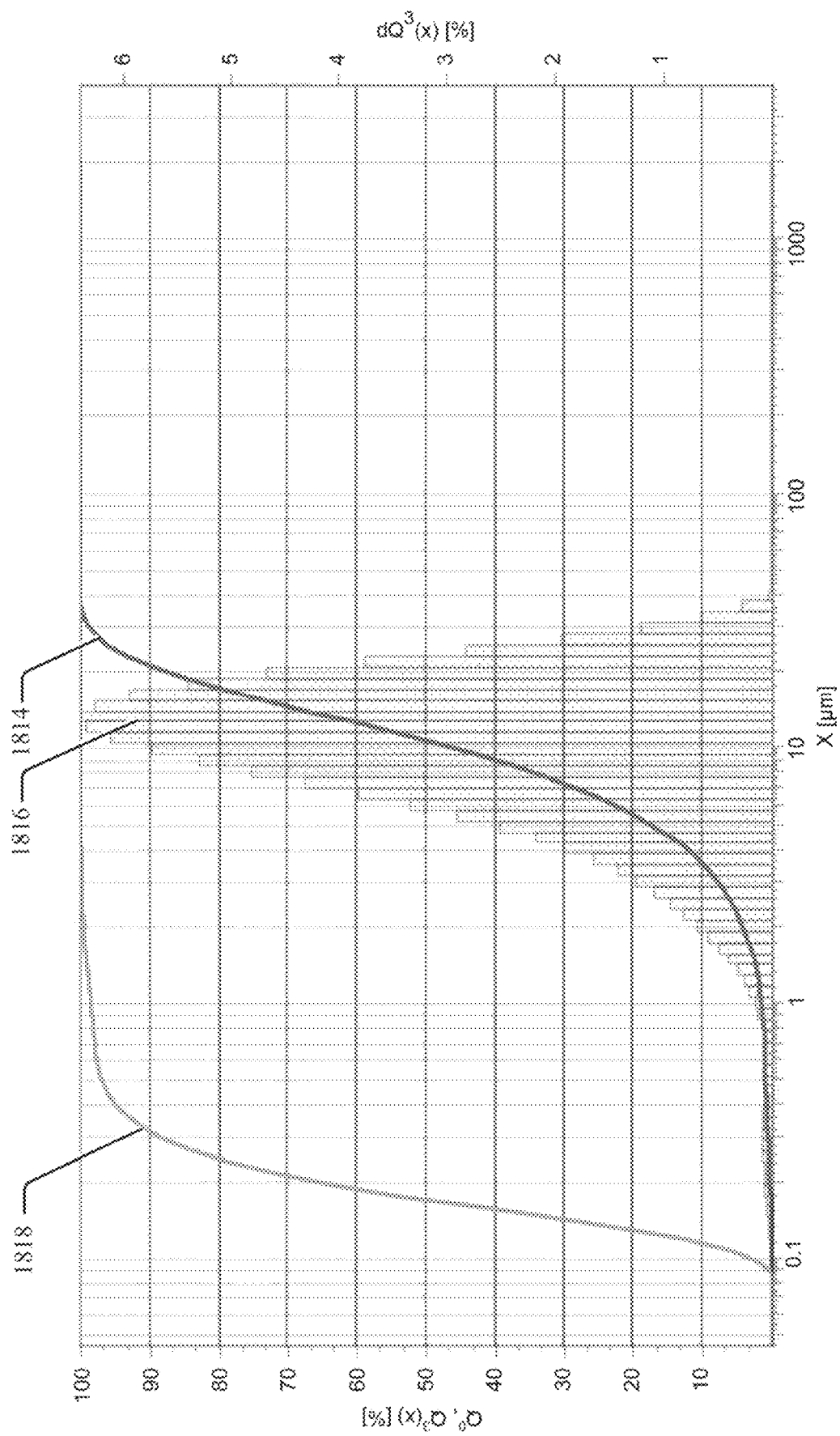
Figure 18R:
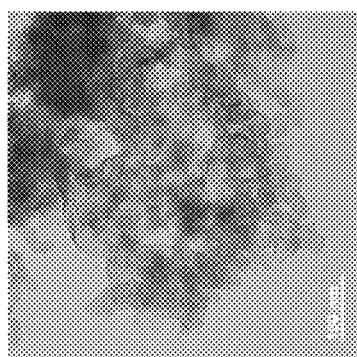
Figure 18S:
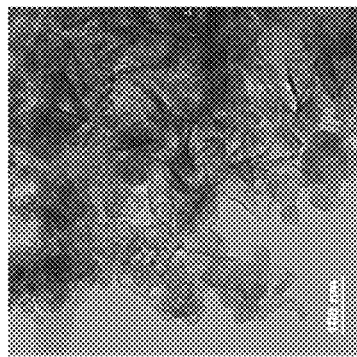
Figure 18T:
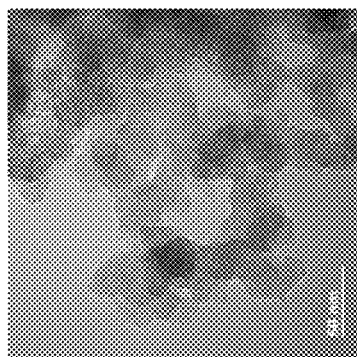
Figure 18U:
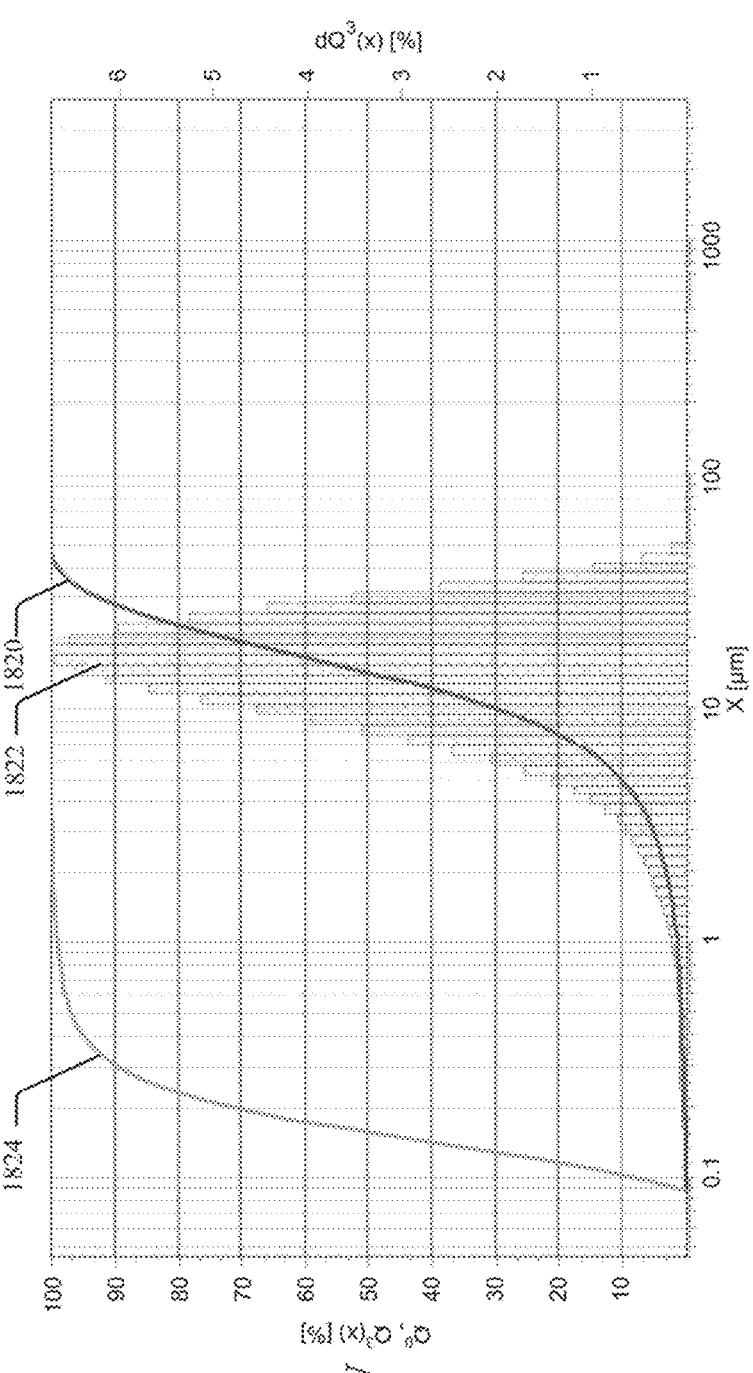
Figure 18V:
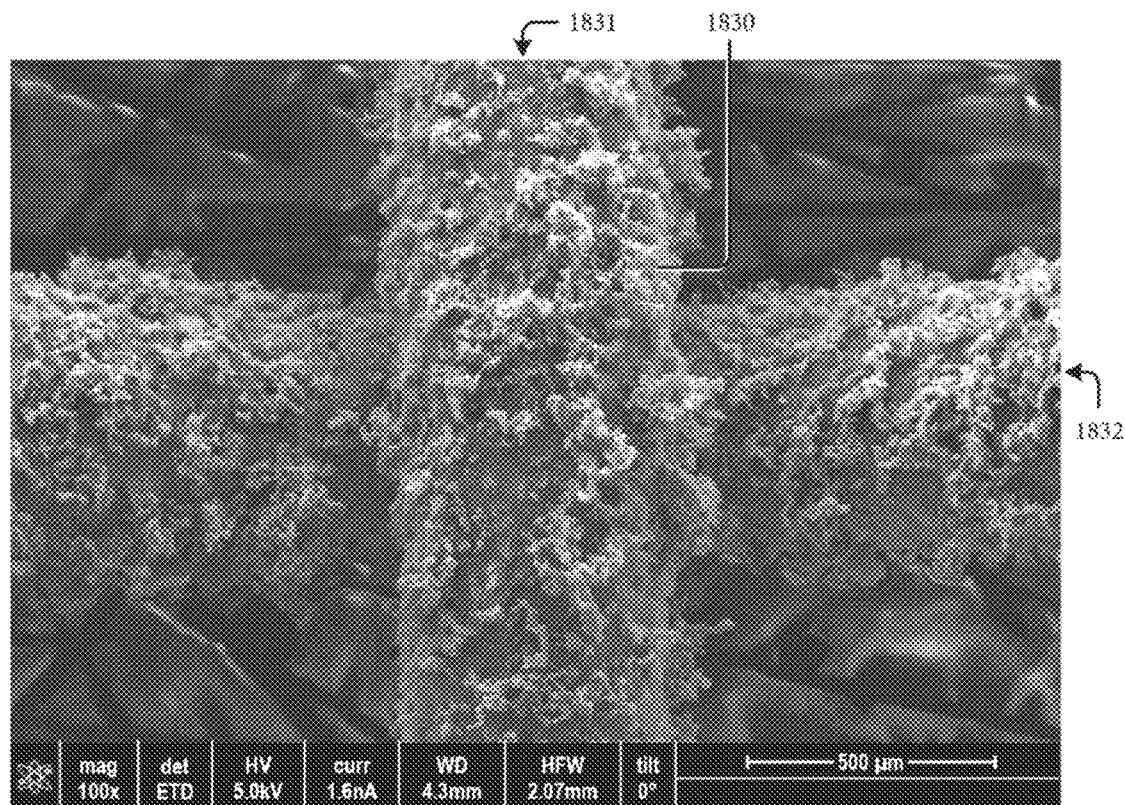
Figure 18W:
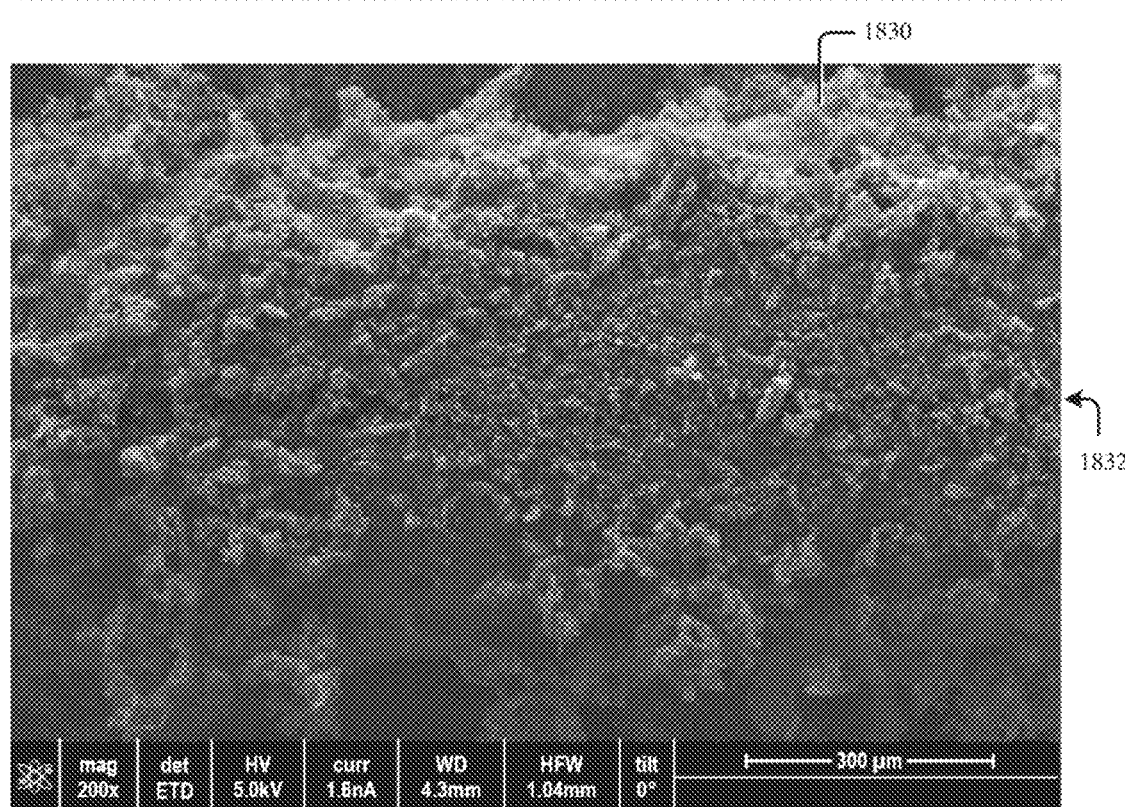
Figure 18X:
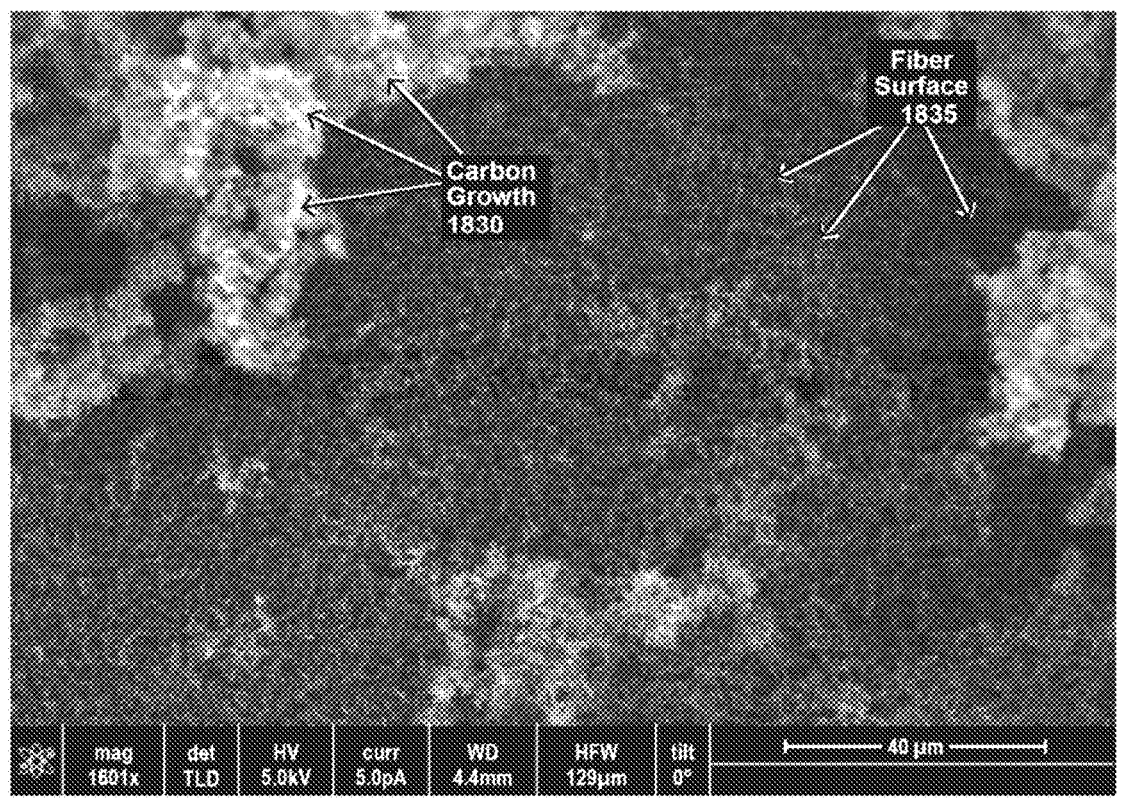
Figure 18Y:
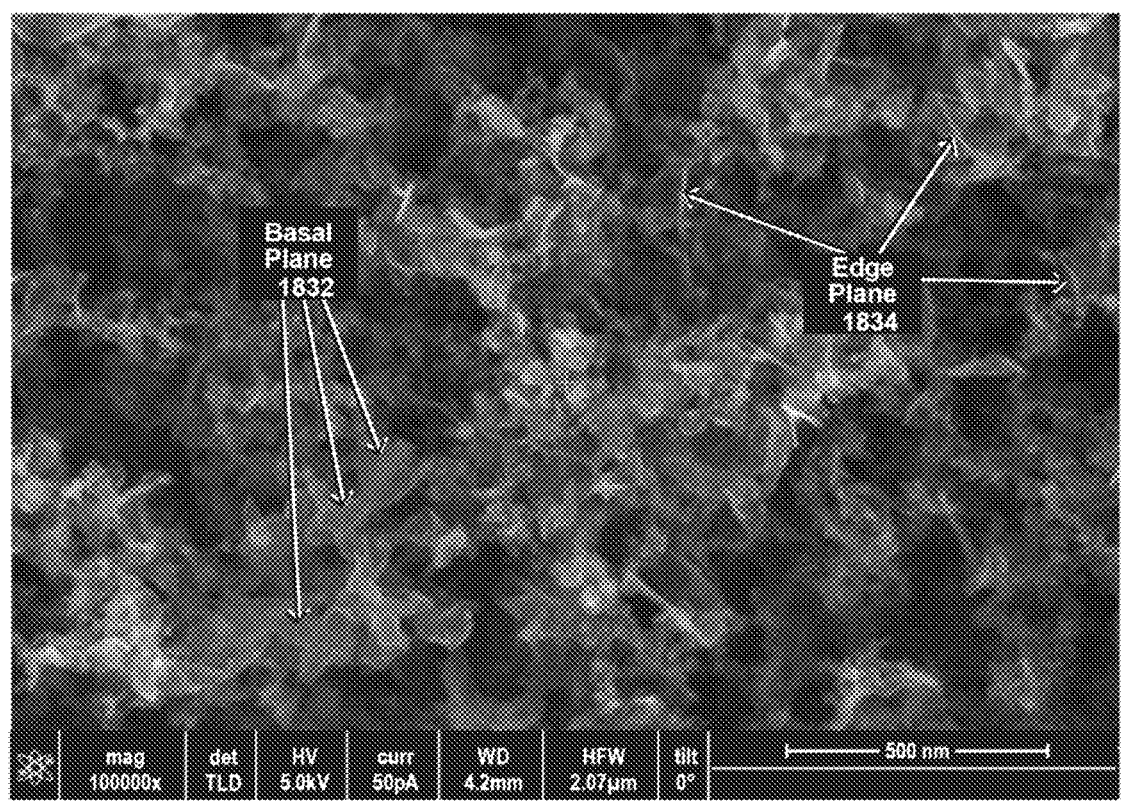

Example carbon-containing structures (e.g., as shown in FIGS. 18A-18Y) that may resonate at a first frequency, which can be correlated to an equivalent electrical circuit comprising a capacitor $C_1$ and an inductor $L_1$. The frequency $f_1$ is given by the equation:

$$f_1 = \frac{1}{2\pi\sqrt{L_1 C_1}} \quad \text{(Eq. 3)}$$

Deformation of the carbon-containing structure may, in turn, change the inductance and/or capacitance of the structure. The changes can be correlated to an equivalent electrical circuit comprising a capacitor $C_2$ and an inductor $L_2$. The frequency $f_2$ is given by the equation:

$$f_2 = \frac{1}{2\pi\sqrt{L_2 C_2}} \quad \text{(Eq. 4)}$$

Figure 3:
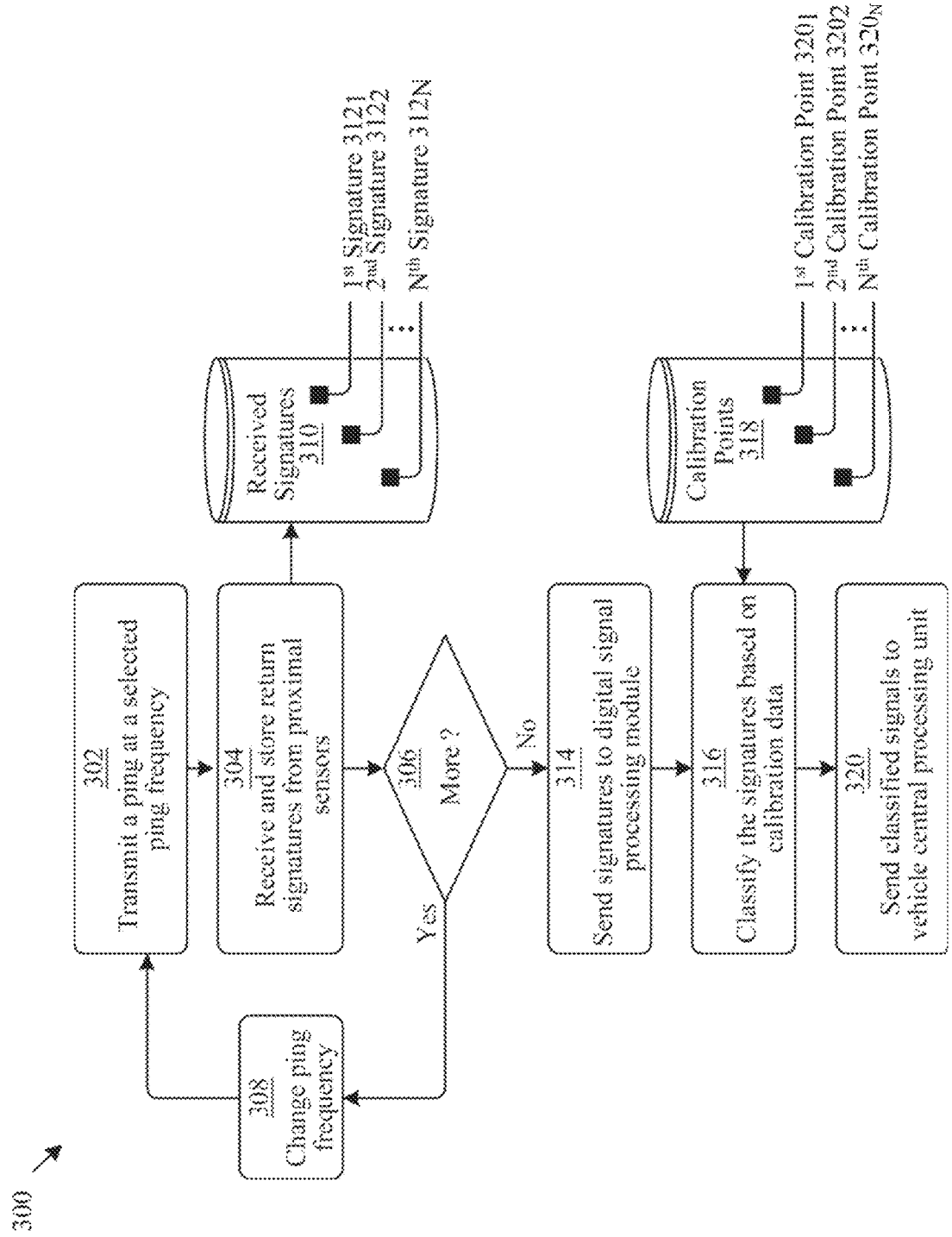
FIG. 3 illustrates a signature classification system, in accordance with one embodiment.

FIG. 3 illustrates a signature classification system 300, in accordance with one embodiment. As an option, the signature classification system 300 may be implemented in the context of any one or more of the embodiments set forth in any previous and/or subsequent figure(s) and/or description thereof. Of course, however, the signature classification system 300 may be implemented in the context of any desired environment. Further, the aforementioned definitions may equally apply to the description below.

The signature classification system 300 processes signals received from sensors formed of carbon-containing tuned resonance materials. The signature classification system 300 can be implemented in any physical environment or weather condition. FIG. 3 relates to incorporating tuned resonance sensing materials into automotive components for classifying signals (such as, signatures) detected by, classified and/or received from sensors installed in vehicles. A ping signal of a selected ping frequency is transmitted at operation 302. The ping signal generation mechanism and the ping transmission mechanism can be performed by any known techniques. For example, a transmitter module can generate a selected frequency of 3 GHZ, and radiate that signal using an antenna or multiple antennae. The design and location of the tuned antenna (such as mounted on and/or within any one or more of the wheel wells or a vehicle) can correspond to any tuned antenna geometry, material and/or location such that the strength of the ping is sufficient to induce (RF) resonance in proximate sensors. Several tuned antennae are disposed upon or within structural members that are in proximity to corresponding sensors. As such, when a proximal surface sensor is stimulated by a ping, it may resonate back with a signature. That signature can be received (at operation 304) and stored in a dataset comprising received signatures 310. A sequence of transmission of a ping, followed by reception of a signature, can be repeated in a loop.

The ping frequency can be changed (operation 308) in iterative passes through the loop. Accordingly, as operation 304 is performed in the loop, operation 304 can store signatures 312, including a first signature 3121, a second signature 3122, up to an $N^{th}$ signature 312N. The number of iterations can be controlled by decision 306. When the "No" branch of decision 306 is taken (such as, when there are no further additional pings to transmit), then the received signatures can be provided (at operation 314) to a digital signal processing module (such as, an instance of signature analysis module 254 shown in FIG. 2). The digital signal processing module classifies the signatures (operation 316) against a set of calibration points 318. The calibrations points can be configured to correspond to particular ping frequencies. For example, calibration points 318 can include a first calibration point 3201 that can correspond to a first ping and first returned signature near 3 GHZ, a second calibration point 3202 that can correspond to a second ping and second returned signature near 2 GHz, and so on for any integer value "N" calibration points (up to a $N^{th}$ calibration point 320N).

At operation 320, classified signals are sent to a vehicle central processing unit (such as, the vehicle central processing unit 116 of FIG. 1). The classified signals can be relayed by the vehicle central processing unit 116 to an upstream repository that hosts a computerized database configured to host and/or run machine learning algorithms. Accordingly, a vast amount of stimulus related to signals, classified signals, and signal responses can be captured for subsequent data aggregation and processing. The database can be computationally prepared, referring to as being "trained", provided a given set of sensed measurements that can be correlated to conditions or diagnoses related to vehicular performance, such as tire degradation due to repeated use. Should, during the operation of the vehicle, the measured deflection (such as, air pressure) of a particular portion of an airfoil component differ from the measured deflection (such as, air pressure) of a different portion of the airfoil component, a potential diagnosis may be that one tire is underinflated and therefore causing vehicle ride height to be non-uniform, resulting in airflow over, on, and/or around the vehicle to demonstrate proportionate non-uniformities, as detected by deflection on the airfoil component. Other potential conditions or diagnoses can be determined by the machine learning system as well. The conditions and/or diagnoses and/or supporting data can be returned to the vehicle to complete a feedback loop. Instrumentation in the vehicle provides visualizations that can be acted upon (such as, by a driver or by an engineer).

Figure 4:
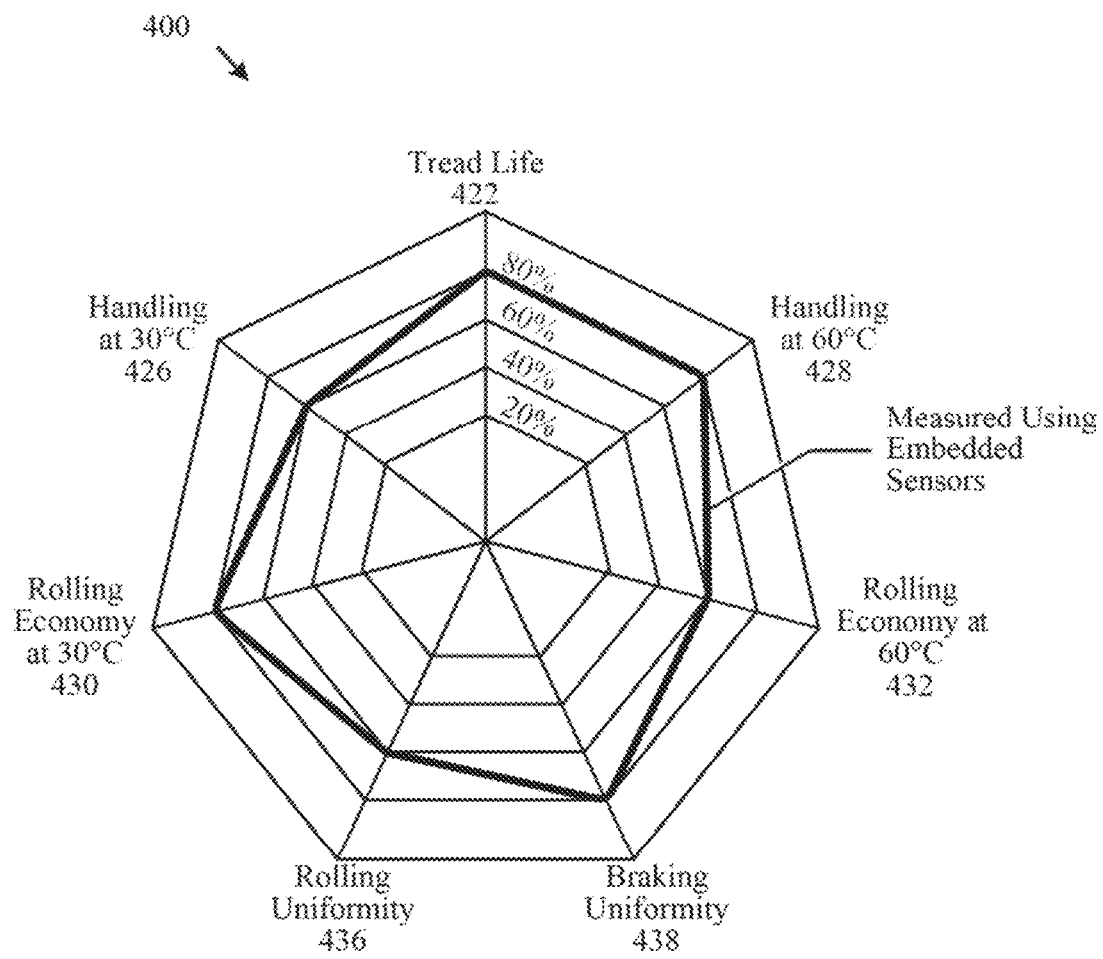
FIG. 4 depicts a series of tire condition parameters that are sensed from changes in RF resonance of various layers of carbon-containing tuned RF resonance materials, in accordance with one embodiment.

FIG. 4 depicts a series of tire condition parameters that are sensed from changes in RF resonance of various layers of carbon-containing tuned RF resonance materials, in accordance with one embodiment.

FIG. 4 depicts a series of tire condition parameters 400 that are sensed from changes in RF resonance of various layers of carbon-containing tuned RF resonance materials, in accordance with one embodiment. As an option, the tire condition parameters 400 may be implemented in the context of any one or more of the embodiments set forth in any previous and/or subsequent figure(s) and/or description thereof. Of course, however, the tire condition parameters 400 may be implemented in the context of any desired environment. Further, the aforementioned definitions may equally apply to the description below.

As shown, FIG. 4 illustrates various physical characteristics or aspects (tire condition parameters 400) pertaining to incorporating tuned resonance sensing materials into automotive components (such as tires). Here, the figure is presented with respect to addressing deployment of survivable sensors in tires, including non-pneumatic tires as well as pneumatic tires. The construction of the tires may correspond to radial tires, bias ply tires, tubeless tires, solid tires, run-flat tires, etc. Tires may be used in any sorts of vehicles and/or equipment and/or accessories pertaining to vehicles. Such vehicles may include aircraft, all-terrain vehicles, automobiles, construction equipment, dump trucks, earthmovers, farm equipment, forklifts, golf carts, harvesters, lift trucks, mopeds, motorcycles, off-road vehicles, racing vehicles, riding lawn mowers, tractors, trailers, trucks, wheelchairs, etc. The tires may, in addition or alternative to that presented, be used in non-motorized vehicles, equipment and accessories such as bicycles, tricycles, unicycles, lawnmowers, wheelchairs, carts, etc.

The parameters shown in FIG. 4 are as an example, and other variants may exist or otherwise be prepared to target specific desirable performance characteristics of many conceivable end-use scenarios, including truck tires designed to offer increased longevity (at the potential expense of road adhesion), or soft racing tires designed to provide maximum road adhesion (at the potential expense of lifespan).

Various carbon structures may be used in different formulations with other non-carbon materials integrated into tires, which then undergo mechanical analysis to determine their respective characteristics of the tires. Some of these characteristics can be determined empirically by direct testing, while other characteristics are determined based on measurements and data extrapolation. For example, rolling uniformity can be determined by sensing changes in force when the tire is subjected to rolling over a uniform surface such as a roller, whereas tread life is based on an abrasion test over a short period, the results of which short term test are extrapolated to yield a predicted tread life value.

More tire characteristics can be measured, but some of these measurement techniques can be physically destructive to the tire, and thus measured at a desired point in the life of the tire. In contrast, using survivable sensors embedded in tires allows for such otherwise destructive measurements to be made throughout the entire lifetime of the tire. For example, detection of response signals based on RF signals pinged against sensors embedded in tires can be used for such sensing. Moreover, each body ply and/or tread layer of a tire can, as discussed herein, include durable (also referred to as "survivable") sensors that are tuned to resonate at a particular frequency.

Ply used in a tire can be formulated to combine carbon-containing structures with other materials to achieve a particular material composition that exhibits desired performance (such as handling and longevity) characteristics. The natural resonance frequency (or frequencies) of the particular material composition can be subjected to spectral analysis to develop a spectral profile for the particular material composition. This spectral profile can be used as a calibration baseline for that material. When the body ply and/or tread layer of the tire undergoes deformation, the spectral profile changes, which spectral profile changes can be used as additional calibration points (such as the calibration points 318). Many such calibration points can be generated by testing, and such calibration points can in turn be used to gauge deformation.

Analysis of the spectral response results in quantitative measurements of many tire parameters. The tire parameters that can be determined from signature analysis, for example, can include tread life 422, handling at a first temperature 428, handling at a second temperature 426, rolling economy at a first temperature 430, rolling economy at a second temperature 432, rolling uniformity 436, and braking uniformity 438.

Responses, such as those spectrally represented based on return ping signals received from sensors embedded in materials in tire ply, can be representative of the deformation observed. That is, a certain type of tire deformation will correspond with a certain type of specific response, such that a mapping between responses or response types can be done to degradation types. Moreover, time-variant changes in the spectral response of a tire as it undergoes in-situ deformation can be used to determine many ambient conditions. In tires that are constructed using multiple ply, each body ply and/or tread layer can be formulated to exhibit a particular tuned frequency or range of frequencies. For example, FIG. 5 (shown hereinbelow) shows a schematic diagram for constructing a tire from multiple ply, each of which has as different a particular tuned frequency or range of frequencies.

FIG. 5 depicts a schematic diagram 500 of an apparatus used for tuning multiple plies of a tire by selecting carbon-containing tuned RF resonance materials from separate and independent reactors for incorporation into the body of a single tire assembly, in accordance with one embodiment. As an option, the schematic diagram 500 may be implemented in the context of any one or more of the embodiments set forth in any previous and/or subsequent figure(s) and/or description thereof. Of course, however, the schematic diagram 500 may be implemented in the context of any desired environment. Further, the aforementioned definitions may equally apply to the description below.

The schematic diagram 500 may be used for fine-adjustment, or tuning, of multiple body plies and/or tread layers of a tire by selecting carbon-containing tuned resonance materials for incorporation into a tire assembly or structure, which can be implemented in any environment. FIG. 5 illustrates how to mix different carbons into tire composite formulations that are in turn assembled into a multi-ply tire. The resulting multi-ply tire exhibits the various resonance-sensitive and frequency-shifting characteristics.

Multiple reactors (such as, reactor $552_1$, reactor $552_2$, reactor $552_3$, and reactor $552_4$) each produce (or otherwise transport or provide) a particular carbon additive/filler to the network that is tuned to yield a particular defined spectral profile. The carbon additives (such as, first tuned carbons 554, second tuned carbons 556, third tuned carbons 558, and fourth tuned carbons 560) can mixed with other (carbon-based or non-carbon based) compositions 550. Any known techniques can be used to mix, heat, pre-process, post-process or otherwise combine the particular carbon additives with the other compositions. Mixers (such as, mixer $562_1$, mixer $562_2$, mixer $562_3$, and mixer $562_4$) are presented to show how different tuned carbons can be introduced into various components of a tire. Other techniques for tire assembly may involve other construction techniques and/or other components that comprise the tire. Any known techniques for multi-ply tires can be used. Moreover, the spectral profile of a particular body ply and/or tread layer (such as a group of body plies and/or tread layers 568, including a body ply and/or tread layer $568_1$, a body ply and/or tread layer $568_2$, a body ply and/or tread layer $568_3$, and a body ply and/or tread layer $568_4$) can be determined based on the characterization of a particular body ply and/or tread layer formulation. For example, based on a stimulus and response characterization, a first body ply and/or tread layer formulation (such as, body ply and/or tread layer formulation $564_1$) might exhibit a first spectral profile, whereas a second body ply and/or tread layer formulation (such as, body ply and/or tread layer formulation $564_2$) might exhibit a second spectral profile.

The resulting different formulations (such as, body ply and/or tread layer formulation $564_1$, body ply and/or tread layer formulation $564_2$, body ply and/or tread layer formulation $564_3$, and body ply and/or tread layer formulation $564_4$), each of which body ply and/or tread layer exhibits a corresponding spectra profile, are used in the different body ply and/or tread layer that are formed into a tire assembly 566.

FIG. 6 depicts sets of example condition signatures 600 that may be emitted from new tires formed of layers of carbon-containing tuned RF resonance materials, in accordance with one embodiment. As an option, the example condition signatures 600 may be implemented in the context of any one or more of the embodiments set forth in any previous and/or subsequent figure(s) and/or description thereof. Of course, however, the example condition signatures 600 may be implemented in the context of any desired environment. Further, the aforementioned definitions may equally apply to the description below.

FIG. 6 shows a second set of example condition signatures 600 that are emitted from tires formed of layers of carbon-containing tuned resonance materials. The example condition signatures 600 or any aspect thereof may be emitted in any environment. FIG. 6 illustrates multiple body ply and/or tread layer (such as, body ply and/or tread layer #1, body ply and/or tread layer #2, and body ply and/or tread layer #3) of a new tire. The term "ply", as used in this example and elsewhere with reference to any one or more of the presented implementations, can refer to a ply or layer within a body of the tire, or—alternatively—a layer of the tire tread protruding radially outward away from the body of the tire intended for contact with hard pavement, or the earth for off-road tires). In one embodiment, the first body ply and/or tread layer may be formulated (referring to being created with a specific formula) with tuned carbons such that the first body ply and/or tread layer resonates at 1.0 GHz when stimulated with a 1.0 GHz ping stimulus (such as, the first ping 602). Similarly, the second body ply and/or tread layer is formulated with tuned carbons such that the second body ply and/or tread layer resonates at 2.0 GHz when stimulated with a 2.0 GHz ping stimulus (such as, the second ping 604). Further, the third body ply and/or tread layer is formulated with tuned carbons such that the third body ply and/or tread layer resonates at 3.0 GHz when stimulated with a 3.0 GHz ping stimulus (such as, the third ping 606). As shown by first response 608, second response 610, and third response 614, all three-body ply and/or tread layer are responsive at their respective tuned frequencies.

A transceiver antenna can be positioned in and/or on the wheel well of the corresponding tire (and/or in any location near the split ring resonator). Systems handling any such generated response signals can be configured to distinguish from other potential responses arising from the other surfaces, such as the remaining non-target tires of the vehicle, for example. For example, even though the right front tire mounted on the right front wheel of the vehicle might respond to a ping that is emitted from a transceiver antenna located in the left front wheel well of the vehicle, the response signal from the right front tire will be significantly attenuated (and recognized as such) as compared to the response signals from the left front tire of the vehicle. In various embodiments, the positioning of the transceiver antenna could be within inches of the split ring resonator, or could be 5-10 meters (or even farther) as needed. Such positioning may be a function of the power of the emitter receiver.

When the transceiver antenna is located in the wheel well of a corresponding tire, the response from the corresponding tire will be attenuated with respect to the ping stimulus. For example, the response from the corresponding tire can be attenuated with respect to the ping stimulus by 9 decibels (−9 dB) or more or can be attenuated with respect to the ping stimulus by 18 decibels (−18 dB) or more or can be attenuated with respect to the ping stimulus by 36 decibels (−36 dB) or more or can be attenuated with respect to the ping stimulus by 72 decibels (−72 dB) or more. In some cases, a ping signal generator is designed to be combined with a transceiver antenna located in the wheel well so as to cause the ping response of a corresponding tire to be attenuated by not more than 75 dB (−75 dB).

FIG. 7 depicts sets of example condition signatures 700 that may be emitted from new tires formed of layers of carbon-containing tuned RF resonance materials, in accordance with one embodiment. As an option, the example condition signatures 700 may be implemented in the context of any one or more of the embodiments set forth in any previous and/or subsequent figure(s) and/or description thereof. Of course, however, the example condition signatures 700 may be implemented in the context of any desired environment. Further, the aforementioned definitions may equally apply to the description below.

As shown, the third set of example condition signatures 700 are emitted from tires after wear-down of some of the carbon-containing tuned resonance materials. As an option, one or more variations of example condition signatures 700 or any aspect thereof may be implemented in the context of the architecture and functionality of the implementations described herein. The example condition signatures 700 or any aspect thereof may be emitted in any environment.

In this example, the tire has undergone wear. More specifically, the outermost body ply and/or tread layer has been worn away completely. As such, a ping stimulus at 1.0 GHz would not result in a response from the outermost ply. This is shown in the chart as a first response attenuation 702. As the tire continues to undergo tread wear, ping responses from the next body ply and/or tread layer and ping responses from the next successive body ply and/or tread layer and so on will be attenuated, which attenuation can be used to measure total tread wear of the tire. As an alternative, the same tuned carbons can be used in all plies. The tread wear of the tire as well as other indications can be determined based on the returned signal signatures from the tire.

Figure 8:
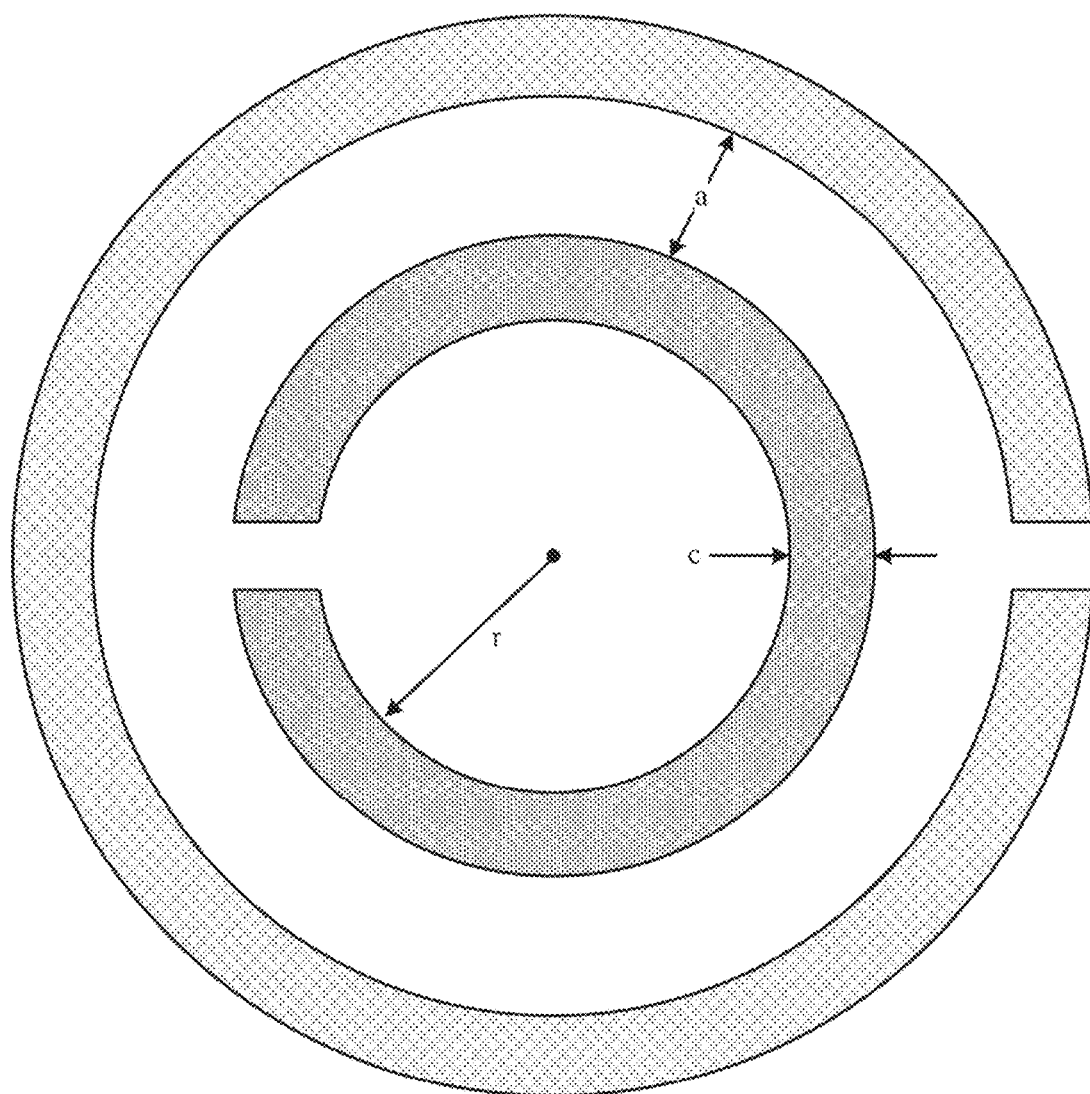
FIG. 8 depicts a top-down schematic view of an example split-ring resonator (split ring resonator) configuration including two concentric split ring resonators, in accordance with one embodiment.

FIG. 8 depicts a top-down schematic view 800 of an example split-ring resonator (split ring resonator) configuration including two concentric split ring resonators, in accordance with one embodiment. As an option, the top-down schematic view 800 may be implemented in the context of any one or more of the embodiments set forth in any previous and/or subsequent figure(s) and/or description thereof. Of course, however, the top-down schematic view 800 may be implemented in the context of any desired environment. Further, the aforementioned definitions may equally apply to the description below.

As shown, FIG. 8 is a top view of two layers, where each layer hosts a split ring resonator (split ring resonator), e.g., forming an example split-ring resonator (split ring resonator) configuration including two concentric split ring resonators. As used herein, split ring resonators (split ring resonators) consist of a pair of concentric rings, disposed on a dielectric substrate, where each ring has slits (e.g., due to a printed pattern). When an array of split ring resonators is excited by means of a time varying magnetic field, the structure behaves as an effective medium with negative effective permeability in a narrow band around the split ring resonator resonance point. Many geometries are possible, e.g., such that dimensions and/or spacings between each split ring resonator including dimensions "a," "r", and/or "c" are selected to achieve particular corresponding spectral response. For example, "a" may be approximately 1 mm, "r" may be 2 mm, and "c" may be approximately 0.6 mm. These dimensions may correspond to producing a desired and/or expected spectral response, e.g., resulting in a relatively wider and/or broader signal response rather than a narrow and/or notched response, facilitating improved spectral analysis leading to improved cost-efficiency in using spectral analysis tools (such as a spectrum analyzer). In addition, or the alternative, any of the dimensions may be further adjusted to achieve particular desired end-result objectives, e.g., applications in racing circuits compared to off-road applications, etc. In one embodiment, a particular geometry may involve gaps between concentric rings. Such gaps may produce a capacitance which in combination with the inductance inherent in the pair of concentric rings introduces a change in the resonance of the ensemble.

A printable, sheet-oriented, cylinder-type, split ring resonator design can be built out of any electrically-conducting materials, including metals, electrically-conducting non-metals, dielectric materials, semiconducting materials, etc. In addition to tuning based on the selection and/or treatment of electrically-conducting materials, split ring resonators can be tuned by varying the geometry such that the effective permittivity accordingly tuned. Effective permittivity as a function of the geometry of a split ring resonator is given in Eq. 5.

$$\mu_{eff} = 1 - \frac{\pi r^2}{a^2}{1 + \frac{2l\sigma_1 i}{\omega r \mu_0} - \frac{3lc_0^2}{\pi\omega^2 r^3 \ln\left(\frac{2c}{d}\right)}} \tag{Eq. 5}$$

where a is the spacing of the cylinders, ω is the angular frequency, μ0 is the permeability of free space, r is the radius, d is the spacing of the concentric conducting sheets, l is a stacking length, c is the thickness of a ring, and σ is the resistance of unit length of the sheets measured around the circumference.

In some situations, the value of a (e.g., the spacing of the cylinders of a cylindrical split ring resonator) can be made relatively small such that the concentric rings absorb EM radiation within a relatively narrow frequency range. In other situations, the value of a can be made relatively large such that the concentric rings each absorb EM radiation at frequencies that are separated by a wide range. In some situations, differently-sized split ring resonators can be disposed on different surfaces of the tire. In some situations, the differently-sized split ring resonators that are disposed on different surfaces of the tire can be used to take measurements of tire conditions (e.g., temperature, aging, wear, etc.).

In some embodiments, the materials that form the split ring resonator are composite materials. Each split ring resonator can be configured to any particular desired tuned response to EM stimulation. At least inasmuch as split ring resonators are designed to mimic the resonance response of atoms (though on a much larger scale, and at lower frequencies), the larger scale of split ring resonators as compared with atoms allows for more control over the resonance response. Moreover, split ring resonators are much more responsive than ferromagnetic materials found in nature. The pronounced magnetic response of split ring resonators carries with it a significant advantage over heavier, naturally occurring materials.

Figure 9:
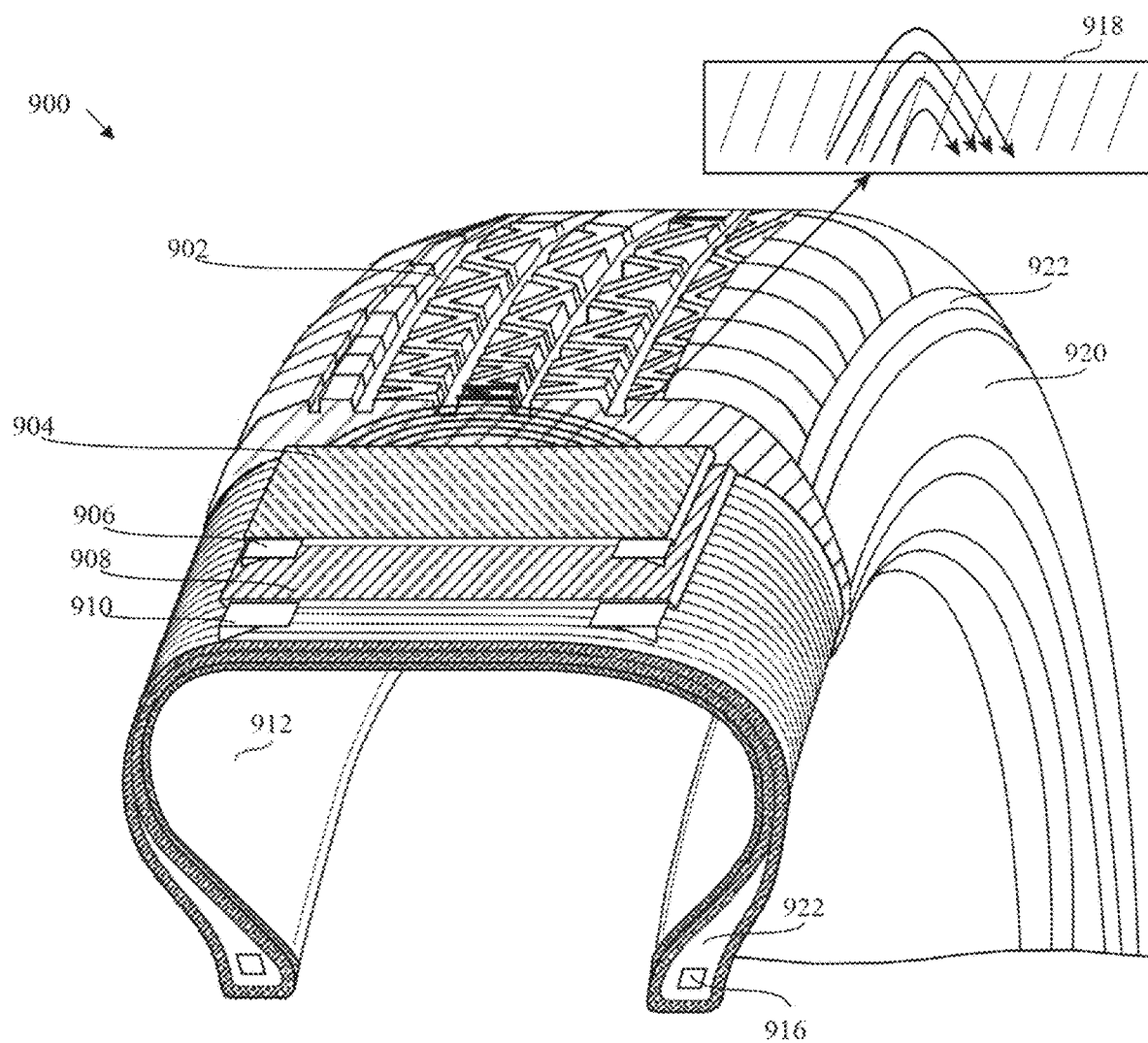
FIG. 9 depicts a schematic diagram showing a complete tire diagnostics system and apparatus for tire wear sensing through impedance-based spectroscopy, in accordance with one embodiment.

FIG. 9 depicts a schematic diagram 900 showing a complete tire diagnostics system and apparatus for tire wear sensing through impedance-based spectroscopy, in accordance with one embodiment. As an option, the schematic diagram 900 may be implemented in the context of any one or more of the embodiments set forth in any previous and/or subsequent figure(s) and/or description thereof. Of course, however, the schematic diagram 900 may be implemented in the context of any desired environment. Further, the aforementioned definitions may equally apply to the description below.

As shown, the schematic diagram 900 of a tire, such as a pneumatic rubber tire filled with air or nitrogen gas ($N_2$), can include traditional tire components including a body 920, an inner liner 912, a bead filler region 922, a bead 916, one or more belt plies 904, 906, 908, and 910, tread 902, and impedance-based spectroscopy wear sensing printed electronics 918 (alternatively sensors including carbon-based microstructures for signal frequency shift and attenuation monitoring by a resonator embedded within any one or more of the belt plies 904-910).

As shown here, a wireless strain sensor can be placed on surfaces or on the sides of the inner liner (or be embedded within) to monitor the tire condition for automobile safety, (such as to detect damaged tires). Tire deformation or strain monitoring can (indirectly) provide information representative of a degree of friction between the tires and contacting road surfaces, which can then be used for the optimization of automobile tire control systems. The tire information can be wirelessly transmitted to a receiver positioned in the wheel well (and/or any location near the split ring resonator) based on a resonant sensor platform. It is to be appreciated that the receiver could be potentially located anywhere that is not opaque to radio frequency (wireless) signaling.

Figure 10:
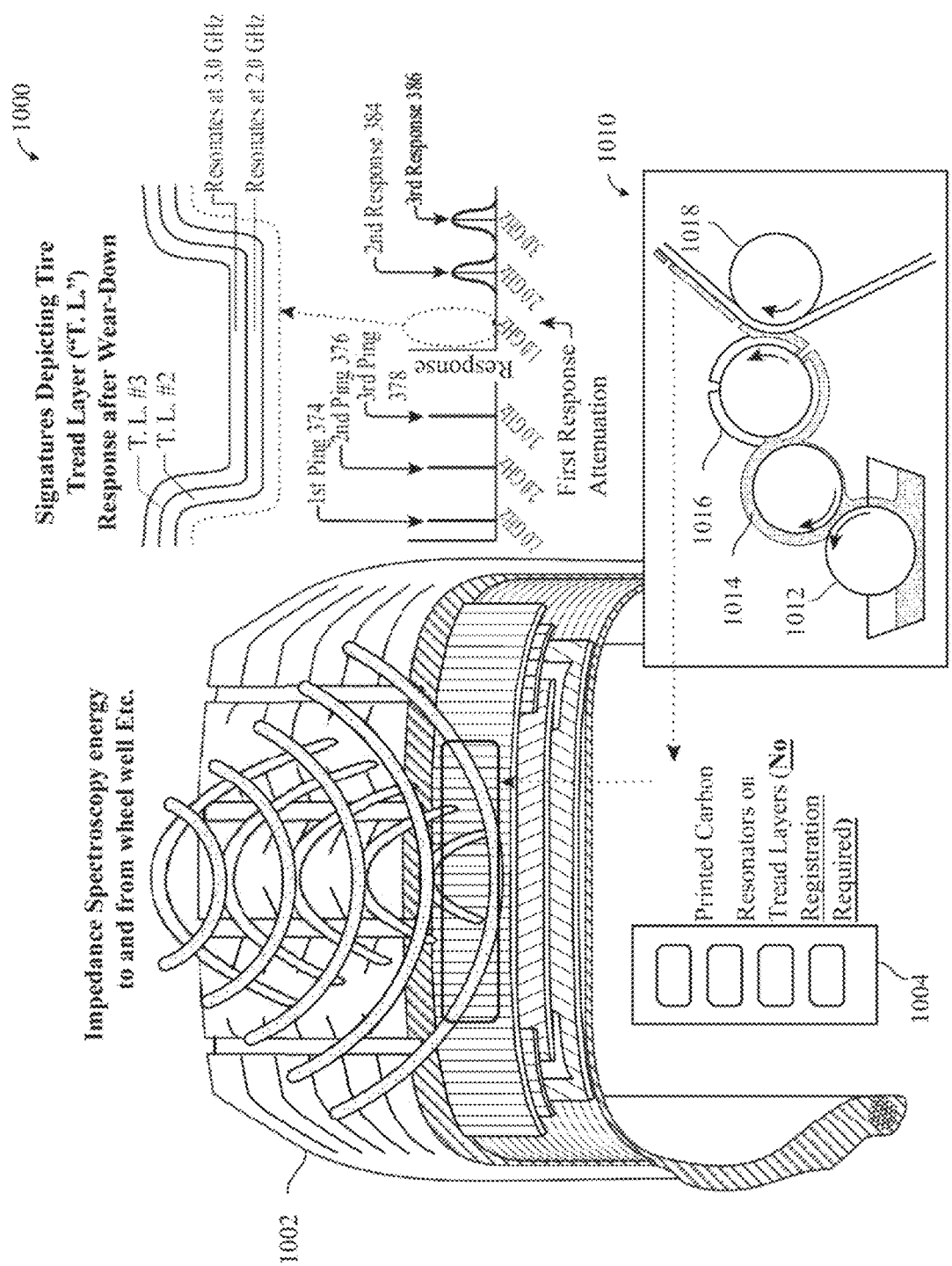
FIGS. 10 and 11 depict schematic diagrams relating to tire information transferred via telemetry into a navigation system, as well as equipment for manufacturing printed carbon-based materials, in accordance with one embodiment.

FIG. 10 depicts a schematic diagram 1000 relating to tire information transferred via telemetry into a navigation system, as well as equipment for manufacturing printed carbon-based materials, in accordance with one embodiment. As an option, the schematic diagram 1000 may be implemented in the context of any one or more of the embodiments set forth in any previous and/or subsequent figure(s) and/or description thereof. Of course, however, the schematic diagram 1000 may be implemented in the context of any desired environment. Further, the aforementioned definitions may equally apply to the description below.

As shown, the schematic diagram 1000 show a system for providing tire wear-related information transferred via telemetry into a navigation system and equipment for manufacturing printed carbon-based materials. The schematic diagram 1000 can function with any one or more of the presently disclosed systems, methods, and materials, such as the sensors including carbon-based microstructures such that a redundant description of the same is omitted. Impedance spectroscopy, also referred to as Electrochemical Impedance Spectroscopy (EIS), refers to a method of impedimetric transduction involving the application of a sinusoidal electrochemical perturbation (potential or current) over a wide range of frequencies when measuring a sample, such as a sensor including carbon-based microstructures incorporated within one or more tire belt plies of a tire 1002. Printed carbon-based resonators 1004 can be incorporated within one or more tire components such as the tire belt plies, with each of the printed carbon-based resonators 1004 having the general oval configuration shown, or some other shape or configuration tailored to achieve specific desirable resonance properties suitable for efficient and accurate vehicle component wear detection through monitoring of frequency shift and/or attenuation (such as a first response attenuation indicative of the wear of a tire body ply and/or tread layer having a natural resonance frequency of approximately 1.0 GHz).

An assembly of rollers 1010 capable of forming the printed carbon-based resonators 1004 includes a repository 1012 (such as a vat) of carbon-based microstructures and/or microstructural material (such as graphene), an anilox roller 1014 (referring to a hard cylinder, usually constructed of a steel or aluminum core which is coated by an industrial ceramic whose surface contains millions of very fine dimples, known as cells), a plate cylinder 1016, and an impression cylinder 1018. In operation, graphene extracted from the repository 1012 can be rolled, pressed, stretched, or otherwise fabricated by the rollers of the assembly of rollers 1010 into the printed carbon-based resonators 1004. No registration (referring to alignment) of the printed carbon-based resonators 1004 may be needed for functioning of the schematic diagram 1000.

As such, any combination of the aforementioned features can be used to manufacture a tire that has a resonator (referring to actual or "equivalent" tank), LC and/or resonant circuit, where carbon-containing microstructures themselves can resonate in response to emitted RF signals from a transceiver, and/or from energy supplied by an advanced energy source, such that other sensors, disposed into or onto any one or more components such as the tread, a ply or plies, an inner liner, etc. of the tire can demonstrate frequency-shifting or signal attenuation properties or behavior. The described resonator is not necessarily required to be embodied as an actual electrical and/or integrated circuit (IC). The described resonator can be realized simply as tuned carbon-containing microstructures, to thus avoid common deterioration concerns that may arise when implementing traditional discrete circuitry in decomposable materials, such as tire tread layers. Such resonators can resonate in response to an externally-supplied 'ping' (such as that supplied by a transceiver located in the wheel well of vehicle), or the resonator can respond to being charged by a co-located (referring to within the same tire tread layer, but possibly at a different location within that tire tread layer), self-powered, self-pinging capability facilitated by any variations or any number of power or charge generators (such as thermoelectric generators, piezoelectric energy generators, triboelectric energy generators, etc.).

At any time when the tire is rolling or otherwise undergoing deformation, any of the described resonators (and other resonators and/or resonant circuits) can be configured to emit and/or further emit oscillating RF signals (or other forms of electromagnetic radiation, depending on the overall configuration). As a vehicle tire experiences wear resultant from usage (such as on or off-road driving), tire tread layers in contact with pavement or ground (earth) may experience deformation, either instantaneously or over time (such as that observed from being "squished", referring to at least partial flattening of sections of the exposed vehicle tire tread layers during rotation or rolling, and/or from lateral motion as experienced during turning, etc.), therefore resultant signal frequency-shift and/or attenuation behavior may change pursuant to such "squishing" as associated signals can oscillate over one or more known amplitude ranges. In addition, or in the alternative, as the tire undergoes deformation, observed signals can oscillate within a known frequency range corresponding to a particular resonator, allowing for precise and accurate identification of the type of deterioration occurring while it is occurring, rather than requiring the driver, passengers, and/or other vehicle occupants to exit the vehicle, while it is stationary, to observe tire tread conditions. Such a frequency-shifting oscillation may be observable as a frequency shift back and forth between two or more frequencies within the known frequency range.

A wireless-capable strain sensor (such as a geometric measure of deformation representing the relative displacement between particles in a material body that may be caused by external constraints or loads) positioned on sides of the inner liner can monitor tire condition for automobile safety (such by detecting damaged tires). Additionally, tire deformation or strain monitoring can indirectly provide information related to the degree of friction between tires and road surface, which can then be used for the optimization of automobile tire control systems. Such tire information can be wirelessly transmitted to a receiver (and/or transceiver) positioned in the wheel hub based on a resonant sensor (such as an impedance spectroscopy, IS, sensor) platform.

Figure 11:
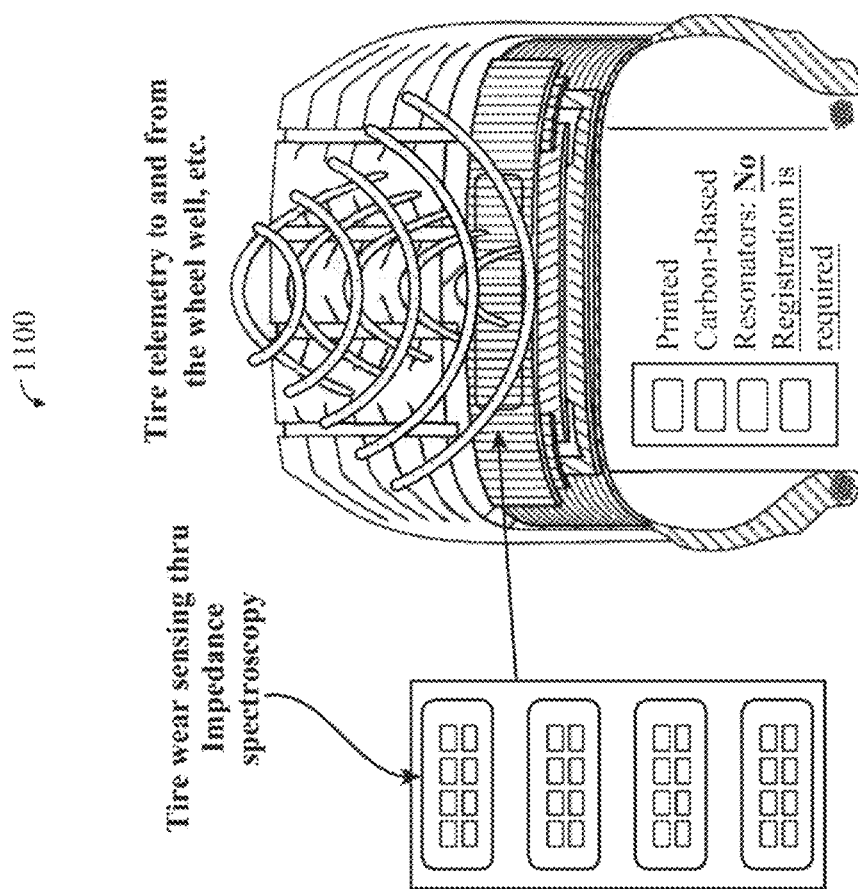

FIG. 11 depicts a schematic diagram 1100 relating to tire information transferred via telemetry into a navigation system, as well as equipment for manufacturing printed carbon-based materials, in accordance with one embodiment. As an option, the schematic diagram 1100 may be implemented in the context of any one or more of the embodiments set forth in any previous and/or subsequent figure(s) and/or description thereof. Of course, however, the schematic diagram 1100 may be implemented in the context of any desired environment. Further, the aforementioned definitions may equally apply to the description below.

In one embodiment, the schematic diagram 1100 may relate to a resonant serial number-based digital encoding system for determining wear of vehicle tires through ply-print encoding. The resonant serial number-based digital encoding system may be incorporated and/or function with any of the presently disclosed systems, methods, and sensors. The resonant serial number-based digital encoding system offers digital encoding of tires through ply-print encoding and thus offers cradle-to-the-grave (referring to a full lifespan) of tracking of tires (and related performance metrics) and a usage profile without requiring traditional electronic devices susceptible to routine wear-and-tear in the tires.

Resonant serial number digital encoding of tire through tire tread layer printing may facilitate, in some implementations, cradle-to-grave tire tracking of tires and usage without necessarily requiring the presence of electronics within the tires. For example, along with tire wear sensing accomplished through impedance spectroscopy, additional resonators may be digitally encoded onto, for example, one or more printed patterns for serial numbers used for telemetry tracking. As a result, so-equipped vehicles can track tread wear, miles driven (e.g., in total), and tire age without requiring radio-frequency identification (RFID) technology.

Along with tire wear sensing thru Impedance Spectroscopy (IS) and/or Electrochemical Impedance Spectroscopy (EIS), additional resonators can be digitally encoded onto a printed pattern to provide a recognizable serial number for telemetry-based tire performance tracking. By being printed onto the body ply and/or tread layer incrementally, tires incorporating the discussed printed carbon-based resonators can be innately serialized.

Figure 12:
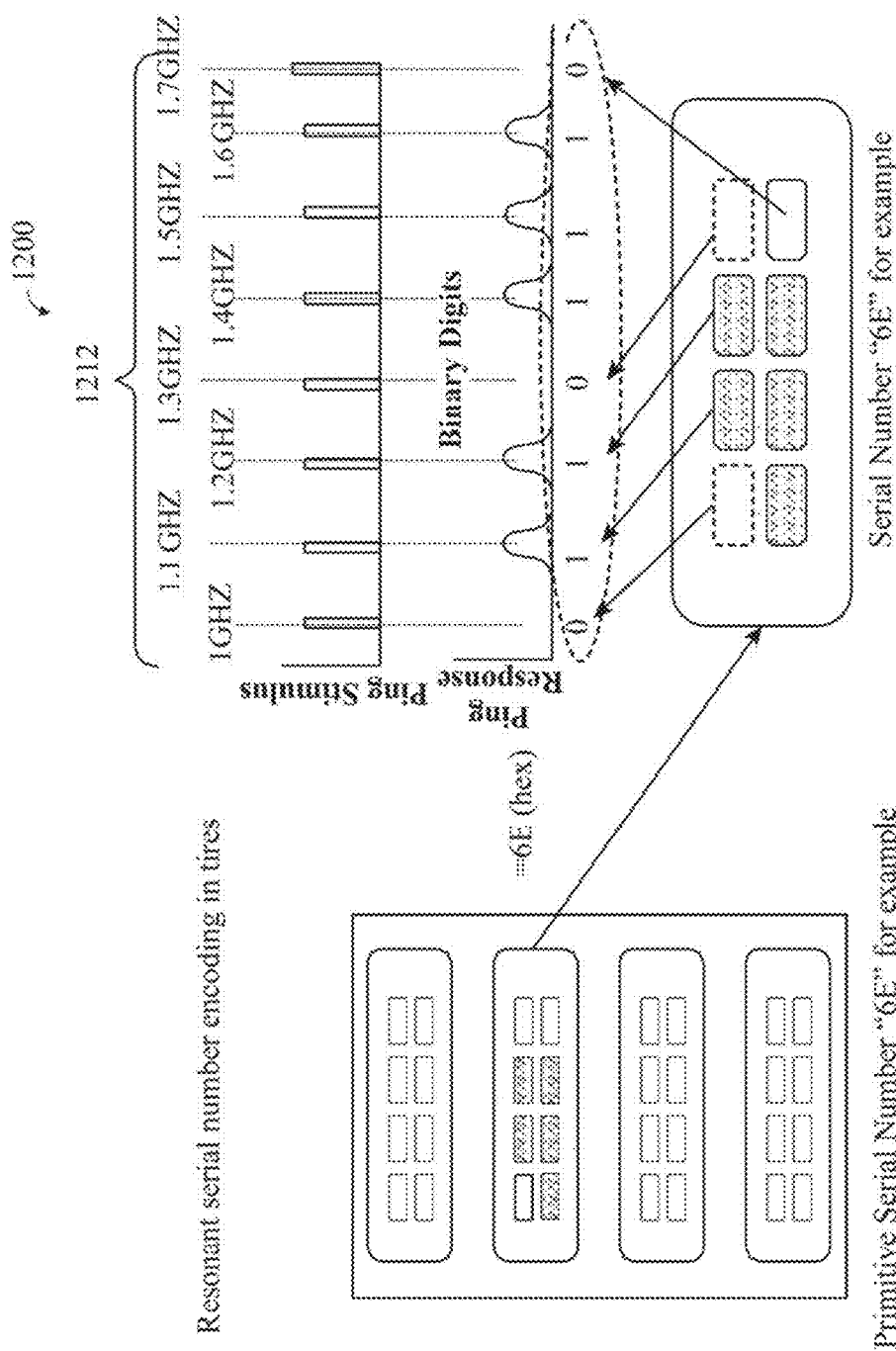
FIG. 12 depicts a schematic diagram for resonant serial number-based digital encoding of vehicle tires through tire tread layer and/or tire body ply-print encoding, in accordance with one embodiment.

FIG. 12 depicts a schematic diagram 1200 for resonant serial number-based digital encoding of vehicle tires through tire tread layer and/or tire body ply-print encoding, in accordance with one embodiment. As an option, the schematic diagram 1200 may be implemented in the context of any one or more of the embodiments set forth in any previous and/or subsequent figure(s) and/or description thereof. Of course, however, the schematic diagram 1200 may be implemented in the context of any desired environment. Further, the aforementioned definitions may equally apply to the description below.

As shown, the serial number "6E" is shown encoded in a specially-prepared array of printed carbon resonators configured to resonate according to the 'ping' stimulus-response diagram 1212 allowing for convenient and reliable identification of that particular body ply and/or tread layer of the so-equipped vehicle tire.

Figure 13:
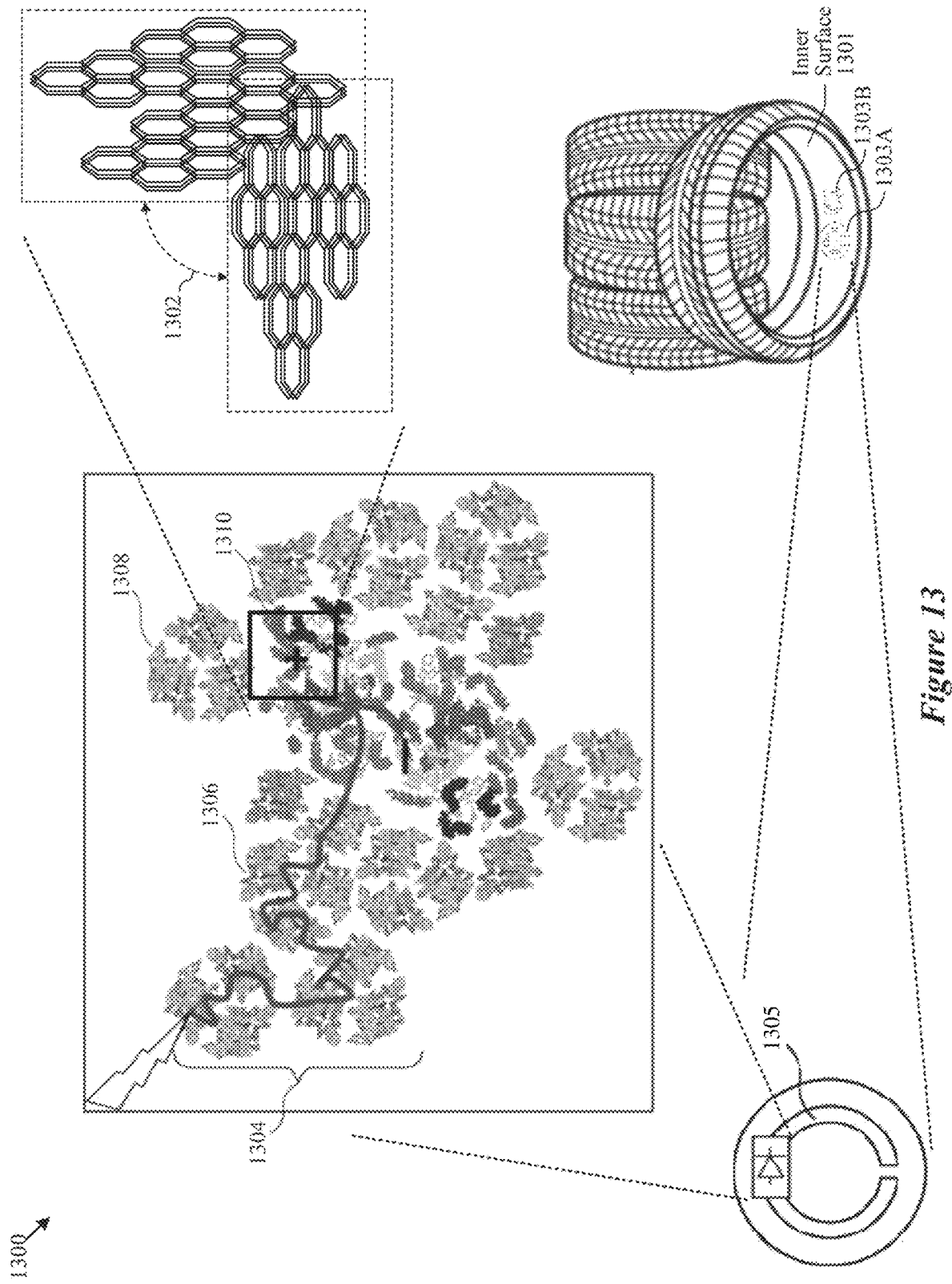
FIG. 13 illustrates resonance mechanisms that contribute to the ensemble phenomenon arising from different proximally-present resonator types, in accordance with one embodiment.

FIG. 13 illustrates resonance mechanisms 1300 that contribute to the ensemble phenomenon arising from different proximally-present resonator types, in accordance with one embodiment. As an option, the resonance mechanisms 1300 may be implemented in the context of any one or more of the embodiments set forth in any previous and/or subsequent figure(s) and/or description thereof. Of course, however, the resonance mechanisms 1300 may be implemented in the context of any desired environment. Further, the aforementioned definitions may equally apply to the description below.

In one embodiment, the resonance mechanisms 1300 may be used to illustrate use of split ring resonators (split ring resonators) as resonance devices that contribute to the ensemble phenomenon arising from different proximally-present resonator types. The figure shows the inner surface 1301 of a tire, where the inner surface has two split ring resonators (e.g., split ring resonator 1303A and split ring resonator 1303B), each of which split ring resonator forms a circuit configuration 1305 that can be tuned to attenuate a signal at a particular frequency and/or to attenuate within a particular range of frequencies. In this embodiment, circuit configuration 1305 is shown as a geometric pattern that corresponds to a substantially-circular split ring resonator; however, alternative circuit configurations can have different geometric patterns (e.g., cylinders, ellipses, rectangles, ovals, squares, etc.), and as such, any conceivable geometric configuration is possible. Variations of the geometric configurations can be selected based on the impact on resonation capabilities of the geometric pattern. In particular, and as shown, the geometric pattern can comprise self-assembled carbon-based particles having various agglomeration patterns (e.g., agglomeration pattern 1306, agglomeration pattern 1308, and agglomeration pattern 1310), any one or more of which can constitute a concentrated region 1304 that can impact the resonation performance of materials within which carbon-based microstructures are incorporated. An agglomeration pattern and/or a series of agglomeration patterns may also impact the resonation performance of materials within which carbon-based microstructures are incorporated.

In various configurations, the carbon-based microstructures may be formed, at least in part, by graphene. In this context, graphene may refer to an allotrope of carbon in the form of a single layer of atoms in a two-dimensional hexagonal lattice in which one atom forms each vertex. Co-location and/or juxtaposition of multiple of such hexagonal lattices into more complex structures introduces further resonance effects. For example, juxtaposition 1302 of two sheets or platelets of graphene may resonate between themselves at a frequency that is dependent on the length, width, spacing, thickness, shape of the spacing, and/or other physical characteristics of the sheets or platelets and/or their relative juxtaposition to each other.

Table 1 depicts one possible chord of attenuations arising from the ensemble effect. As shown in the table, each of the structures has a different resonant frequency domain that corresponds to its scale designation.

TABLE 1

Ensemble effect examples

| Structure | Scale Designation | Resonant Frequency Domain |
|---|---|---|
| Printed Pattern (e.g., split ring resonator geometry) | Macro-scale | Lower GHz |
| Agglomeration pattern | Meso-scale | Higher GHz |
| Juxtaposition of graphene sheets or platelets | Micro-scale | Very high GHz |
| Molecule | Nano-scale | THz |

Any number of different split ring resonators can be printed onto a surface of a tire. Moreover, any number of different sizes of split ring resonators can be printed onto any of the surfaces of a tire. The choice of materials and/or the size and/or other structural or dimensional characteristics of a particular split ring resonator can be used to control the resonation frequency of that particular resonator split ring. A series of differently-sized split ring resonators can be printed such that the pattern corresponds to a digitally encoded value. Stimulating the series of differently-sized split ring resonators with via electromagnetic signal communication, for example, sweeping through a range from 8 GHz to 9 GHz or similar, and measuring the attenuation response through a range of the return may lead to a recognizable encoded serial number. Many different encoding schemes are possible, and as such, the non-limiting example of Table 2 is merely for illustration.

TABLE 2

Example encoding scheme

| Size (outer diameter) | 1 mm | 2 mm | 2.5 mm | 3 mm | 4 mm | 5 mm | 6 mm | 7 mm |
|---|---|---|---|---|---|---|---|---|
| Bit Assignment | 8 | 7 | 6 | 5 | 4 | 3 | 2 | 1 |
| Calibrated Attenuation Point (GHz) | 8.890 | 8.690 | 8.655 | 8.570 | 8.470 | 8.380 | 8.350 | 8.275 |
| Encoded 6E split ring resonator pattern | | Present | Present | | Present | Present | Present | |
| Encoded 6E bit pattern | 0 | 1 | 1 | 0 | 1 | 1 | 1 | 0 |
| Encoded 4E split ring resonator pattern | | Present | | | Present | Present | Present | |
| Encoded 4E bit pattern | 0 | 1 | 0 | 0 | 1 | 1 | 1 | 0 |
| Encoded E1 split ring resonator pattern | Present | Present | Present | | | | | Present |
| Encoded E1 bit pattern | 1 | 1 | 1 | 0 | 0 | 0 | 0 | 1 |

Figure 14:
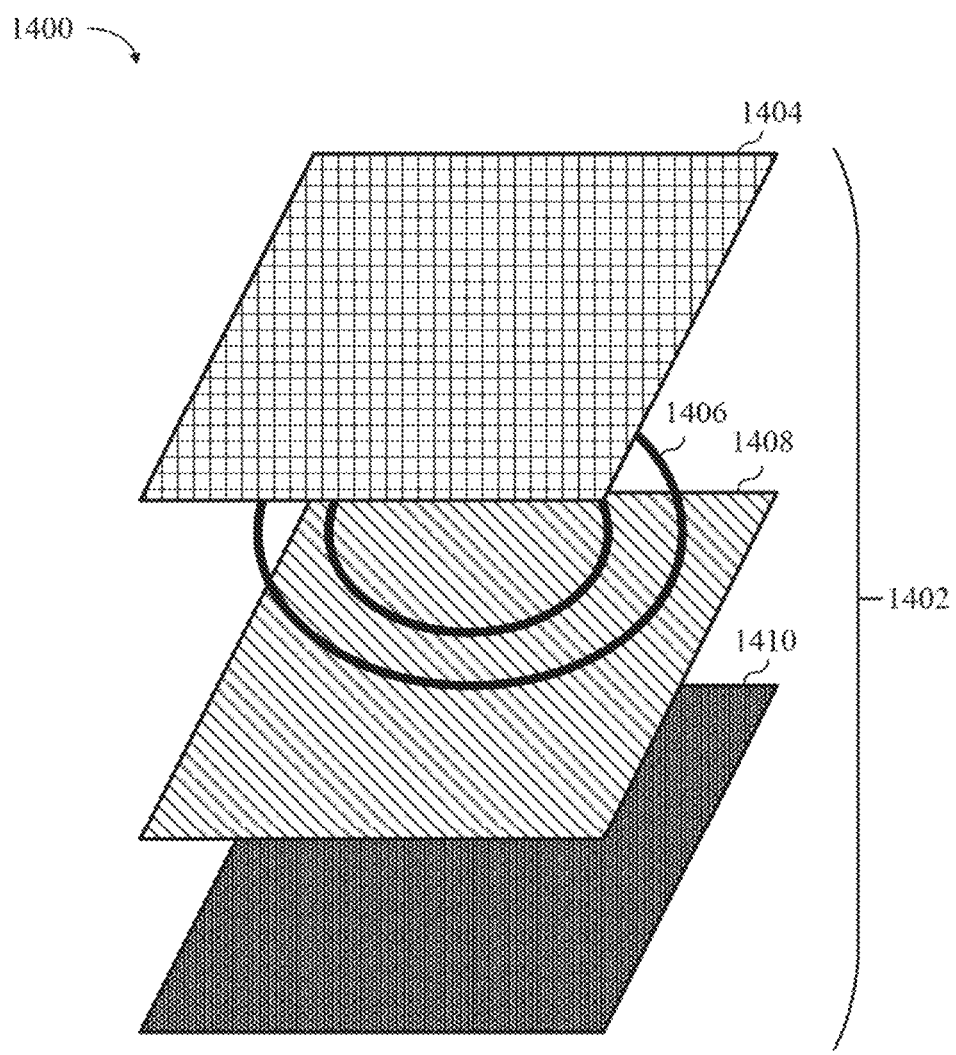
FIG. 14 is an example temperature sensor including one or more of the presently disclosed split ring resonators, in accordance with one embodiment.

FIG. 14 is an example temperature sensor 1400 including one or more of the presently disclosed split ring resonators, in accordance with one embodiment. As an option, the example temperature sensor 1400 may be implemented in the context of any one or more of the embodiments set forth in any previous and/or subsequent figure(s) and/or description thereof. Of course, however, the example temperature sensor 1400 may be implemented in the context of any desired environment. Further, the aforementioned definitions may equally apply to the description below.

Figure 16:
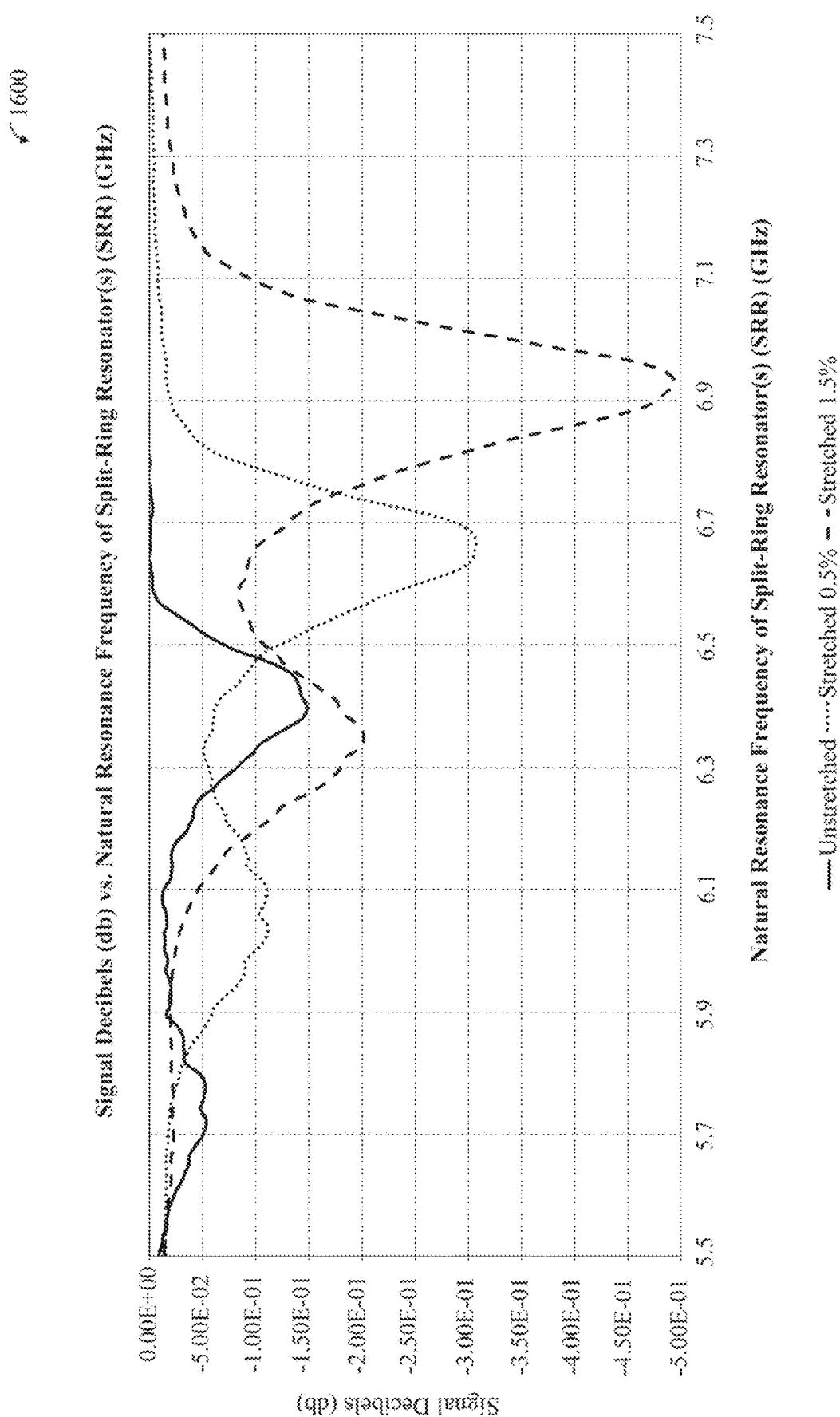
FIG. 16 is a graph of measured resonant signature signal intensity (in decibels, dB) relative to the natural resonance frequency of split ring resonators showing resonance response shift proportionate to tire ply deformation, in accordance with one embodiment.

In one implementation, the example temperature sensor 1400 may include a section 1402 of a tire body (e.g., as shown in FIG. 9) with multiple tire plies. The example temperature sensor 1400 may detect a temperature 1408 of a tire ply, e.g., in which the example temperature sensor 1400 is incorporated. In one implementation, the tire sensor may include a ceramic material 1404 (e.g., organized as a matrix), and one or more split ring resonators 1406, such as shown in FIG. 8 and elsewhere in the present disclosure). Each of the one or more split ring resonators 1406 may have a natural resonance frequency (e.g., as shown in FIG. 16) that may shift in response to one or more of a change in an elastomeric property or a change in the temperature of the respective tire. An electrically-conductive layer 1410 may be dielectrically separated from a respective split ring resonator of the one or more split ring resonators 1406. In some implementations, the example temperature sensor 1400 may be produced and shipped without being incorporated in a tire, such that later incorporation within a tire and/or tire ply is possible.

In addition, or in an alternative embodiment, the example temperature sensor 1400 may be incorporated into a system (not shown in FIG. 14) configured to detect tire strain (e.g., as shown in FIG. 16) in a vehicle. The system may include an antennae (e.g., as discussed in the present disclosure relating to emission and/or propagation of electromagnetic signals) disposed on one or more of the vehicle or a vehicle component. The antennae may be configured to output an electromagnetic ping. The system may also include a tire having a body (e.g., as shown in FIG. 9) formed of one or more tire plies. Any one or more of the tire plies may include split-ring resonators (split ring resonators), e.g., as discussed in the present disclosure. In one implementation, each split ring resonator may have a natural resonance frequency configured to proportionately shift (e.g., as shown in FIG. 16) in response to a change in an elastomeric property of a respective one or more tire plies, e.g., reversible deformation, stress, and/or strain.

In some implementations, the described system may function to detect changes in physical properties of materials outside of configurations relating to tires and/or vehicles, e.g., automobiles and trucks. For example, the system may detect changes in surface temperature of an airplane wing and/or other type of airfoil, e.g., associated with spacecraft and/or the like. Also, the system may permit for instances where the one or more split ring resonators 1406 may be removably adhered onto patients in a hospital setting, such that body temperature readings of the respective patient may be obtained without the usage of conventional thermal sensors (e.g., relying on radiative heat transfer technology, etc.). In any of these examples, as well as others, such a system may detect a physical property associated with a surface.

In one implementation, the system may include a single antennae configured to output an electromagnetic ping and one or more flexible substrates. Each of the flexible substrates may include a first side including a plurality of split-ring resonators (split ring resonators) (e.g., such as the one or more split ring resonators 1406) disposed on the flexible substrate. Each split ring resonator may have a natural resonance frequency that may proportionately shift (e.g., as shown in FIG. 16) in response to a change in an elastomeric property of a respective one or more tire plies. The elastomeric property may include one or more of a reversible deformation, stress, strain, or temperature. In this way, the system may generate an absorption profile (e.g., referring to unique changes in absorption phenomena of the electromagnetic ping output by the antennae). The system may include a second side positioned opposite to the first side. The second side may attach to the surface. The single antenna may analyze data associated with the absorption profile and output a topography of the physical property.

Figure 15:
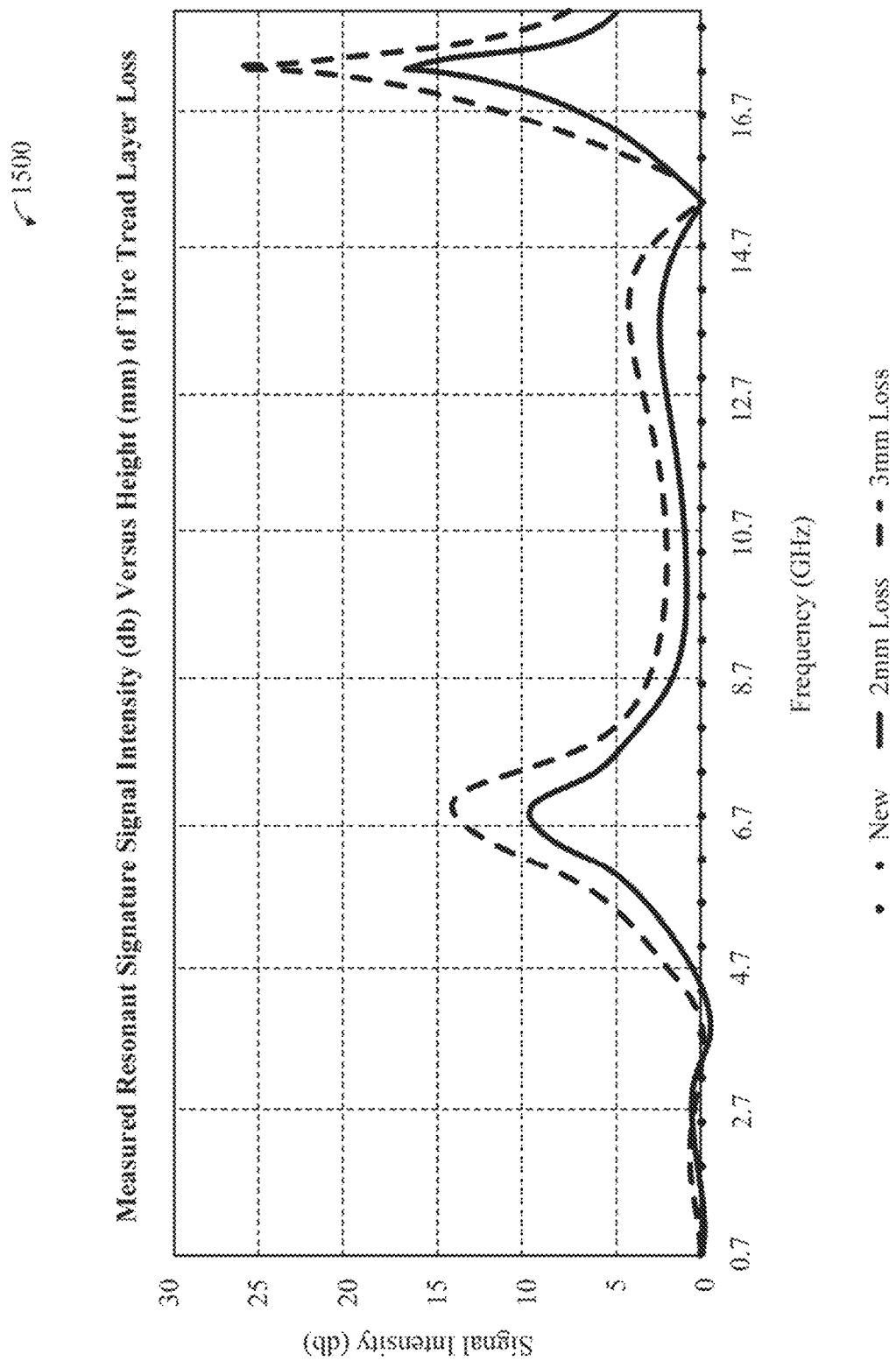
FIG. 15 is a graph of measured resonant signature signal intensity (in decibels, dB) relative to height (in millimeters, mm) of tire tread layer loss, in accordance with one embodiment.

FIG. 15 is a graph 1500 of measured resonant signature signal intensity (in decibels, dB) relative to height (in millimeters, mm) of tire tread layer loss, in accordance with one embodiment. As an option, the graph 1500 may be implemented in the context of any one or more of the embodiments set forth in any previous and/or subsequent figure(s) and/or description thereof. Of course, however, the graph 1500 may be implemented in the context of any desired environment. Further, the aforementioned definitions may equally apply to the description below.

As shown here, carbon-containing microstructures and/or microstructural materials can be incorporated into sensors or, in some configurations, entire layers of one or more tire treads at a given concentration level, or multiple dissimilar concentration levels (in each of the one or more tire tread layers) to achieve the unique deterioration profile shown. That is, the measure resonance signature (referring to the identifying "signature" of a particular tire tread layer in question) can be 'pinged', as so described herein, by one or more RF signals to demonstrate the attenuation of that emitted signal as shown.

A new tire tread layer can be configured to indicate a signal intensity (measured in decibels, dB) of approximately 0. That intensity can change proportionate to the extent of deterioration of that tire tread layer. For instance, a 2 mm height loss of a tire tread layer, presumedly the tire tread layer in contact with pavement, can correspond with the measure resonant signature signal intensity profile shown. A 'ping' signal at 6.7 GHz can be measured at an intensity level of about 9 dB, etc., and so on and so forth.

Accordingly, unique concentration levels, chemistries, dispersions, distributions and/or the like of the carbon-containing microstructures can be embedded (or, in some cases, placed on one or more surfaces of) tire tread layers to achieve a unique and readily identifiable measured resonant signature signal intensity as shown. A user of such a system can therefore immediately be notified to the exact extent and location of tire tread wear as it occurs during driving, rather than being restricted to observe the tires while the vehicle is in a stationary condition, a process that can be both time-consuming and cumbersome.

FIG. 16 is a graph 1600 of measured resonant signature signal intensity (in decibels, dB) relative to the natural resonance frequency of split ring resonators showing resonance response shift proportionate to tire ply deformation, in accordance with one embodiment. As an option, the graph 1600 may be implemented in the context of any one or more of the embodiments set forth in any previous and/or subsequent figure(s) and/or description thereof. Of course, however, the graph 1600 may be implemented in the context of any desired environment. Further, the aforementioned definitions may equally apply to the description below.

In one embodiment, the graph 1600 shows measured resonant signature signal intensity (in decibels, dB) against the natural resonance frequency of split-ring resonator(s) (split ring resonators) incorporated into tire treads and/or tire plies (e.g., as discussed in the present disclosure), in accordance with one embodiment. As shown here, carbon-containing and/or carbonaceous microstructures and/or microstructural materials can be incorporated into sensors or, in some configurations, entire layers of one or more tire treads at a given concentration level, or multiple dissimilar concentration levels (in each of the one or more tire tread layers) to achieve the unique deterioration profile shown. That is, the measure resonance signature (referring to the identifying "signature" of a particular tire tread layer in question) can be 'pinged', as so described herein, by one or more RF signals to demonstrate the shift of that emitted signal as shown, e.g., representative and/or proportionate to an extent of reversible tire deformation, e.g., stress and/or strain (as may be encountered in drifting scenarios). In this way, split ring resonator "response" signal behavior can be modeled as a function of tire deformation, e.g., strain (associated with drifting), allowing for a complete picture of tire condition and performance. Real-world scenarios resulting in lateral tire stiction loss may include drifting and/or hydroplaning, e.g., implying phenomena that occurs when a layer of water builds between the wheels of the vehicle and the road surface, leading to a loss of traction that prevents the vehicle from responding to control inputs. If hydroplaning occurs to all contact wheels simultaneously, the vehicle becomes, in effect, an uncontrolled sled. Usage of the presently disclosed split ring resonators and/or resonators in combination with antennae and/or signal processing equipment may effectively eliminate the need to rely on conventional hydroplaning detection techniques, e.g., through usage of a vibration detection unit coupled with surfaces of a tire which may deteriorate and become compromised through extended usage. In addition, FIG. 16 shows spectral response (in signal decibels) associated with lateral tire movement encountered during striction loss while drifting. In real-world scenarios, such as temporary stiction loss may be audibly heard through a high-pitched "screech," as opposed to other sounds heard during rapid forward rotation only. This type of periodic stiction loss (prior to the drifting vehicle regaining stiction and/or traction) may be exhibited (not shown in FIG. 16) as a periodic and/or cyclical shift in the natural resonance frequency of corresponding split ring resonators. Further yet, with respect to FIG. 16, "screech" type circumstances may be visually depicted by minor periodic and/or cyclical shifts in frequency of the various troughs and/or peaks of the curves.

As can be seen, the real-time multi-modality resonator supports methods for measuring stiction using resonant materials-containing sensors for elastomer property change detection. In one setting, one or more resonant materials-containing sensors for elastomer property change detection are disposed in a location proximal to a transducer. A stimulation signal may be emitted so as to excite the one or more resonant materials-containing sensors for elastomer property change detection. The emissions comprise electromagnetic energy that spans a known frequency range. A calibration signal is captured under a known stiction condition. After receiving return signals that comprise, at least in part, frequencies that are responsive to the stimulation signal, various signal processing techniques are applied to the return signal. For example, various signal processing techniques are applied to the return signal to compare with respect to the stimulation signal. Wherever frequencies and/or amplitude of the return signal differs from the calibration signal, a corresponding interfacial indirect permittivity (e.g., at the interface between a tire and the driving surface) is calculated. Absolute and/or relative values of the interfacial indirect permittivity are correlated to a stictional value (e.g., using a calibration table). Changes in the stictional value over time are in turn correlated to road and/or tire conditions.

The static and/or dynamic values that make up the aforementioned calibration signal and/or calibration table can be based at least in part on analysis of the stimulation signal, and/or analysis of an environment proximal to the transducer. Moreover, the aforementioned calibration signal and/or calibration table can encompass permittivity calibration signals, permeability calibration signals, temperature calibration signals, vibration calibration signals, doping calibration signals, etc. In one implementation, calibration procedures may be performed under known and/or controlled environmental conditions, e.g., dry pavement and in clear weather, to generate baseline data at various forward-facing angular velocities (such that the test vehicle is only moving directly forward with no lateral skidding and/or sliding movement). This baseline data then serves as one or more calibration curves from which deformation values may be subsequently compared and/or calculated. In this way, clear performance changes may be observed relative to the initial unstretched (baseline) calibration curve, e.g., as shown in FIG. 16.

Whenever and wherever the return signal differs from the calibration signal further analysis of the return signal with respect to the stimulation signal can serve to identify which of the frequencies of the return signal are different than the calibration signal. The differences can be observed/measured as an attenuation of a frequency or frequencies with respect to the calibration signal. Additionally, or alternatively, the differences can be observed/measured as a frequency shift (as shown in FIG. 16 relative to data corresponding stretched at 0.5%, etc.) of peaks with respect to peaks of the calibration signal.

Figure 17:
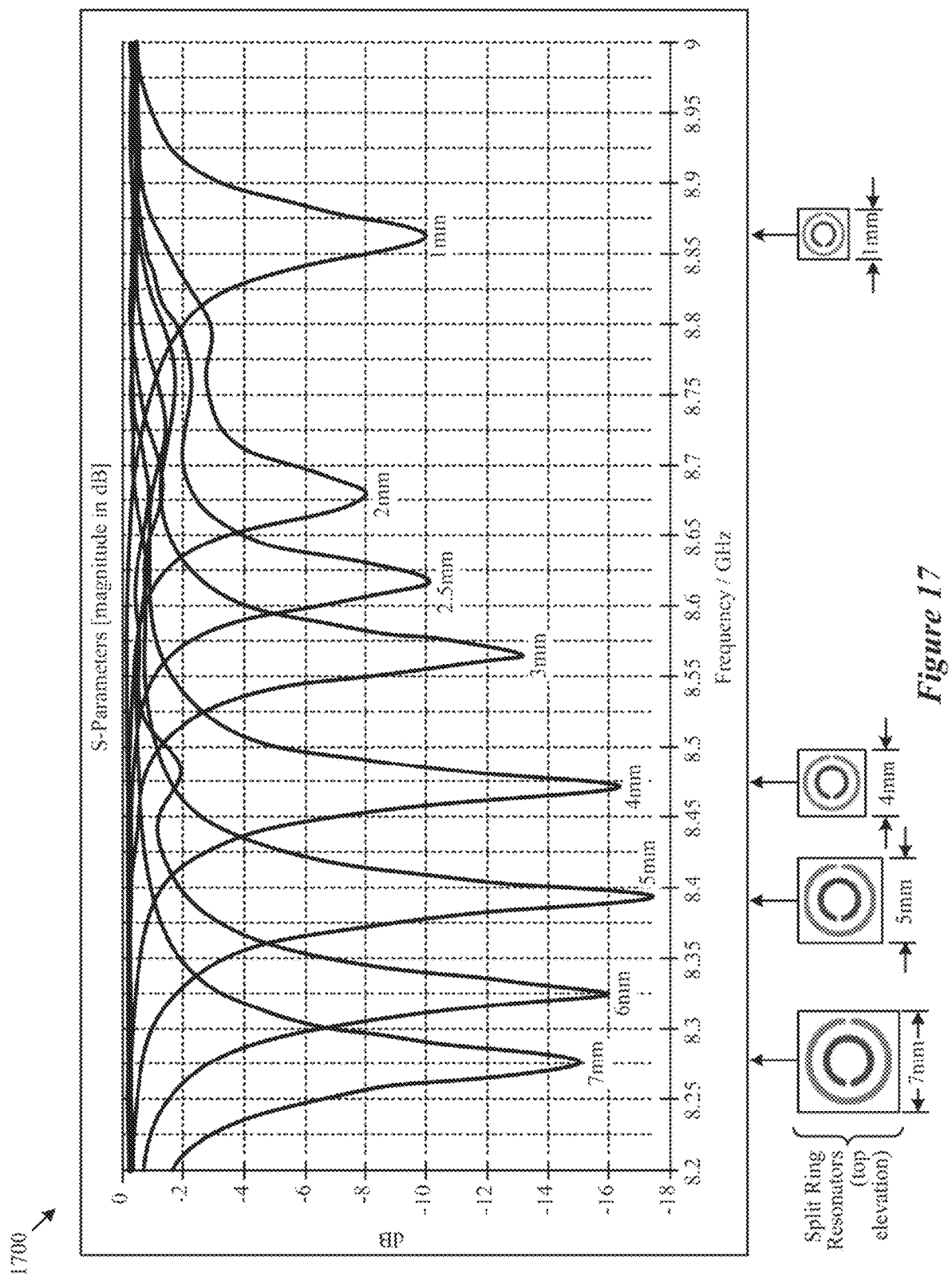
FIG. 17 is a graph of signal intensity relative to chirp signal frequency for split ring resonators that may resonate corresponding to an encoded serial number, in accordance with one embodiment.

FIG. 17 is a graph 1700 of signal intensity relative to chirp signal frequency for split ring resonators that may resonate corresponding to an encoded serial number, in accordance with one embodiment. As an option, the graph 1700 may be implemented in the context of any one or more of the embodiments set forth in any previous and/or subsequent figure(s) and/or description thereof. Of course, however, the graph 1700 may be implemented in the context of any desired environment. Further, the aforementioned definitions may equally apply to the description below.

In one embodiment, the graph 1700 shows use of split ring resonant structures that are configured to resonate in a manner that corresponds to an encoded serial number. Such a pattern of split ring resonant structures can be printed on tires or other elastomers. As shown, the encoded serial number "E1" is shown by the presence of split ring resonators of four different sizes. The graph 1700 shows EM stimulus in a range of about 8 GHz to about 9 GHz, whereas the response is shown as attenuation in a range from about −8 dB to about −18 dB. Stimulating the series of different sized split ring resonators with via electromagnetic signal communication across the range and measuring the S-parameters of the return across the range, leads to convenient and reliable identification of that particular printed pattern. It follows then that, if a unique pattern is printed onto each one of a run of tires, and if the pattern is associated with an encoded serial number, then a determination of the specific tire can be made based on the pattern's response to the EM interrogation.

More specifically, if a unique pattern is printed onto each one of a run of tires, and if the pattern is associated with an encoded serial number, then a determination of the specific tire can be made based on measured S-parameters (e.g., S-parameter ratios that correspond to attenuation) in response to EM interrogation over an EM stimulus in a range corresponding to the encoding scheme. In the example of FIG. 17, the attenuations fall in a range from about −8 dB to about −18 dB however, in other measurements the attenuations fall in a range of about −1 dB to about −9 dB. In other measurements the attenuations fall in a range of about −10 dB to about −19 dB. In other measurements the attenuations fall in a range of about −20 dB to about −35 dB. In empirical experimentation, the attenuations are substantially independent of the number of differently-configured resonators that are proximally collocated on a tire surface. More particularly, in some experimentation, the attenuations may be particularly pronounced when the resonators are proximally collocated on a tire surface that may be on the tread-side of a steel belt (e.g., in a steel belted radial tire).

The foregoing encoding and printing techniques can be used in tires and other elastomer-containing components. In some cases, printing the resonators is carried out at relatively high temperatures and/or with chemical agents (e.g., catalysts) such that chemical bonds are formed between the carbon atoms of the resonators and the elastomers. The chemical bonds that are formed between the carbon atoms of the resonators and the elastomers contribute to ensemble effect, and as such, calibration curves may be taken to account for the type and extent of the aforementioned chemical bonds.

The elastomer may contain any one or more types of rubber. Isoprene, for example, is a common rubber formulation. Isoprene has its own single C—C bonds and double bonds between the other molecular elements in the ligands.

Additional double carbon bonds formed by the high-temperature printing of the split ring resonators has the effect of increased conductivity, which effect can be exploited to form larger, lower frequency resonators. Additionally, or alternatively, agglomerations can be tuned into specific sizes, which would give rise to overtones that contribute to the ensemble effect, which in turn results in very high sensitivity given EM interrogation in a tuned range. In some cases, the response of the materials to EM interrogation is sufficiently discernable such that the age or other aspect of the elastomer's health can be determined (e.g., by comparison to one or more calibration curves).

More specifically, as elastomers age, the molecular spacing changes and coupling and/or percolation of energy decreases correspondingly, thus shifting the response frequencies as the conductive localities become more and more isolated with respect to adjacent localities. In some cases, attenuation and/or return signal strength will change at specific frequencies. Such changes can be determined over time, and the changes can be used to construct calibration curves.

The design of tires supports many possible locations for printing of the split ring resonators. As examples, split ring resonators can be located on any inner surface of a tire, including but not limited to the cap ply, and/or on or near the steel belts (e.g., on the tread side of a steel belt), and/or on or near a radial ply, and/or on the sidewall, and/or on the bead chafers, and/or on the beads, etc.

Use of the split ring resonator techniques are not limited to only tires. The techniques can be applied to any elastomer-containing components such belts and hoses. Moreover, the use of the split ring resonator techniques is not limited to only vehicles. That is, since consumables exist in organic powertrain and/or drive train components in a wide range of motive devices (e.g., in industrial mechanical systems), the split ring resonator techniques can be applied to such consumables as well. Some aspects of wear phenomena are a consequence of friction, heat, heat cycling and corrosion, any of which can result in and/or accelerate changes in the molecular structure of the materials. Changes in the molecular structure of the materials is detectable under EM interrogation. More specifically, by calculating a frequency shift, a particular sample's response (e.g., an aged sample's response) under a particular EM interrogation regime with respect to a calibration curve, the age or health of the material can be assessed based on the magnitude of the frequency shift.

FIGS. 18A through 18Y depict carbonaceous materials used as a formative material to produce any of the presently disclosed resonators (e.g., split ring resonators), in accordance with one embodiment. As an option, FIGS. 18A through 18Y may be implemented in the context of any one or more of the embodiments set forth in any previous and/or subsequent figure(s) and/or description thereof. Of course, however, FIGS. 18A through 18Y may be implemented in the context of any desired environment. Further, the aforementioned definitions may equally apply to the description below.

As shown, FIG. 18A through FIG. 18Y depict carbon-based materials, growths, agglomerates, aggregates, sheets, particles and/or the like, such as those self-nucleated in-flight in a reaction chamber or reactor from a carbon-containing gaseous species such as methane ($CH_4$), as disclosed by Stowell, et al., in U.S. patent application Ser. No. 16/785,020 entitled "3D Self-Assembled Multi-Modal Carbon-Based Particle" filed on Feb. 7, 2020, the contents of which are hereby incorporated by reference for all purposes.

The shown carbon-based nanoparticles and aggregates can be characterized by a high degree of "uniformity" (such as a high mass fraction of desired carbon allotropes), a high degree of "order" (such as a low concentration of defects), and/or a high degree of "purity" (such as a low concentration of elemental impurities), in contrast to the lower uniformity, less ordered, and lower purity particles achievable with conventional systems and methods.

The nanoparticles produced using the methods described herein can contain multi-walled spherical fullerenes (MWSFs) or connected MWSFs and have a high uniformity (such as, a ratio of graphene to MWSF from 20% to 80%), a high degree of order (such as, a Raman signature with an $I_D/I_G$ ratio from 0.95 to 1.05), and a high degree of purity (such as, the ratio of carbon to other elements (other than hydrogen) is greater than 99.9%). The nanoparticles produced using the methods described herein contain MWSFs or connected MWSFs, and the MWSFs do not contain a core composed of impurity elements other than carbon. The particles produced using the methods described herein can be aggregates containing the nanoparticles described above with large diameters (such as greater than 10 μm).

Conventional methods have been used to produce particles containing multi-walled spherical fullerenes with a high degree of order but can lead to end products with a variety of shortcomings. For example, high temperature synthesis techniques lead to particles with a mixture of many carbon allotropes and therefore low uniformity (such as less than 20% fullerenes relative to other carbon allotropes) and/or small particle sizes (such as less than 1 μm, or less than 100 nm in some cases). Methods using catalysts can lead to products that include the catalyst elements and therefore have relatively lower purity (referring to less than 95% carbon to other elements) as well. These undesirable properties also often lead to undesirable electrical properties of the resulting carbon particles (such as, electrical conductivity of less than 1,000 S/m).

The carbon nanoparticles and aggregates described herein can be characterized by Raman spectroscopy that is indicative of the high degree of order and uniformity of structure. The uniform ordered and/or pure carbon nanoparticles and aggregates described herein can be produced using relatively high speed, low cost improved thermal reactors and methods, as described below.

The term "graphene", as both commonly understood and as referred to herein, implies an allotrope of carbon in the form of a two-dimensional, atomic-scale, hexagonal lattice in which one atom forms each vertex. The carbon atoms in graphene are $sp^2$-bonded. Additionally, graphene has a Raman spectrum with two main peaks: a G-mode at approximately 1580 $cm^{-1}$ and a D-mode at approximately 1350 $cm^{-1}$ (when using a 532 nm excitation laser).

The term "fullerene", as both commonly understood and as referred to herein, implies a molecule of carbon in the form of a hollow sphere, ellipsoid, tube, or other shapes. Spherical fullerenes can also be referred to as Buckminsterfullerenes, or buckyballs. Cylindrical fullerenes can also be referred to as carbon nanotubes. Fullerenes are similar in structure to graphite, which is composed of stacked graphene sheets of linked hexagonal rings. Fullerenes may also contain pentagonal (or sometimes heptagonal) rings.

The term "multi-walled fullerene", as both commonly understood and as referred to herein, implies fullerenes with multiple concentric layers. For example, multi-walled nanotubes (MWNTs) contain multiple rolled layers (concentric tubes) of graphene. Multi-walled spherical fullerenes (MWSFs) contain multiple concentric spheres of fullerenes.

The term "nanoparticle", as both commonly understood and as referred to herein, implies a particle that measures from 1 nm to 989 nm. The nanoparticle can include one or more structural characteristics (such as, crystal structure, defect concentration, etc.), and one or more types of atoms. The nanoparticle can be any shape, including but not limited to spherical shapes, spheroidal shapes, dumbbell shapes, cylindrical shapes, elongated cylindrical type shapes, rectangular and/or prism shapes, disk shapes, wire shapes, irregular shapes, dense shapes (such as, with few voids), porous shapes (such as, with many voids), etc.

The term "aggregate", as both commonly understood and as referred to herein, implies a plurality of nanoparticles that are connected together by Van der Waals forces, by covalent bonds, by ionic bonds, by metallic bonds, or by other physical or chemical interactions. Aggregates can vary in size considerably, but in general are larger than about 500 nm.

A carbon nanoparticle can include two (2) or more connected multi-walled spherical fullerenes (MWSFs) and layers of graphene coating the connected MWSFs and can be formed to be independent of a core composed of impurity elements other than carbon. A carbon nanoparticle, as described herein, can include two (2) or more connected multi-walled spherical fullerenes (MWSFs) and layers of graphene coating the connected MWSFs. In such a configuration, where the MWSFs do not contain a void (referring to a space with no carbon atoms greater than approximately 0.5 nm or greater than approximately 1 nm) at the center. The connected MWSFs can be formed of concentric, well-ordered spheres of $sp^2$-hybridized carbon atoms (which is in favorable contrast to conventional spheres of haphazardly-ordered, non-uniform, amorphous carbon particles, which can otherwise fail to achieve any one or more of the unexpected and favorable properties disclosed herein).

The nanoparticles containing the connected MWSFs have an average diameter in a range from 5 to 500 nm, or from 5 to 250 nm, or from 5 to 100 nm, or from 5 to 50 nm, or from 10 to 500 nm, or from 10 to 250 nm, or from 10 to 100 nm, or from 10 to 50 nm, or from 40 to 500 nm, or from 40 to 250 nm, or from 40 to 100 nm, or from 50 to 500 nm, or from 50 to 250 nm, or from 50 to 100 nm.

The carbon nanoparticles described herein form aggregates, wherein many nanoparticles aggregate together to form a larger unit. A carbon aggregate can a plurality of carbon nanoparticles. A diameter across the carbon aggregate can be a range from 10 to 500 µm, or from 50 to 500 µm, or from 100 to 500 µm, or from 250 to 500 µm, or from 10 to 250 µm, or from 10 to 100 µm, or from 10 to 50 µm. The aggregate can be formed from a plurality of carbon nanoparticles, as defined above. Aggregates can contain connected MWSFs, such as those with a high uniformity metric (such as a ratio of graphene to MWSF from 20% to 80%), a high degree of order (such as a Raman signature with an $I_D/I_G$ ratio from 0.95 to 1.05), and a high degree of purity (such as greater than 99.9% carbon).

Aggregates of carbon nanoparticles, referring primarily to those with diameters in the ranges described above, especially particles greater than 10 µm, are generally easier to collect than particles or aggregates of particles that are smaller than 500 nm. The ease of collection reduces the cost of manufacturing equipment used in the production of the carbon nanoparticles and increases the yield of the carbon nanoparticles. Particles greater than 10 µm in size also pose fewer safety concerns compared to the risks of handling smaller nanoparticles, such as, potential health and safety risks due to inhalation of the smaller nanoparticles. The lower health and safety risks, thus, further reduce the manufacturing cost.

A carbon nanoparticle, in reference to that disclosed herein, can have a ratio of graphene to MWSFs from 10% to 90%, or from 10% to 80%, or from 10% to 60%, or from 10% to 40%, or from 10% to 20%, or from 20% to 40%, or from 20% to 90%, or from 40% to 90%, or from 60% to 90%, or from 80% to 90%. A carbon aggregate has a ratio of graphene to MWSFs is from 10% to 90%, or from 10% to 80%, or from 10% to 60%, or from 10% to 40%, or from 10% to 20%, or from 20% to 40%, or from 20% to 90%, or from 40% to 90%, or from 60% to 90%, or from 80% to 90%. A carbon nanoparticle has a ratio of graphene to connected MWSFs from 10% to 90%, or from 10% to 80%, or from 10% to 60%, or from 10% to 40%, or from 10% to 20%, or from 20% to 40%, or from 20% to 90%, or from 40% to 90%, or from 60% to 90%, or from 80% to 90%. A carbon aggregate has a ratio of graphene to connected MWSFs is from 10% to 90%, or from 10% to 80%, or from 10% to 60%, or from 10% to 40%, or from 10% to 20%, or from 20% to 40%, or from 20% to 90%, or from 40% to 90%, or from 60% to 90%, or from 80% to 90%.

Raman spectroscopy can be used to characterize carbon allotropes to distinguish their molecular structures. For example, graphene can be characterized using Raman spectroscopy to determine information such as order/disorder, edge and grain boundaries, thickness, number of layers, doping, strain, and thermal conductivity. MWSFs have also been characterized using Raman spectroscopy to determine the degree of order of the MWSFs.

Raman spectroscopy is used to characterize the structure of MWSFs or connected MWSFs used in reference to that incorporated within the various tire-related plies of tires as discussed herein. The main peaks in the Raman spectra are the G-mode and the D-mode. The G-mode is attributed to the vibration of carbon atoms in $sp^2$-hybridized carbon networks, and the D-mode is related to the breathing of hexagonal carbon rings with defects. In some circumstances, defects may be present, yet may not be detectable in the Raman spectra. For example, if the presented crystalline structure is orthogonal with respect to the basal plane, the D-peak will show an increase. Alternatively, if presented with a perfectly planar surface that is parallel with respect to the basal plane, the D-peak will be zero.

When using 532 nm incident light, the Raman G-mode is typically at 1582 cm$^{-1}$ for planar graphite, however, can be downshifted for MWSFs or connected MWSFs (such as, down to 1565 cm$^{-1}$ or down to 1580 cm$^{-1}$). The D-mode is observed at approximately 1350 cm$^{-1}$ in the Raman spectra of MWSFs or connected MWSFs. The ratio of the intensities of the D-mode peak to G-mode peak (such as, the $I_D/I_G$) is related to the degree of order of the MWSFs, where a lower $I_D/I_G$ indicates a higher degree of order. An $I_D/I_G$ near or below 1 indicates a relatively high degree of order, and an $I_D/I_G$ greater than 1.1 indicates a lower degree of order.

A carbon nanoparticle or a carbon aggregate containing MWSFs or connected MWSFs, as described herein, can have and/or demonstrate a Raman spectrum with a first Raman peak at about 1350 cm$^{-1}$ and a second Raman peak at about 1580 cm$^{-1}$ when using 532 nm incident light. The ratio of an intensity of the first Raman peak to an intensity of the second Raman peak (such as, the $I_D/I_G$) for the nanoparticles or the aggregates described herein can be in a range from 0.95 to 1.05, or from 0.9 to 1.1, or from 0.8 to 1.2, or from 0.9 to 1.2, or from 0.8 to 1.1, or from 0.5 to 1.5, or less than 1.5, or less than 1.2, or less than 1.1, or less than 1, or less than 0.95, or less than 0.9, or less than 0.8.

A carbon aggregate containing MWSFs or connected MWSFs, as defined above, has a high purity. The carbon aggregate containing MWSFs or connected MWSFs has a ratio of carbon to metals of greater than 99.99%, or greater than 99.95%, or greater than 99.9%, or greater than 99.8%, or greater than 99.5%, or greater than 99%. The carbon aggregate has a ratio of carbon to other elements of greater than 99.99%, or greater than 99.95%, or greater than 99.9%, or greater than 99.5%, or greater than 99%, or greater than 90%, or greater than 80%, or greater than 70%, or greater than 60%. The carbon aggregate has a ratio of carbon to other elements (except for hydrogen) of greater than 99.99%, or greater than 99.95%, or greater than 99.9%, or greater than 99.8%, or greater than 99.5%, or greater than 99%, or greater than 90%, or greater than 80%, or greater than 70%, or greater than 60%.

A carbon aggregate containing MWSFs or connected MWSFs, as defined above, has a high specific surface area. The carbon aggregate has a Brunauer, Emmett and Teller (BET) specific surface area from 10 to 200 m$^2$/g, or from 10 to 100 m$^2$/g, or from 10 to 50 m$^2$/g, or from 50 to 200 m$^2$/g, or from 50 to 100 m$^2$/g, or from 10 to 1000 m$^2$/g.

A carbon aggregate containing MWSFs or connected MWSFs, as defined above, has a high electrical conductivity. A carbon aggregate containing MWSFs or connected MWSFs, as defined above, is compressed into a pellet and the pellet has an electrical conductivity greater than 500 S/m, or greater than 1,000 S/m, or greater than 2,000 S/m, or greater than 3,000 S/m, or greater than 4,000 S/m, or greater than 5,000 S/m, or greater than 10,000 S/m, or greater than 20,000 S/m, or greater than 30,000 S/m, or greater than 40,000 S/m, or greater than 50,000 S/m, or greater than 60,000 S/m, or greater than 70,000 S/m, or from 500 S/m to 100,000 S/m, or from 500 S/m to 1,000 S/m, or from 500 S/m to 10,000 S/m, or from 500 S/m to 20,000 S/m, or from 500 S/m to 100,000 S/m, or from 1000 S/m to 10,000 S/m, or from 1,000 S/m to 20,000 S/m, or from 10,000 to 100,000 S/m, or from 10,000 S/m to 80,000 S/m, or from 500 S/m to 10,000 S/m. In some cases, the density of the pellet is approximately 1 g/cm$^3$, or approximately 1.2 g/cm$^3$, or approximately 1.5 g/cm$^3$, or approximately 2 g/cm$^3$, or approximately 2.2 g/cm$^3$, or approximately 2.5 g/cm$^3$, or approximately 3 g/cm$^3$. Additionally, tests have been performed in which compressed pellets of the carbon aggregate materials have been formed with compressions of 2,000 psi and 12,000 psi and with annealing temperatures of 800° C. and 1,000° C. The higher compression and/or the higher annealing temperatures generally result in pellets with a higher degree of electrical conductivity, including in the range of 12,410.0 S/m to 13,173.3 S/m.

The carbon nanoparticles and aggregates described herein can be produced using thermal reactors and methods. Further details pertaining to thermal reactors and/or methods of use can be found in U.S. Pat. No. 9,862,602, issued Jan. 9, 2018, entitled "CRACKING OF A PROCESS GAS", which is hereby incorporated by reference in its entirety for all purposes. Additionally, carbon-containing and/or hydrocarbon precursors (referring to at least methane, ethane, propane, butane, and natural gas) can be used with the thermal reactors to produce the carbon nanoparticles and the carbon aggregates described herein.

The carbon nanoparticles and aggregates described herein are produced using the thermal reactors with gas flow rates from 1 slm to 10 slm, or from 0.1 slm to 20 slm, or from 1 slm to 5 slm, or from 5 slm to 10 slm, or greater than 1 slm, or greater than 5 slm. The carbon nanoparticles and aggregates described herein are produced using the thermal reactors with gas resonance times from 0.1 seconds(s) to 30 s, or from 0.1 s to 10 s, or from 1 s to 10 s, or from 1 s to 5 s, from 5 s to 10 s, or greater than 0.1 seconds, or greater than 1 s, or greater than 5 s, or less than 30 s.

The carbon nanoparticles and aggregates described herein can be produced using the thermal reactors with production rates from 10 g/hr to 200 g/hr, or from 30 g/hr to 200 g/hr, or from 30 g/hr to 100 g/hr, or from 30 g/hr to 60 g/hr, or from 10 g/hr to 100 g/hr, or greater than 10 g/hr, or greater than 30 g/hr, or greater than 100 g/hr.

Thermal reactors (or other cracking apparatuses) and thermal reactor methods (or other cracking methods) can be used for refining, pyrolyzing, dissociating or cracking feedstock process gases into its constituents to produce the carbon nanoparticles and the carbon aggregates described herein, as well as other solid and/or gaseous products (such as, hydrogen gas and/or lower order hydrocarbon gases). The feedstock process gases generally include, for example, hydrogen gas ($H^2$), carbon dioxide ($CO^2$), $C^1$ to $C^{10}$ hydrocarbons, aromatic hydrocarbons, and/or other hydrocarbon gases such as natural gas, methane, ethane, propane, butane, isobutane, saturated/unsaturated hydrocarbon gases, ethene, propene, etc., and mixtures thereof. The carbon nanoparticles and the carbon aggregates can include, for example, multi-walled spherical fullerenes (MWSFs), connected MWSFs, carbon nanospheres, graphene, graphite, highly ordered pyrolytic graphite, single-walled nanotubes, multi-walled nanotubes, other solid carbon products, and/or the carbon nanoparticles and the carbon aggregates described herein.

Methods for producing the carbon nanoparticles and the carbon aggregates described herein can include thermal cracking methods that use, for example, an elongated longitudinal heating element optionally enclosed within an elongated casing, housing, or body of a thermal cracking apparatus. The body can include, for example, one or more tubes or other appropriate enclosures made of stainless steel, titanium, graphite, quartz, or the like. The body of the thermal cracking apparatus is generally cylindrical in shape with a central elongate longitudinal axis arranged vertically and a feedstock process gas inlet at or near a top of the body. The feedstock process gas can flow longitudinally down through the body or a portion thereof. In the vertical configuration, both gas flow and gravity assist in the removal of the solid products from the body of the thermal cracking apparatus.

The heating element can include any one or more of a heating lamp, one or more resistive wires or filaments (or twisted wires), metal filaments, metallic strips, or rods, and/or other appropriate thermal radical generators or elements that can be heated to a specific temperature (such a, a molecular cracking temperature) sufficient to thermally crack molecules of the feedstock process gas. The heating element can be disposed, located, or arranged to extend centrally within the body of the thermal cracking apparatus along the central longitudinal axis thereof. In configurations having only one heating element can include it placed at or concentric with the central longitudinal axis; alternatively, for configurations having multiple heating elements can include them spaced or offset generally symmetrically or concentrically at locations near and around and parallel to the central longitudinal axis.

Thermal cracking to produce the carbon nanoparticles and aggregates described herein can be achieved by flowing the feedstock process gas over, or in contact with, or within the vicinity of, the heating element within a longitudinal elongated reaction zone generated by heat from the heating element and defined by and contained inside the body of the thermal cracking apparatus to heat the feedstock process gas to or at a specific molecular cracking temperature.

The reaction zone can be considered to be the region surrounding the heating element and close enough to the heating element for the feedstock process gas to receive sufficient heat to thermally crack the molecules thereof. The reaction zone is thus generally axially aligned or concentric with the central longitudinal axis of the body. The thermal cracking is performed under a specific pressure. The feedstock process gas is circulated around or across the outside surface of a container of the reaction zone or a heating chamber to cool the container or chamber and preheat the feedstock process gas before flowing the feedstock process gas into the reaction zone.

The carbon nanoparticles and aggregates described herein and/or hydrogen gas are produced without the use of catalysts. Accordingly, the process can be entirely catalyst free.

Disclosed methods and systems can advantageously be rapidly scaled up or scaled down for different production levels as may be desired, such as being scalable to provide a standalone hydrogen and/or carbon nanoparticle producing station, a hydrocarbon source, or a fuel cell station, to provide higher capacity systems, such as, for a refinery and/or the like.

A thermal cracking apparatus for cracking a feedstock process gas to produce the carbon nanoparticles and aggregates described herein include a body, a feedstock process gas inlet, and an elongated heating element. The body has an inner volume with a longitudinal axis. The inner volume has a reaction zone concentric with the longitudinal axis. A feedstock process gas can be flowed into the inner volume through the feedstock process gas inlet during thermal cracking operations. The elongated heating element can be disposed within the inner volume along the longitudinal axis and is surrounded by the reaction zone. During the thermal cracking operations, the elongated heating element is heated by electrical power to a molecular cracking temperature to generate the reaction zone, the feedstock process gas is heated by heat from the elongated heating element, and the heat thermally cracks molecules of the feedstock process gas that are within the reaction zone into constituents of the molecules.

A method for cracking a feedstock process gas to produce the carbon nanoparticles and aggregates described herein can include at least any one or more of the following: (1) providing a thermal cracking apparatus having an inner volume that has a longitudinal axis and an elongated heating element disposed within the inner volume along the longitudinal axis; (2) heating the elongated heating element by electrical power to a molecular cracking temperature to generate a longitudinal elongated reaction zone within the inner volume; (3) flowing a feedstock process gas into the inner volume and through the longitudinal elongated reaction zone (such as, wherein the feedstock process gas is heated by heat from the elongated heating element); and (4) thermally cracking molecules of the feedstock process gas within the longitudinal elongated reaction zone into constituents thereof (such as, hydrogen gas and one or more solid products) as the feedstock process gas flows through the longitudinal elongated reaction zone.

The feedstock process gas used to produce the carbon nanoparticles and aggregates described herein can include a hydrocarbon gas. The results of cracking can, in turn, further include hydrogen in gaseous form (such as, $H^2$) and various forms of the carbon nanoparticles and aggregates described herein. The carbon nanoparticles and aggregates include two or more MWSFs and layers of graphene coating the MWSFs, and/or connected MWSFs and layers of graphene coating the connected MWSFs. The feedstock process gas is preheated (such as, to 100° C. to 500° C.) by flowing the feedstock process gas through a gas preheating region between a heating chamber and a shell of the thermal cracking apparatus before flowing the feedstock process gas into the inner volume. A gas having nanoparticles therein is flowed into the inner volume and through the longitudinal elongated reaction zone to mix with the feedstock process gas, to form a coating of a solid product (such as, layers of graphene) around the nanoparticles.

The carbon nanoparticles and aggregates containing multi-walled spherical fullerenes (MWSFs) or connected MWSFs described herein can be produced and collected without requiring the completion of any post-processing treatments or operations. Alternatively, some post-processing can be performed on one or more of the presently disclosed MWSFs. Some examples of post-processing involved in making and using resonant materials include mechanical processing such as ball milling, grinding, attrition milling, micro fluidizing, and other techniques to reduce the particle size without damaging the MWSFs. Some further examples of post-processing include exfoliation processes (referring to the complete separation of layers of carbon-containing material, such as the creation or extraction of layers of graphene from graphite, etc.) including sheer mixing, chemical etching, oxidizing (such as the Hummer method), thermal annealing, doping by adding elements during annealing (such as sulfur and/or nitrogen), steaming, filtering, and lyophilization, among others. Some examples of post-processing include sintering processes such as spark plasma sintering (SPS), direct current sintering, microwave sintering, and ultraviolet (UV) sintering, which can be conducted at high pressure and temperature in an inert gas. Multiple post-processing methods can be used together or in a series. The post-processing produces functionalized carbon nanoparticles or aggregates containing multi-walled spherical fullerenes (MWSFs) or connected MWSFs.

Materials can be mixed together in different combinations, quantities and/or ratios. Different carbon nanoparticles and aggregates containing MWSFs or connected MWSFs described herein can be mixed together prior to one or more post-processing operations, if any at all. For example, different carbon nanoparticles and aggregates containing MWSFs or connected MWSFs with different properties (such as, different sizes, different compositions, different purities, from different processing runs, etc.) can be mixed together. The carbon nanoparticles and aggregates containing MWSFs or connected MWSFs described herein can be mixed with graphene to change the ratio of the connected MWSFs to graphene in the mixture. Different carbon nanoparticles and aggregates containing MWSFs or connected MWSFs described herein can be mixed together after post-processing. Different carbon nanoparticles and aggregates containing MWSFs or connected MWSFs with different properties and/or different post-processing methods (such as, different sizes, different compositions, different functionality, different surface properties, different surface areas) can be mixed together in any quantity, ratio and/or combination.

The carbon nanoparticles and aggregates described herein are produced and collected, and subsequently processed by mechanical grinding, milling, and/or exfoliating. The processing (such as, by mechanical grinding, milling, exfoliating, etc.) can reduce the average size of the particles. The processing (such as, by mechanical grinding, milling, exfoliating, etc.) increases the average surface area of the particles. The processing by mechanical grinding, milling and/or exfoliation shears off some fraction of the carbon layers, producing sheets of graphite mixed with the carbon nanoparticles.

The mechanical grinding or milling is performed using a ball mill, a planetary mill, a rod mill, a shear mixer, a high-shear granulator, an autogenous mill, or other types of machining used to break solid materials into smaller pieces by grinding, crushing, or cutting. The mechanical grinding, milling and/or exfoliating is performed wet or dry. The mechanical grinding is performed by grinding for some period of time, then idling for some period of time, and repeating the grinding and idling for a number of cycles. The grinding period is from 1 minute (min) to 20 mins, or from 1 min to 10 mins, or from 3 mins to 8 mins, or approximately 3 mins, or approximately 8 mins. The idling period is from 1 min to 10 mins, or approximately 5 mins, or approximately 6 mins. The number of grinding and idling cycles is from 1 min to 100 mins, or from 5 mins to 100 mins, or from 10 mins to 100 mins, or from 5 mins to 10 mins, or from 5 mins to 20 mins. The total amount of time of grinding and idling is from 10 mins to 1,200 mins, or from 10 mins to 600 mins, or from 10 mins to 240 mins, or from 10 mins to 120 mins, or from 100 mins to 90 mins, or from 10 mins to 60 mins, or approximately 90 mins, or approximately mins minutes.

The grinding steps in the cycle are performed by rotating a mill in one direction for a first cycle (such as, clockwise), and then rotating a mill in the opposite direction (such as, counterclockwise) for the next cycle. The mechanical grinding or milling is performed using a ball mill, and the grinding steps are performed using a rotation speed from 100 to 1000 rpm, or from 100 to 500 rpm, or approximately 400 rpm. The mechanical grinding or milling is performed using a ball mill that uses a milling media with a diameter from 0.1 mm to 20 mm, or from 0.1 mm to 10 mm, or from 1 mm to 10 mm, or approximately 0.1 mm, or approximately 1 mm, or approximately 10 mm. The mechanical grinding or milling is performed using a ball mill that uses a milling media composed of metal such as steel, an oxide such as zirconium oxide (zirconia), yttria stabilized zirconium oxide, silica, alumina, magnesium oxide, or other hard materials such as silicon carbide or tungsten carbide.

The carbon nanoparticles and aggregates described herein are produced and collected, and subsequently processed using elevated temperatures such as thermal annealing or sintering. The processing using elevated temperatures is done in an inert environment such as nitrogen or argon. The processing using elevated temperatures is done at atmospheric pressure, or under vacuum, or at low pressure. The processing using elevated temperatures is done at a temperature from 500° C. to 2,500° C., or from 500° C. to 1,500° C., or from 800° C. to 1,500° C., or from 800° C. to 1,200° C., or from 800° C. to 1,000° C., or from 2,000° C. to 2,400° C., or approximately 8.00° C., or approximately 1,000° C., or approximately 1,500° C., or approximately 2,000° C., or approximately 2,400° C.

The carbon nanoparticles and aggregates described herein are produced and collected, and subsequently, in post processing operations, additional elements or compounds are added to the carbon nanoparticles, thereby incorporating the unique properties of the carbon nanoparticles and aggregates into other mixtures of materials.

Either before or after post-processing, the carbon nanoparticles and aggregates described herein are added to solids, liquids or slurries of other elements or compounds to form additional mixtures of materials incorporating the unique properties of the carbon nanoparticles and aggregates. The carbon nanoparticles and aggregates described herein are mixed with other solid particles, polymers, or other materials.

Either before or after post-processing, the carbon nanoparticles and aggregates described herein are used in various applications beyond applications pertaining to making and using resonant materials. Such applications including but not limited to transportation applications (such as, automobile and truck tires, couplings, mounts, elastomeric "o"-rings, hoses, sealants, grommets, etc.) and industrial applications (such as, rubber additives, functionalized additives for polymeric materials, additives for epoxies, etc.).

FIGS. 18A and 18B show transmission electron microscope (TEM) images of as-synthesized carbon nanoparticles. The carbon nanoparticles of FIG. 18A (at a first magnification) and FIG. 18B (at a second magnification) contain connected multi-walled spherical fullerenes (MWSFs) with graphene layers that coat the connected MWSFs. The ratio of MWSF to graphene allotropes in this example is approximately 80% due to the relatively short resonance times. The MWSFs in FIG. 18B are approximately 5 nm to 10 nm in diameter, and the diameter can be from 5 nm to 500 nm using the conditions described above. The average diameter across the MWSFs is in a range from 5 nm to 500 nm, or from 5 nm to 250 nm, or from 5 nm to 100 nm, or from 5 nm to 50 nm, or from 10 nm to 500 nm, or from 10 nm to 250 nm, or from 10 nm to 100 nm, or from 10 nm to 50 nm, or from 40 nm to 500 nm, or from 40 nm to 250 nm, or from 40 nm to 100 nm, or from 50 nm to 500 nm, or from 50 nm to 250 nm, or from 50 nm to 100 nm. No catalyst was used in this process, and therefore, there is no central seed containing contaminants. The aggregate particles produced in this example had a particle size of approximately 10 μm to 100 μm, or approximately 10 μm to 500 μm.

FIG. 18C shows the Raman spectrum of the as-synthesized aggregates in this example taken with 532 nm incident light. The $I_D/I_G$ for the aggregates produced in this example is from approximately 0.99 to 1.03, indicating that the aggregates were composed of carbon allotropes with a high degree of order.

FIG. 18D and FIG. 18E show example TEM images of the carbon nanoparticles after size reduction by grinding in a ball mill. The ball milling was performed in cycles with a 3-minute (min) counter-clockwise grinding operation, followed by a 6 min idle operation, followed by a 3-min clockwise grinding operation, followed by a 6-min idle operation. The grinding operations were performed using a rotation speed of 400 rpm. The milling media was zirconia and ranged in size from 0.1 mm to 10 mm. The total size reduction processing time was from 60 mins to 120 mins. After size reduction, the aggregate particles produced in this example had a particle size of approximately 1 μm to 5 μm. The carbon nanoparticles after size reduction are connected MWSFs with layers of graphene coating the connected MWSFs.

FIG. 18F shows a Raman spectrum from these aggregates after size reduction taken with a 532 nm incident light. The $I_D/I_G$ for the aggregate particles in this example after size reduction is approximately 1.04. Additionally, the particles after size reduction had a Brunauer, Emmett and Teller (BET) specific surface area of approximately 40 $m^2/g$ to 50 $m^2/g$.

The purity of the aggregates produced in this sample were measured using mass spectrometry and x-ray fluorescence (XRF) spectroscopy. The ratio of carbon to other elements, except for hydrogen, measured in 16 different batches was from 99.86% to 99.98%, with an average of 99.94% carbon.

In this example, carbon nanoparticles were generated using a thermal hot-wire processing system. The precursor material was methane, which was flowed from 1 slm to 5 slm. With these flow rates and the tool geometry, the resonance time of the gas in the reaction chamber was from approximately 20 second to 30 seconds, and the carbon particle production rate was from approximately 20 g/hr.

Further details pertaining to such a processing system can be found in the previously mentioned U.S. Pat. No. 9,862,602, titled "CRACKING OF A PROCESS GAS," which is hereby incorporated by reference for all purposes.

Example 1

FIG. 18G, FIG. 18H, and FIG. 18I show TEM images of as-synthesized carbon nanoparticles of this example. The carbon nanoparticles contain connected multi-walled spherical fullerenes (MWSFs) with layers of graphene coating the connected MWSFs. The ratio of multi-walled fullerenes to graphene allotropes in this example is approximately 30% due to the relatively long resonance times allowing thicker, or more, layers of graphene to coat the MWSFs. No catalyst was used in this process, and therefore, there is no central seed containing contaminants. The as-synthesized aggregate particles produced in this example had particle sizes of approximately 10 µm to 500 µm. FIG. 18J shows a Raman spectrum from the aggregates of this example. The Raman signature of the as-synthesized particles in this example is indicative of the thicker graphene layers which coat the MWSFs in the as-synthesized material. Additionally, the as-synthesized particles had a Brunauer, Emmett and Teller (BET) specific surface area of approximately 90 m$^2$/g to 100 m$^2$/g.

Example 2

FIG. 18K and FIG. 18L show TEM images of the carbon nanoparticles of this example. Specifically, the images depict the carbon nanoparticles after performance of size reduction by grinding in a ball mill. The size reduction process conditions were the same as those described as pertains to the foregoing FIGS. 18G-18J. After size reduction, the aggregate particles produced in this example had a particle size of approximately 1 µm to 5 µm. The TEM images show that the connected MWSFs that were buried in the graphene coating can be observed after size reduction. FIG. 18M shows a Raman spectrum from the aggregates of this example after size reduction taken with 532 nm incident light. The $I_D/I_G$ for the aggregate particles in this example after size reduction is approximately 1, indicating that the connected MWSFs that were buried in the graphene coating as-synthesized had become detectable in Raman after size reduction, and were well ordered. The particles after size reduction had a Brunauer, Emmett and Teller (BET) specific surface area of approximately 90 m$^2$/g to 100 m$^2$/g.

Example 3

FIG. 18N is a scanning electron microscope (SEM) image of carbon aggregates showing the graphite and graphene allotropes at a first magnification. FIG. 18O is a SEM image of carbon aggregates showing the graphite and graphene allotropes at a second magnification. The layered graphene is clearly shown within the distortion (wrinkles) of the carbon. The 3D structure of the carbon allotropes is also visible.

The particle size distribution of the carbon particles of FIG. 18N and FIG. 18O is shown in FIG. 18P. The mass basis cumulative particle size distribution 1806 corresponds to the left y-axis in the graph ($Q^3$(x) [%]). The histogram of the mass particle size distribution 1808 corresponds to the right axis in the graph (d$Q^3$ (x)[%]). The median particle size is approximately 33 µm. The 10th percentile particle size is approximately 9 µm, and the 90th percentile particle size is approximately 103 µm. The mass density of the particles is approximately 10 g/L.

Example 4

The particle size distribution of the carbon particles captured from a multiple-stage reactor is shown in FIG. 18Q. The mass basis cumulative particle size distribution 1814 corresponds to the left y-axis in the graph ($Q^3$(x) [%]). The histogram of the mass particle size distribution 1816 corresponds to the right axis in the graph (d$Q^3$(x) [%]). The median particle size captured is approximately 11 µm. The 10th percentile particle size is approximately 3.5 µm, and the 90th percentile particle size is approximately 21 µm. The graph in FIG. 18Q also shows the number basis cumulative particle size distribution 1818 corresponding to the left y-axis in the graph ($Q^0$ (x) [%]). The median particle size by number basis is from approximately 0.1 µm to approximately 0.2 µm.

Returning to the discussion of FIG. 18P, the graph also shows a second set of example results. Specifically, in this example, the particles were size-reduced by mechanical grinding, and then the size-reduced particles were processed using a cyclone separator. The mass basis cumulative particle size distribution 1810 of the size-reduced carbon particles captured in this example corresponds to the left y-axis in the graph ($Q^3$(x) [%]). The histogram of the mass basis particle size distribution 1812 corresponds to the right axis in the graph (d$Q^3$(x) [%]). The median particle size of the size-reduced carbon particles captured in this example is approximately 6 µm. The 10th percentile particle size is from 1 µm to 2 µm, and the 90th percentile particle size is from 10 µm to 20 µm.

Further details pertaining to making and using cyclone separators can be found in U.S. patent application Ser. No. 15/725,928, filed Oct. 5, 2017, titled "MICROWAVE REACTOR SYSTEM WITH GAS-SOLIDS SEPARATION", which is hereby incorporated by reference in its entirety for all purposes.

In some cases, carbon particles and aggregates containing graphite, graphene and amorphous carbon can be generated using a microwave plasma reactor system using a precursor material that contains methane, or contains isopropyl alcohol (IPA), or contains ethanol, or contains a condensed hydrocarbon (such as, hexane). In some other examples, the carbon-containing precursors are optionally mixed with a supply gas (such as, argon). The particles produced in this example contained graphite, graphene, amorphous carbon, and no seed particles. The particles in this example had a ratio of carbon to other elements (other than hydrogen) of approximately 99.5% or greater.

In one particular example, a hydrocarbon was the input material for the microwave plasma reactor, and the separated outputs of the reactor comprised hydrogen gas and carbon particles containing graphite, graphene, and amorphous carbon. The carbon particles were separated from the hydrogen gas in a multi-stage gas-solid separation system. The solids loading of the separated outputs from the reactor was from 0.001 g/L to 2.5 g/L.

Example 5

FIG. 18R, FIG. 18S, and FIG. 18T are TEM images of as-synthesized carbon nanoparticles. The images show examples of graphite, graphene, and amorphous carbon allotropes. The layers of graphene and other carbon materials can be clearly seen in the images.

The particle size distribution of the carbon particles captured is shown in FIG. 18U. The mass basis cumulative particle size distribution 1820 corresponds to the left y-axis in the graph ($Q^3(x)$ [%]). The histogram of the mass particle size distribution 1822 corresponds to the right axis in the graph ($dQ^3(x)$ [%]). The median particle size captured in the cyclone separator in this example was approximately 14 µm. The 10th percentile particle size was approximately 5 µm, and the 90th percentile particle size was approximately 28 µm. The graph in FIG. 18U also shows the number basis cumulative particle size distribution 1824 corresponding to the left y-axis in the graph ($Q^0(x)$ [%]). The median particle size by number basis in this example was from approximately 0.1 µm to approximately 0.2 µm.

FIG. 18V, FIG. 18W, and FIGS. 18X, and 18Y are images that show three-dimensional carbon-containing structures that are grown onto other three-dimensional structures. FIG. 18V is a 100× magnification of three-dimensional carbon structures grown onto carbon fibers, whereas FIG. 18W is a 200× magnification of three-dimensional carbon structures grown onto carbon fibers. FIG. 18X is a 1601× magnification of three-dimensional carbon structures grown onto carbon fibers. The three-dimensional carbon growth over the fiber surface is shown. FIG. 18Y is a 10000× magnification of three-dimensional carbon structures grown onto carbon fibers. The image depicts growth onto the basal plane as well as onto edge planes.

More specifically, FIGS. 18V-18Y show example SEM images of 3D carbon materials grown onto fibers using plasma energy from a microwave plasma reactor as well as thermal energy from a thermal reactor. FIG. 18V shows an SEM image of intersecting fiber 1831 and fiber 1832 with 3D carbon material 1830 grown on the surface of the fibers. FIG. 18W is a higher magnification image (the scale bar is 300 µm compared to 500 µm for FIG. 18V) showing the 3D carbon material 1830 on the fiber 1832. FIG. 18X is a further magnified view (scale bar is 40 µm) showing the 3D carbon material 1830 on fiber surface 1835, where the 3D nature of the 3D carbon material 1830 can be clearly seen. FIG. 18Y shows a close-up view (scale bar is 500 nm) of the carbon alone, showing interconnection between basal planes of the fiber 1832 and edge planes 1834 of numerous sub-particles of the 3D carbon material grown on the fiber. FIGS. 18V-18Y demonstrate the ability to grow 3D carbon on a 3D fiber structure, such as 3D carbon growth grown on a 3D carbon fiber.

3D carbon growth on fibers can be achieved by introducing a plurality of fibers into the microwave plasma reactor and using plasma in the microwave reactor to etch the fibers. The etching creates nucleation sites such that when carbon particles and sub-particles are created by hydrocarbon disassociation in the reactor, growth of 3D carbon structures is initiated at these nucleation sites. The direct growth of the 3D carbon structures on the fibers, which themselves are three-dimensional in nature, provides a highly integrated, 3D structure with pores into which resin can permeate. This 3D reinforcement matrix (including the 3D carbon structures integrated with high aspect ratio reinforcing fibers) for a resin composite results in enhanced material properties, such as tensile strength and shear, compared to composites with conventional fibers that have smooth surfaces, and which smooth surfaces typically delaminate from the resin matrix.

Carbon materials, such as any one or more of the 3D carbon materials described herein, can have one or more exposed surfaces prepared for functionalization, such as that to promote adhesion and/or add elements such as oxygen, nitrogen, carbon, silicon, or hardening agents. Functionalization refers to the addition of functional groups to a compound by chemical synthesis. In materials science, functionalization can be employed to achieve desired surface properties; for instance, functional groups can also be used to covalently link functional molecules to the surfaces of chemical devices. The carbon materials can be functionalized in-situ—that is, on site within the same reactor in which the carbon materials are produced. The carbon materials can be functionalized in post-processing. For example, the surfaces of fullerenes or graphene can be functionalized with oxygen- or nitrogen-containing species which form bonds with polymers of the resin matrix, thus improving adhesion and providing strong binding to enhance the strength of composites.

Functionalizing surface treatments can be performed on any one or more of the disclosed carbon-based materials (such as, CNTs, CNO, graphene, 3D carbon materials such as 3D graphene) utilizing plasma reactors (such as, microwave plasma reactors) described herein. Such treatments can include in-situ surface treatment during creation of carbon materials that can be combined with a binder or polymer in a composite material, or surface treatment after creation of the carbon materials while the carbon materials are still within the reactor.

Some of the foregoing embodiments include resonators that include a plurality of three-dimensional (3D) aggregates formed of carbon-containing material that is embedded within a ply or plies of tire. However, some embodiments include resonators that are printed or otherwise disposed on an inner surface of a tire (e.g., on an inner liner of the tire).

FIG. 19A1 provides a depiction 19A100 of a split ring resonator, or plurality of split ring resonators, being placed in concrete before the concrete is to be poured into a given structural form, in accordance with one embodiment. As an option, the depiction 19A100 may be implemented in the context of any one or more of the embodiments set forth in any previous and/or subsequent figure(s) and/or description thereof. Of course, however, the depiction 19A100 may be implemented in the context of any desired environment. Further, the aforementioned definitions may equally apply to the description below.

As shown in FIG. 19A1, split ring resonators can be incorporated into the concrete pour 1902. A split ring resonator, or a plurality of split ring resonators 1904, can be mixed into the concrete 1906 while in a mixing vessel, or a split ring resonator, or a plurality of split ring resonators, can be mixed into the concrete while the concrete is mid-stream during the pouring process.

The split ring resonator, or a plurality of split ring resonators 1904, can be captured within the concrete pour 1902. The split ring resonators can be captured within the form in any orientation, but may likely settle near the bottom of the structural element; for instance, where any given split ring resonator can be oriented such that the normal vector from the plane of the split ring resonator is substantially vertical, or any given split ring resonator can be oriented such that the normal vector from the plane of the split ring resonator is substantially horizontal, or any given split ring resonator can be oriented such that the normal vector from the plane of the split ring resonator is on an angle between vertical and horizontal.

In certain situations, the split ring resonator will be captured within the form at a location that is relatively proximal to a form boundary. In other cases, the split ring resonator will end up within the form at a location that is relatively distal to a form boundary. This is because of the natural tendencies (e.g., fluid dynamics) of foreign object (e.g., split ring resonators) to locate randomly within a concrete pour 1902. Regardless of the location of the split ring resonator in the form, the techniques for pinging a split ring resonator with a signal and for receiving a return signal are operable. More specifically, since the signal to noise ratio is so wide (see the 18 dB separation as shown in FIG. 17), the return signal from any given split ring resonator at any particular location can be received and processed so as to facilitate comparison to a calibration signal. This technique can be applied to various structures, one such example can be seen in FIG. 19A1 which illustrates a vertically oriented concrete structural member.

The foregoing example pertains to a vertically-oriented concrete structural member, however the herein-disclosed techniques also apply when forming a horizontally oriented concrete structural member (or a concrete structure member at any angle).

FIG. 19A2 provides a depiction 19A200 of a split ring resonator, or plurality of split ring resonators, being placed in concrete before the concrete is to be poured into a given structural form, in accordance with one embodiment. As an option, the depiction 19A200 may be implemented in the context of any one or more of the embodiments set forth in any previous and/or subsequent figure(s) and/or description thereof. Of course, however, the depiction 19A200 may be implemented in the context of any desired environment. Further, the aforementioned definitions may equally apply to the description below.

In one embodiment, FIG. 19A2 shows a split ring resonator, or a plurality of split ring resonators 1904 that can be incorporated onto the concrete pour 1902 when pouring for a slab 1910. A split ring resonator, or a plurality of split ring resonators 1904 can be mixed into the concrete 1906 while in a mixing vessel, or a split ring resonator, or a plurality of split ring resonators 1904 can be mixed into the concrete 1906 while the concrete is mid-stream during the pouring process.

The split ring resonator, or a plurality of split ring resonators 1904 can be captured within the concrete pour 1902, and within the form at any orientation. For example, any given split ring resonator can be oriented such that the normal vector from the plane of the split ring resonator is substantially vertical, or any given split ring resonator can be oriented such that the normal vector from the plane of the split ring resonator is substantially horizontal, or any given split ring resonator can be oriented such that the normal vector from the plane of the split ring resonator is on an angle between vertical and horizontal. The split ring resonator, or a plurality of split ring resonators 1904 may be, in one embodiment, distributed closer to the walls of the horizontally-oriented concrete structural member 1914. In certain embodiments, the split ring resonator, or a plurality of split ring resonators 1904 may end up within the form at a location that is relatively proximal to the top surface of the horizontally-oriented concrete structural member 1914. In certain other embodiments, the split ring resonator, or a plurality of split ring resonators 1904 may relatively be proximal to bottom surface of the horizontally-oriented concrete structural member 1914. Still yet, the split ring resonator, or a plurality of split ring resonators 1904 may be oriented, integrated into, and/or affixed to rebar (or other support structure within the concrete member) such that a location of the split ring resonator, or a plurality of split ring resonators 1904 may be maintained during the concrete pour 1902 to the concrete member.

In various embodiments, FIGS. 19A1 and 19A2 depict one embodiment of a split ring resonator, or multiple split ring resonators, being placed in concrete before the concrete is to be poured into a given structural form (e.g., vertically-oriented concrete structural member, horizontally-oriented concrete structural member). Further, FIGS. 19A1 and 19A2 are presented to illustrate, in one embodiment, how a split ring resonator (e.g., of a ring-type, or of a cylinder-type), or a plurality of split ring resonators 1904 (e.g., of ring-types, or of cylinder-types, or of combinations thereof) can be incorporated into a concrete mixture in advance of pouring the concrete into a form. The form can be of any shape. Strictly as examples, and as shown in FIG. 19A1, the form can be configured to receive a pour for a vertically-oriented concrete structural member 1912 (e.g., the shown column or wall 1908). Additionally, or alternatively, and as shown in FIG. 19A2, the form can be configured to receive a pour for a horizontally-oriented concrete structural member 1914 (e.g., the shown slab 1910).

Regardless of the location of the split ring resonator in the form (e.g., at the top surface, at the bottom, within the concrete, etc.), the techniques for pinging a split ring resonator with a signal and for receiving a return signal may be maintained and operable. More specifically, since the signal to noise ratio is so wide (see the 18 dB separation as shown in FIG. 17), the return signal from any given split ring resonator at any particular location may be received and processed so as to facilitate comparison to an earlier captured calibration signal.

In one embodiment, the aforementioned calibration signal may be captured once the pour has cured. Such a calibration signal can be stored in a database, and/or any system that holds specified information. At a later time, the structural member may be interrogated with a ping signal and its then-current return signal can be compared to the corresponding calibration signal. In one embodiment, a difference between the later-captured signal and the calibration signal may be indicative of a change in compression between the time that the calibration signal was captured and the time that the interrogation is carried out.

A similar approach can be applied in the presence of a plurality of split ring resonators that are dispersed throughout the structural member. Specifically, pinging in a region of the structural member where there are many split ring resonators in substantially the same location would return a calibration signal that can also be stored in a database, or any other system that can store information. Again, at any later time, the structural member can be interrogated with a ping signal and its then-current return signal can be compared to a corresponding calibration signal. If a difference is determined between the two signals, this phenomenon can be indicative of a change in the structure and or its constituent materials. There are many possible techniques for analyzing a change in response (e.g., due to compression, or due to flexure, etc.), some of which techniques are shown and described as pertains to FIG. 19B1.

FIG. 19B1 shows a depiction 19B00 of columns containing the split ring resonator, or plurality of split ring resonators, and an equation for measuring the change within the structural members, in accordance with one embodiment. As an option, the depiction 19B00 may be implemented in the context of any one or more of the embodiments set forth in any previous and/or subsequent figure(s) and/or description thereof. Of course, however, the depiction 19B00 may be implemented in the context of any desired environment. Further, the aforementioned definitions may equally apply to the description below.

As shown, the depiction 19B00 shows cured columns containing a split ring resonator, or plurality of split ring resonators 1904, and various equations for measuring the change within the structural members. Additionally, a change in the compression 1916 of the materials surrounding the split ring resonators 1904 initiates a change in response 1922 from the split ring resonators (as shown in FIG. 19B2). Further, FIG. 19B1 shows an example equation for measuring the degree of compression within the structural members (as a function of change in compression) Eq. 6. Additionally, although Eq. 6 is shown relating to compression, and Eq. 7 (hereinbelow) is shown relating to change in response, it is to be appreciated that any change torsion, hygrometry (humidity), flexion, response, material property, etc. may be the basis for determining and/or measuring a change of the split ring resonator(s).

In one embodiment, one use model may support structural assessment of an infrastructure's concrete foundation (e.g., apartment complex, condominiums, homes, hotels). Additionally, a one use model may support structural assessment of a building's infrastructure in general, including monitoring of steel beams, support columns/pillars, and other aspects of structural health monitoring. Ongoing or periodic monitoring of the integrity of the material over time can indicate whether or not the material that forms the structure has been altered, for example due to aging, excessive or related stresses, and/or due to physical damage, etc. In some cases, it may be possible to prevent imminent failure of the materials so as to avoid a catastrophe. In some situations, multiple structural members can combine into one load-bearing structure, the entirety of which load-bearing structure is to be monitored over time. Calibration and periodic monitoring could be accomplished, for example, in a two-step fashion. In a first step, a technician operating a signal generator (or similar tool), tunes the signal generator to a selected frequency and emits a signal proximal to the split ring resonators in a structural member. A return signal and/or its characteristics (e.g., attenuation, single frequency resonance, multiple frequency resonance, etc.) from the split ring resonators is captured. The technician stores the return signal and/or its characteristics as a calibration point pertaining to a ping of that location and at that given point in time. The return signal and/or its characteristics is later used as a calibration signature corresponding to the point in time when the material is deemed to have a baseline state of structural integrity.

In a second step, carried out at any later time after the first step, the technician may repeat the pinging and signature capturing process to gather then-current data returned by the split ring resonators in the structural member. A comparison between the calibration signature and the then-current data may potentially be indicative of changes in the integrity of the material. In one embodiment, a change in response 1918 might be merely indicative of a change in compression. Certain ranges of changes of compression over time may be considered to be normal, and may occur in normal use (e.g., as the structure flexes under stresses from Earth movements such as earth tremors). In addition to the foregoing technique for measuring changes in compression, further techniques are presented hereunder as pertains to measuring changes in flexure.

FIG. 19B2 shows a depiction 19B02 of columns containing the split ring resonator, or plurality of split ring resonators, and an equation for measuring the change within the structural members, in accordance with one embodiment. As an option, the depiction 19B02 may be implemented in the context of any one or more of the embodiments set forth in any previous and/or subsequent figure(s) and/or description thereof. Of course, however, the depiction 19B02 may be implemented in the context of any desired environment. Further, the aforementioned definitions may equally apply to the description below.

In one embodiment, the depiction 19B02 shows a cured slab containing the split ring resonator, or plurality of split ring resonators 1904, and an example equation for measuring the degree of flexion within the structural members (as a function of change in flexion) Eq. 7. Additionally, a change in the flexion 1920 of the materials surrounding the split ring resonators 1904 causes a change in response 1922 from the split ring resonators resulting in a differing signal response than initially determined. This information is deemed imperative for monitoring the integrity of the material in its application.

As previously mentioned in the given case, a split ring resonator or split ring resonators 1904 would be implemented in the concrete foundation to allow for monitoring of material. This could be accomplished, as an example, in a two-step fashion. In a first step, a technician operating a signal generator (or similar tool), tunes the signal generator to a selected frequency, which may emit a signal proximal to the split ring resonators in a structural member. A return signal and/or its characteristics (e.g., attenuation, single frequency resonance, multiple frequency resonance, etc.) from the split ring resonators is captured. The technician stores the return signal and/or its characteristics as a calibration point pertaining to a ping of that location and at that given point in time. The return signal and/or its characteristics is later used as a calibration signature corresponding to the point in time when the material is deemed to have a baseline state of structural integrity.

When implementing the split ring resonator or split ring resonators into the member, the exact orientation and location may not be controllable during the pour, however the foregoing two-step procedure can still be used. This is because, when pinging the plurality of split ring resonators, an ensemble effect signal (the return from the multiple split ring resonators) can be used as a calibration. Again, in the second step, carried out at any later time after the first step, the technician would repeat the pinging and signature capturing process to gather then current data returned by the split ring resonators in the structural member. A comparison between the calibration signature and the then-current data may potentially be indicative of changes in the integrity of the material. On the one hand, a change in response 1918 might be merely indicative of a change in compression. Certain ranges of changes of compression over time may be considered to be normal, and may occur in normal use (e.g., as the structure flexes under stresses from earth movements such as earth tremors). In addition to the foregoing technique for measuring changes in compression, further techniques are presented hereunder as pertains to measuring changes in flexure.

If the structural member is already in a given use, a split ring resonator or plurality of split ring resonators 1904 can still be implemented on the structural member, regardless of physical characteristics (e.g. shape, size, location). Examples of such are shown and described as pertains to FIG. 20.

Figure 20:
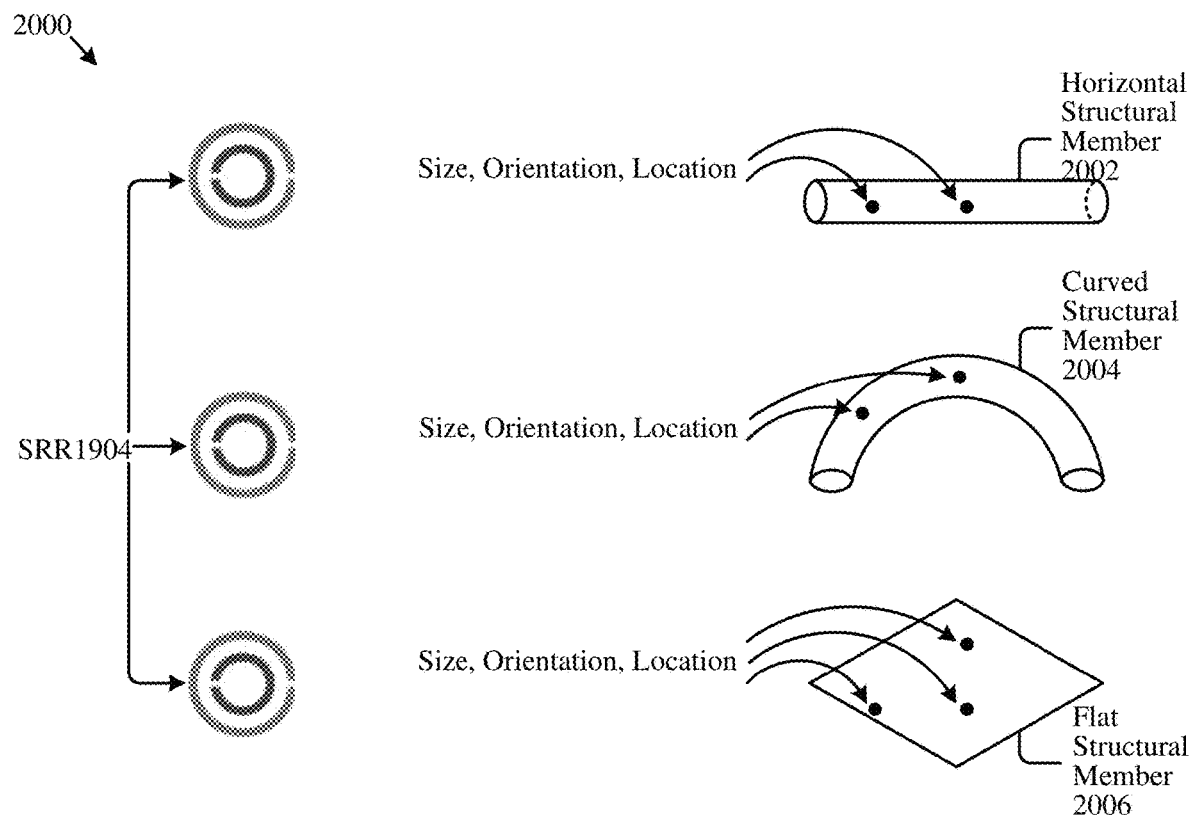
FIG. 20 illustrates the utilization of split ring resonators externally on structural members varying in shapes that already in use.

FIG. 20 illustrates the utilization 2000 of split ring resonators externally on structural members varying in shapes that already in use, in accordance with one embodiment. As an option, the utilization 2000 may be implemented in the context of any one or more of the embodiments set forth in any previous and/or subsequent figure(s) and/or description thereof. Of course, however, the utilization 2000 may be implemented in the context of any desired environment. Further, the aforementioned definitions may equally apply to the description below.

In one embodiment, FIG. 20 also displays examples of possible factors and equations that may be vital in determining the size, orientation, location, and application of the split ring resonator or split ring resonators on the structural member. Additionally, FIG. 20 illustrates the utilization of split ring resonators that are applied externally to structural members of varying shapes. FIG. 20 displays examples of possible factors and equations that may be vital in determining the size, orientation, location, and application of the split ring resonator or split ring resonators on the structural member.

More specifically, FIG. 20 depicts a horizontal member 2002 where the split ring resonator 1904 can be attached (e.g., using ultrasonic welding) and used in a given application (e.g., an axle component, a tie rod component, a push rod, rebar, etc.). In addition to the horizontal elongated members, the split ring resonator could also be attached to a curved member 2004 (e.g., bucket handle, suspension part, a portion of spring, rebar, etc.).

In one specific case, a split ring resonator 1904 or a plurality of spaced split ring resonators can be applied to rebar using any known technique, after which the rebar may be situated into a form. When the concrete or other construction composition is poured into the form, the juxtaposition of the split ring resonators on the rebar and the juxtaposition of the split ring resonators in the form remains substantially the same as when the split ring resonators were applied to the rebar and situated in the form. As such, the split ring resonators can be positioned so as to be substantially aligned into a horizontally-oriented plane (i.e., in an 'X' direction), or so as to be substantially aligned into a vertically-oriented plane (i.e., in a 'Y' direction), or so as to be substantially aligned into a depth-oriented plane (i.e., in an 'Z' direction).

Additionally, or alternatively, a split ring resonator could be attached to a flat structural member 2006 (e.g., the hood of a car). In this given application the split ring resonator could be used in order to measure the flex of a hood of a car dynamically, and at any given moment in time. This method has many advances as compared to the use of a wind tunnel in order to measure the flex of the hood of the car. This is because, in the wind tunnel case, the vehicle is stationary, whereas in the contemplated use model where the vehicle is actually underway, actual real time responses can be calculated. Thus, the split ring resonator or split ring resonators 1904 provide instant feedback during actual driving conditions.

The determined size of the split ring resonator or split ring resonators for each of the structural members may be dependent on the size of the member as well as the application. This is shown by Eq. 8. Specifically, different sizes of the split ring resonator or split ring resonators resonate at correspondingly different frequencies. The different sizes can be accounted for during the initial calibration test.

In certain situations (e.g., when applying a split ring resonator to a straight horizontal member, or when applying a split ring resonator to a curved member, or when applying a split ring resonator to a flat member) the optimal location (Eq. 10) and/or orientation (Eq. 9) can be determined or inferred from analysis of a finite element model (e.g., using CAD software such as SOLIDWORKS, AGROS2D, CALCILIX). More specifically, the results from the finite element analysis will yield flexure vectors, compression vectors, and expansion vectors depending upon the application and desired properties that are of interest. Based on the results from the finite element analysis, a particular structural member can be configured with the split ring resonator at a corresponding location (Eq. 10) and/or orientation (Eq. 9).

Figure 21:
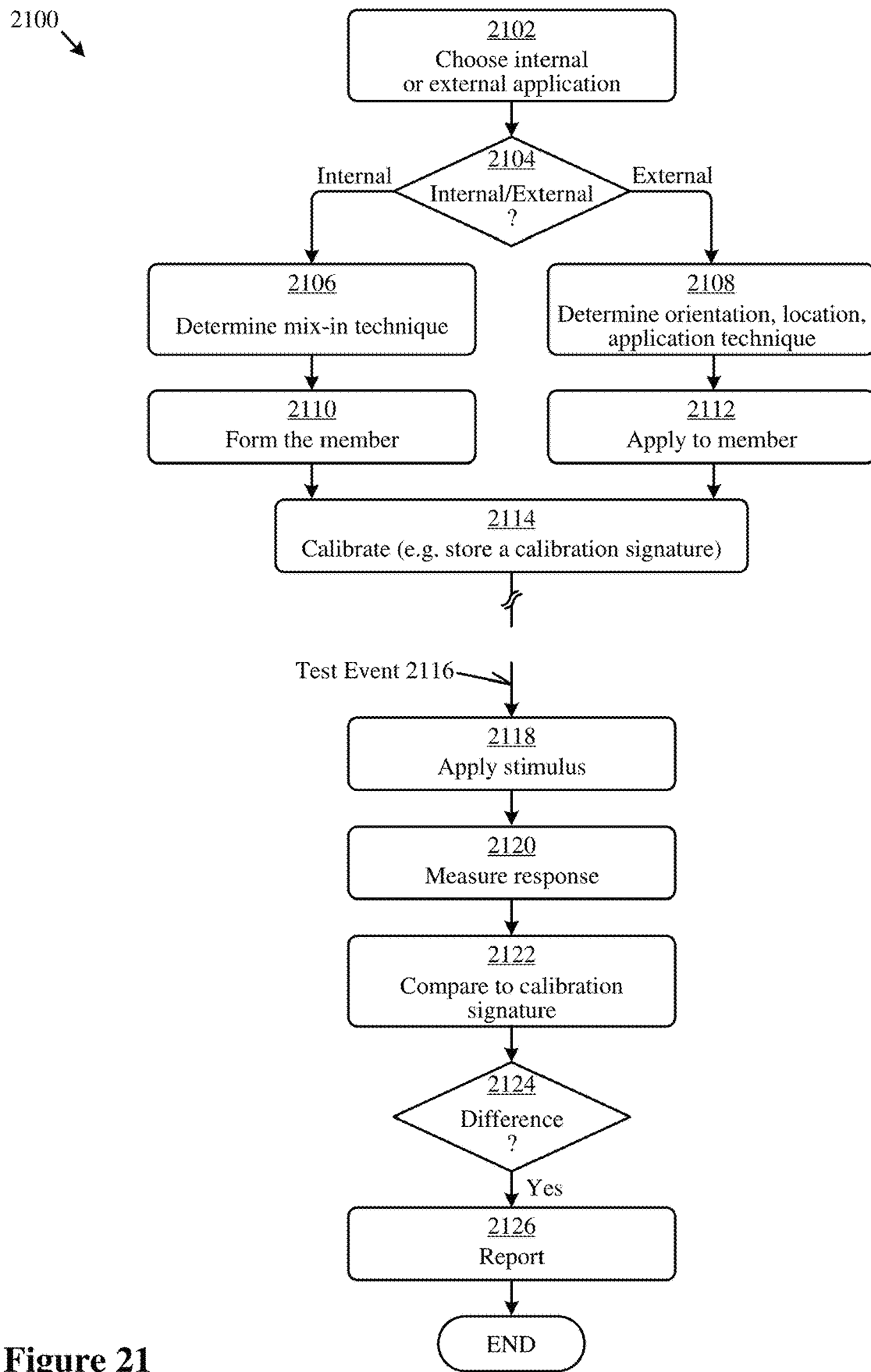
FIG. 21 is a flow chart representing the process in which the split ring resonator is implemented in the given applications, in accordance with one embodiment.

FIG. 21 is a flow chart 2100 representing the process in which the split ring resonator is implemented in the given applications, in accordance with one embodiment. As an option, the flow chart 2100 may be implemented in the context of any one or more of the embodiments set forth in any previous and/or subsequent figure(s) and/or description thereof. Of course, however, the flow chart 2100 may be implemented in the context of any desired environment. Further, the aforementioned definitions may equally apply to the description below.

As shown, the first step of the process is to determine whether the scenario admits either an internal or external disposition of the split ring resonators (step 2102). In the event of an internal application (step 2104) of the split ring resonator or split ring resonators, the mix-in technique would need to be determined (step 2106). In one embodiment, the split ring resonator or split ring resonators may be combined with an aggregate mixture or cement. The aggregate mixture or cement may then be poured into a structure or foundation and the split ring resonators would disperse randomly throughout the mixture ultimately forming the member (step 2110).

Once the foundation or structure has cured the split ring resonators can be calibrated, and an initial state or calibration signature can be gathered (step 2114). To achieve the calibration signature a unique signal may used to ping a response from the split ring resonators. Based upon the characteristics of the medium in which the split ring resonators are immersed, a response as a function of the medium's parameters (compression, density, frequency, etc.) may be generated. This initial reading when the structure is in some initial state may become the calibration signature and reference parameter for future comparisons. Of course, it is to be appreciated that the initial reading may be reset (and/or recalibrated) at a later point of time (such as recasting of cement, seismic upgrades, etc.).

In the event of an external application (e.g., via ultrasonic welding) the split ring resonator or split ring resonators would be integrated onto a component in a fashion that would not compromise the accuracy of the split ring resonator. The orientation, location, and application of the split ring resonator can be used to gather correct data from the split ring resonator (step 2108) (for example, the installment of a split ring resonator to a motor vehicle axle). The orientation of the split ring resonator to the axle can be used to achieve a normal, horizontal, or angled vector from the plane of the split ring resonator which does not compromise the signal to noise ratio and allows for operable return of calibration signature or point. The location of the split ring resonator on the axle may be placed in zones of failure and fluctuating stress for appropriate monitoring of the integrity of the axle. Sonic welding of the split ring resonators (step 2112) to the axle may be employed to ensure accuracy of the split ring resonators calibration signature and points. Sonic welding which allows for dissimilar materials to bind does not use solder or other materials to form a weld that could dampen or alter the response of the split ring resonators. Of course, it is to be appreciated that any type of affixing may also be used in lieu of welding.

As shown in the flowchart, both external and internal processes converge to test event (step 2116). During the test event a stimulus is applied (step 2118) and a response is measured (step 2120). The test event is used to gather and compare calibration points against the calibration signature (step 2122). After a given amount of time has elapsed and, strictly as example, a stressful event to the structure or component has taken place, or routine maintenance check, or a visual observation of the component or structure renders need for testing a test is performed. This test returns calibration points which may be similar in nature to calibration signatures taken later when the structure or component may differ in the structure's integrity. A two-step technique could be used to accomplish obtaining the necessary calibrations. In a first step (step 2120), a technician operating a signal generator (or similar tool), tunes the signal generator to a selected frequency, and emits a signal proximal to the split ring resonators in a structural member. A return signal and/or its characteristics (e.g., attenuation, single frequency resonance, multiple frequency resonance, etc.) from the split ring resonators is captured. The technician stores the return signal and/or its characteristics as a calibration point pertaining to a ping of that location and at that given point in time. The return signal and/or its characteristics is later used as a calibration signature corresponding to the point in time when the material is deemed to have a baseline state of structural integrity.

In a second step (step 2122), carried out at any later time after the first step, the technician would repeat the pinging and signature capturing process to gather then current data returned by the split ring resonators in the structural member. A comparison between the calibration signature and the then-current data may potentially be indicative of changes in the integrity of the material. On the other hand, a change in response 1918 might be merely indicative of a change in compression. Certain ranges of changes of compression over time may be considered to be normal, and may occur in normal use (e.g., as the structure flexes under stresses from earth movements such as earth tremors. In addition to the foregoing technique for measuring changes in compression, further techniques are presented hereunder as pertains to measuring changes in flexure. Regardless of the shape of the member the previously technique, or any related technique disclosed herein, can be used to gather the necessary information.

The calibration points are then compared against the calibration signature. If the difference of the two signals is outside of the acceptable error threshold or tolerance (the "Yes" option of decision 2124) then the "YES" branch of decision 2124 is taken and a report is made (step 2126). Additionally, FIGS. 22A1-22A3 illustrates other embodiments where the aforementioned is applied.

FIGS. 22A1 through 22A3 are being presented to illustrate use of split ring resonators or a plurality of split ring resonators within roadside barriers, in accordance with one embodiment. As an option, the FIGS. 22A1 through 22A3 may be implemented in the context of any one or more of the embodiments set forth in any previous and/or subsequent figure(s) and/or description thereof. Of course, however, the FIGS. 22A1 through 22A3 may be implemented in the context of any desired environment. Further, the aforementioned definitions may equally apply to the description below.

As shown, FIG. 22A1 depicts a roadway 2202 containing a concrete barrier 2206 and/or metal barrier 2204, or possibly both, that use a split ring resonator or a plurality of split ring resonators. Roadside barriers are meant to reduce the severity of potential vehicle accidents (e.g., going over a cliff, into a body of water, etc.) by absorbing the force from an oncoming car and stopping the car from continuing on its path by allowing the body of the barrier to deform in its shape. After this has been accomplished, the integrity of the material of the barrier may be altered and possibly may need to be replaced due to the deformation of the material. Even if the outside physical aspect of the barrier seems to be unaltered, there may be deformities within the material causing it to have weakened as a result of the impact, thus requiring the barrier to be replaced.

To determine when and how often the given barrier may need to be replaced, split ring resonators may be placed within the concrete barriers as shown in FIG. 22A2 (e.g., an example of the technique depicted in FIG. 19A). Once the foundation or structure has cured, the split ring resonators can be calibrated, and an initial state or calibration signature can be gathered, for example, by a two-step fashion technique. In a first step, a technician operating a signal generator (or similar tool), tunes the signal generator to a selected frequency, and emits a signal proximal to the split ring resonators in the concrete barrier. A return signal and/or its characteristics (e.g., attenuation, single frequency resonance, multiple frequency resonance, etc.) from the split ring resonators is captured. The technician stores the return signal and/or its characteristics as a calibration point pertaining to a ping of that location and at that given point in time. The return signal and/or its characteristics is later used as a calibration signature corresponding to the point in time when the material is deemed to have a baseline state of structural integrity.

Figure 22B:
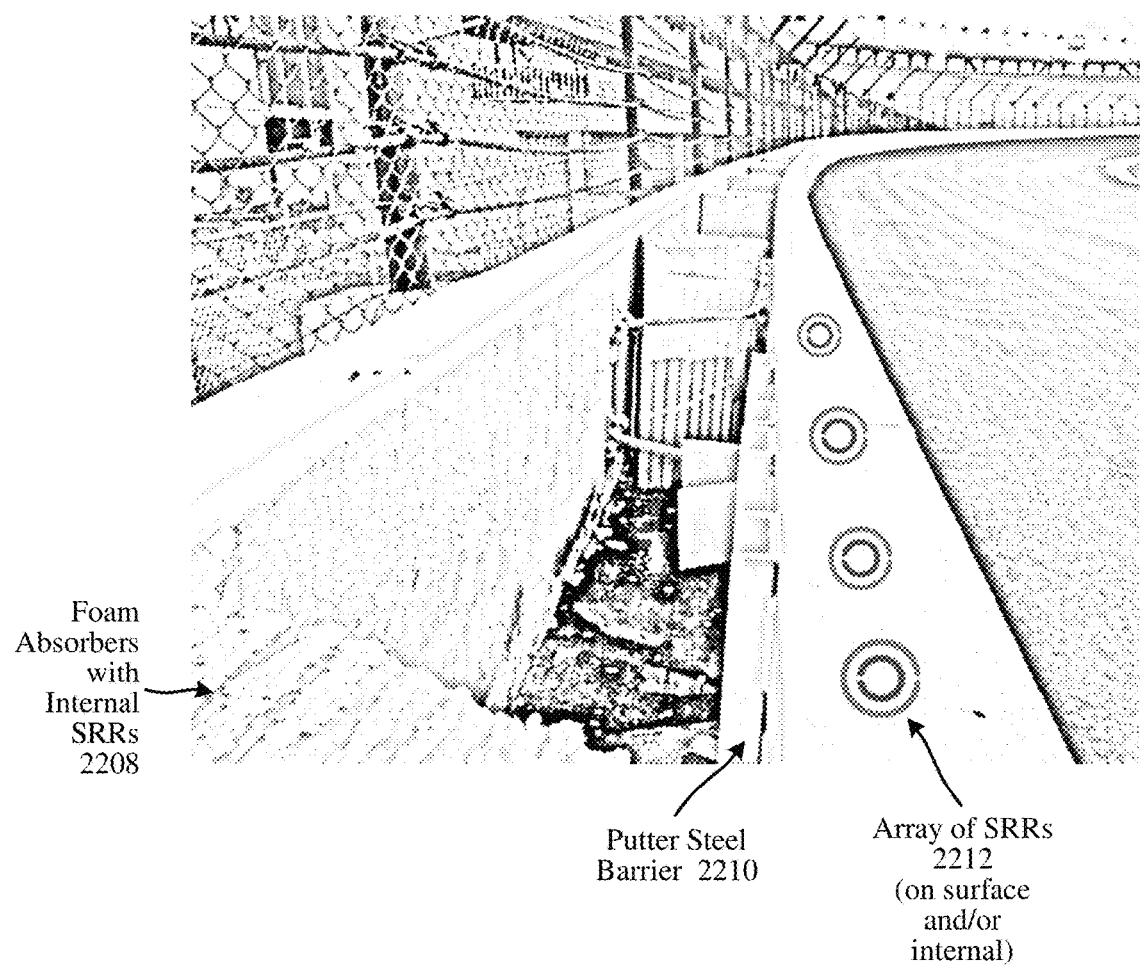
FIG. 22B depicts a roadside barrier used in a racetrack showing structural components that constitute the roadside barrier in which a split ring resonator or split ring resonators can be placed, in accordance with one embodiment.

The same can be applied to a metal barrier represented in FIG. 22A3. The split ring resonators may also be attached with an application technique (e.g., ultrasonic welding) of step 2112. Once attached to the metal barrier, the split ring resonators can be calibrated, and an initial state or calibration signature can be gathered using the previously two-step technique. Similarly, a racetrack barrier can also use a plurality of split ring resonators to monitor the integrity of the barrier which is depicted in FIG. 22B.

Of course, it is to be appreciated that split ring resonators may be embedded in other materials (other than concrete barriers of FIG. 22A2 and/or metal barriers of FIG. 22A3), including but not limited to: aviation related embodiments (e.g., wings, landing gear, plane component, etc.), nautical related embodiments (e.g., sails, masts, buoys, structural steel, etc.), utilities related embodiments (e.g., power line structure, transmission line, delivery pipelines, etc.), construction related embodiments (e.g., beams, concrete pylons, etc.), biomedical related embodiments (e.g., prosthetics, implants, orthotics, etc.), professional sports equipment related embodiments (e.g., helmets, protective pads, handheld implements, footwear, etc.), forging or smelting related embodiments (e.g., metals, composites, alloys, etc.), power production related embodiments (e.g., solar arrays, hydro-electric dams, wind-powered turbines, natural gas housing and transport, etc.), automobile related safety and/or performance embodiments (e.g., engine performance, suspension, chassis and body integrity, etc.), manufacturing related embodiments (e.g., assembly, 3D printing, component amalgamation, testing, etc.), agriculture related embodiments (e.g., growth rates, temperature control, moisture saturation, ultraviolet light exposure, etc.), and/or space travel related embodiments (e.g., air lock performance, propellant receptacle integrity, launch effect tolerance measurements, capsule/fuselage distortion during flight, etc.). In short, use of split ring resonators for determining deformation of the material to which it is affixed or in which it is incorporated may relate to any application where it can be imbedded and/or affixed, where the substrate to which it is affixed or in which it is embedded is of a sufficient permanent state that any deformation of the substrate would be an indication of material fatigue.

With respect to one specific example, drilling rigs are often exposed to high temperature and corrosive environments for offshore application. Such conditions often cause drillpipe failures, which result predominately from metal fatigue. Having split ring resonators embedded, in one embodiment, within the drillpipe itself, would allow metal fatigue to be detected in advance of causing a drillpipe failure (and the inherent complications that arise from such failure). Consistent with the description herein, the split ring resonators embedded in the drillpipe may be initially calibrated, where an initial state or calibration signature can be gathered (consistent with the two-step fashion technique). A signal generator (or similar tool) may tune the signal generator to a selected frequency, and emit a signal next to the split ring resonators in the drillpipe. A return signal and/or its characteristics may be captured, which in turn, may be stored as a calibration signature of the material at that state in time. At a later time period (consistent with step 2116), a stimulus may be applied (per step 2118) and a response may be measured (per step 2120), which in turn may be compared to the calibration signature (per step 2122). It is to be appreciated that the stimulus may be applied at any time period rate (e.g. every minute, day, week, month, etc.) as predetermined by a user. In this manner, deformation (which may be indicated of fatigue crack, crack propagation, etc.) may be measured within the drillpipe, and detected before actually causing a drillpipe failure.

FIG. 22B depicts a roadside barrier 22B00 used in a racetrack showing structural components that constitute the roadside barrier in which a split ring resonator or split ring resonators can be placed, in accordance with one embodiment. As an option, the roadside barrier 22B00 may be implemented in the context of any one or more of the embodiments set forth in any previous and/or subsequent figure(s) and/or description thereof. Of course, however, the roadside barrier 22B00 may be implemented in the context of any desired environment. Further, the aforementioned definitions may equally apply to the description below.

In one embodiment, the roadside barrier 22B00 may include a steel and foam energy reduction barrier. As shown, the racetrack is to the side of the foam absorbers (with internal split ring resonators 2208). Steel and foam energy reduction barriers may be used in the high speed section of certain tracks and work by absorbing the kinetic energy during impact to reduce severity of accidents as well as to separate the spectating crowd from possible hazards in the case of a collision of cars and/or to prevent hazardous material from being launched into the crowd. When the barrier contacts the car or cars, the absorbed energy travels along the sides of the wall reducing the damage to the cars and preventing injury to the spectators.

Additionally, an array of split ring resonators 2212 can be placed either on the surface and/or internally on the putter steel barrier 2210 in order to obtain needed information to determine the integrity of the barrier after, for example, one or more collisions, or to determine the integrity of the barrier over a certain period of time. In exemplary cases, the array of split ring resonators 2212 can be placed in the front and back of the putter steel barriers, and/or embedded in foam absorbers and/or on or in any of the cement walls.

In one specific embodiment, after the array of split ring resonators 2212 has been disposed (e.g., placed in the foam absorbers with internal split ring resonators 2208 and/or externally or internally placed in the putter steel barrier 2210, and/or externally or internally placed in the foam absorbers, etc.), they can be calibrated by way of the two-step technique detailed herein.

In a first step, a technician operating a signal generator (or similar tool), tunes the signal generator to a selected frequency, which emits a signal proximal to the split ring resonators in the foam absorbers with internal or external split ring resonators 2008 and/or externally or internally in the putter steel barrier 2210. A return signal and/or its characteristics (e.g., attenuation, single frequency resonance, multiple frequency resonance, etc.) from the split ring resonators is captured. The technician stores the return signal and/or its characteristics as a calibration point pertaining to a ping of that location and at that given point in time. The return signal and/or its characteristics is later used as a calibration signature corresponding to the point in time when the material is deemed to have a baseline state of structural integrity.

In a second step, carried out at any later time after the first step, the technician would repeat the pinging and signature capturing process to gather the then-current data returned by the split ring resonators in the structural member. A comparison between the calibration signature and the then-current data may potentially be indicative of changes in the integrity of the material. On the other hand, a change in response 1918 might be merely indicative of a change in compression. Certain ranges of changes of compression over time may be considered to be normal, and may occur in normal use (e.g., as the structure flexes under stresses from earth movements such as earth tremors. In addition to the foregoing technique for measuring changes in compression, further techniques are presented hereunder as pertains to measuring changes in flexure. After analysis of the gathered data, a report can be constructed in which replacement of the barriers can be determined.

Figure 23:
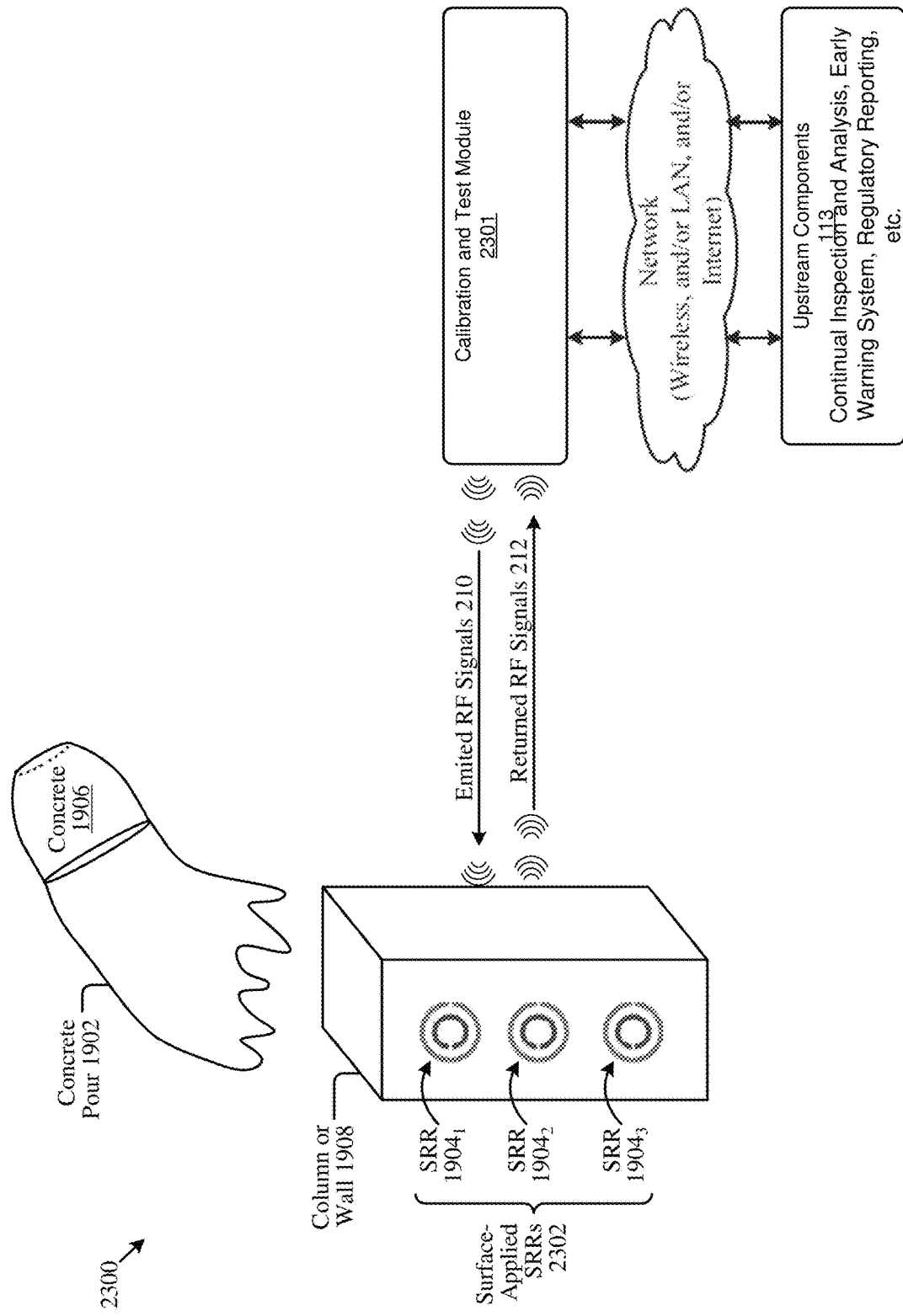
FIG. 23 shows a depiction of split ring resonators disposed on the surface of a concrete structure after the concrete has been poured into a given structural form, in accordance with one embodiment.

FIG. 23 shows a depiction 2300 of split ring resonators disposed on the surface of a concrete structure after the concrete has been poured into a given structural form, in accordance with one embodiment. As an option, the depiction 2300 may be implemented in the context of any one or more of the embodiments set forth in any previous and/or subsequent figure(s) and/or description thereof. Of course, however, the depiction 2300 may be implemented in the context of any desired environment. Further, the aforementioned definitions may equally apply to the description below.

As shown, the depiction 2300 includes split ring resonators (e.g., split ring resonator $1904_1$, split ring resonator $1904_2$, split ring resonator $1904_3$) disposed on the surface of a concrete structure (e.g., column or wall 1908) after the concrete has been poured into a given structural form. Placement of such split ring resonators (e.g., the shown surface-applied split ring resonators 2302) can be done as a "retrofit", in some cases long after the pour has cured, and in some cases long after a building has been erected using columns and/or walls. The construction, placement of, and means of affixing surface-applied split ring resonators 2302 to a structure can be accomplished using any known technique. For example, such surface-applied split ring resonators 2302 can be printed or silk-screened onto a substrate in a roll, and that roll of substrate or portions thereof can be applied, possibly with an adhesive to a surface of a column or wall. In some cases, the substrate is lifted off, leaving the surface-applied split ring resonators 2302 affixed to the surfaces of the column or wall. In some cases, the surface-applied split ring resonators 2302 can be printed directly onto the rebar. In some cases, the surface-applied split ring resonators 2302 can be printed onto a substrate using a inkjet or bubble jet printer. In some cases, the surface-applied split ring resonators 2302 can be printed onto a substrate using offset or printing (e.g., multi-color offset printing). In some cases, the surface-applied split ring resonators 2302 can be printed onto a substrate using gravure printing techniques.

A calibration and test module 2301 can be situated proximal to any location where there are surface-applied split ring resonators 2302. One or more calibration signatures based on a particular combination of occurrences of emitted RF signals 210 and corresponding occurrences of returned RF signals 212 can be communicated over a network to upstream components 113. Strictly as examples that are pertinent to this and other embodiments, an upstream component may include, but not be limited to, modules that perform continual inspection and analysis of the structures, modules that combine to serve in the capacity of an early warning system, modules that comport with governance, and/or modules that comport with any regulatory reporting requirements.

Any of the foregoing techniques for making and using split ring resonators can be combined. For example, surface-applied split ring resonators can be retrofitted onto surfaces of a roadside barriers and/or components thereof. Additionally, for example, the upstream components might include a racetrack safety monitoring unit. Further, split ring resonators of a first geometry of split ring resonators (e.g., concentric rings) can be combined (e.g., proximally-juxtaposed) with split ring resonators of a second geometry (e.g., concentric cylinders). Strictly as yet another embodiment, a roadside barrier made of steel and/or other barrier components made of steel of another electrically-conducting material can serve as an electrically-conductive layer that is dielectrically separated (e.g., via an adhesive) from any one or more split ring resonators that are disposed onto the surface of the roadside barrier.

The foregoing discloses various ways to incorporate or otherwise embed split ring resonators into the base materials that form the intended structural member (e.g., such as in cement pours). Further, the foregoing discloses various ways to affix split ring resonators onto a surface of a structural member (e.g., such as a tie-rod of a steering mechanism in an automobile). It is additionally envisioned to use a RF "horn" to emit a particular signal and measure the response of the embedded split ring resonators, as discussed herein as well.

Some methods include disposing split ring resonators onto a (possibly printed) "ground plane" which forms an assembly that is in turn applied onto a surface of the structural member. This greatly may increase sensitivity of the split ring resonator over a broad range of EM.

The foregoing methods support static non-destructive testing merely by comparing a current response/signature to a previously-taken calibration response/signature and then classifying the differences between the two signatures. More particularly, certain differences that are apparent between the signatures can be correlated to corresponding physical property changes. In some cases, the physical property changes are indicative of aging (e.g., brittle-ization). In some cases, the physical property changes are indicative of stretching, compression, other deformation, etc.

In some cases, the physical property changes are indicative of dynamically changing property changes (e.g., vibration). Capturing a series of a dynamically-taken series of responses/signatures to a previously-taken series of calibration responses/signatures supports dynamic non-destructive testing. Difference that are apparent between the two sets signatures can be correlated to physical property changes such as cyclical deformations. In some cases, the physical property changes are indicative of aging (e.g., changes in the elastic deformation curve). In some cases, the physical property changes that occur between readings and/or the physical property changes that are measured when comparing one series of readings to another series of readings can be indicative of elastic versus plastic deformations, which are sometimes indicative of imminent failure. Strictly as one example, imminent failure of a component might be indicated when a measured elasticity curve (e.g., based on a series of readings) resembles a region of an elasticity curve that has been designated as preceding a failure event.

FIG. 24A depicts a sensing laminate 24A00 including alternating layers of carbon-containing resin and carbon fiber in contact with one-another, in accordance with one embodiment. As an option, the sensing laminate 24A00 may be implemented in the context of any one or more of the embodiments set forth in any previous and/or subsequent figure(s) and/or description thereof. Of course, however, the sensing laminate 24A00 may be implemented in the context of any desired environment. Further, the aforementioned definitions may equally apply to the description below.

As shown, the sensing laminate 24A00 includes a schematic side-view cutaway diagram composed of multiple layers disposed on each other, including (sequentially) a carbon-containing resin $2404_2$, a carbon fiber $2402_2$, a carbon-containing resin $2404_1$, and a carbon fiber $2402_1$. In one embodiment, the sensing laminate 24A00 can be representative of any sensor discussed with relation to that shown in FIGS. 24A-24C. The term "resin" (in polymer chemistry and materials science), generally, refers to a solid or highly viscous substance of plant or synthetic origin that is typically convertible into polymers (a large molecule, or macromolecule, composed of many repeated subunits). Synthetic resins may be industrially produced resins, typically viscous substances that convert into rigid polymers by the process of curing. In order to undergo curing, resins typically contain reactive end groups, such as acrylates or epoxides. The term "carbon fiber", refers to fibers about 5-10 micrometers (µm) in diameter and composed mostly of carbon atoms. Carbon fibers have several advantages including high stiffness, high tensile strength, low weight, high chemical resistance, high temperature tolerance and low thermal expansion.

Any one or more of the carbon-containing resin $2404_2$, the carbon fiber $2402_2$, the carbon-containing resin $2404_1$, and the carbon fiber $2402_1$ can be tuned to demonstrate or exhibit one or more specific resonance frequencies upon being pinged by RF signals by incorporating specific concentration levels of the any one or more of the aforementioned carbon-containing microstructures. The sensing laminate can include any configuration, orientation, order, or layering of any one or more of the carbon-containing resin $2404_2$, the carbon fiber $2402_2$, the carbon-containing resin $2404_1$, and the carbon fiber $2402_1$ and/or fewer or additional layers comprising similar or dissimilar materials. Additional layers of resin can be layered interstitially between additional layers of carbon fiber.

Each layer of carbon-containing resin can be formulated differently to resonate at a different expected or desired tuned frequency. The physical phenomenon of material resonation can be described with respect to a corresponding molecular composition. For example, a layer having a first defined structure, such as a first molecular structure will resonate at a first frequency, whereas a layer having a second, different molecular structure can resonate at a second, different frequency Material having a particular molecular structure and contained in a layer will resonate at a first tuned frequency when that layer is in a low energy state, and will resonate at a second different frequency when the material in the layer is in an induced higher-energy state. For example, material in a layer that exhibits a particular molecular structure can be tuned to resonate at a 3 GHz when the layer is in a natural, undeformed, low energy state. In contrast, that same layer can resonate at 2.95 GHz when the layer is at least partially deformed from its natural, undeformed, low energy state. As a result, this phenomenon can be adjusted to accommodate the needs for detecting, with a high degree of fidelity and accuracy, even the most minute aberration to, for example, a tire surface contacting against a road surface such as pavement and experiencing enhanced wear at a certain localized region of contact. Race cars racing on demanding race circuits (referring to highly technical, windy tracks featuring tight turns and rapid elevational changes) can benefit from such localized tire wear or degradation information to make informed tire-replacement decisions, even in time-sensitive race-day conditions. As described herein, the phenomenon may be applied to any context and/or application where split ring resonators can be integrated within or affixed to a substrate.

FIGS. 24B1 and 24B2 depict a frequency-shifting phenomenon as demonstrated by a sensing laminate including carbon-containing tuned RF resonance materials, in accordance with one embodiment. As an option, the FIGS. 24B1 and 24B2 may be implemented in the context of any one or more of the embodiments set forth in any previous and/or subsequent figure(s) and/or description thereof. Of course, however, the FIGS. 24B1 and 24B2 may be implemented in the context of any desired environment. Further, the aforementioned definitions may equally apply to the description below.

The frequency-shifting phenomenon referred to above (with respect to FIG. 24A, such as transitioning from resonating at a frequency of 3 GHz to 2.95 GHZ) is shown and discussed with reference to FIGS. 24B1-24B2. FIG. 24B2 depicts a frequency-shifting phenomenon as exhibited in a sensing laminate that includes carbon-containing tuned resonance materials.

As generally understood, atoms emit electromagnetic radiation at a natural frequency for a given element. That is, an atom of a particular element has a natural frequency that corresponds to characteristics of the atom. For example, when a Cesium atom is stimulated, a valence electron jumps from a lower energy state (such as, a ground state) to a higher energy state (such as, an excited energy state). When the electron returns to its lower energy state, it emits electromagnetic radiation in the form of a photon. For Cesium, the photon emitted is in the microwave frequency range; at 9.192631770 THz. Structures that are larger than atoms, such as molecules formed of multiple atoms also resonate (such as by emitting electromagnetic radiation) at predictable frequencies. For example, liquid water in bulk resonates at 109.6 THz. Water that is in tension (such as, at the surface of bulk, in various states of surface tension) resonates at 112.6 THz. Carbon atoms and carbon structures also exhibit natural frequencies that are dependent on the structure. For example, the natural resonant frequency of a carbon nanotube (CNT) is dependent on the tube diameter and length of the CNT. Growing a CNT under controlled conditions to control the tube diameter and length leads to controlling the structure's natural resonant frequency. According, synthesizing or otherwise "growing" CNTs is one way to tune to a desired resonant frequency.

Other structures formed of carbon can be formed under controlled conditions. Such structures include but are not limited to carbon nano-onions (CNOs), carbon lattices, graphene, carbon-containing aggregates or agglomerates, graphene-based, other carbon containing materials, engineered nanoscale structures, etc. and/or combinations thereof, any one or of which being incorporated into sensors of vehicle components according to the presently disclosed implementations. Such structures can be formed to resonate at a particular tuned frequency and/or such structures can be modified in post-processing to obtain a desired characteristic or property. For example, a desired property such as a high reinforcement value can be brought about by selection and ratios of combinations of materials and/or by the addition of other materials. Moreover, co-location of multiples of such structures introduces further resonance effects. For example, two sheets of graphene may resonate between themselves at a frequency that is dependent on the length, width, spacing, shape of the spacing and/or other physical characteristics of the sheets and/or their juxtaposition to each other.

As is known in the art, materials have specific, measurable characteristics. This is true for naturally occurring materials as well as for engineered carbon allotropes. Such engineered carbon allotropes can be tuned to exhibit physical characteristics. For example, carbon allotropes can be engineered to exhibit physical characteristics corresponding to: (a) a particular configuration of constituent primary particles; (b) formation of aggregates; and (c) formation of agglomerates. Each of these physical characteristics influence the particular resonant frequencies of materials formed using corresponding particular carbon allotropes.

In addition to tuning a particular carbon-based structure for a particular physical configuration that corresponds to a particular resonant frequency, carbon-containing compounds can be tuned to a particular resonant frequency (or set of resonant frequencies). A set of resonant frequencies is termed a resonance profile.

FIG. 24B1 depicts a first carbon-containing structure that resonates at a first frequency, which can be correlated to an equivalent electrical circuit comprising a capacitor $C_1$ and an inductor $L_1$ (note that the context of Eq. 3, provided below, can also be found hereinabove with respect to FIG. 2, and/or the carbon-containing structures of FIGS. 18A-18Y, in particular). The frequency $f_1$ is given by the equation:

$$f_1 = \frac{1}{2\pi\sqrt{L_1 C_1}} \quad \text{(Eq. 3)}$$

FIG. 24B2 depicts a slight deformation of the same first carbon-containing structure of FIG. 24B1. The deformation causes a change to the physical structure, which in turn, changes the inductance and/or capacitance of the structure. The changes can be correlated to an equivalent electrical circuit comprising a capacitor $C_2$ and an inductor $L_2$. The frequency $f_2$ may given by the equation:

$$f_2 = \frac{1}{2\pi\sqrt{L_2 C_2}} \qquad \text{(Eq. 4)}$$

FIG. 24B3 is a graph 24B300 depicting idealized changes in RF resonance as a function of deflection, in accordance with one embodiment. As an option, the graph 24B300 may be implemented in the context of any one or more of the embodiments set forth in any previous and/or subsequent figure(s) and/or description thereof. Of course, however, the graph 24B300 may be implemented in the context of any desired environment. Further, the aforementioned definitions may equally apply to the description below.

As shown, the graph 24B300 depicts idealized changes in measured resonance as a function of deflection. As an option, one or more variations of graph 24B300 or any aspect thereof may be implemented in the context of the implementations described herein. The graph 24B300 (or any aspect thereof) may be implemented in any environment.

The implementation shown in FIG. 24B3 is merely one example. The shown graph depicts one aspect of deformation, specifically deflection. As a member or surface undergoes deformation by deflection (such as curving), the deformation can change the demonstrated resonance frequency of the member upon being pinged by a signal, such as an RF signal. The shape of the curve can depend on characteristics of the member, such as on characteristics of the laminate that forms the member or surface. The curve can be steep at small variations, whereas the curve flattens as the deflection reaches a maximum. Moreover, the shape of the curve depends in part on the number of layers of the laminate, the geometry of the carbon structures, how the carbon is bonded into the laminate, etc.

FIG. 24B4 is a graph 24B400 depicting changes in RF resonance for 4-layer and 5-layer laminates, in accordance with one embodiment. As an option, the graph 24B400 may be implemented in the context of any one or more of the embodiments set forth in any previous and/or subsequent figure(s) and/or description thereof. Of course, however, the graph 24B400 may be implemented in the context of any desired environment. Further, the aforementioned definitions may equally apply to the description below.

As shown, the graph 24B400 depicts changes in resonance for 4-layer laminates 292 and for 5-layer laminates 294. As an option, one or more variations of graph 24B400 or any aspect thereof can be implemented in the materials and systems described herein. Materials such as the described laminates can be deployed into many applications. One particular application may be for surface sensors, which can be deployed into, on, or over many locations throughout a vehicle. An example of such deployments may be shown and described as pertains to FIG. 24C.

Figure 24C:
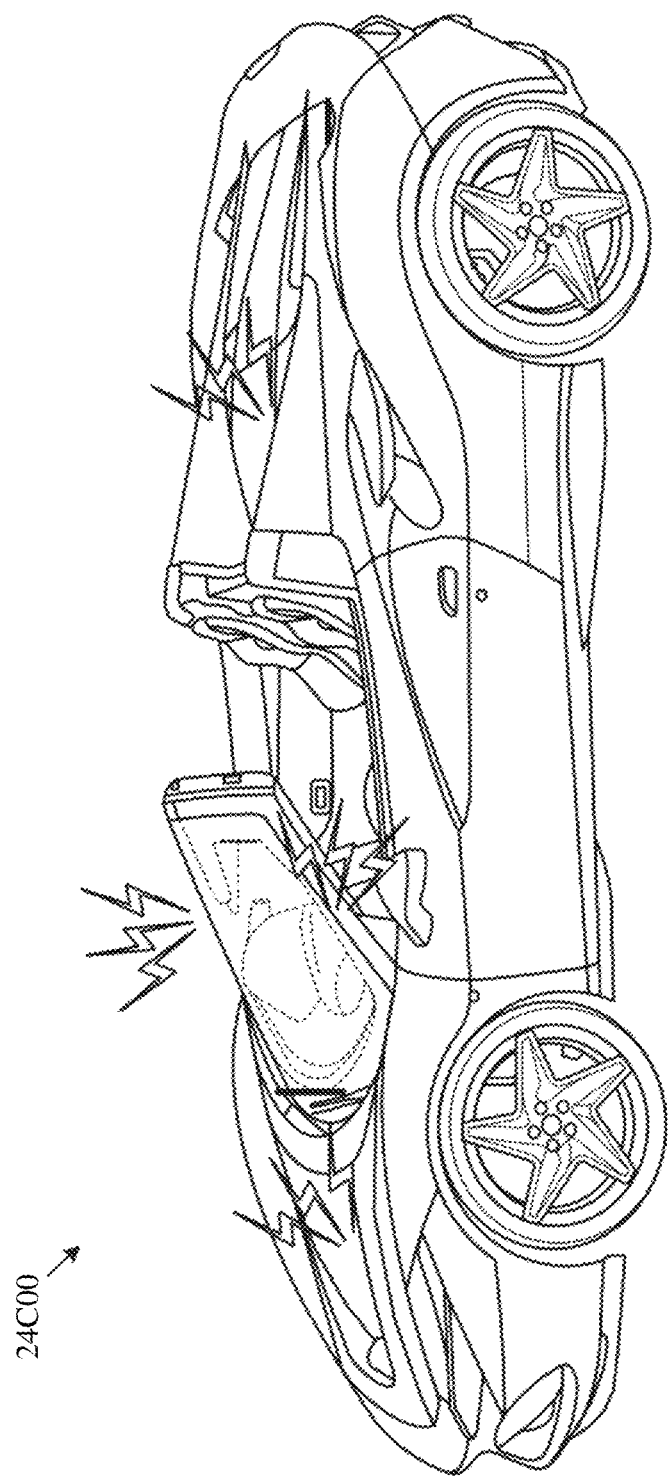
FIG. 24C depicts surface sensor deployments in areas of a vehicle, in accordance with one embodiment.

FIG. 24C depicts surface sensor deployments in areas of a vehicle 24C00, in accordance with one embodiment. As an option, the vehicle 24C00 may be implemented in the context of any one or more of the embodiments set forth in any previous and/or subsequent figure(s) and/or description thereof. Of course, however, the vehicle 24C00 may be implemented in the context of any desired environment. Further, the aforementioned definitions may equally apply to the description below.

As shown, the vehicle 24C00 shows example surface sensor deployments in selected locations of a vehicle. Such example surface sensor deployments, or any aspect thereof, may be implemented in or on a vehicle exposed to any possible exterior environmental condition, such as snow, sleet, hail, etc.

Tuned resonance sensing carbon-containing materials can be incorporated into or with automotive features, surfaces, and/or components in the context of durable sensors in various exterior surfaces of vehicles. As shown, the vehicle is equipped with surface sensors on the front faring (such as, hood) of the vehicle, on support members of the vehicle, and on the roof of the vehicle. Each of the foregoing locations of the vehicle can be subjected to stresses and accompanying deformations during operation of the vehicle. As examples, the surface sensors on the front faring will undergo air pressure changes when the vehicle is in operation (such as, during forward motion). Under the forces of the air pressure, the material that composes the surface can deform slightly and, in accordance with the phenomenon described as pertains to FIG. 24B1 and FIG. 24B2, demonstrate a change in resonant frequency of the material proportionate to the degree of change or deformation of the material. Such a change can be detected using the 'ping" and observation techniques described earlier.

Observed emitted signals can collectively define a signature for a particular material or surface and can be further classified. Specific characteristics of the signal can be isolated for comparison and measurement to determine calibration points that correspond to the specific isolated characteristics. Accordingly, aspects of the environment surrounding a vehicle can be accurately and reliably determined.

For example, if the deformation of the surface sensor results in a frequency shift from 3 GHz to 2.95 GHz, the difference can be mapped to a calibration curve, which in turn can yield a value for air pressure. A vehicle component such as a panel, roof, hood, trunk, or airfoil component can provide a relatively large surface area. In such cases, transceiver antennas can be distributed on the observable side of the component. Several transceiver antennas can be distributed into an array, where each element of the array corresponds to a section of the large surface area. Each transceiver antenna can be installed on or within the wheel wells of the surface sensor deployments 24C00 as shown and be independently stimulated by pings/chirps. In some cases, each element of the array can be stimulated sequentially, whereas, in other cases, each element of the array is stimulated concurrently. Aerodynamics of the vehicle can be measured over large surface areas by signal processing employed to distinguish signature returns from proximal array elements.

Signature returns from a particular array element can be analyzed with respect to other environmental conditions and/or other sensed data. For example, deflection of a particular portion of an airfoil component might be compared with deflection of a different portion of the airfoil component, which in turn might be analyzed with respect to then-current temperatures, and/or then-current tire pressure, and/or any other sensed aspects of the vehicle or its environment. As heretofore described, a resonator circuit (such as is shown in 24B1 and 24B2) can be implemented by situating a resonator in a surface panel of the vehicle (as is shown in 24C). Configurations of other embodiments are specifically tuned to be able to locate resonators (e.g. Split ring resonators) across the vehicle's surface. An array, or matrix of surface sensors varying in size, can be deployed into or on over many locations throughout a vehicle in order for the vehicle's conditions to be analyzed in present time. One such deployment may be found, for example, in FIG. 29, described hereinbelow.

Figure 25A:
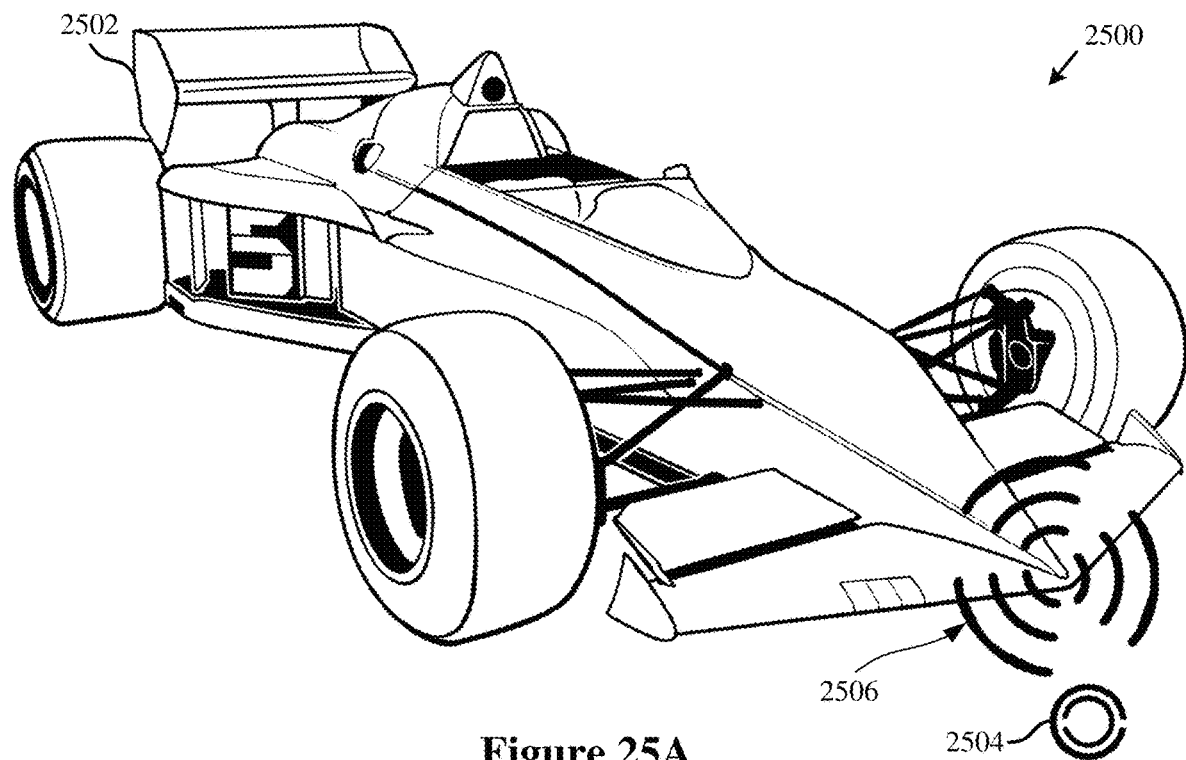
FIG. 25A provides a depiction of interaction between a vehicle and split ring resonators disposed in roadway asphalt and/or on the surface of a road, in accordance with one embodiment.

FIG. 25A provides a depiction 2500 of interaction between a vehicle and split ring resonators disposed in roadway asphalt and/or on the surface of a road, in accordance with one embodiment. As an option, the depiction 2500 may be implemented in the context of any one or more of the embodiments set forth in any previous and/or subsequent figure(s) and/or description thereof. Of course, however, the depiction 2500 may be implemented in the context of any desired environment. Further, the aforementioned definitions may equally apply to the description below.

As shown, the depiction 2500 may include a vehicle 2502, split ring resonators 2504 located in and/or on a road surface, and road surface to vehicle interaction 2506. In one embodiment, the depiction 2500 may be used to determine tire stiction (and/or rolling friction). For example, maintaining static contact with the road enables control of the vehicle (whereas losing static contract with the road can lead to lost of control of the vehicle). The split ring resonators 2504 may be used to measure tire (and/or interfacial) stiction (as a function of tire tread thickness). The process for determining tire stiction is explained in greater detail below with reference to FIG. 27.

Figure 25B:
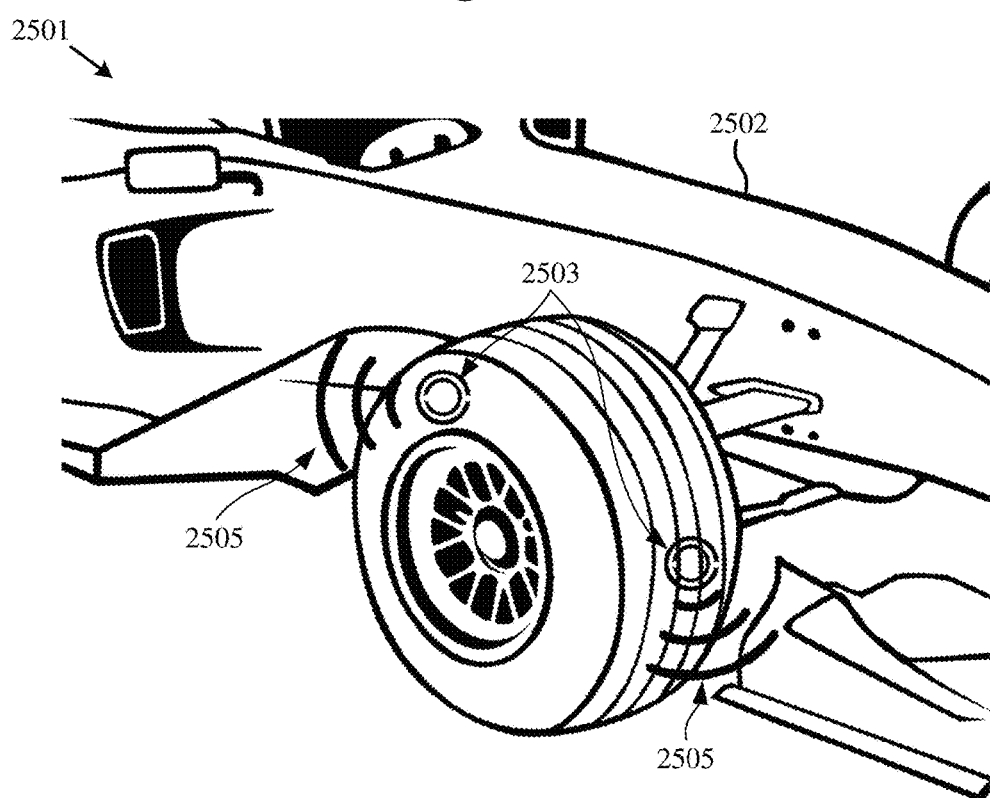
FIG. 25B provides a depiction of how split ring resonators disposed within or on a tire can be used to measure tire stiction, in accordance with one embodiment.

FIG. 25B provides a depiction of how split ring resonators disposed within or on a tire can be used to measure tire stiction, in accordance with one embodiment. As an option, the depiction 2500 may be implemented in the context of any one or more of the embodiments set forth in any previous and/or subsequent figure(s) and/or description thereof. Of course, however, the depiction 2500 may be implemented in the context of any desired environment. Further, the aforementioned definitions may equally apply to the description below.

As shown, the depiction 2501 may include the vehicle 2502, split ring resonators 2503 located in and/or on a tire, and tire interaction 2505. In one embodiment, the depiction 2501 may be used to determine tire stiction (and/or rolling friction). For example, the split ring resonators 2503 located in and/or on a tire may be used to measure tire (and/or interfacial) stiction (as a function of tire tread thickness).

In various embodiments, the split ring resonators 2504 located in and/or on a road surface, and the split ring resonators 2503 located in and/or on a tire may be used to measure a tire's actual stiction to the surface of the road, as well as measure a tire's actual thickness on the surface of the road. Such measurements may occur in real-time, even while the vehicle 2502 is being operated. In this manner, tire stiction may be measured continuously (or near continuously) with high accuracy, given the fact that the split ring resonators 2504 and 2503 do not rely on electronics (which are more prone to failure and other mechanical issues).

As an example, with the car racing industry, while the vehicle 2502 is being driven, split ring resonators (located in and/or on the car, such as the tire, and/or in and/or on the road) may provide real-time data to drivers and pit crews of real-time permittivity relating to tire stiction. Such real-time data may allow for immediate feedback to how the tire is responding and interacting with the surface of the road, which in turn, may allow the driver and pit crew to adjust and fine-tune the vehicle (e.g. tire tread type, power to tires, wind shield, wing, spoiler, etc.) to allow for greater tire stiction (to maximize control and performance of the vehicle, at a minimum). Of course, any other fine-tuning of the vehicle may be performed to ensure tire stiction.

In one embodiment, the split ring resonators 2504 and 2503 may be low-cost sensor due to the fact that it does not rely on electronics for function. As such, the split ring resonators 2504 and 2503 may not only improve real-time data gathering (at higher accuracy), but at a lower cost than current alternatives.

Figure 26:
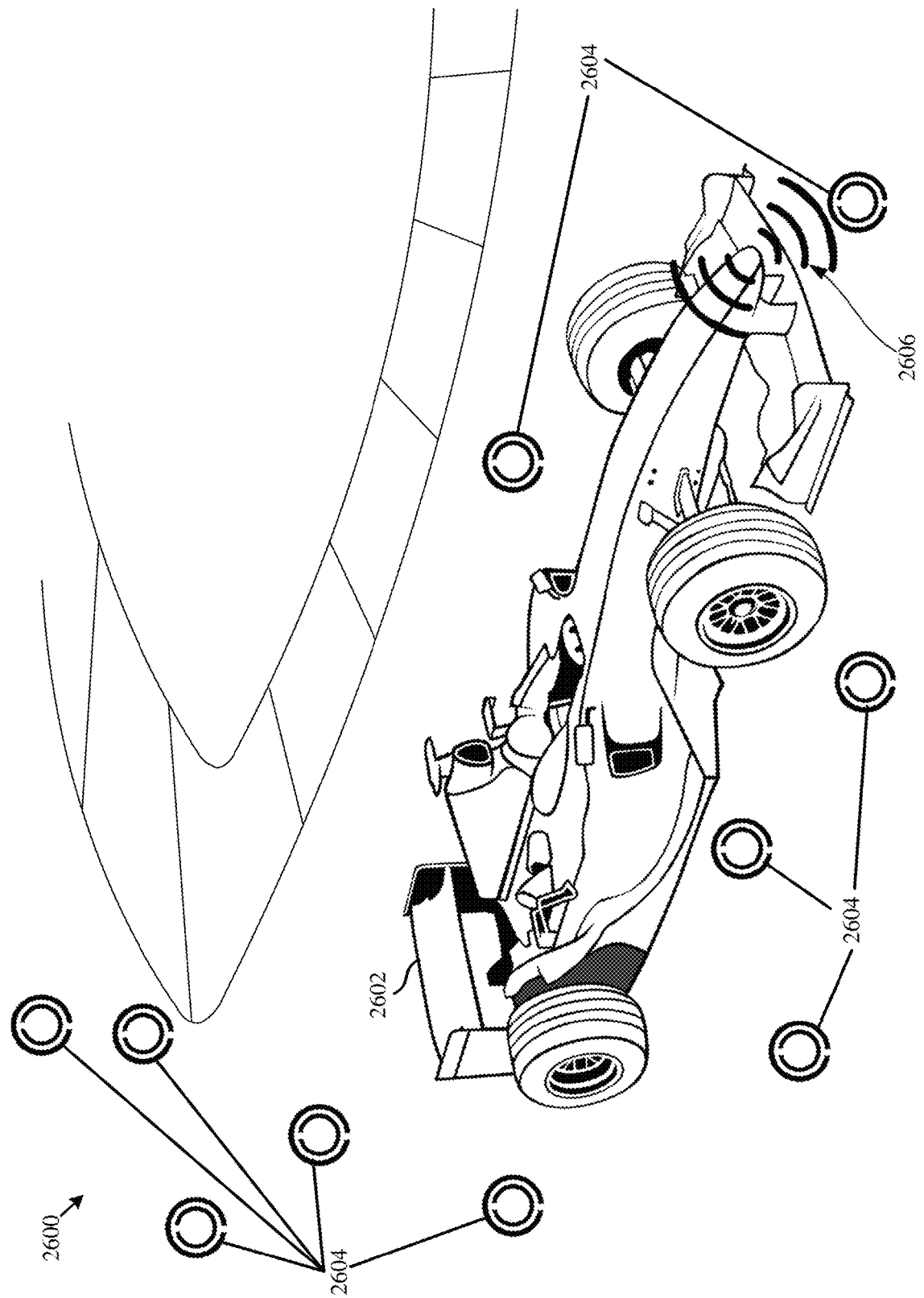
FIG. 26 depicts placement of split ring resonators disposed in roadway asphalt and/or on the surface of a road, in accordance with one embodiment.

FIG. 26 depicts placement 2600 of split ring resonators disposed in roadway asphalt and/or on the surface of a road, in accordance with one embodiment. As an option, the placement 2600 may be implemented in the context of any one or more of the embodiments set forth in any previous and/or subsequent figure(s) and/or description thereof. Of course, however, the placement 2600 may be implemented in the context of any desired environment. Further, the aforementioned definitions may equally apply to the description below.

As shown, the placement 2600 includes a vehicle 2602, split ring resonators 2604, and vehicle interaction 2606. The location of the split ring resonators 2604 (as shown within FIG. 26) is arbitrary. The key take-away of the location of such split ring resonators 2604 is that they may be placed anywhere in or on the surface of the road. In one embodiment, FIG. 26 may apply to a race car track, which may necessitate a greater number of split ring resonators 2604 (for increased data gathering and performance fine-tuning). In contrast, in other applications, such as on a normal highway or thoroughfare, the location of split ring resonators 2604 may be spaced at a greater amount (as fine tuning of performance may not be needed).

As discussed herein, the split ring resonators 2604 may be used to collect data in relation to tire stiction. Such data may be used, in turn, to modify parameters associated with the car. Additionally, such data may be used for safety (of the vehicle and/or of the road). For example, if the split ring resonators 2604 determined that real-time stiction levels have reduced (indicating a loss of traction), traffic advisories may immediately alert other drivers of hazardous road conditions (and likewise decrease the speed limit in and/or around the area where loss of traction was detected). In this manner, the split ring resonators 2604 may be used for traffic management and/or safety.

Further, split ring resonators, such as those located in and/or a tire (such as the split ring resonators 2503) may be used as an alternative to conventional anti-lock braking systems (which typically rely on wheel speed sensors and vehicle speed sensors to determine if the tire has stopped turning). The split ring resonators 2503 may provide more accurate data with less latency (between time of detecting to time of reporting out to a control module, such as millisecond). Further, once again, because the split ring resonators 2503 do not rely on electronics to function (contrary to conventional sensor systems), they would be less prone to error and failure.

In another embodiment, the split ring resonators 2604 may be used to determine driver capability and/or track driver performance. For example, if an overenthusiastic driver accelerates rapidly, or an aggressive driver brakes forcefully, such data may be used to create a driver profile (of driver performance). For drivers that are training (and need objective data feedback), such data may be used to assist the driver in training (to learn to drive in a more pleasant manner). Further, such data may be tied to an auto-insurance carrier, where preferential rates may be associated with less aggressive driving historical tendencies.

In this manner, the split ring resonators 2604 may be used in a variety of scenarios and ways such that measuring tire stiction may be used not only to better control the vehicle (ensure traction between the vehicle and the surface of the road), but based on such data gathered, may be used for safety, driver training, insurance carrier rates, etc.

Figure 27:
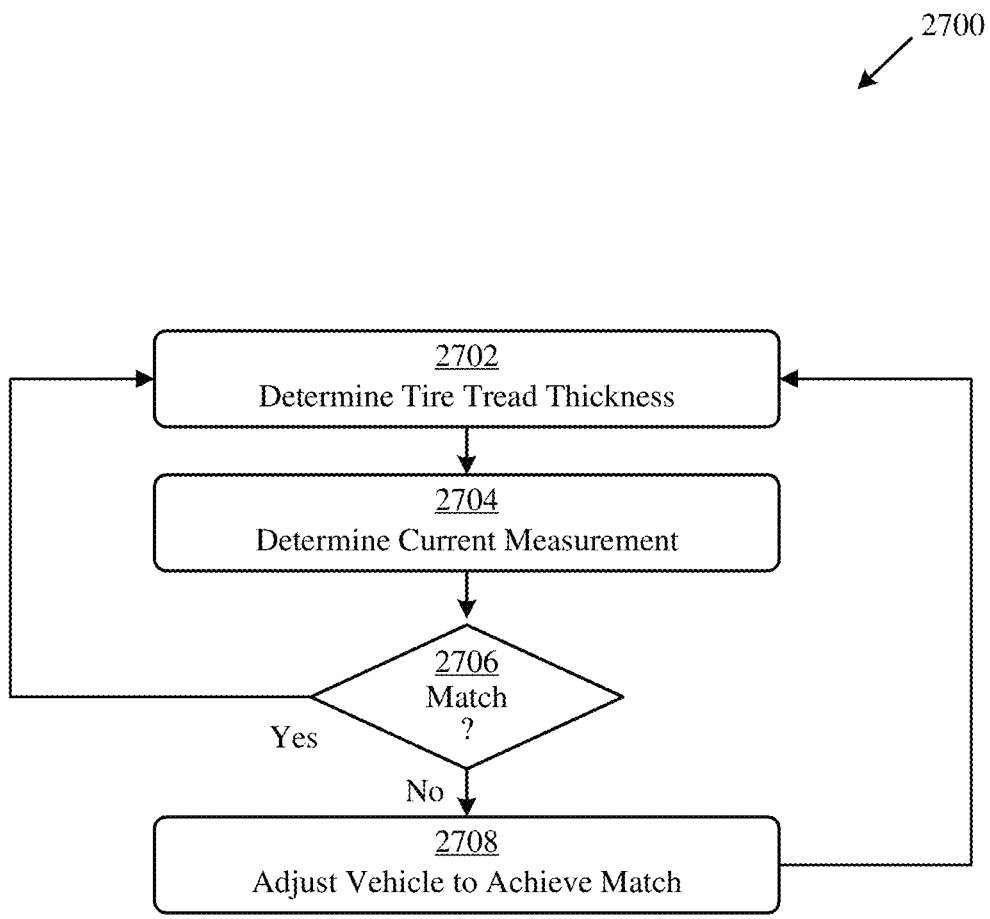
FIG. 27 is a flow chart representing the process to determine tire stiction, in accordance with one embodiment.

FIG. 27 is a flow chart 2700 representing the process to determine tire stiction, in accordance with one embodiment. As an option, the flow chart 2700 may be implemented in the context of any one or more of the embodiments set forth in any previous and/or subsequent figure(s) and/or description thereof. Of course, however, the flow chart 2700 may be implemented in the context of any desired environment. Further, the aforementioned definitions may equally apply to the description below.

As shown, the flow chart 2700 begins with determining tire tread thickness (step 2702). Next, a current measurement is determined (step 2704). For example, a current measurement may include a deformation of a split-ring resonator at the point that the tire meets the road. Such deformation may be measured (in the form of a frequency shift), and the ensemble effect (things associated with and/or effected by the action causing the deformation) may track a permittivity of the surroundings, including but not limited to water, tar, blacktop (asphalt), concrete, etc. If the current measurement is a match with a baseline measurement (per decision 2706), then the method returns back to step 2702 to determine tire tread thickness, and step 204 to determine refractive index. When the refractive index is not a match (per decision 2706), then the method 2700 proceeds to step 2708 and the vehicle is adjusted to achieve a match.

In one embodiment, the refractive index may relate to measuring reflectivity (which may use the refractive index) for each tire layer and determining the permittivity of each tire layer. When the tire stiction is high, the tread thickness (and hence the reflectivity and permittivity) will increase proportionally. If tire stiction has been lost (i.e. traction has been lost), a mismatch (i.e. a non proportional reflectivity and permittivity) will exist with respect to the tire tread thickness. In this manner, tire tread thickness can be used to determine tire stiction as a function of refractive index (and hence reflectivity), and permittivity.

Additionally, a refractive index mismatch in compounded materials (particularly in tires, asphalt, plastics, rubber, metal alloy, etc.) may be used to detect variations of scattering parameters (or S-parameters, elements of a scattering matrix, etc.) for stiction levels. Such scattering parameters may relate to stimulating (via wireless signals) one or more split ring resonators located in or on a tire (or a vehicle, a vehicle component, a surface of a road, etc.). Such one or more split ring resonators may be used to obtain an immediate read of tire tread thickness (which in turn may be used to determine tire stiction, as described hereinabove).

Further, use of the split ring resonators (as a basis to determine tire stiction) provides a very economical small form factor solution that does not rely on electronics to function. Such factors, therefore, in combination with high accuracy with low latency, make split ring resonators a viable solution for a plethora of applications.

Figure 28:
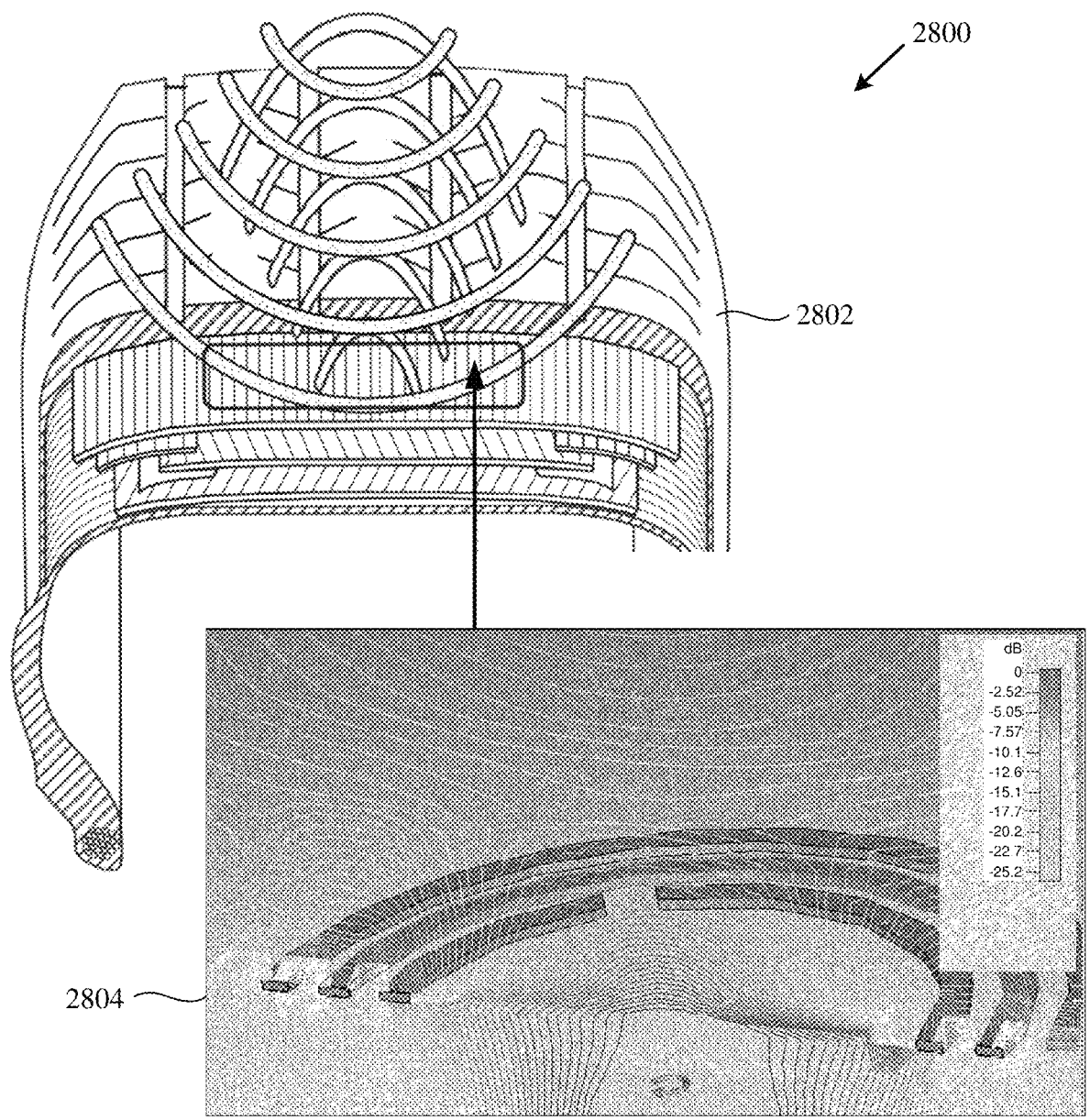
FIG. 28 shows a correlation between measured frequencies and tread thickness, in accordance with one embodiment.

FIG. 28 shows a correlation 2800 between measured frequencies and tread thickness, in accordance with one embodiment. As an option, the correlation 2800 may be implemented in the context of any one or more of the embodiments set forth in any previous and/or subsequent figure(s) and/or description thereof. Of course, however, the correlation 2800 may be implemented in the context of any desired environment. Further, the aforementioned definitions may equally apply to the description below.

As shown, a tire 2802 includes multiple one or more tire belt plies (in a manner consistent with the tire 1002). The carbon-based microstructures incorporated within the tire 2802 may includes split ring resonators. Such split ring resonators may have a natural resonance (such as approximately 1.0 GHz), and in response to external conditions (such as driving the tire), the tire 2802 may deform and/or otherwise be altered. The deformation and/or alteration within the tire 2802 may be measured (in terms of a response attenuation) as a frequency response of the split ring resonators.

The frequency response is shown in model 2804. In one embodiment, the model 2804 may correlate with impedance spectroscopy energy to and from a tire. Such energy (measured in terms of frequency) may be used to determine tire stiction. For example, tire thickness of the tire 2802 may alter, such as between a natural state and an in-use driving state. During in-use driving state, the tire 2802 may have stiction (and traction) with the surface of a road. Such a state (of having tire stiction) may be correlated with a matching frequency model (shown, in one example, in the model 2804). However, when tire stiction is lost (i.e. a lost of tire traction occurs), the corresponding model 2804 may no longer match. For example, when stiction is lost, then permittivity may decrease rapidly. A calibration of how stiction works under different conditions may allow comparison of then-current readings (and changes in readings) to be compared to the calibration curves.

In this manner, impedance spectroscopy may be used to measure frequencies samples of split ring resonators found in or on a tire. It is to be appreciated that although the correlation 2800 is shown with respect to one embodiment of a tire, other applications (such as in relation to car components, car skin, road surface conditions, metal fatigue conditions, construction material, etc.) are envisioned in a similar manner.

As such, split ring resonators may be disposed in and/or on a material (including internal components such as wiring or external components such as road asphalt) and can be used to provide information pertaining to the material in and/or on which it is located.

Figure 29:
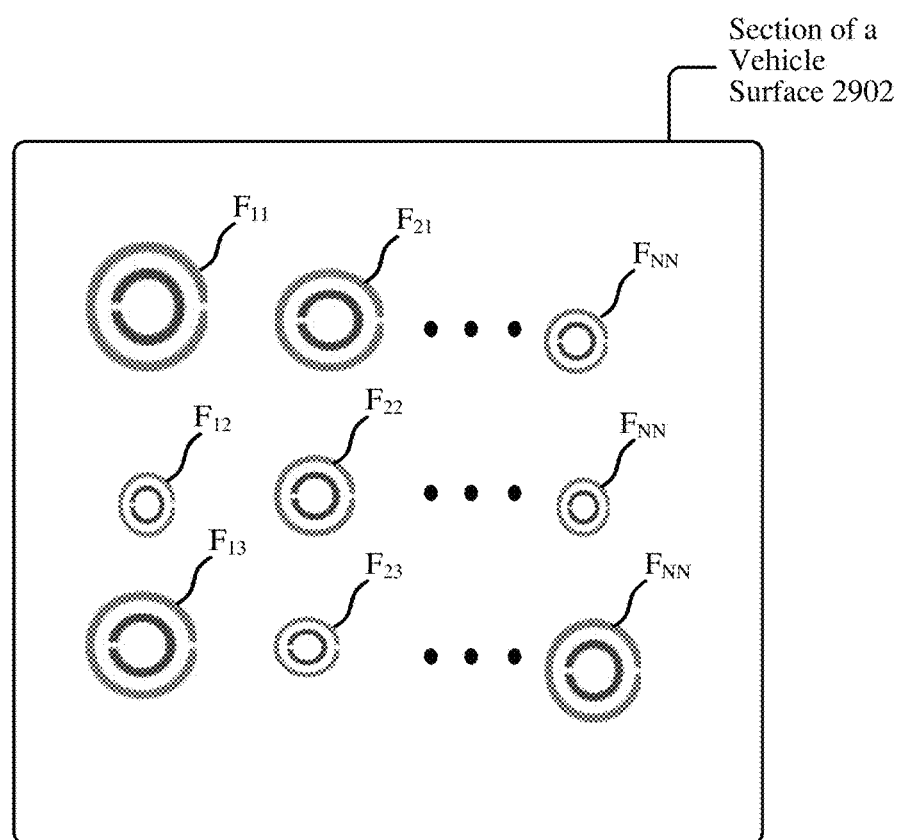
FIG. 29 shows a section of a vehicle surface where an array of individually configured split ring resonators are disposed, in accordance with one embodiment.

FIG. 29 shows a section 2900 of a vehicle surface where an array of individually configured split ring resonators are disposed, in accordance with one embodiment. As an option, the section 2900 may be implemented in the context of any one or more of the embodiments set forth in any previous and/or subsequent figure(s) and/or description thereof. Of course, however, the section 2900 may be implemented in the context of any desired environment. Further, the aforementioned definitions may equally apply to the description below.

As shown, the section of a vehicle surface 2902 may be subjected to stresses and accompanying deformations during operation of the vehicle, and split ring resonators (split ring resonators) (shown in FIG. 29 as $F_{11}$, $F_{12}$, $F_{13}$, $F_{21}$, $F_{22}$, $F_{23}$, up and to $F_{NN}$) can be used to detect possible changes within the material under such environmental stresses and deformations. The split ring resonators may be printed or applied onto the spongy material of the vehicle (e.g. vinyl wrap of vehicle), and/or the combination of the resonators and spongy material may be placed all over a vehicle or section of a vehicle surface of interest.

For example, the split ring resonators on the front bumper may undergo air pressure changes when the vehicle is in operation (such as, during forward motion, thus creating a downward force on this section of the vehicle). Under the forces of the air pressure, the material that composes the surface can deform slightly and, in accordance with the phenomenon described as pertains to FIG. 24B1 and FIG. 24B2, demonstrate a change in resonant frequency of the material proportionate to the degree of change or deformation of the material. While all the split ring resonators will be resonating simultaneously, a difference in one of the split ring resonators or multiple of split ring resonators can be determined due to a change in the pitch that can be detected by a stimulus/response comparator, such as may be implement in whole or in part by a horn/receiver or similar device.

An array or matrix of split ring resonators over the vehicle surface 2902 and the constituents are configured in such a way that the frequency responses of any of the constituent members of the array do not collide with the neighboring split ring resonators. One such configuration is shown and described as pertains to FIG. 30.

Figure 30:
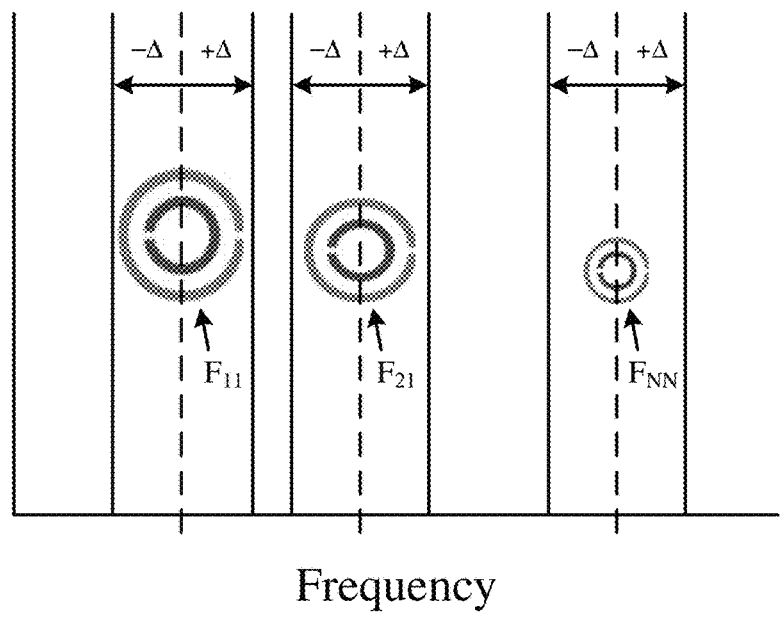
FIG. 30 depicts a configuration of the split ring resonators in a frequency bin, in accordance with one embodiment.

FIG. 30 depicts a configuration 3000 of the split ring resonators in a frequency bin, in accordance with one embodiment. As an option, the configuration 3000 may be implemented in the context of any one or more of the embodiments set forth in any previous and/or subsequent figure(s) and/or description thereof. Of course, however, the configuration 3000 may be implemented in the context of any desired environment. Further, the aforementioned definitions may equally apply to the description below.

As shown, the split ring resonators (shown as $F_{11}$, $F_{21}$, up and to $F_{NN}$) may each reside in frequency bins. As the surface containing the split ring resonators undergoes deformation by deflection, the positive deflection or negative deflection can change physical characteristics of the split ring resonator, thereby changing the inherent center frequency of the member. The variation in the frequency response of a member is represented in FIG. 30 by the Δ symbols. This change in the resonant frequency, even at its maximum, may not collide with the neighboring split ring resonators, as shown. Measuring the cyclic deflection over time facilitates detection of cyclical stress (e.g. buffeting) as it occurs on the vehicle surface. One such example for detecting time-based deflection variations is shown and described as pertains to FIG. 31.

Figure 31:
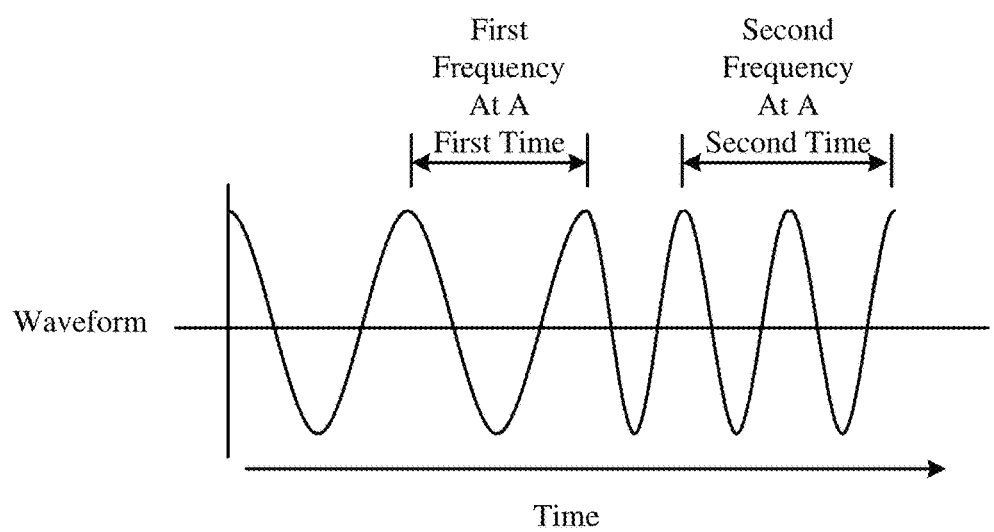
FIG. 31 shows a chart of detection of time-based variation of deflection, as indicated by time-based variation of the resonant frequency, in accordance with one embodiment.

FIG. 31 shows a chart 3100 of detection of time-based variation of deflection, as indicated by time-based variation of the resonant frequency, in accordance with one embodiment. As an option, the chart 3100 may be implemented in the context of any one or more of the embodiments set forth in any previous and/or subsequent figure(s) and/or description thereof. Of course, however, the chart 3100 may be implemented in the context of any desired environment. Further, the aforementioned definitions may equally apply to the description below.

As shown, the chart 3100 shows detection of time-based variations of deflection through ongoing measurement of cyclic deflection of the split ring resonators, which may allow for performing analysis of pressures over a given control surface of the vehicle. For example, the foregoing techniques of disposing an array of split ring resonators across a control surface vehicle, in combination with the technique of analyzing the combined return from individual split ring resonators of that control surface, may allow identification of regions of the surface that are experiencing cyclical stresses (e.g. buffeting). In some cases, the physical property changes are indicative of relatively high frequency, dynamically changing property variations (e.g., vibration). Capturing a series of a dynamically-taken series of responses/signatures, and comparing such to a previously-taken series of calibration responses/signatures may facilitate dynamic non-destructive testing. Differences that are apparent between the two sets signatures may be correlated to physical property changes, such as cyclical deformations (e.g. buffeting).

Figure 32:
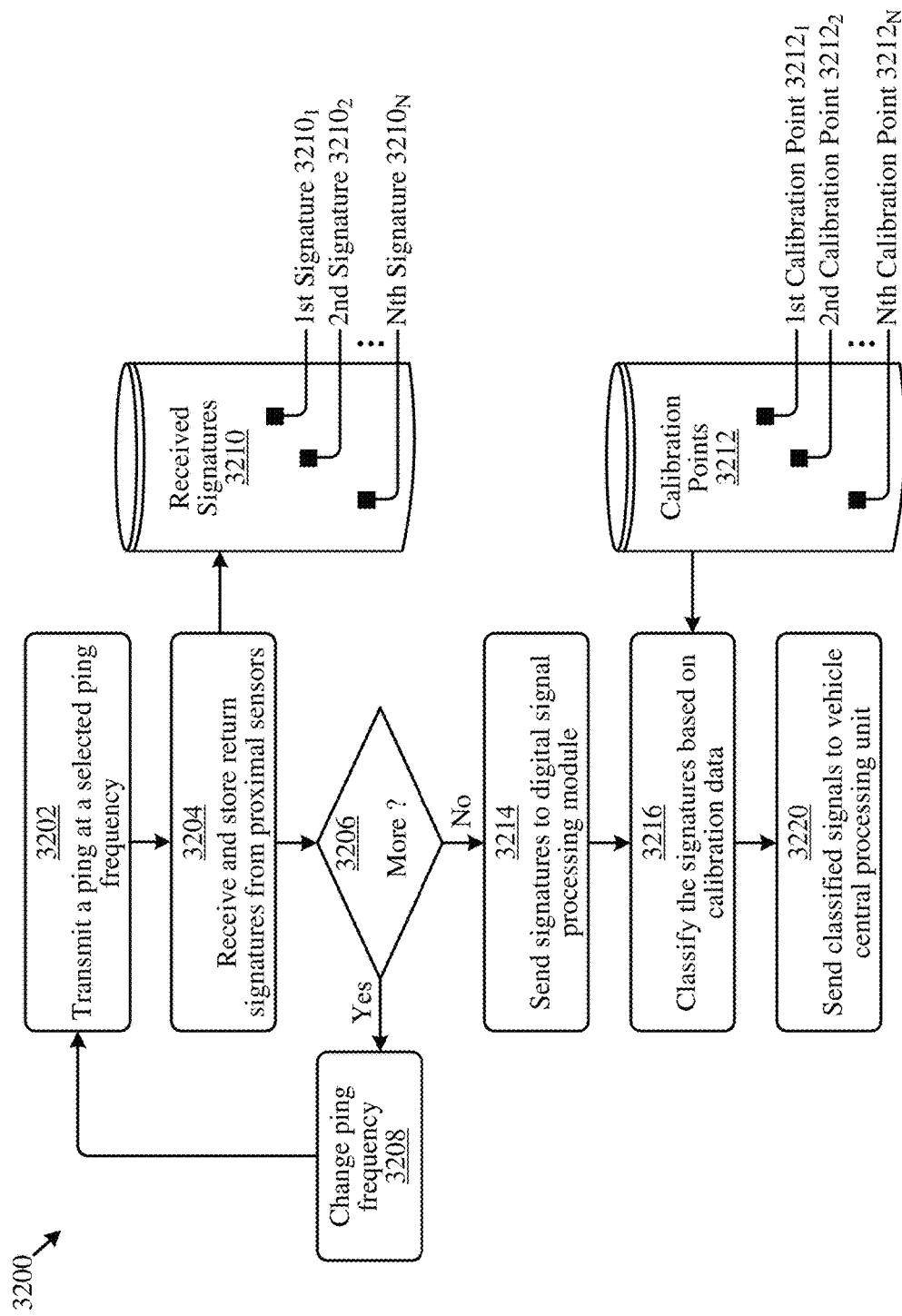
FIG. 32 depicts a signature classification system that processes signals received from sensors formed of carbon-containing tuned resonance materials, in accordance with one embodiment.

FIG. 32 depicts a signature classification system 3200 that processes signals received from sensors formed of carbon-containing tuned resonance materials, in accordance with one embodiment. As an option, the signature classification system 3200 may be implemented in the context of any one or more of the embodiments set forth in any previous and/or subsequent figure(s) and/or description thereof. Of course, however, the signature classification system 3200 may be implemented in the context of any desired environment. Further, the aforementioned definitions may equally apply to the description below.

In one embodiment, the signature classification system 3200 can be implemented in any physical environment. More specifically, the signature classification system 3200 depicts one example of how to classify signals (such as, signatures). As shown, a ping signal of a selected ping frequency is transmitted at operation 3202. The ping signal generation mechanism and the ping transmission mechanism can be performed by any known techniques. For example, a transmitter module can generate a selected frequency of 3 GHZ, and radiate that signal using a horn or multiple horns and multiple receiving antennae. The designs and locations of the tuned antennae can correspond to any tuned antenna geometry, material and/or location such that the strength of the ping is sufficient to induce (RF) resonance in proximate sensors. In some embodiments, several tuned antennae are disposed upon or within structural members that are in proximity to corresponding sensors (such as mounted on and/or within any one or more of the wheel wells or a vehicle). As such, when a proximal surface sensor is stimulated by a ping, it may resonate back with a signature. At operation 3204, that signature can be received and stored in a dataset comprising received signatures 3210. A sequence of transmission of a ping, followed by reception of a signature, can be repeated in a loop so as to capture a set of calibration signals, which in turn may be stored as calibration points 3212.

The ping frequency can be changed (at operation 3208) in iterative passes through decision 3206. Accordingly, as operation 3202 is performed in the loop (via decision 3206), operation 3204 can receive and then store the signatures 3210 (including a first signature 32101, a second signature 32102, up to an Nth signature 3210N). The number of iterations may be controlled by decision 3206. When the "No" branch of decision 3206 is taken (such as, when there are no further additional pings to transmit in the iteration loop), then the received signatures can be provided (operation 3214) to a digital signal processing module. The digital signal processing module classifies the signatures (operation 3216) against a set of calibration points 3212. The calibrations points can be configured to correspond to particular ping frequencies. For example, calibration points 3212 can include a first calibration point 32121 that can correspond to a first ping and first returned signature near 3 GHZ, a second calibration point 32122 that can correspond to a second ping and second returned signature near 2 GHz, and so on for any integer value "N" calibration points.

At operation 3220, classified signals are sent to a vehicle central processing unit. The classified signals can be relayed by the vehicle central processing unit (such as vehicle central processing unit 116) to an upstream repository (such as upstream components 113) that hosts a computerized database configured to host and/or run machine learning algorithms. Accordingly, a vast amount of stimulus related to signals, classified signals, and signal responses can be captured for subsequent data aggregation and processing. A database of the machine learning subsystem (e.g., a training model) can be formed or "trained" by providing a set of sensed measurements which in turn are correlated to conditions related to vehicular performance. Once the database has been computationally prepared, or "trained", then during the operation of the vehicle, the measured deflection (such as, air pressure) of a particular portion of an airfoil component can be compared to the calibration points, and the comparison yields a delta in frequency that corresponds to a variation in deflection which in turn corresponds to a particular air pressure. Other potential conditions or diagnoses can be determined by the machine learning system. The conditions and/or diagnoses and/or supporting data can be made available to instrumentation in the vehicle to complete a feedback loop. In some cases, instrumentation in the vehicle provides visualizations that can be acted upon (such as, by a driver or by an engineer).

Figure 33:
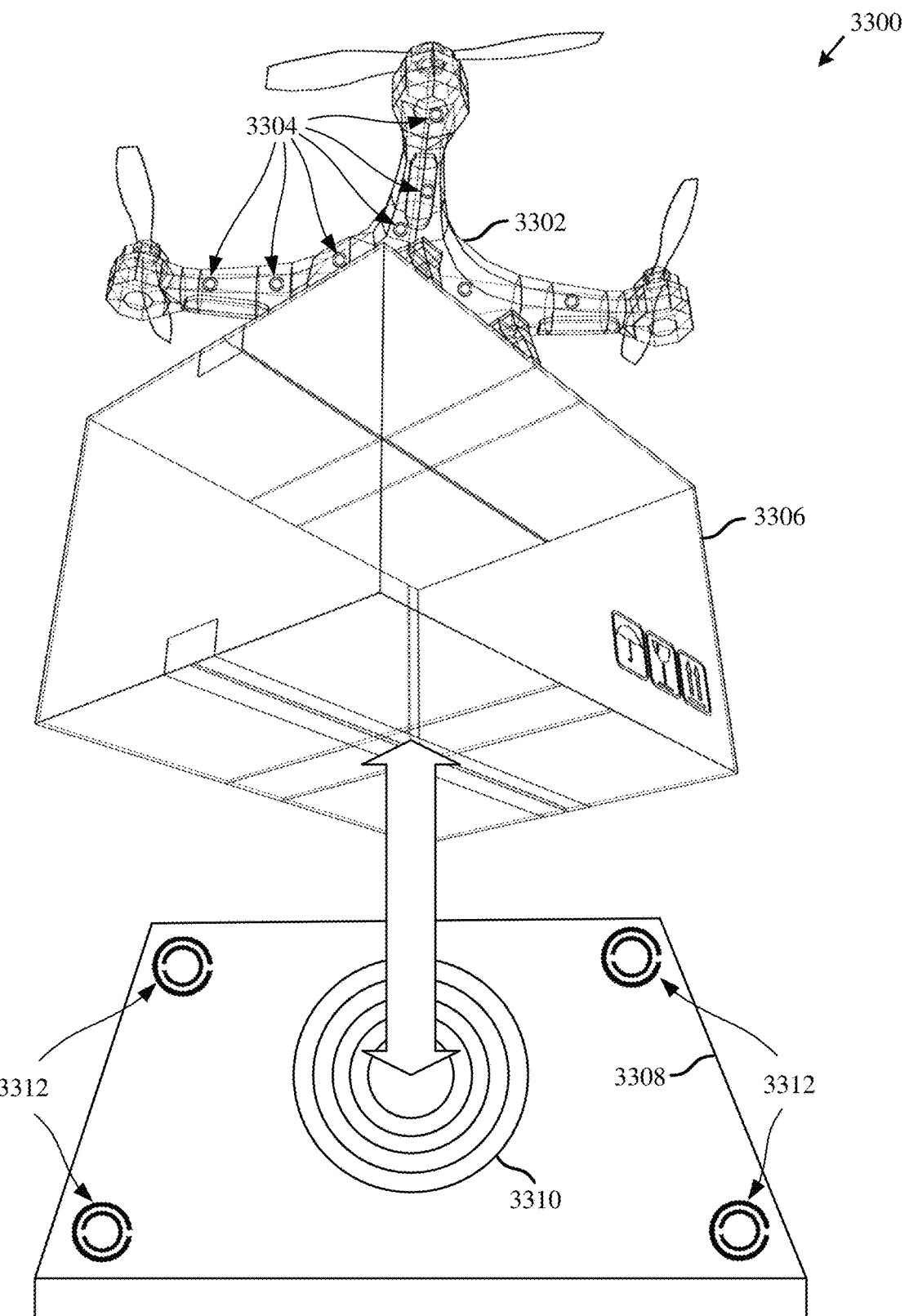
FIG. 33 shows a depiction of split ring resonators disposed in and/or on a drone, and/or a drone platform, in accordance with one embodiment.

FIG. 33 shows a depiction 3300 of split ring resonators disposed in and/or on a drone, and/or a drone platform, in accordance with one embodiment. As an option, the depiction 3300 may be implemented in the context of any one or more of the embodiments set forth in any previous and/or subsequent figure(s) and/or description thereof. Of course, however, the depiction 3300 may be implemented in the context of any desired environment. Further, the aforementioned definitions may equally apply to the description below.

As shown, a drone 3302 may include one or more split ring resonators 3304. In one embodiment, the drone 3302 may be used to transport a package 3306. Of course, it is to be appreciated that the drone 3302 may be configured for transport of other items (such as a camera, weather sensing instruments, animals, medical supplies, food, goods, cargo, payloads, etc.). Additionally, in other embodiments, the drone 3302 may be configured for military or tactical purposes (including configured as an unmanned combat aerial vehicle). Further, as described hereinbelow, the drone 3302 may be configured as a passenger drone, an unmanned aerial vehicle (UAV), and/or an autonomous aerial vehicle (AAV). In one embodiment, the drone 3302 may be capable of vertical take-off and landing (VTOL) and/or electric vertical take-off and landing (eVTOL).

Additionally, a drone landing pad 3308 is provided, which may include one or more split ring resonators 3312. A target location 3310 to align the drone 3302 and the drone landing pad 3308 is also provided.

In various embodiments, the one or more split ring resonators 3304 may be used to facilitate real-time sensing of a physical state of the drone 3302 and/or environmental conditions external to the drone 3302. Such real-time sensing may occur millisecond-by-millisecond, and may be used to detect structural changes within the drone 3302 before it becomes a problem, and/or to alter a course of the drone 3302 to reach an intended destination (such as the target location 3310). For example, in one embodiment, should a propeller on the drone 3304 suffer material fatigue (and be prone to break), a split ring resonator located on the propeller may determine a structural change (in terms of a change of frequency). Additionally, any element of the drone 3302 may be monitored such that any structural change can be detected before the negative effects of the change are observed.

In another embodiment, the drone 3302 may initiate a takeoff or landing on the drone landing pad 3308. Real-time sensing of the state of the drone 3302 (by the one or more split ring resonators 3304) may protect both the drone 3302 and/or the drone landing pad 3308. In this manner, the one or more split ring resonators 3304 may detect changes before and/or after takeoff. It is to be noted that the one or more split ring resonators 3312 on the drone landing pad 3308 may additionally be used to sense both a state of the landing pad 3308 and/or a position of the drone 3302 (regardless of whether the drone 3302 has the one or more split ring resonators 3304). Further, when landing, the one or more split ring resonators 3304 on the drone 3302 or the one or more split ring resonators 3312 on the drone landing pad 3308 may be used to determine, in real-time, a pinpoint location of the drone 3302 as it approaches the drone landing pad 3308. In this manner, the one or more split ring resonators 3304 and/or 3312 may be used for precision landing capabilities.

The one or more split resonators 3312 of the drone landing pad 3308 may additionally be used to determine a state of the drone landing pad 3308 such that material fatigue and/or component failure can be detected before visually manifested.

In another scenario, after landing, a state of the drone 3302 may be assess by receiving health related data from the one or more split ring resonators 3304. For example, the drone 3302 may pass through a drone health system which may broadcast a wireless signal. Each of the one or more split ring resonators 3304 may provide a frequency response that may correspond with structure health (in terms of material fatigue and component failure) of the drone 3302. In this manner, the split ring resonators 3304 may be used to detect a state of health of the drone 3302 before, during, and after takeoff and/or landing. The state of the health may be used to alert and/or be communicated to a human/user and/or an autonomous system.

In this manner, an autonomous system of heath checking for a fleet of drone may be achieved. When a drone arrives at a landing location, it may be inspected and assessed. If a split ring resonator indicates a structural issue with the drone, it may be further inspected (e.g. manual inspection, etc.) and/or repaired. If no issues are found with the drone, it may receive a "good health" designation and be ready to be sent out again. In this manner, continual management of the drones may be achieved with respect to health integrity of the fleet, which in turn, may satisfy legal and social constraints on use of drones (particularly within consumer air space).

Figure 34:
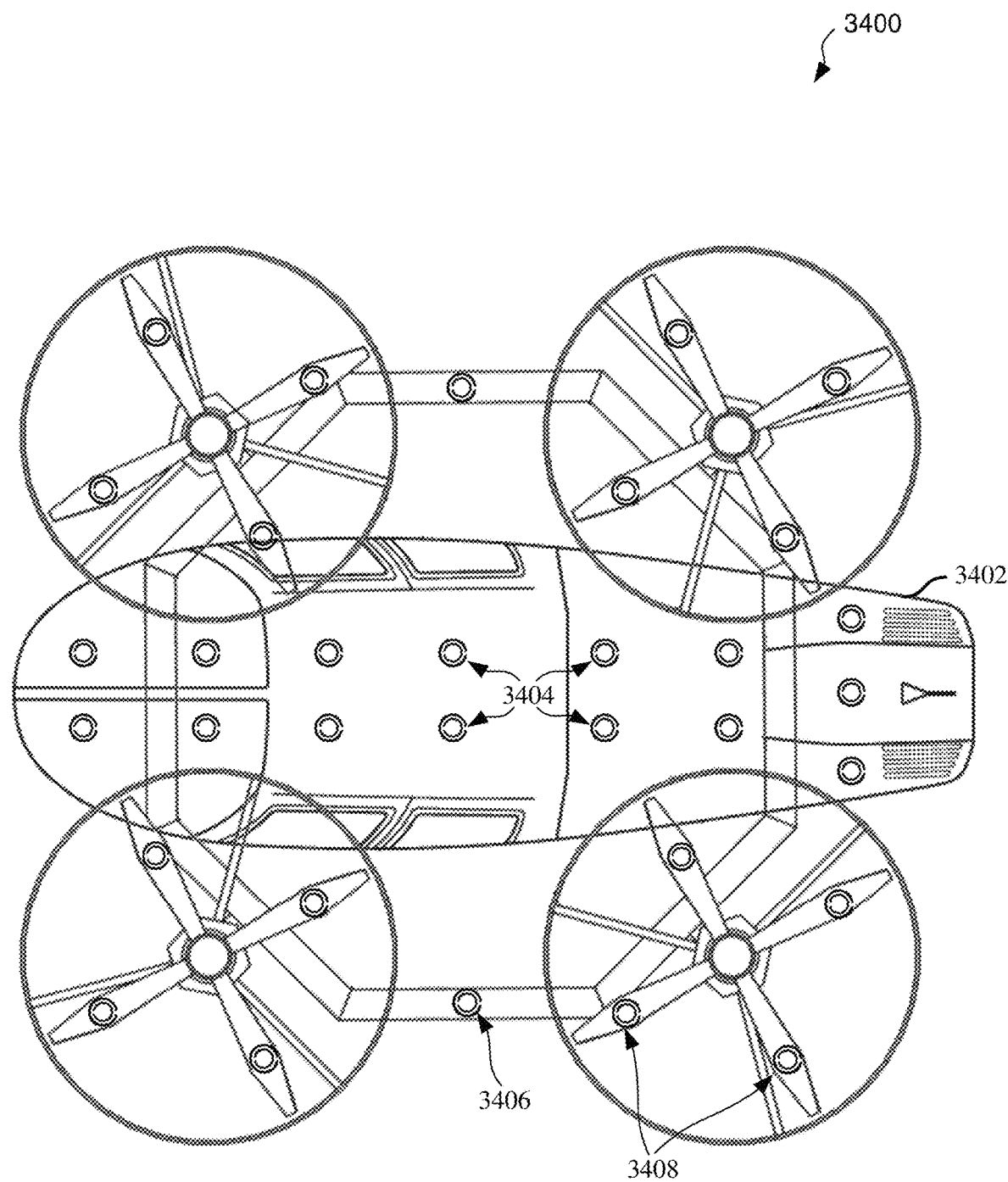
FIG. 34 shows a depiction of split ring resonators disposed in and/or on an aerial vehicle, in accordance with one embodiment.

FIG. 34 shows a depiction 3400 of split ring resonators disposed in and/or on an aerial vehicle, in accordance with one embodiment. As an option, the depiction 3400 may be implemented in the context of any one or more of the embodiments set forth in any previous and/or subsequent figure(s) and/or description thereof. Of course, however, the depiction 3400 may be implemented in the context of any desired environment. Further, the aforementioned definitions may equally apply to the description below.

As shown, an unmanned aerial vehicle (UAV) 3402 may include split ring resonators located on the aerial vehicle body 3404, structural components 3406, and/or propeller components 3408. Of course, it is to be appreciated that split ring resonators may be located in and/or on any and/or all components of the drone 3404.

In various embodiments, the split ring resonators (such as those located on the aerial vehicle body 3404, structural components 3406, and/or propeller components 3408) may be used to obtain real-time (with millisecond time granularity) measurements associated with the unmanned aerial vehicle 3402, including but not be limited to vibration, strain, dimensional and/or material property changes, pressure, and temperature.

For example, with respect to vibration, the split ring resonators may read vibrational frequency (from Hz level to 100s of KHz level). Additionally, in one embodiment, accelerometers and other noncontact displacement sensors may be used to measure low through high frequency vibration (e.g., from very low frequencies in the low hertz range such as in large bridge-like structures to higher vibrations such as are found in supersonic applications—up to 100s of kilohertz). With respect to strain, the split ring resonators may detect component flexion/torsion, as well as structural fatigue/failure. With respect to dimensional and/or material property changes, the split ring resonators may determine whether elastomer components (such as those found, for example, in tires, belts, hoses, etc.) need to be replaced (due to wear and aging). Further, dimensional and/or material property changes may be used to determine a distance to ground for landing (as described hereinabove FIG. 33). With respect to pressure, the split ring resonators may be used to detect air pressure, differential air pressure, and/or cyclical changes in air pressure. Additionally, with respect to temperature, the split ring resonators may detect surface and component internal temperatures.

As such, split ring resonators found in or on components through the unmanned aerial vehicle 3402 may be used to detect parametric measurements associated with a state of health of the unmanned aerial vehicle 3402. Further, more than one measurement may be simultaneously received. For example, in response to a wireless ping, each of the split ring resonators may provide a frequency response. Such frequency response may be calibrated, in one instance, to a measurement of pressure, whereas another frequency response may be calibrated, in another instance, to material property changes. As such, responses from all of the split ring resonators may be received, which in turn, may provide a simultaneous result of all sensor parameters associated with the unmanned aerial vehicle 3402.

Figure 35:
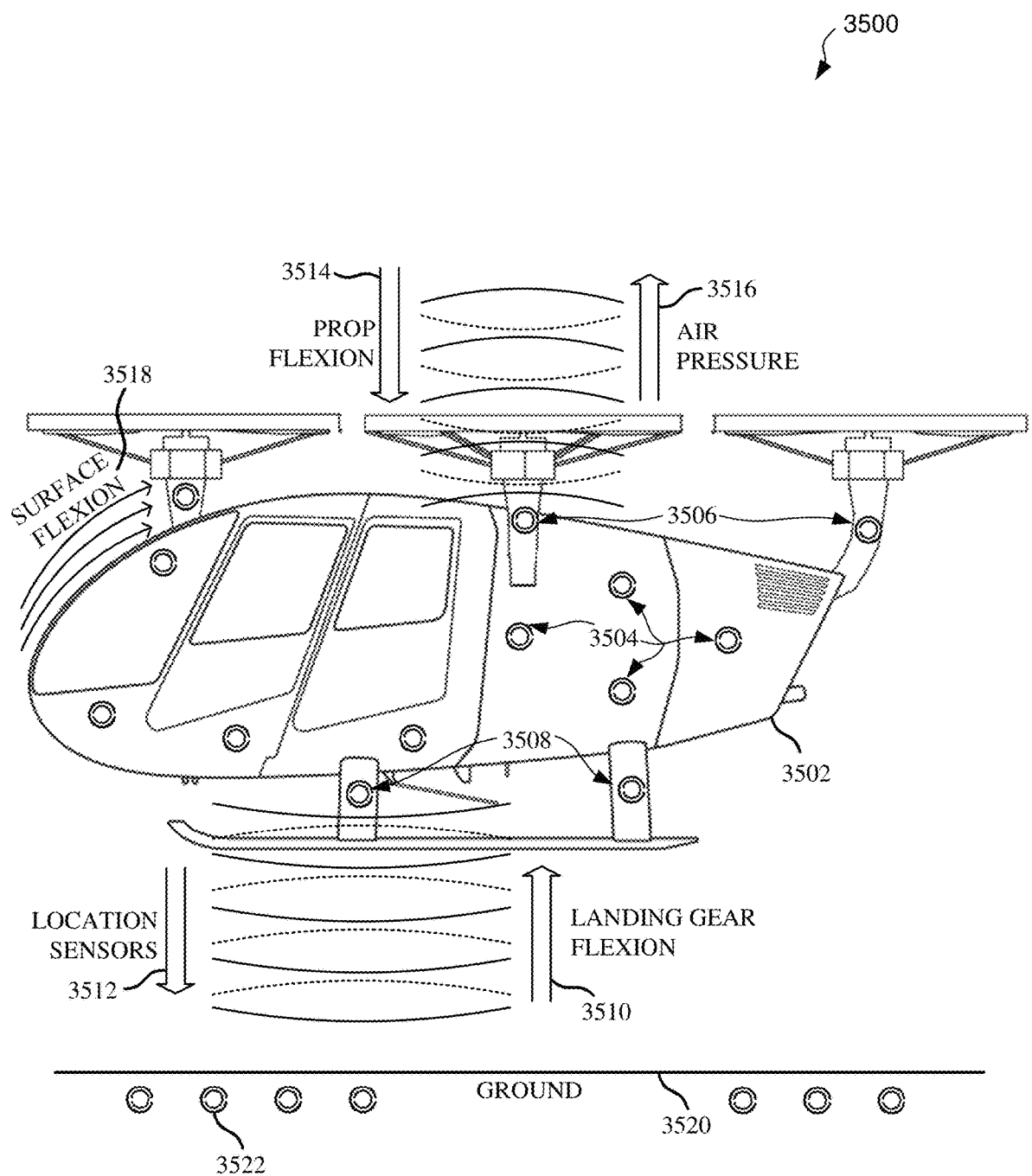
FIG. 35 shows a depiction of split ring resonators disposed in and/or on an aerial vehicle, as well as landing location sensors, in accordance with one embodiment.

FIG. 35 shows a depiction 3500 of split ring resonators disposed in and/or on an aerial vehicle, as well as landing location sensors, in accordance with one embodiment. As an option, the depiction 3500 may be implemented in the context of any one or more of the embodiments set forth in any previous and/or subsequent figure(s) and/or description thereof. Of course, however, the depiction 3500 may be implemented in the context of any desired environment. Further, the aforementioned definitions may equally apply to the description below.

As shown, an unmanned aerial vehicle 3502 may be capable of vertical take-off and/or landing (VTOL and/or eVTOL). It is to be appreciated that, in other embodiments, the unmanned aerial vehicle 3502 may be configured for other takeoff capabilities (e.g. conventional takeoff and landing, short takeoff and landing, etc.).

One or more split resonators may be found on the unmanned aerial vehicle 3502 including being located on the aerial vehicle body 3504, structural components 3506, and/or landing gear 3508. Of course, consistent with FIG. 34, the one or more split resonators may be located anywhere (and in any degree of quantity) on the unmanned aerial vehicle 3502, and may be used to provide sensor related information.

As an example, the split ring resonators located on the unmanned aerial vehicle 3502 may be distributed throughout the surface. Additionally, lightweight antennas may additionally be distributed throughout the unmanned aerial vehicle 3502. In one embodiment, the split ring resonators and antennas may be redundant (especially for mission-critical components, for safety constraints, etc.). Such split ring resonators may provide real-time simultaneous sensing (in milliseconds). Further, condition signatures may be associated with simultaneous feedback responses from the split ring resonators. For example, a condition signature may be associated with a component failure, an external condition (weather, flying pattern, etc.), etc. Further, the split ring resonators may be arranged to allow for triangulation positioning to assist with pinpoint landings (consistent with as described herein with respect to FIG. 33).

To that end, the split ring resonators may include location sensors 3512, may be used to calculate landing gear flexion 3510, surface flexion 3518, propeller flexion 3514, and/or air pressure 3516. As emphasized elsewhere, the split ring resonators may be used in any capacity in relation to takeoff, flight, landing, management, etc. of the unmanned aerial vehicle 3502, including but not limited to torsion, tire wear, air speed, air pressure, flexion of vehicle component, etc.

In one embodiment, the location sensors 3512 may operate to pinpoint a location for precise landing. Further, split ring resonators 3522 located in and/or on the surface of the ground 3520 may additionally be used to assist with achieving a precise landing.

Figure 36A:
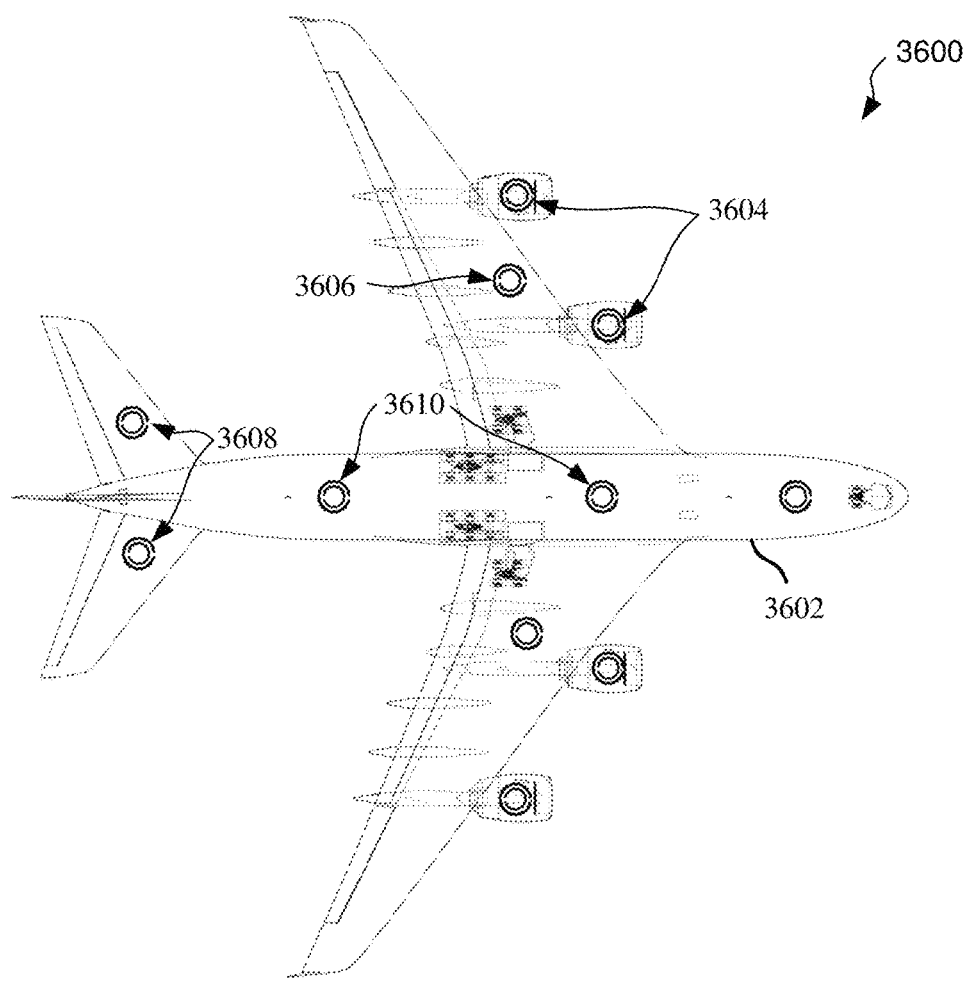
FIGS. 36A and 36B show two depictions of split ring resonators disposed in and/or on aircraft, in accordance with one embodiment.
Figure 36B:
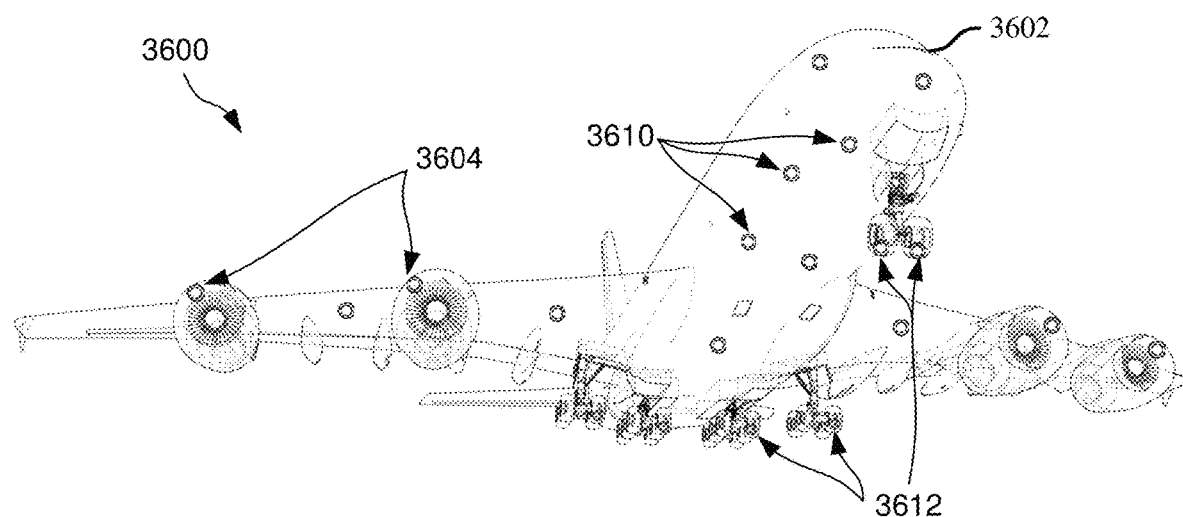

FIGS. 36A and 36B show two depictions 3600 of split ring resonators disposed in and/or on aircraft, in accordance with one embodiment. As an option, the two depictions 3600 may be implemented in the context of any one or more of the embodiments set forth in any previous and/or subsequent figure(s) and/or description thereof. Of course, however, the two depictions 3600 may be implemented in the context of any desired environment. Further, the aforementioned definitions may equally apply to the description below.

As shown, an aircraft 3602 includes one or more split ring resonators that are located in and/or on various locations of the aircraft 3602, including, but not limited to an engine 3604 (jet, propeller, etc.), a wing 3606, a horizontal stabilizer 3608, a fuselage 3610, and/or tires 3612. It is to be appreciated that any number of split ring resonators may be found on the aircraft 3602, and a purpose of the split ring resonator may differ. For example, split ring resonators located at the front of the aircraft 3602 may be used to gather external weather conditions (air pressure, temperature, wind speed, etc.), split ring resonators located on tires may be used to determine tread life and state, and/or split ring resonators located in the engine may be used to ensure safety and lack of material fatigue. In some embodiments, a condition signature may be created and correlated with known conditions (weather patterns, signs of material fatigue, etc.). Additionally, a frequency from a split ring resonator may be used for more than one condition signature simultaneously. For example, a split-ring resonator may be used for determining tread thickness, and may also be used for stiction measurements, hydroplaning detection, etc.

It is to be appreciated that although a commercial aircraft is shown in the two depictions 3600, any aircraft (commercial, military, personal, etc.) may be applicable. Additionally, use of split ring resonators in aircraft may provide continuous millisecond-by-millisecond changes before takeoff, continuously during flight, and during landing. Such changes may include structural parameter changes (e.g. fatigue thresholds, impending component failure, etc.), which in turn, may cause alerts to systems and personnel.

For example, triggering an alert may cause an aircraft to avoid aircraft, or to land safely before an impending failure event occurs.

Figure 37A:
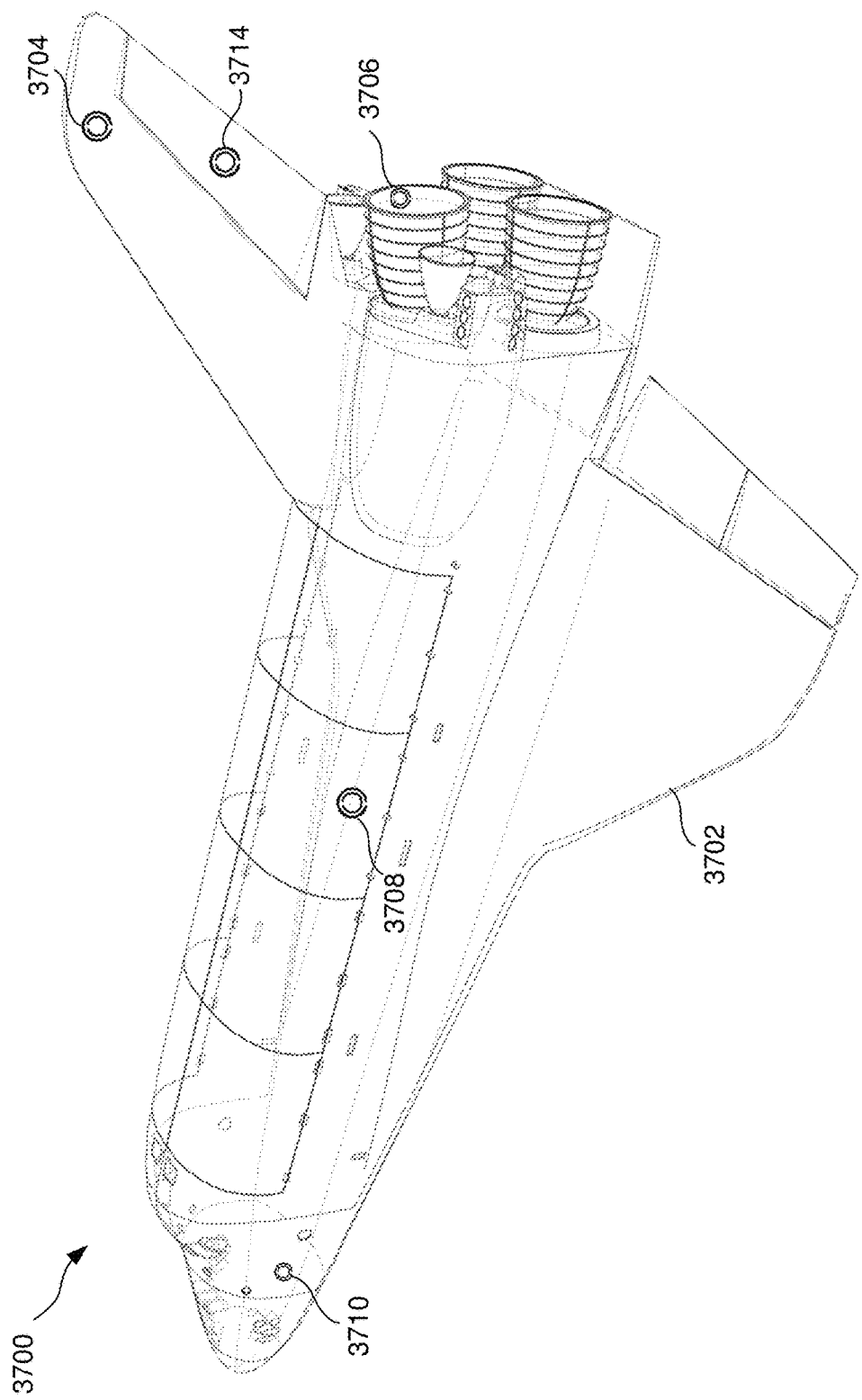
FIG. 37A shows a depiction of split ring resonators disposed in and/or on a rocket, in accordance with one embodiment.

FIG. 37A shows a depiction 3700 of split ring resonators disposed in and/or on a rocket, in accordance with one embodiment. As an option, the depiction 3700 may be implemented in the context of any one or more of the embodiments set forth in any previous and/or subsequent figure(s) and/or description thereof. Of course, however, the depiction 3700 may be implemented in the context of any desired environment. Further, the aforementioned definitions may equally apply to the description below.

As shown, a spaceship 3702 may include one or more split ring resonators located through the spaceship 3702, including, but not limited to, the wing 3704, the elevon 3714, the engine 3708, the flight deck 3710, and/or the cargo bay 3708. It is to be appreciated that any number of split ring resonators may be found on the spaceship 3702.

Use of split ring resonators in spaceships may provide continuous millisecond-by-millisecond changes before takeoff, continuously during flight, and during reentry. Such changes may include structural parameter changes (e.g. fatigue thresholds, impending component failure, etc.), which in turn, may cause alerts to systems and personnel. Further, spaceships (often termed orbiters) are often attached to a rocket booster. Generally, a structural failure to any component on either of the spaceship or the rocket booster would often result in complete failure for both the spaceship and the rocket booster. Use of split ring resonators, however, would ensure that any structural parameter change (to either the spaceship or the rocket booster) could be detected before impacting either the spaceship or the rocket booster. In some embodiments, a structural parameter change may cause the spaceship and the rocket booster to disengage to preserve the one or the other (based on the structural parameter change identified).

Figure 37B:
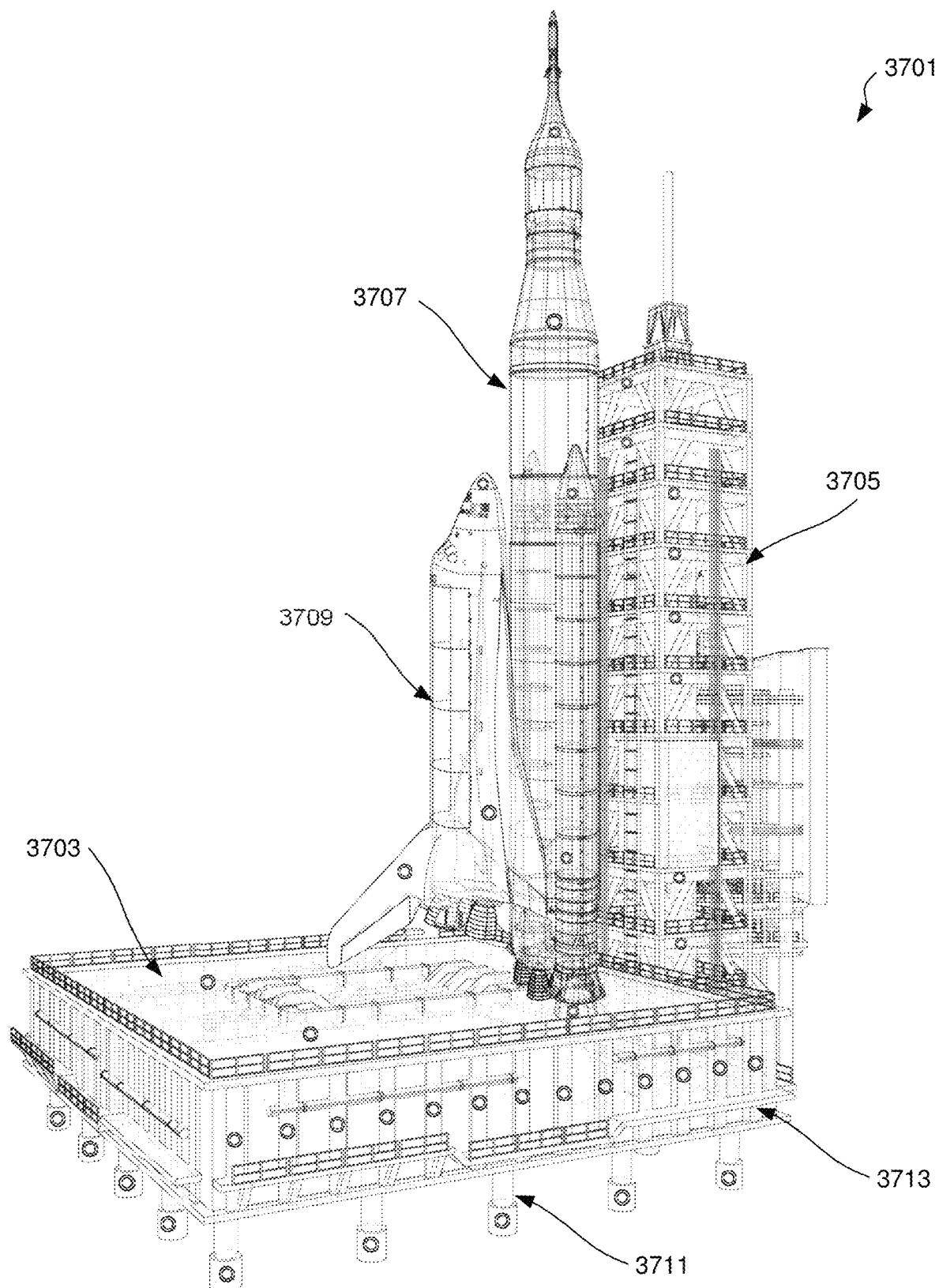
FIG. 37B shows a depiction of split ring resonators disposed in and/or on a rocket, and/or a landing platform, as well as landing location sensors, in accordance with one embodiment.

FIG. 37B shows a depiction 3701 of split ring resonators disposed in and/or on a rocket, and/or a landing platform, in accordance with one embodiment. As an option, the depiction 3701 may be implemented in the context of any one or more of the embodiments set forth in any previous and/or subsequent figure(s) and/or description thereof. Of course, however, the depiction 3701 may be implemented in the context of any desired environment. Further, the aforementioned definitions may equally apply to the description below.

As shown, a spaceship 3709 may be attached to a rocket booster 3707. Split ring resonators may be located and found on each of the spaceship 3709 and the rocket booster 3707. Further a launch pad for the spaceship 3709 and the rocket booster 3707 is shown, including a launcher platform 3703, a flame pit 3711, platform trusses 3713, and/or a launcher service structure 3705. Split ring resonators may be located and found throughout each component of the launch pad of the depiction 3701. In this manner, split ring resonators located in and/or on parts of the launch pad may be used to detect structural parameter changes (e.g. fatigue thresholds, impending component failure, etc.), which in turn, may cause alerts to systems and personnel. For example, a structural fail (in any of the components) may cause a launch to be aborted. Additionally, after the launch has commenced (but before liftoff), a structural fail may additional cause a launch to be aborted. Thus, any structural fail (at any point) may be the basis for a launch to be aborted, and/or for corrective action to be implemented.

In this manner, early warning systems may be based on split ring resonators found through the launch pad, the spaceship, and/or the rocket booster, and/or any component related thereto, and real-time data may be obtained to ensure safe remediation of any detected change.

Further, for any type of airborne vehicle, split ring resonators may be used as low-cost resonant sensors for safety. For example, split ring resonators may be used to detect excess vibration on components, detect and monitor microcracks in materials, monitor local temperatures of nonmetallic component surfaces (in providing instantaneous values as well as historical/cyclical changes), monitor local temperatures within nonmetallic components (in providing instantaneous values as well as historical/cyclical changes), provide pinpoint position accuracy (for precise landings, as an example), and/or may be installed into materials, onto surfaces and/or below surfaces (such as painted surfaces).

Figure 38A:
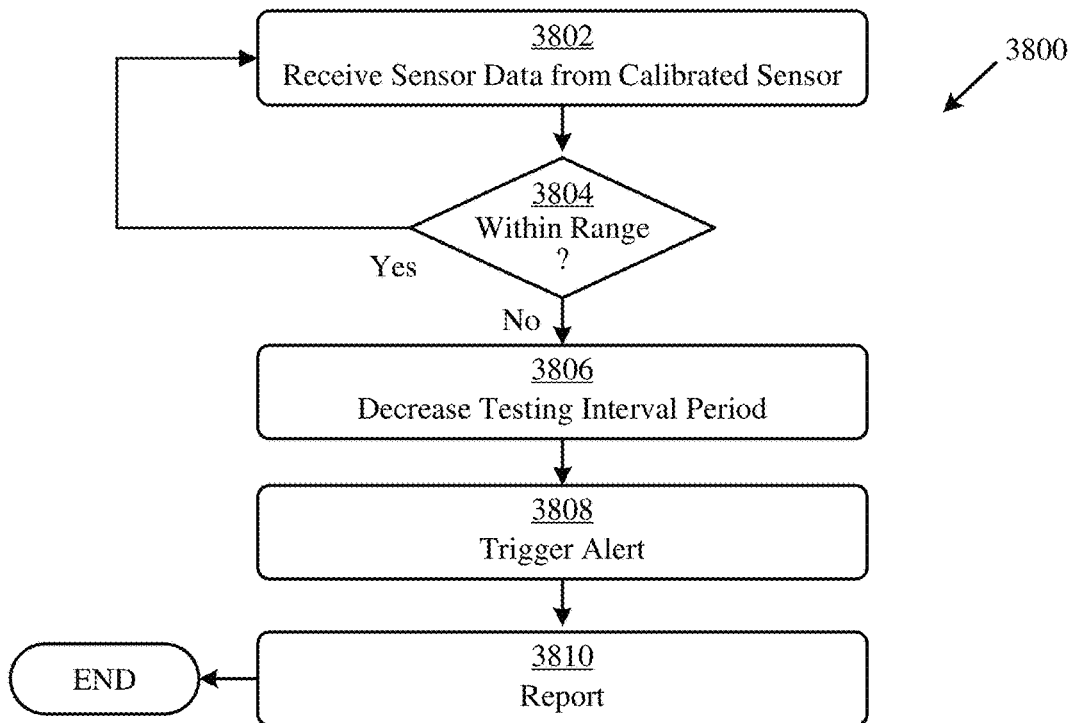
FIG. 38A is a flow chart relating to reporting feedback from split ring resonators, in accordance with one embodiment.

FIG. 38A is a flow chart 3800 relating to reporting feedback from split ring resonators, in accordance with one embodiment. As an option, the flow chart 3800 may be implemented in the context of any one or more of the embodiments set forth in any previous and/or subsequent figure(s) and/or description thereof. Of course, however, the flow chart 3800 may be implemented in the context of any desired environment. Further, the aforementioned definitions may equally apply to the description below.

The flow chart 3800 relates to one embodiment where sensor data is received from one or more split ring resonators, and one or more actions are taken in response.

As shown, the flow chart 3800 begins with receiving sensor data from a calibrated sensor (step 3802). The calibrated sensor may include one or more split ring resonators, calibrated based on a natural resonance. It is determined (decision 3804) whether the sensor data is within a predetermined range. For example, the sensor data may be correlated with a condition signature (where known deviations are correlated with known failures and/or conditions). If the sensor data is within range (or within an allowed condition signature), the method returns to continuously receiving sensor data (per step 3802). Of course, the interval for receiving sensor data may be predetermined and/or adjusted as needed.

If the sensor data is not within range, then the flow chart 3800 advances to decreasing testing interval period (step 3806). In one embodiment, step 3806 may be optional. For example, the testing interval period may already be near continuous (per step 3802), in which case there may not be a need to decrease the testing interval period. In response (or simultaneous with) to step 3806, an alert may be triggered (step 3808), and a report may be generated (step 3810).

In some embodiments, an alert and/or a report in relation to the not-in-range sensor data may be used to inform and/or alert a human (e.g. operator, supervisor, etc.), saved to a repository (e.g. storage, etc.), inform and/or alert an organization (e.g. Environmental Protection Agency, Department of Motor Vehicles, etc.), etc., It is envisioned that such not-in-range sensor data may also be used to trigger automated actions (e.g. AI integrated systems, etc.), cause automated setting alteration(s) on the vehicle (or an apparatus in which the split ring resonators are located), and/or take any other automated action (without intervention of a human).

Figure 38B:
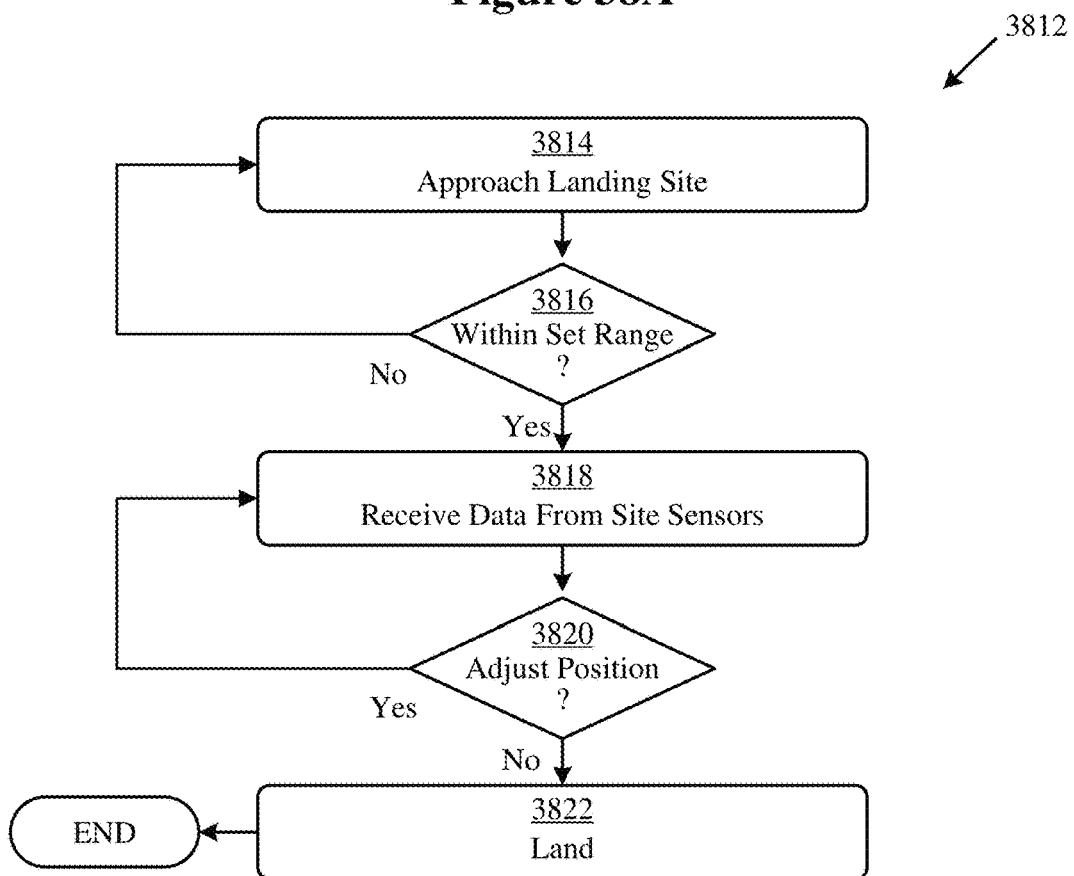
FIG. 38B is a flow chart relating to landing an aerial vehicle and/or drone using split ring resonators, in accordance with one embodiment.

FIG. 38B is a flow chart 3812 relating to landing an aerial vehicle and/or drone using split ring resonators, in accordance with one embodiment. As an option, the flow chart 3812 may be implemented in the context of any one or more of the embodiments set forth in any previous and/or subsequent figure(s) and/or description thereof. Of course, however, the flow chart 3812 may be implemented in the context of any desired environment. Further, the aforementioned definitions may equally apply to the description below.

The flow chart 3812 relates to one embodiment where sensor data is received from one or more split ring resonators (located on site) to assist with pinpoint landing capabilities. It is to be appreciated that as similar flow could be created for use of split ring resonators located on an aerial vehicle (rather than relying on site-based sensors).

As shown, the flow chart 3812 starts with an aerial vehicle approaching a landing site (step 3814). It is determined whether the aerial vehicle is within a set range (such as a predetermined distance from the landing pad) (decision 3816). In one embodiment, determining whether an aerial vehicle is within a set range (per decision 3816) may rely, at least in part, on split ring resonators located on the aerial vehicle.

Once the aerial vehicle is within a set range, data may be received from site sensors (step 3818). Data from such site sensors may be sent to the aerial vehicle such that position adjustments may be affected (decision 3820). When the position does not need further alteration, the aerial vehicle may be landed (step 3822). Of course, it is to be appreciated that decision 3820 may occur continuously as the aerial vehicle approaches the landing pad, such that real-time adjustments to the position of the aerial vehicle may be made.

In one embodiment, the site sensors (per step 3818) may be used to triangulate the exact position of the aerial vehicle. As can be appreciated, the flow chart 3812 provides just one example of how split ring resonators may be used and assist in landing an aerial vehicle.

FIG. 39 shows a depiction 3900 of meta-materials in a dielectric matrix, and circuitry relating thereto, in accordance with one embodiment. As an option, the depiction 3900 may be implemented in the context of any one or more of the embodiments set forth in any previous and/or subsequent figure(s) and/or description thereof. Of course, however, the depiction 3900 may be implemented in the context of any desired environment. Further, the aforementioned definitions may equally apply to the description below.

Within the context of the present description, meta-materials may include any material engineered to have a physical property that is not found in naturally occurring materials.

As shown, in SEM image 3902, meta-materials may be tuned in a dielectric matrix. For example, meta-materials may be selected for frequency selective properties, including where the meta-materials are innately tuned and constructed in application. Additionally, the meta-materials may provide frequency selective conductivity without being direct current conductive. Further, such meta-materials may conduct and maintain a connection without touching (unlike standard conductive ink/flakes/coating which must touch in order conduct and maintain a connection).

The arrangement of meta-materials tuned in a dielectric matrix (per SEM image 3902) may be shown via lumped circuits 3904, where a series resistance with minimum impedance at resonant frequency, or a parallel resistance with maximum impedance at resonant frequency may be achieved. It is to be appreciated that the arrangement of meta-materials may be arranged in either a series resistance and/or a parallel resistance.

In various embodiments, the meta-materials in a dielectric matrix may be arranged in a split ring resonator 3906 which may be represented in a circuitry type configuration 3908. Such configuration 3908 may include an inductor associated with the ring, and a capacitor associated with the gap of the split ring resonator. Such configuration should be construed in a manner consistent with FIGS. 24B1 and 24B2 discussed hereinabove.

Use of meta-materials as frequency selective materials may allow for continued flexing (of the material) without degradation in conductance. Additionally, frequency tuning may allow for increased signal to noise ratio for better detection and resolution. Further, other parameters (temperature, stress strain, etc.) may be directly measured through the stretching, deforming, and/or temperature readings of the dielectric matrix.

In this manner, meta-materials may be used in and/or on a split ring resonator, which in turn, may provide frequency selective conductivity without being DC conductive. Further, high frequency conductivity of meta-materials may allow for use in split ring resonators.

Figure 40:
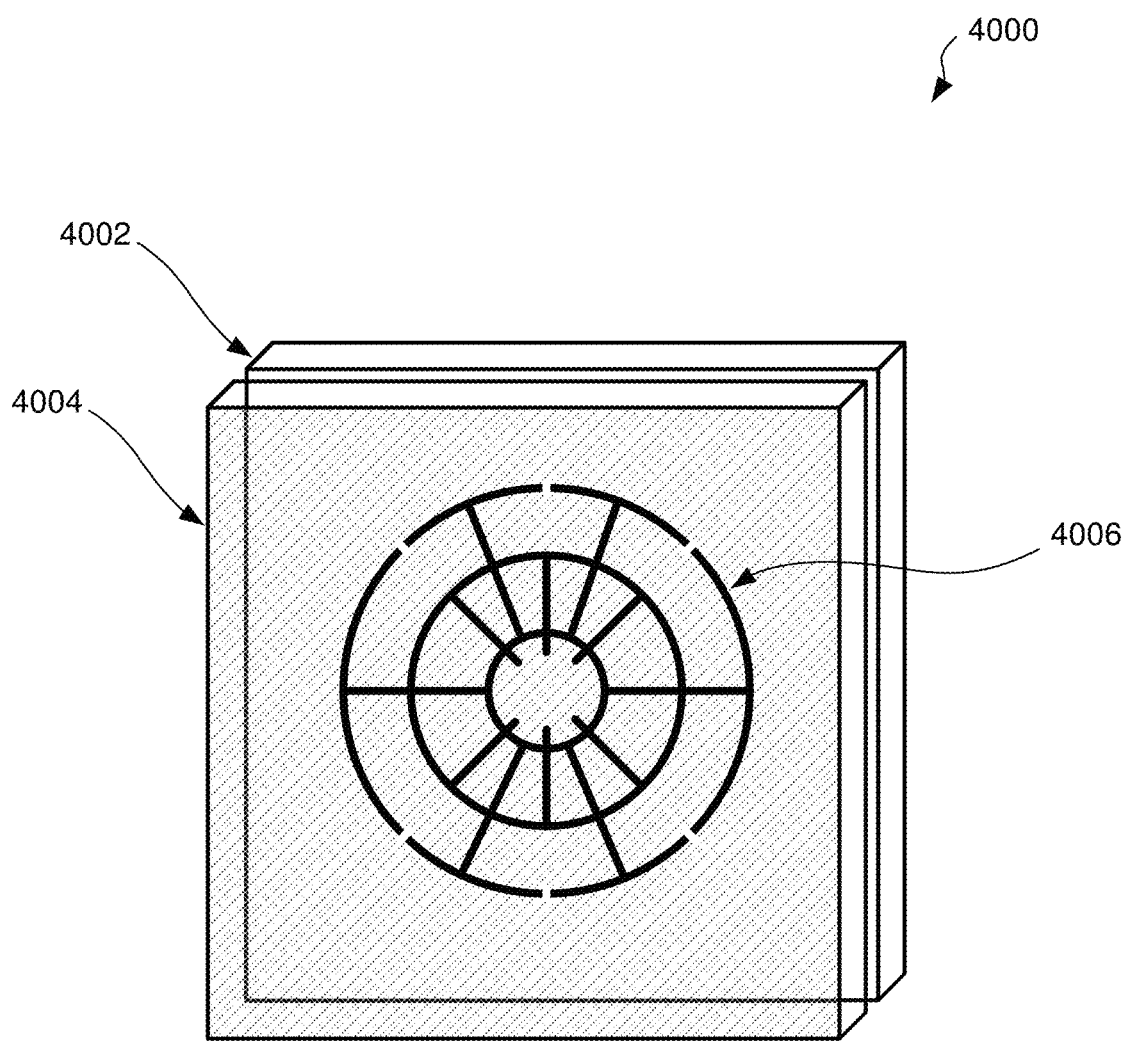
FIG. 40 shows a depiction of a split ring resonator embedded within an open or closed cell material, in accordance with one embodiment.

FIG. 40 shows a depiction 4000 of a split ring resonator embedded within an open or closed cell material, in accordance with one embodiment. As an option, the depiction 4000 may be implemented in the context of any one or more of the embodiments set forth in any previous and/or subsequent figure(s) and/or description thereof. Of course, however, the depiction 4000 may be implemented in the context of any desired environment. Further, the aforementioned definitions may equally apply to the description below.

As shown, a split ring resonator 4006 may be embedded between a first layer 4002 and a second layer 4004. In various embodiments, the material of the first layer and/or the second layer may include open or closed cell (selected or coated) material. Such material may have a specific permittivity that is a mix of the material and of air in the pores within the material itself, such that when the air flow compresses the foam drives out the air and the aggregate permittivity becomes that of the material (the open or closed cell foam). As a result of the fact that the material's permittivity is much higher than the air, the compression of the material would result in a downshift of frequency.

To describe it from an alternative perspective, embedding the split ring resonator 4006 in a foam-based material allows for a greater resonance frequency (compared to if the split ring resonator responded by itself). This greater resonance frequency is due, at least in part, to the foam-based material deforming, and when the deformation occurs, there is a direct and great correlation with a change of permittivity of the foam-based material.

Additionally, in another embodiment, a split ring resonator may be printed onto the top of the open or closed cell material foam, with a ground plane on the back with foam material in-between the top and ground plane levels. The distance between the front sensor to the ground plane (with the foam in-between) may cause a frequency shift (like a capacitor). In this manner, the foam material may function as a pressure sensor and the presence of the foam may serve to shift the resonant frequency up or down. For example, if the foam element(s) is deformed or deflected (push in or pulled out), the foam elements can be measured as a change of the split ring resonators.

As such, as detailed herein, a split ring resonator may provide a response to a wireless ping/chirp/query. Additionally, using a foam-based material to encase the split ring resonator may amplify the split ring resonator's response. Again, the deformation of the foam-based material is greater than, for example, a semi-rigid material, which in turn, translates to a greater permittivity difference (comparing again a foam-based material to a semi-rigid material). Within the context of FIG. 24B4, a foam-based material may have a similar type response (with the y-axis coordinate measuring permittivity rather than frequency). Additionally, in one embodiment, such permittivity may be unipolar or bi-polar. For example, in some cases (e.g., in turbulent situations), a positive pressure as well as negative pressure may exist on the surface. Within the context of the present description, a semi-rigid material refers to a stiff material that is capable of flexing. A foam-based material refers to a cellular spongy material. Comparing a semi-rigid material to a foam-based material, the foam-based material is capable of greater compression and deformation (given its spongy form). As such, using foam-based material in combination with split ring resonators (as detailed herein) may allow for greater amplification of the response (which in turn may correlate with instrumentation that can operate at lower frequency and power levels).

The combination, therefore, of a split ring resonator with an accompanying material and/or substrate (e.g. semi-rigid material, foam-based material, concrete, rubber, polymers, etc.) may have an ensemble effect. Within the context of the present description, an ensemble effect refers to the frequency response of a split ring resonator in combination with an accompanying material and/or substrate.

Figure 41:
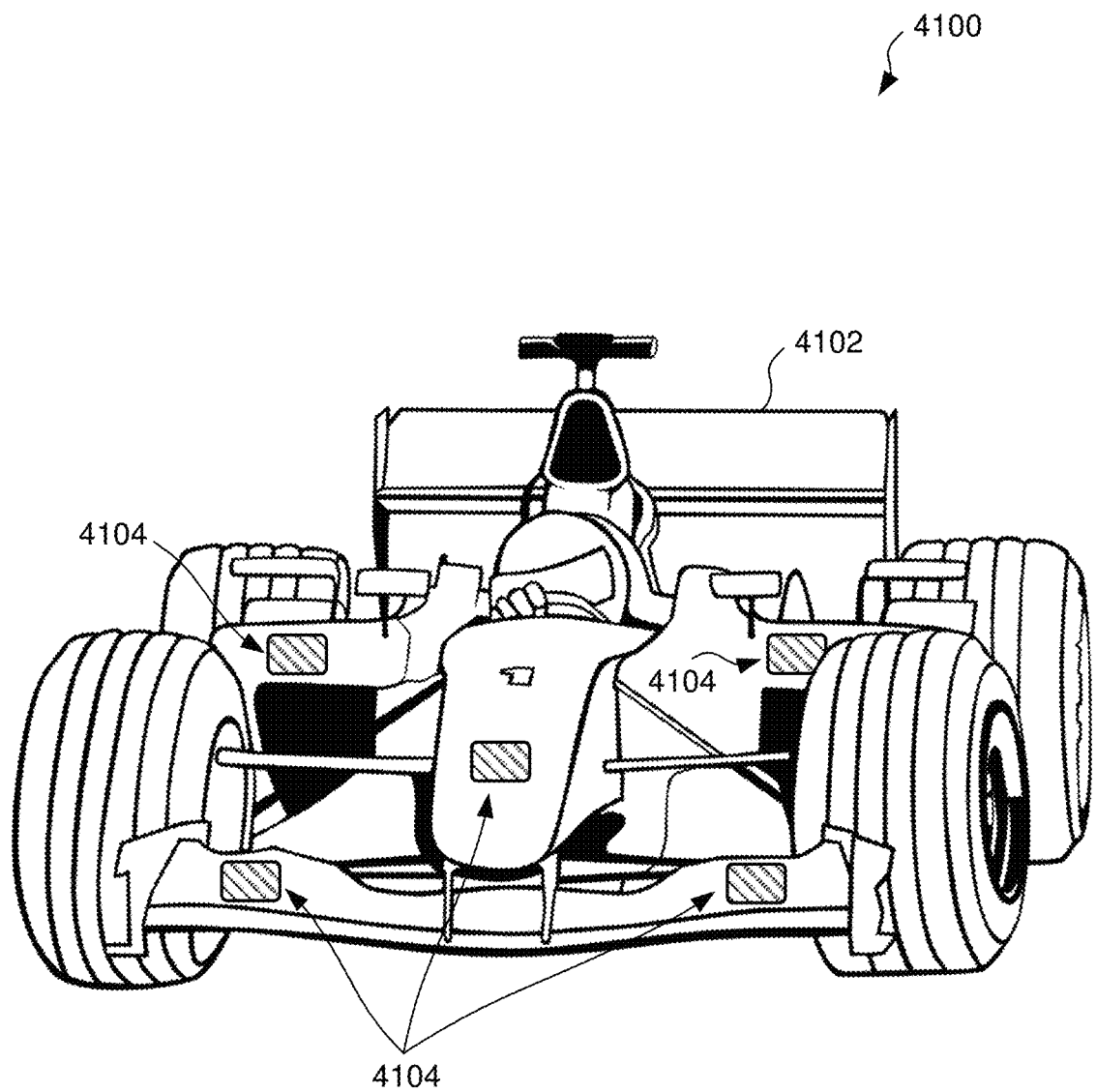
FIG. 41 shows a depiction of pressure sensors using open or closed cell material, in accordance with one embodiment.

FIG. 41 shows a depiction 4100 of pressure sensors using open or closed cell material, in accordance with one embodiment. As an option, the depiction 4100 may be implemented in the context of any one or more of the embodiments set forth in any previous and/or subsequent figure(s) and/or description thereof. Of course, however, the depiction 4100 may be implemented in the context of any desired environment. Further, the aforementioned definitions may equally apply to the description below.

In function, a wave pulse may propagate from an antenna (located on the vehicle 4104 and/or a surrounding object/location), which in turn may impinge on an object (such as the unoptimized sensors 4104) that has real and imaginary physical materials components that either reflect or absorb the energy. This, in turn, may produce a form of analog telemetry via wireless communication (where transmission of temperature, pressure, and/or other measurements may occur by reflection or absorption of the wave pulse), which in turn, may provide a remote low-cost parameter sensing of the physical world.

Figure 42:
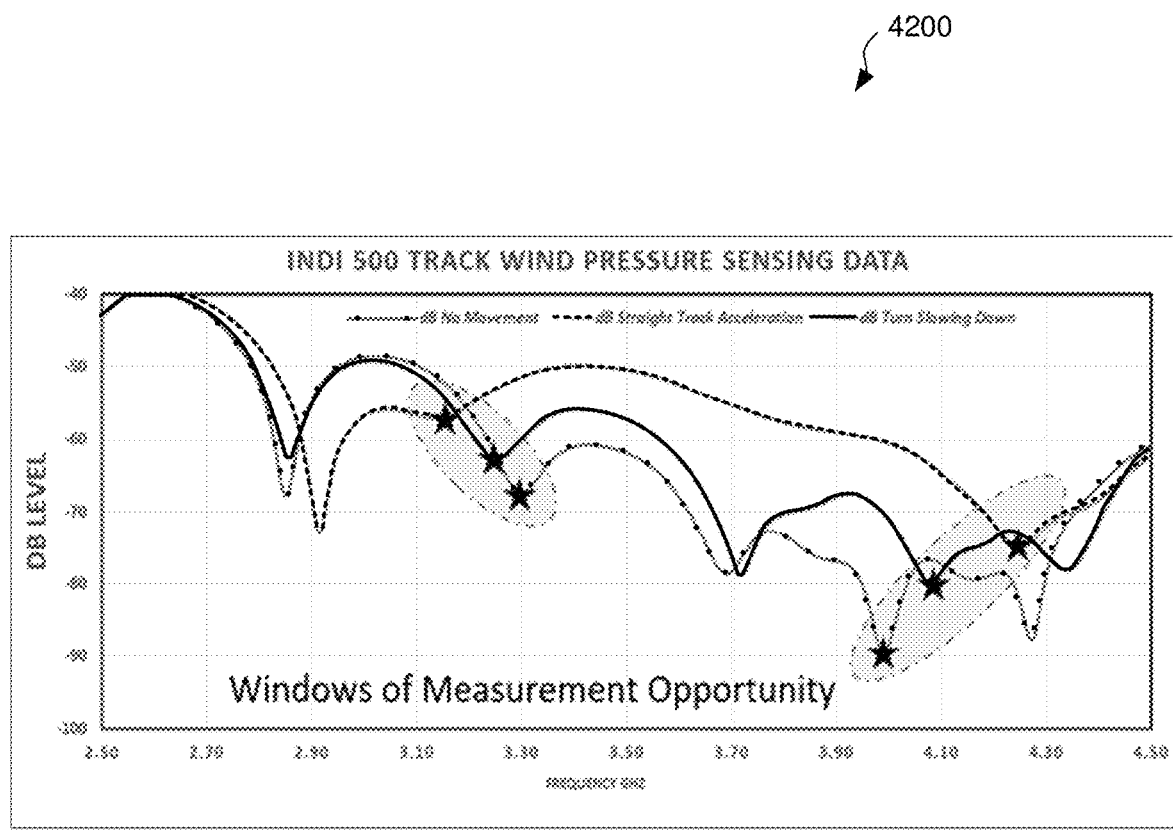
FIG. 42 shows a depiction of wind pressure sensing data using open or closed cell material, in accordance with one embodiment.

Real-world testing of the vehicle 4102 with sensing data is shown in FIG. 42.

FIG. 42 shows a depiction 4200 of wind pressure sensing data using open or closed cell material, in accordance with one embodiment. As an option, the depiction 4200 may be implemented in the context of any one or more of the embodiments set forth in any previous and/or subsequent figure(s) and/or description thereof. Of course, however, the depiction 4200 may be implemented in the context of any desired environment. Further, the aforementioned definitions may equally apply to the description below.

As shown, the depiction 4200 is of wind pressure sensing data based on a vehicle (such as the vehicle 4102). The wind pressure sensor may be constructed in a manner consistent with FIG. 40. Additionally, it is to be appreciate that FIG. 42 displays a single use case scenario (for wind pressure). Similar sensing data may be obtained for other metrics (temperature, pressure, speed, etc.).

Figure 43:
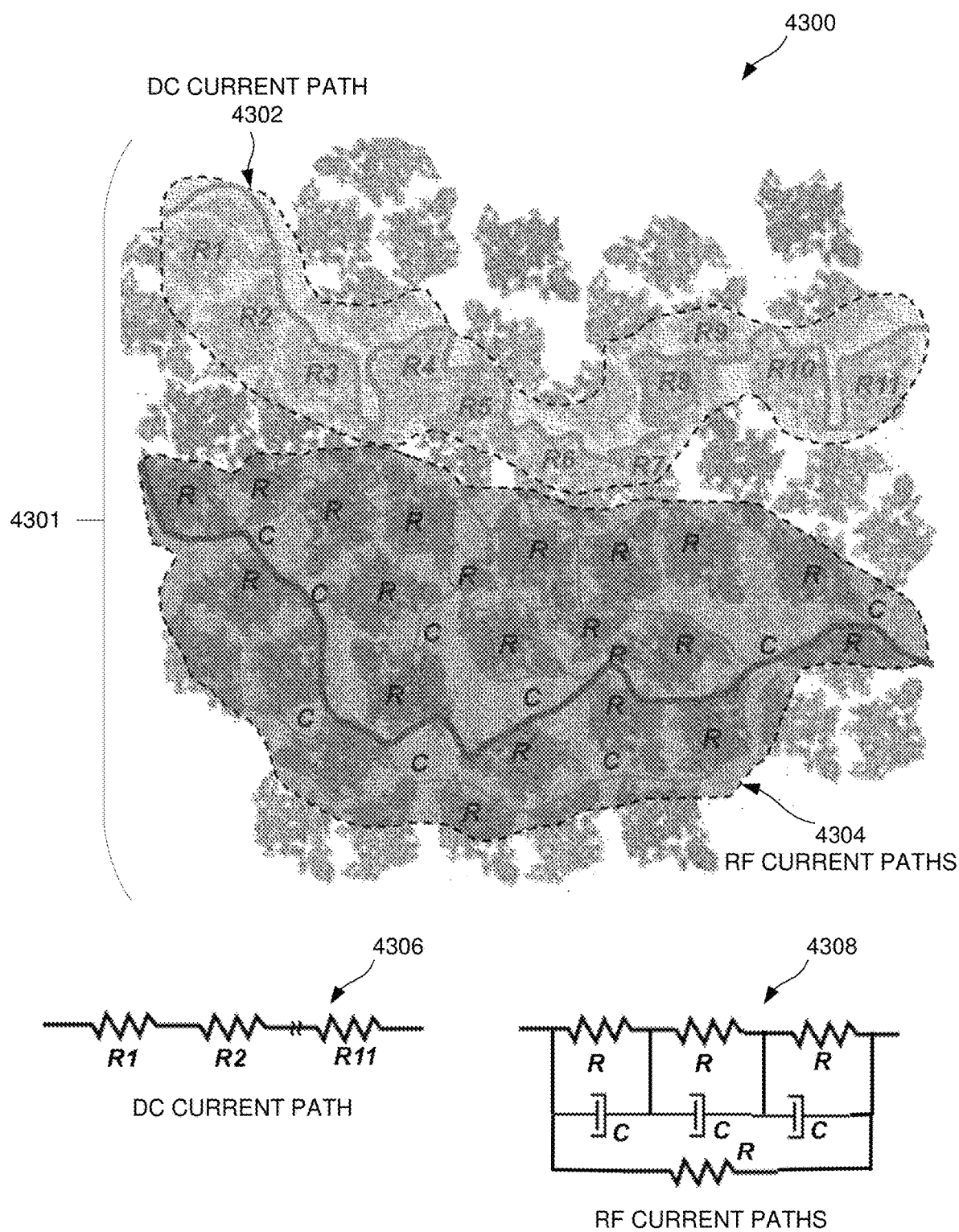
FIG. 43 shows a depiction of a path and circuitry relating to frequency selective conductivity, in accordance with one embodiment.

The depiction 4200 shows three case scenarios: (1) frequency based on no movement of the vehicle; (2) frequency based on straight track acceleration of the vehicle; and (3) frequency based on the vehicle slowing down on a turn. As can be observed, each of the case scenarios produces a separate and distinct frequency measurement. Such frequency measurement may be correlated with a condition signature, as described hereinabove. Additionally, the stars found on each of the lines are indicative of maxima/minima data points, FIG. 43 shows a depiction 4300 of a path and circuitry relating to frequency selective conductivity, in accordance with one embodiment. As an option, the depiction 4300 may be implemented in the context of any one or more of the embodiments set forth in any previous and/or subsequent figure(s) and/or description thereof. Of course, however, the depiction 4300 may be implemented in the context of any desired environment. Further, the aforementioned definitions may equally apply to the description below.

As shown, the depiction 4300 includes an image 4301 of current materials 4302 and meta-materials 4304. As can be observed, current materials require a DC current based on a direct connection which allows current to flow. Such current materials may be represented by circuit 4306. In contrast to such conventional systems, use of meta-materials 4304 may allow conductivity to be achieved through resistive and reactive pathways. Such pathways may be based on a non-direct connection (where each pathway and/or node does not need to be touching) in order to be conductive. Circuit 4308 represents use of the meta-materials to establish conductivity.

Figure 44:
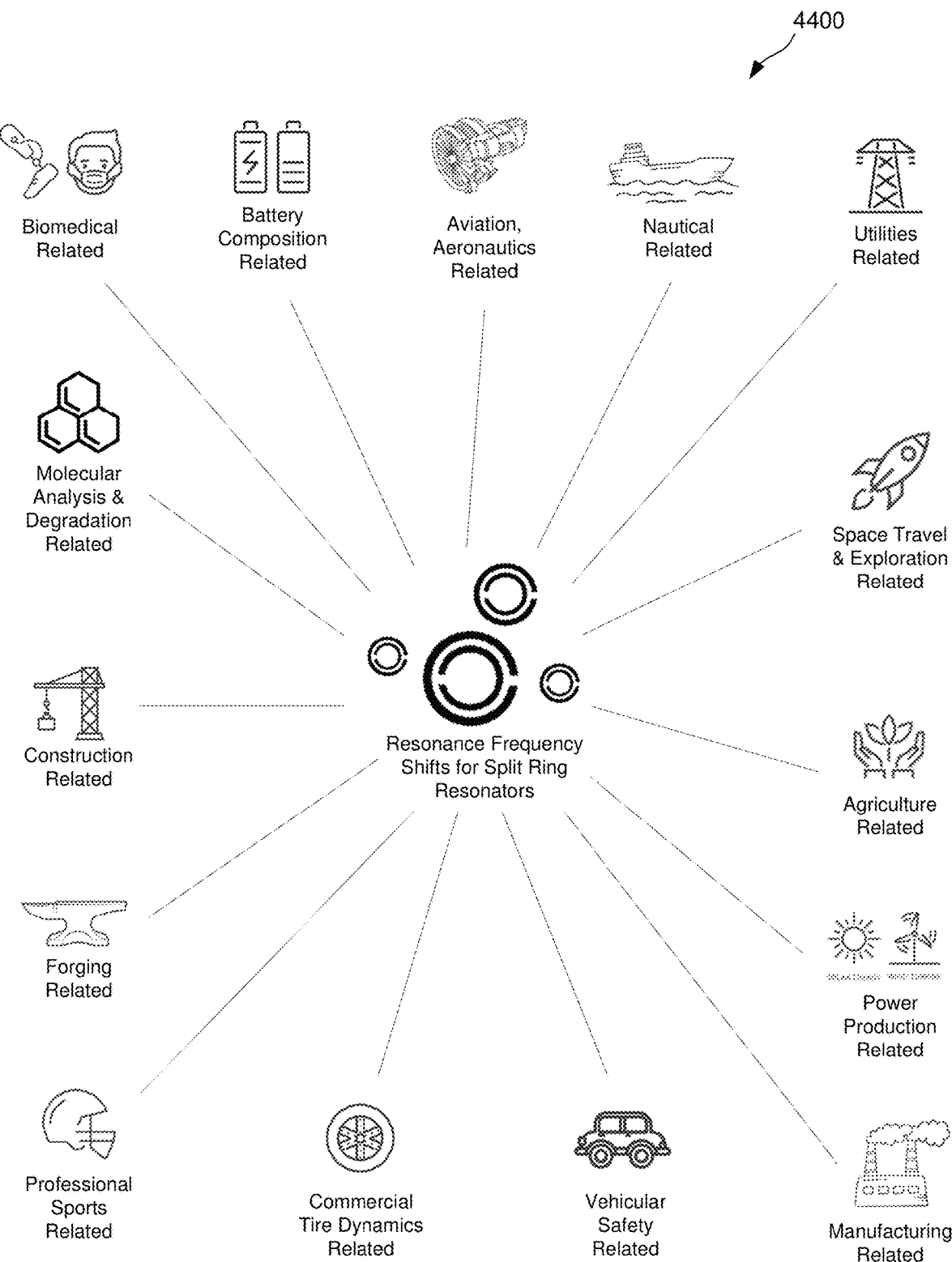
FIG. 44 shows a depiction of many industries in which the use of split ring resonators may be applicable, in accordance with one embodiment.

FIG. 44 shows a depiction 4400 of many industries in which the use of split ring resonators may be applicable, in accordance with one embodiment. As an option, the depiction 4400 may be implemented in the context of any one or more of the embodiments set forth in any previous and/or subsequent figure(s) and/or description thereof. Of course, however, the depiction 4400 may be implemented in the context of any desired environment. Further, the aforementioned definitions may equally apply to the description below.

As shown, the depiction 4400 includes a variety of exemplary world-wide industry applications where resonance frequency shifts associated with split ring resonator(s) may offer early detection capabilities with regard to literally hundreds of potential scenarios, thus providing the ability to remediate and adjust where potential issues may be discovered. Data associated with resonance frequency shifts of split ring resonator(s) may apply to nearly every industry and market, including but not limited to: utilities, space travel and exploration, agriculture, power production, manufacturing, vehicular safety, commercial tire dynamics, professional sports, forging, construction, molecular analysis and degradation, biomedical, battery composition, aviation and/or aeronautics, nautical, consumer packaged goods, bridges and roadways, etc. Some of such industries (and applicability of split ring resonators) have been detailed herein.

For purposes of being as precise as possible, as well as showing potential applicability of use of split ring resonators (and resonance frequency shifts relating thereto) to many other industries, additional material is provided hereinbelow.

As discussed earlier, split ring resonators may be embedded in or printed on other materials (other than concrete barriers of FIG. 22A2 and/or metal barriers of FIG. 22A3) encompassing a wide range of applications within equally wide range of global industries. In this manner, measuring resonance frequency shifts may occur in nearly any application where split ring resonators can be embedded or printed (on a surface, within a material, etc.). Further, split ring resonators may be used not only to determine a shift in resonance frequency (which may be associated with a signature indicative of a physical condition), but may also be used to control an aspect in response to receipt of such input. For example, a temperature sensor may have split ring resonators embedded therein such that when a predetermined temperature is reached, an external unit (air conditioner, heater, air vent, etc.) may be activated until the ambient temperature reaches the predetermined temperature. In some instances, taking an action may be dependent on a processor which may interpret the data from the resonance frequency shift of the split ring resonator, and in response, initiate an action (e.g. a command to take action to modify an environmental condition, etc.). In other embodiments, taking an action may occur without use of an external processor. For example, an item may be transported which must be kept within a predetermined temperature. In order to determine a test the integrity of the temperature while the item is transported, a temperature sensor embedded with split ring resonators may be affixed to the item, and if the temperature exceeds a predetermined threshold, deformation of the sensor may cause a physical manifestation (change in color, deformed indicator, etc.). As such, an environmental change or manifestation may be directly associated with a state of the split ring resonator.

In one embodiment, aviation related applications may include detection of material stress, temperature or vibration levels approaching or exceeding known tolerances as the aircraft experiences subsonic, transonic, supersonic, and hypersonic speeds. Employing split ring resonators within and over the surface of the wings, including aileron(s), elevator(s), and rudder(s), may detect air pressure both above and below the wing surface, temperature increases and decreases, surface area distortions, and even potential material fractures or failures, thus providing opportunity to alert both the pilot and ground personnel to potential danger to the aircraft and provide adequate time to respond and correct airspeed, lift, flight posture, payload disbursal, and so forth before any catastrophic event may occur. Additionally, applicable embodiments may include fixed wing constructions conjoined with aero-foil blades within and upon which split ring resonators are used to measure air pressure above and beneath the aero-foil surface to determine optimal extension or retraction of said aero-foil, thus providing opportunity to adjust flight parameters and maximize aircraft performance. In another embodiment for aviation, employing split ring resonators within and over the surface of the wings, including aileron(s), elevator(s), and rudder(s), may detect at what point the harmonics or geometry of the wing surface begin to deform and turn smooth air into turbulent.

In yet another embodiment, aviation related applications may include aircraft jet engine turbo fan and propeller engine fault tolerance measurements and the potential dangers of exceeding those tolerances. For example, split ring resonators may be employed in virtually every engine part, including housings and cowlings, to provide temperature shift, vibration frequency increases and decreases, material flex or distortion, air intake, fuel intake, combustion, manifold pressure, oil pressure, compression, and/or exhaust measurements. By way of example, split ring resonators on the surface area of an engine's propeller may detect and provide indication of ordinary measurements like speed of angular rotation, axial and/or centrifugal airflow, and torque, and more potentials threat-analytical measurements like undue stress or flex experienced by propeller and fan blades, microscopic stress fractures developing in the same, excessive temperature, engine lubricant viscosity breakdown rate and degree, and so forth, thus alerting pilots to potentially immediate need of corrective action to prevent imminent or eventual engine failure and enabling maintenance personnel to determine possibly appropriate remediation measures to undertake in maintenance cycles.

In still another embodiment, aviation related applications may include both fixed and separable (modular) fuselage integrity measurement parameters and changes thereto from inside and outside forces during flight and on the ground. Split ring resonators may be used within and on the surface of the fuselage to detect varying levels of distortion from internal and external air pressure, temperature shifts, vibration frequency increases and decreases experienced during take-off (or launch), increases and decreases in altitude, and/or increases and decreases in airspeed, and provide early warnings of possible structural failures in the metals and/or composites associated therewith before a catastrophic event may occur.

In one embodiment, biomedical related applications may include detecting slight alterations and/or undue wear in components in a patient's prosthetic limb(s). Through the use of split ring resonators, small (even microscopic) changes in the composition and/or shape of a prosthesis component may be detected and addressed very early, perhaps even before any pain or discomfort manifests itself to the patient. For example, a fixed-bearing or mobile-bearing knee prosthesis used in knee replacement surgery may develop slight misalignment or contortion as a result of stress from weight-bearing and/or other environmental effects resulting in possible pain or discomfort experienced by the recipient. More specifically, employing split ring resonators in conjunction with the contact surfaces of a femoral and/or tibial component of a prosthetic knee may reveal slight differentiations in pressure and/or stress points as well as possible degradation of the polyethylene articulating surfaces associated therewith, thus alerting medical staff to a potential need for adjustment, maintenance, and/or outright retrofit to maximize comfort and stability for the patient.

In another embodiment, biomedical related applications may include detecting possible shifts in the position, flow, and/or range of motion with regard to any one of dozens or hundreds of medical implants in a post-operative setting. In one example, one or more split ring resonators may be utilized to ensure that an artificial heart valve implant does not move or shift position during operation and/or does not seize up and possibly restrict the free flow of non-oxygenated or oxygenated blood to or from the heart itself, thus risking significant injury or fatal consequences for the patient. If placed on or within both the valve implant and the arterial wall adjacent thereto, split ring resonators may alert the patient and/or medical personnel to minor or major aberrations requiring adjustment or refitting to restore proper heart valve function, possibly even before the patient experiences any overt symptoms at all.

In yet another embodiment, biomedical related applications may include detecting the effectiveness or need to adjust orthotics designed to improve, restrict, attenuate and/or brace or bolster patents' range of motion and comfort. The use of split ring resonators with regard to the application of orthotics may assist in helping correct or counterbalance loss or impairment of a patients' otherwise normal gait affected by significant neurological dysfunction and/or injury or trauma. In one such example, split ring resonators installed within and upon carbon fiber and/or other composite ankle and/or foot orthosis, with a counterpart knee orthosis featuring an extension swing assist mechanism, may detect stress, pressure, and/or range of motion outside of acceptable parameter values, thus indicating that further adjustment is required to achieve the desired level of foot drop correction, knee support, improved balance, enhanced proprioception, and improved gait biomechanics for the patient.

In still another embodiment, personal protective equipment (PPE) related applications may include improving effectiveness of said PPEs to detect certain compounds and/or viral strains within moisture droplets that come into contact with the material of, for example, a face mask. By way of specific example, because split ring resonators based on carbonaceous growth can be tuned serve a specific detection-related purpose, such split ring resonators may be infused within the fibrous materials of an N-95-type face mask (or any type of face mask) with a variety of differently-tuned split ring resonators capable of detecting specific types of molecular compounds and/or viral stains, thus enabling the wearer, and (particularly) medical personnel, to quickly determine whether a risk of contagion and/or imminent illness might be an immediate threat and engage appropriate quarantine, treatment, or remedial protocols to minimize negative effects.

For example, in one embodiment, the face mask may be used to detect a specific strain (such as COVID), and when the specific strain is detected, the face mask (or a specific portion of it) may visibly change a color, at least in part. Such may be indicative that the user of the mask has contracted the specific strain. Additionally, other virus sensors may be installed in any location (e.g. bus entryway, metro car, subway entrance, etc.) such that based on ambient air passing by, if the specific strain is detected, it may change colors, indicative that an individual has passed by that sensor who has the specific strain.

Further applicability of use of split ring resonators for detecting biomaterials may be found in U.S. patent application Ser. No. 17/382,661, entitled "METHOD OF MANUFACTURING A GRAPHENE-BASED BIOLOGICAL FIELD-EFFECT TRANSISTOR," filed Jul. 22, 2021, the contents of which is herein incorporated by reference for all purposes.

Within the context of airport security, such sensors could be embedded within typical metal detection systems such that when an individual is being scanned, the air being expelled from the individual may be analyzed to determine the presence of the specific strain. In one context, a low-cost fabric-based sensor could be hung within the metal detector such that when an individual passes by the air may be automatically analyzed, and a color change may occur on the low-cost fabric if the specific strain is detected. Such detection may occur even without requiring electronic configuration or parts. Alternatively, the sensor may be electronically attached to a processor such that when the air is analyzed, if the specific strain is detected, a response (e.g. alarm, notification, etc.) may occur.

In one embodiment, utilities related applications may include detecting slowly and/or suddenly developing faults in high-power line conductor structures and/or housing/insulating sleeves. As an example, split ring resonators may detect stress flexing or fractures in protective power line insulation and/or housing sleeves that could possibly become a contributing factor in allowing sparks or other direct effects to potentially impact or ignite wildfires due to a relative proximity of dry vegetation (e.g., grasses, trees, leaves, etc.) to power line structures. More specifically, the use of split ring resonators installed within and around one or more layers of housings and/or sleeves installed radially around the master conductor cable may detect the development of small (even microscopic) faults over time that, if left unchecked, might leave the master conductor wire(s) dangerously exposed to natural elements.

In another embodiment, utilities related applications may include measuring liquid and/or gas flow through one or more forms of delivery apparatus (pipelines) and measure any changes in the shape, temperature, structural integrity, and stress (due to internal and/or external pressures) possibly affecting performance of said delivery system. In particular, split ring resonators may be employed to help maintain optimal operational pressure levels in delivery pipelines by detecting and alerting operation and maintenance personnel to changes in the composition of the delivery mechanisms' physical structure (cylindrical and otherwise) and possibly detect even microscopic faults in structure material that, if diagnosed and handled at an early state, will not mature and manifest into catastrophic loss or damage to the pipeline delivery system as a whole. By way of a different example, split ring resonators may detect over-pressurized delivery segments, thus allowing operation and maintenance personnel the opportunity to make upstream and/or downstream adjustments to keep such pressure within standard operational thresholds and alleviate undue stress leading to additional maintenance, repair, and/or even replacement.

In one embodiment, construction related applications may include the use of split ring resonators to detect stress, unforeseen or uncalculated load-bearing, and/or other environmentally-based effects on performance, including but not limited to ambient temperature changes, moisture indices and/or saturation, and relative physical size of the raw materials employed to provide requisite support, load balancing, and stability. By way of example, split ring resonators positioned along the long axis of a support beam and/or joist in the rafters of a rooftop construction may reveal unforeseen flexing of said beams or joists, thus alerting the builder and/or occupant to potentially hazardous conditions of flex stemming from the method of construction relative to weigh borne by said construction. In addition, where structural materials other than natural wood are employed (including but not limited to composite steel, plywood, or oriented strand board, etc.) split ring resonators embedded within the structure of the load-bearing material itself may detect small imperfections or faults developing over time that could eventually lead to failure of the support structure should fault severity rise above a predetermined threshold.

In another embodiment, construction related applications may include detecting changes in the composition and structure of extremely high-level load-bearing steel-reinforced or purely concrete support pylons for pedestrian as well as vehicular bridges, elevated railways, parking structures, multi-level housing and commercial structures, etc. More specifically, split ring resonators integrated as part of the composite material of a reinforced concrete pylon structure, as well as surface-installed split ring resonators capable of detecting changes in composition, may be employed to detect the initial development of small defects, and/or presence of existing slight defects following casting, that could possibly require further external support and/or other remediation measures necessary to preserve the integrity of the structure and continue providing adequate load-bearing according to the design thereof.

In still another embodiment, construction related applications may include ensuring adherence to fire-prevention and other safety measures required by governmental standards and regulations. In such a capacity, split ring resonators may help detect the unlikely occurrence of, for example, unforeseen and unnoticeable alterations in constructed "firewalls" and/or other fire-resistant assembly systems comprising metal frames and lightweight structural cementitious (SCP) panels. Specifically, split ring resonators may detect small "gaps" developing in the installation of the firewalls or SCPs and alert builders and/or maintenance personnel to those protective measures having fallen out of compliance with the aforementioned governmental regulations where otherwise casual visual affirmation measures may not detect said non-compliance.

In one embodiment, nautical related applications may include detecting any changes in the structural integrity and/or wind pressure applied to the sailcloth of an unfurled sail as the draft of the sail opens up under wind loading. Employing split ring resonators on the surface of, and/or in between multiple cloth layers comprising, a sail may provide critical real-time information to the sailing crew of a potential problem with the integrity of the sail when in use. In one specific example, split ring resonators may be able to detect material distortions or faults within and upon a spinnaker sail composition under the stresses associated with wind loading during casual and/or competitive sailing, thus enabling the crew to more quickly affect necessary adjustments to the spinnaker sail posture with regard to its tethering to the mast, spar, and/or stay.

In another embodiment, nautical related applications may include detecting changes in solid and/or tubular mast compression when a main sail (or main sheet) experiences varying degrees of wind loading during normal operation. By way of example, the use of split ring resonators affixed to the surface of a bendable/flexible mast may assist the sailing crew in determining whether the optimal level of wind load applied to the main sail is being achieved and/or whether an adjustment therefore is required. Additionally, the use of split ring resonators affixed to a rigid mast construction may detect degrees of undue/unplanned flexing of the mast during operation, possibly indicating an excess of wind loading force upon the main sail that the crew may diagnose and make appropriate adjustments to return to optimal performance. Further, the use of split ring resonators employed both within and attached to the exterior of sold and/or tubular masts may aid the crew in detecting early signs of stress faults developing in the mast's material construction, thus enabling the crew to more accurately determine a window for more comprehensive testing, maintenance, and even outright replacement where fatigue has passed beyond a predetermined "safe" threshold.

In yet another embodiment, nautical related applications may include detecting changes and/or aberrations in the construction of vessel components (particularly the hull) due to outside forces like temperature (both in and out of the water), small and large strains possibly affecting metal, composite, and/or alloy material construction performance when both anchored as well as under propulsion. By way of one example, the use of split ring resonators may detect changes or distortions of the pontoons of a catamaran, for instance, when sailing over calm and/or challenging waters. Specifically, where multi-hull designed watercraft are generally employed due to superior ability to travel at higher speeds and remain relatively more stable than their monohull counterparts, part of that comparison equation between the two may involve hull surface areas in contact with the water during operation. Employing split ring resonators on the surface of the hull(s) of such a watercraft may detect temporary changes, aberrations, and/or distortions in the shape of the hull(s) due to changes in water temperature, impact of wake, material flex during in operation, etc. that might lead to increased drag potentially translating to a lower achievable speed than when optimal hull surface shape is maintained. With that information, watercraft crews may have the ability to possibly adjust one or more environmental parameters in an effort to return to optimal performance. In one embodiment, such environmental parameters (e.g. angle of sail, length of cord, etc.) may occur automatically (based on an actuator attached to a process to process the data from the split ring resonator(s)).

In one embodiment, forging related applications may include detecting minor aberrations in the consistency/density of forged metals, composites, and/or alloys. The arena of forging metals, composites, and/or alloys may span two major stages of implement production: applying high levels of heat and casting of ingot blanks, and the actual shaping and creation of the end-result implement derived from the forged materials. The first example may involve using split ring resonators to help detect very small (even microscopic) deformities and/or aberrations in the raw metal, composite, and/or alloy that could potentially affect the quality, strength, and reliability of the finished product exemplified by the second example. The second example, the end product of the forging process, may benefit from split ring resonators both within the metal, composite, and/or alloy raw material as well as affixed to the exterior of the finished product because the resonators may help detect surface shape, density, and/or consistency variations outside of acceptable established parameters. By way of a specific example, employing split ring resonators in the forging of the shaft and/or head of a golf club (an "iron," for example) may alert the manufacturer and designer to a slightly inaccurate club head angle or possibly weaker-than-expected coupling between the golf club shaft and head when assembled, or the split ring resonators may detect a club head shape that is slightly inconsistent with the strict design guidelines, thus requiring a reforging or other material adjustment to bring the club back into compliance with manufacturing standards.

In one embodiment, power production related applications may include establishing and maintaining consistency and optimal performance of individual solar cells within a large solar panel array. For example, split ring resonators may be integrated into the actual material of individual solar cells when fabricated which can detect when the material of the cell may be degrading or performing outside of established norms during regular operation/collection and retention periods. Additionally, split ring resonators may be employed adjacent to the array of solar cells (between the cells and the encapsulant, for example) to detect whether the solar array as a whole is experiencing compromised performance, or merely one or more individual cells.

In another embodiment, power production related applications may include detection of environmental conditions related to the structure and operation of a hydroelectric dam and/or the power plant(s) associated therewith. Using split ring resonators within the construction of a dam may provide the ability to detect changes in the composition of dam construction materials (including, but not limited to, components such as antiseepage armored concrete, concrete stake, first sealing metallic plate, metal connecting plate, second sealing metallic plate, and second antiseepage armored concrete) and enable builders, operations personnel, and maintenance personnel to analyze real-time data about the current state of the dam's structure, perhaps providing early warnings of potential faults that, left unaddressed, may mature into full-fledged catastrophic breaches in the dam's primary function. Specifically, constructing the dam with split ring resonators installed within the raw cement pours that constitute the dam's primary structure may enable sensors installed in and around the dam to provide early warning of slight changes, distortions, and or deformities in the anti-seepage armored concrete structure (s), thus enabling the operation and maintenance personnel an opportunity to remediate or mitigate any potential issues before any real problems surface.

In yet another embodiment, power production related applications may include constantly monitoring and assessing the viability and condition of horizontal-axis wind turbine stands, blades, and/or energy generators. The use of split ring resonators may detect changes in fan blade durability, wear, and posture, shape, strength, and durability of vertical stands, and/or standard operation of the turbine itself. By way of specific example, placement of split ring resonators on both the blades of a horizontal-axis wind turbine apparatus, as well as the hub to which those blades are attached, may provide early indications that an individual blade's (which may consist, in one embodiment, of aluminum-fiberglass hybrid construction) connection to the hub is weakening over time, thus requiring possible maintenance and even replacement, barring appropriate remedial measures. Early detection of these types of possible faults saves time and money in that "an ounce of prevention may be worth a pound of cure," and maximized operation time may be directly related to sustained, or even increased electric energy production.

In still another embodiment, power production related applications may include detecting and tracking changes in natural gas storage and transport conduits. As one of the costliest, (in terms of time, capital expenditure, potential energy loss, and additional maintenance cycles) issues with natural gas storage and transfer, leakage along any of the wide range of physical systems involved in delivering natural gas energy sources is a problem that may be minimized or alleviated altogether with the use of split ring resonators deployed throughout the system. By way of example, split ring resonators applied to the physical delivery conduit(s) that transport natural gas from point A to point B can detect potential leaks early by providing indications to operations and maintenance personnel that potential faults, distortions, and/or aberrations are forming within the material of the transport conduit(s) directly and/or any joints or junctions where a piece of transport conduit may be physically attached to one or more additional components. Additionally, being able to detect leakage of a predetermined gas (e.g. methane, etc.) may have green applicability in that environmentally harmful gases may be detected and stopped before causing significant damage.

In one embodiment, manufacturing related applications may include displaying information about component amalgamation and/or final assembly status (conforming or non-confirming) of a given product at the end of the build and assembly process. Employing split ring resonators in precise locations on individual parts brought together to form a complete machine or other product can detect if and where possible inaccuracies and/or misalignment may be present in the final assembly. For example, if three parts A, B, and C of an end product are to be assembled according to known strict tolerance guidelines with regard to spacing and/or alignment, split ring resonators positioned so as to detect the presence (or absence) of other precisely placed split ring resonators—for the purpose of affirming whether the two pieces A and B (or B and C, or A and C, as the case may be) are correctly connected to one another without undue variance in specified gaps or alignment—may detect where an assembly fault may be present based on proximity measurements between the split ring resonators falling outside of acceptable tolerances.

In another embodiment, manufacturing related applications may include detecting any potential faults or errors within an apparatus by way of post-production testing. The use of split ring resonators affixed to crucial locations of a newly-manufactures supersonic-capable jet engine afterburner assembly may provide critical information to the engineers and maintenance personnel regarding the accuracy of said assembly when performing its function in otherwise real-world conditions. Specifically, affixing split ring resonators to the longitudinally-movable shroud and variable area exit nozzle comprising the afterburner "thrust-shaping" mechanism can provide vital information regarding that assemblies post-production performance by relaying whether said shroud and nozzle functions are performing within established optimal tolerances, thus ensuring proper functionality prior to ultimately introducing said afterburner assembly to the supersonic jet fighter on which the assembly will perform its intended function.

In one embodiment, agriculture related applications may include detecting and tracking growth rates among a sample of agricultural products to determine whether those specimens are growing at rates within established guidelines (e.g., not growing too slowly, but also not growing too fast). Because it would be difficult, and perhaps unreasonable, to place split ring resonators within the actual fiber of plant specimens, themselves, split ring resonators employed on key external points of the non-edible portion(s) of such agricultural specimens may detect growth rates when pinged at the correct intervals over the span of a typical growth cycle of said plant specimen. In addition, split ring resonators employed may be used to simply detect and report on surface temperature readings over the course of a set polling period by reporting the surface temperature back to the polling mechanism each time a ping is conducted thereon, thus allowing the growers and botanists information relevant to the temperature of given agricultural specimens over the course of a growth cycle period. Further, split ring resonators may be employed to also provide key information about moisture saturation of agricultural specimens to which the split ring resonators are affixed. That is, whenever the polling and recording mechanism seeks a response form the one or more split ring resonators affixed to a given group of agricultural specimens, personnel monitoring the growth process may be able to discover whether, and by how much, the moisture saturation of one or more agricultural specimens demonstrates a measurement outside (either too little or too much) of acceptable parameters and possibly learn something about the effects of said moisture aberrations. Further still, split ring resonators may be able to detect whether, and by how much, agricultural specimens may be exposed to inadequate, inadequate, or excessive ultraviolet light during a growth cycle. When affixed to key external points of the non-edible portion(s) of such agricultural specimens, split ring resonators affixed to plants both within and out from under shaded areas may closely track each specimen's exposure to direct, indirect, or obscured light sources by way of readings returned during regular polling by polling and recording mechanisms.

In one embodiment, space travel related applications may include determining whether spacecraft modules are fitting together and as designed and remain safe for astronauts as well as other sensitive beings and/or inanimate payload on the ship. By way of one specific example, split ring resonators may be employed in conjunction with two spacecraft vehicles and/or spacecraft modules which are at some point connected or conjoined while operating in a zero-gravity setting. The split ring resonators may detect whether the conjoining processes (where controllers are designed to articulate the coupling system in order for the active half of the coupling system to successfully capture the target component, align the two, and establish an otherwise static/rigid connection) are completed accurately and safely by alerting astronauts and/or other monitoring personnel to potentially hazardous conditions based on proximity, air pressure, temperature reading tolerances are or are not within acceptable guidelines.

In another embodiment, space travel related applications may include constant solid rocket propellant integrity monitoring and reporting for all launch stages (before, during, and after) of a space vehicle. For example, solid rocket propellant (SRB) composites must remain crack/defect-free, as propellant composites which contain cracks present a risk of explosive failure of the vehicle. If not properly monitored for potential faults/cracks/defects, solid propellant systems may be inadvertently ignited by multiple possible causes including mechanical shock and static electricity. The possibility of employing split ring resonators in both the actual composite fuel mix, as well as upon the surface of the solid fuel element, can provide a detection medium for astronauts and ground crew to receive early warning of possible faults in an SRB fuel source before launch of the vehicle and subsequent potentially devastating failure.

In another embodiment, space travel related applications may include detecting and tracking the effects of external forces on the framing, body, and components of a rocket-propelled vessel during launch. Extreme heat, vibration, air pressure increases and decreases, and/or torque introduced by lift-off are just a few of the outside forces that may have potentially negative impact on the launch vehicle during actual launch. Such forces may lead to changes and/or distortions in the surface shape of the launch vehicle which could impose potentially dangerous results if not detected early and mitigated effectively. Thus, employing split ring resonators over the surface and within the components of a launch vehicle may help provide real-time data about changes in conditions and/or other unexpected circumstances to the astronauts and ground personnel who can then affect minor ad hoc adjustments in telemetry, etc. to keep the launch process progressing according to design parameters.

In one embodiment, professional sports equipment related applications may include monitoring and tracking raw data from a professional athlete's protective (and non-protective) equipment during competition. One high-profile example involves the use of a football helmet in professional football contests (as well as other sports requiring helmet use) and the necessity for that helmet to provide adequate protection to the wearer against concussion (or worse) brought on when the wearer's head experiences both linear acceleration and rotational acceleration due to a variety of impact types over the course of a contest. By way of a specific example, split ring resonators may be installed in the crown energy attenuation assembly (or "padding") formed from absorbent foam, air, gel, or a combination thereof and integrated into the construction of a player's helmet. In fact, split ring resonators may be a part of the actual material composition (of the absorbent foam, for example) in the helmet and used to detect extreme compression within one or more specific pressure points within the helmet during impact. Thus, athletic training staff on the sideline of a contest in progress may conceivably receive real-time "alerts" that one or more absorbent foam inserts within a particular player's helmet have just received a potentially excessive (dangerous) impact without the player, themselves, even needing to alert said personnel to the potential issue as all.

In one embodiment, professional sports equipment related applications may include monitoring the integrity of other perhaps lesser safety-oriented equipment required for success in a particular player's given competition. By way of specific example, professional hockey players may be prevented from playing (in the course of normal competition) without a suitable hockey stick used to manipulate the puck around the ice during competition. If and when a stick breaks, that player may be required to immediately discard the broken implement (which nearly always culminates in the player dropping the remnants of the broken stick in question wherever they happen to be on the ice at that moment), thus rendering the player essentially ineffective for any time he/she is on the ice during competition. Using split ring resonators both within the construct and on the outside of graphite hockey sticks (and attached to the exterior of a natural wood hockey stick) would enable bench personnel to learn whether the integrity of a hockey stick in use may be approaching a breaking point before that stick actually breaks, thus allowing the player to switch to a brand new stick before any such failure. In addition, another hockey-oriented application may involve snap-on-snap-off replaceable skate blades. If a replaceable skate blade were to unexpectedly release and/or become detached from its housing during competition, the results could be fatal. The use of split ring resonators on the two conjoining elements that constitute a replaceable skate blade connection may detect whether a separation is imminent based on a change of proximity of the two split ring resonators, thus allowing the player and/or bench staff to affect a necessary adjustment and/or reconnection in order to prevent such a separation during competition.

In one embodiment, lubricant (and other vital fluids including but not limited to fuel, coolants, and other process fluids) viscosity and/or molecular degradation related applications may include detecting, at a molecular level, when a vital fluid (such as motor oil) begins to break down within an engine during operation. By way of one specific example, microscopic split ring resonators infused within the actual composition of the liquid may detect molecular degradation of the fluid over the course of regular engine operation by, for example, detecting increased levels of foreign matter within the liquid (e.g., carbon deposits from the many thousands of ignition chamber combustion events, etc.), thus enabling an outside monitoring component the ability to display a report or initiate an alarm to alert operations and maintenance personnel when a potential threshold level of foreign particulates have become "part of" the lubricant pool within the engine requiring flushing and refreshing of lubricant to prolong the life of the machine in question. It should be noted that similar split ring resonator use may be applicable to the known other aforementioned engine-operation liquids including fuel, coolant, and process fluids like hydraulic fluid, etc.

In one embodiment, rechargeable battery composition, charging, and recharging related applications may include detecting when and how severe changing conditions within the membrane components (cathodes, anodes, separators, etc.) of a rechargeable battery may be in real time. For example, electrodes attached to the external casing of a rechargeable battery may receive detection information from split ring resonators integrated throughout the cathode (and/or anode) of a lithium battery during the initial charging, discharge, and recharging phases of battery operation.

Detection of anomalies or inconsistencies in the material make-up of the cathode (and/or anode) membranes by the split ring resonators may, thus, alert operations personnel to a potential problem with a single cell, or even a block of lithium cells, in a larger battery housing which could potentially affect overall performance.

Additionally, in some embodiments, pinging the split ring resonators may occur by an external source (such as a ping to a split ring resonator located on a surface of a vehicle). In other instances, pinging the split ring resonators may be prevented by a surrounding impediment (such as when the split ring resonators are embedded in a liquid, or within a steel structure such as an engine, etc.). In those instances, data may be collected where the split ring resonators are located. For example, if split ring resonators are within a liquid traveling through an apparatus, such split ring resonators may be pinged during the course of travel by a microprocessor (located also within the liquid) and data may be recorded during the course of travel. In this manner, when the liquid exits the apparatus, data collected during the course of travel may be provided. Further, such data may be correlated with signatures and conditions associated with the apparatus in which it was traveling. For example, if split ring resonators are embedded within a lubricant, such lubricant may be sent through an engine, and after exiting, data associated with the split ring resonators as it traveled through the engine may have a timestamp associated with each ping such that a particular location of the split ring resonator may be correlated with the timestamp. In this manner, an aberration detected internally may be ascertained after the lubricant has exited the apparatus. Additionally, in another embodiment, data obtained from pinging the split ring resonators may be received internally (within the system in which the split ring resonators are embedded) and communicated via a hard wired connection to an external antenna which, in turn, may communicate the data to an external data collecting source.

With respect to fleet management, split ring resonators may be used in a variety of contexts. For example, maintaining a fleet (e.g. drone, vehicles, trucks, planes, etc.) in good working condition may be based on individual readings of split ring resonators in each item. Knowing when an item needs to be taken from use and serviced is often based on 1) predetermined time or travel thresholds; or 2) device failure (indicative that it needs to be repaired). Having split ring resonators embedded within such fleet item would allow for precise management of a fleet such that an item is serviced whenever a sensor on the item detects a change in state 3) with respect to fleet management, individual vehicle or part wear and failure data can be communicated into the fleet's and part manufacture's warehouse and factory order system (CRM) to better synchronize just in time parts in advance of a scheduled service to improve more accurate forecasting of needed parts at the manufacturing site or warehouse site. Additionally, mass management (service warehouse, real estate houses, commercial properties, etc.) can be time and cost intensive to maintain. Split ring resonators can be tuned for specific sensitivities (such as detecting when a layer of dust is found on a floor). Such an applicability could apply even to research facilities (which operate in no dust zones).

In various embodiments, operation of the split ring resonators may be used for triangulation (or location positioning). Additionally, a response from a split ring resonator may, in turn, cause a response in a second split ring resonator, which may, in turn, generate another response in a third split ring resonator, and so on and so forth. In this manner, a response from a single split ring resonator may be sequenced through other split ring resonators as needed. In another embodiment, operation of the split ring resonators may be used for triangulation (or location positioning) in areas where GPS data is nonexistent, compromised or insufficiently accurate for precise navigation and location.

In another embodiment, the mattress industry may use split ring resonators to modify the contours of a mattress to match a preference of a user. For example, a user may want to decrease pressure at a certain point of the mattress (to alleviate back pain, etc.). As a user lies on the mattress, the split ring resonators (which may be embedded within the mattress, within a foam material, etc.) may indicate pressure points across the entire mattress. A processor associated with the mattress may be used to interpret such data and modify the contours of the mattress (including by mechanical manipulation, expansion/retraction of foam in the amount of compression, etc.) to achieve the desired outcome (a specific pressure at the specific point indicated). Additionally, a doctor may provide a specific set of mattress pressure points (to alleviate a condition) which may be inputted into the mattress such that when a user lies on the mattress, the mattress may be configured in real time to meet the prescribed pressure points. Further, as a user changes position in bed (from side to back sleeping, etc.), the mattress may continually adjust the contours of the bed to meet the predetermined pressure points, regardless of the position taken by the user.

Still yet, in one embodiment, the split ring resonators could be used to detect a growth on an object. For example, the split ring resonators may be embedded into fiber and composite fiber such that if black mold grew, for example, on the surface of wall (such as an inside wall that is not outwardly facing), the black mold may be detected on the surface of the wall. Additionally, the split ring resonators may be used to detect a leak (such as a water leak in a basement of a house). Thus, within the context of house maintenance and safety, split ring resonators may be used to detect the state of the house.

Further, split ring resonators may be used to detect integrity of medication (such as medication spoilage). Additionally, it may be used in a sensor to detect a physical condition (presence of gangrene, blood sugar levels for diabetes, etc.).

Further applicability of use of resonant frequency shifts of split ring resonators may apply within the context of U.S. patent application Ser. No. 17/884,735, entitled "BATTERY SAFETY SYSTEM FOR DETECTING ANALYTES," filed Aug. 10, 2022, and U.S. patent application Ser. No. 17/182,006, entitled "ANALYTE SENSING DEVICE," filed Feb. 22, 2021, the contents of all of which are herein incorporated by reference for all purposes.

Further, split ring resonators may be used to detect can be placed on individual containers of consumer packaged goods, e.g. laundry detergent, milk, etc or consumer RX containers to determine the amount of product remaining in the container and then relay that information into a patient's medical management system or automatic re-ordering system.

In the foregoing specification, the disclosure has been described with reference to specific implementations thereof. It will however be evident that various modifications and changes may be made thereto without departing from the broader spirit and scope of the disclosure. For example, the above-described process flows are described with reference to an ordering of process actions. However, the ordering of many of the described process actions may be changed without affecting the scope or operation of the disclosure. The specification and drawings are to be regarded in an illustrative sense rather than in a restrictive sense.

What is claimed is:

1. A structural building component, comprising:
   at least one meso-scale or micro-scale resonator embedded within a material of the structural building component, or placed on a surface of the material;
   wherein the at least one meso-scale or micro-scale resonator is formed from a three-dimensional (3D) monolithic carbonaceous growth and wherein the at least one meso-scale or micro-scale resonator is configured to respond to a wireless electromagnetic stimulus; and
   wherein the at least one meso-scale or micro-scale resonator is configured to resonate at one or more corresponding unique frequencies, the frequencies indicating a state of the material at a position proximate to the at least one meso-scale or micro-scale resonator.

2. The structural building component of claim 1, wherein the material is concrete or steel.

3. The structural building component of claim 2, wherein a first frequency of the one or more corresponding unique frequencies is associated with a calibration signature of the material.

4. The structural building component of claim 3, wherein the calibration signature is measured after the concrete has been poured, cured, and hardened.

5. The structural building component of claim 3, wherein a second signature is measured at a time after the calibration signature was measured.

6. The structural building component of claim 5, wherein the second signature is associated with a second frequency.

7. The structural building component of claim 5, wherein the second signature indicates at least one of a deformation, a change in compression, a change in flexion, a change in response, a fracture, a strain, or a stress.

8. The structural building component of claim 1, wherein the at least one meso-scale or micro-scale resonator is configured to resonate at a first frequency in response to the wireless electromagnetic stimulus when the material is in a first state, and is configured to resonate at a second frequency in response to the wireless electromagnetic stimulus when the material is in a second state.

9. The structural building component of claim 1, wherein a tuned resonant frequency of the 3D monolithic carbonaceous growth is based at least in part on one or more physical characteristics of the material.

10. The structural building component of claim 1, wherein the at least one meso-scale or micro-scale resonator is configured to indicate a first condition of the material by generating a first wireless electromagnetic return signal in response to the wireless electromagnetic stimulus, and is configured to indicate a second condition of the material by generating a second wireless electromagnetic return signal in response to the wireless electromagnetic stimulus.

11. The structural building component of claim 10, wherein the first wireless electromagnetic return signal has a first frequency, and the second wireless electromagnetic return signal has a second frequency different than the first frequency.

12. The structural building component of claim 1, wherein the state of the material includes a deformation of the material.

13. The structural building component of claim 12, wherein the at least one meso-scale or micro-scale resonator is configured to indicate the deformation of the material by generating a first electromagnetic return signal in response to the wireless electromagnetic stimulus, and is configured to indicate a lack of deformation of the material by generating a second electromagnetic return signal in response to the wireless electromagnetic stimulus.

14. The structural building component of claim 1, wherein at least one meso-scale or micro-scale resonator includes a resonance portion.

15. The structural building component of claim 14, wherein the resonance portion is configured to resonate at a first frequency in response to the wireless electromagnetic stimulus when the state of the material exceeds a threshold, and is configured to resonate at a second frequency in response to the wireless electromagnetic stimulus when the state of the material is beneath the threshold.

16. The structural building component of claim 1, wherein a resonant frequency of 3D monolithic carbonaceous growth is based at least in part on either or both of a permittivity and a permeability of the material.

17. The structural building component of claim 1, wherein at least one of:
   the at least one meso-scale or micro-scale resonator further comprises a first meso-scale or micro-scale resonator including a plurality of first carbon particles configured to uniquely resonate in response to the wireless electromagnetic stimulus based at least in part on a concentration level of the first carbon particles within the first meso-scale or micro-scale resonator;
   the at least one meso-scale or micro-scale resonator further comprises a second meso-scale or micro-scale resonator and includes a plurality of second carbon particles configured to uniquely resonate in response to the wireless electromagnetic stimulus based at least in part on a concentration level of the second carbon particles within the second meso-scale or micro-scale resonator;
   each of the first carbon particles and second carbon particles is chemically bonded with the material;
   the first carbon particles include first aggregates forming a first porous structure; or
   the second carbon particles include second aggregates forming a second porous structure.

18. The structural building component of claim 1, wherein the at least one meso-scale or micro-scale resonator comprises a first meso-scale or micro-scale resonator and a second meso-scale or micro-scale resonator.

19. The structural building component of claim 18, wherein at least one of:
   the first meso-scale or micro-scale resonator is configured to resonate at a first frequency in response to the wireless electromagnetic stimulus;
   the second meso-scale or micro-scale resonator is configured to resonate at a second frequency in response to the wireless electromagnetic stimulus;
   the first frequency is different than the second frequency;
   an amplitude of resonance of the first meso-scale or micro-scale resonator or the second meso-scale or micro-scale resonator is indicative of an extent of wear of the material; or
   an extent of shift of a natural resonance frequency in response to the wireless electromagnetic stimulus of the first meso-scale or micro-scale resonator and the second meso-scale or micro-scale resonator is indicative of an amount of deformation of the material.

20. The structural building component of claim 18, wherein each of the first meso-scale or micro-scale resonator and the second meso-scale or micro-scale resonator has an attenuation point, wherein the attenuation point of each the first meso-scale or micro-scale resonator and the second meso-scale or micro-scale resonator is associated with a frequency response to the wireless electromagnetic stimulus.

21. The structural building component of claim 1, wherein the structural building component comprises a load-bearing element of a building structure selected from the group consisting of: a foundation element, a wall, a column, a beam, a roof component, a bridge component, and a dam component.

22. The structural building component of claim 1, wherein the structural building component is configured to provide at least one of: structural support, load distribution, or structural integrity to a building structure, and wherein the material comprises at least one of: concrete, steel, wood, composite materials, or reinforced polymers.

23. The structural building component of claim 1, wherein the structural building component is a foundation, wall, column, beam, or roof element of a building.

24. The structural building component of claim 1, wherein the structural building component is made of concrete or steel and is configured to support or distribute loads in a building structure.

25. The structural building component of claim 1, wherein the structural building component is a load-bearing element that provides structural integrity to a building.

26. The structural building component of claim 1, wherein the structural building component is a primary structural element that transfers loads to a foundation or supporting structure, and wherein the at least one meso-scale or micro-scale resonator is positioned at a location on or within the structural building component that experiences stress concentration during normal use of the building structure.

27. The structural building component of claim 1, wherein the at least one meso-scale or micro-scale resonator is configured to detect changes in material properties that would compromise a structural integrity of the building structure.

28. The structural building component of claim 1, wherein the structural building component is selected from the group consisting of: a foundation element, a load-bearing wall, a column, a beam, a roof component, a bridge component, a concrete panel, a reinforced concrete element, a steel frame element, and combinations thereof, wherein the structural building component is configured to provide structural support, load distribution, or structural integrity to a building structure.

* * * * *